US009133166B2

(12) United States Patent
Kanouni et al.

(10) Patent No.: US 9,133,166 B2
(45) Date of Patent: Sep. 15, 2015

(54) HISTONE DEMETHYLASE INHIBITORS

(71) Applicant: Quanticel Pharmaceuticals, Inc., San Diego, CA (US)

(72) Inventors: Toufike Kanouni, La Jolla, CA (US); Zhe Nie, San Diego, CA (US); Jeffrey Alan Stafford, San Diego, CA (US); James Marvin Veal, Apex, NC (US)

(73) Assignee: QUANTICEL PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 14/210,006

(22) Filed: Mar. 13, 2014

(65) Prior Publication Data

US 2014/0275084 A1 Sep. 18, 2014

Related U.S. Application Data

(60) Provisional application No. 61/783,563, filed on Mar. 14, 2013.

(51) Int. Cl.
*C07D 401/04* (2006.01)
*C07D 401/14* (2006.01)

(52) U.S. Cl.
CPC ............ *C07D 401/14* (2013.01); *C07D 401/04* (2013.01)

(58) Field of Classification Search
CPC .................................................... C07D 401/04
USPC ........................................ 546/274.1; 514/341
See application file for complete search history.

(56) References Cited

U.S. PATENT DOCUMENTS

| 6,846,834 | B2 | 1/2005 | Browner et al. |
| 7,186,841 | B2 | 3/2007 | Browner et al. |
| 7,977,334 | B2 | 7/2011 | Trieselmann et al. |
| 2004/0127733 | A1 | 7/2004 | Trieselmann et al. |
| 2005/0245526 | A1 | 11/2005 | Trieselmann et al. |
| 2007/0135464 | A1 | 6/2007 | Browner et al. |
| 2009/0221589 | A1 | 9/2009 | Trieselmann et al. |
| 2011/0111046 | A1 | 5/2011 | Bagley et al. |

FOREIGN PATENT DOCUMENTS

WO WO00/39108 7/2000

OTHER PUBLICATIONS

Berge et al., "Pharmaceutical Salts", Journal of Pharmaceutical Sciences, Jan. 1977, vol. 66, No. 1, pp. 1-19.
Lachner et al., "An epigenetic road map for histone lysine methylation" Jun. 1, 2003 Journal of Cell Science vol. 116, pp. 2117-2124.
Lin, et al. "Loss of the retinoblastoma binding protein 2 (RBP2) histone demethylase supresses tumorigenesis in mice lacking RB1 or Men1" Aug. 16, 2011, Proc. Natl. Acad. Sci. vol. 108, Issue 33 pp. 13379-13386.
Klose et al. "JmjC-domain-containing proteins and histone demethylation" Sep. 2006, Nature Reviews Genetics vol. 7, pp. 715-727.
Mangueron et al. "The key to development: interpreting the histone code?" 2005, Current Opinion Genet. Dev. vol. 15, pp. 163-176.
P. H. Stahl & C. G. Wermuth "Handbook of Pharmaceutical Salts", Verlag Helvetica Chimica Acta, Zurich, 2002.
PCT/US2014/26710 International Search Report and Written Opinion Dated Jul. 14, 2014.
PUBCHEM SureCN11168572, CID 70529681, pp. 1-3, Create Date: Dec. 1, 2012; p. 1; [retrieved on Jun. 4, 2014]. Retrieved from the Internet: <URL: http://pubchem.ncbi.nlm.nih.gov/summary/summary.cgi?cid=70529681&loc=ec_rcs>.
PUBCHEM SureCN12075252, CID 13320858, pp. 1-5, Create Date: Feb. 8, 2007; p. 1; [retrieved on Jun. 4, 2014]. Retrieved from the Internet: <URL: http://pubchem.ncbi.nlm.nih.gov/summary/summary.cgi?cid=13320858&loc=ec_rcs>.
PUBCHEM SureCN12427208, CID 60046595, pp. 1-5, Create Date: Aug. 20, 2012; p. 1; [retrieved on Jun. 4, 2014]. Retrieved from the Internet: <URL: http://pubchem.ncbi.nlm.nih.gov/summary/summary.cgi?cid=60046595&loc=ec_rcs>.
PUBCHEM SureCN14499331, CID 20753075, pp. 1-6, Create Date: Dec. 5, 2007; p. 1; [retrieved on Jun. 4, 2014]. Retrieved from the Internet: <URL: http://pubchem.ncbi.nlm.nih.gov/summary/summary.cgi?cid=20753075&loc=ec_rcs>.
PUBCHEM SureCN1899117, CID 57525825, pp. 1-6, Create Date: Aug. 16, 2012; p. 1; [retrieved on Jun. 4, 2014]. Retrieved from the Internet: <URL: http://pubchem.ncbi.nlm.nih.gov/summary/summary.cgi?cid=57525825&loc=ec_rcs>.
PUBCHEM SureCN6808551, CID 9859560, pp. 1-3, Create Date: Oct. 25, 2006; p. 1; [retrieved on Jun. 4, 2014]. Retrieved from the Internet: <URL: http://pubchem.ncbi.nlm.nih.govisummary/summary.cgi?cid=98595608Jocrec_rcs>.

*Primary Examiner* — Patricia L Morris
(74) *Attorney, Agent, or Firm* — Wilson Sonsini Goodrich & Rosati

(57) ABSTRACT

The present invention relates generally to compositions and methods for treating cancer and neoplastic diseases. Provided herein are substituted imidazole-pyridine derivative compounds and pharmaceutical compositions comprising said compounds. The subject compounds and compositions are useful for inhibition of histone demethylase enzymes. Furthermore, the subject compounds and compositions are useful for the treatment of cancer, such as prostate cancer, breast cancer, bladder cancer, lung cancer and/or melanoma and the like.

17 Claims, No Drawings

HISTONE DEMETHYLASE INHIBITORS

CROSS REFERENCE

This application claims the benefit of U.S. Provisional Application 61/783,563, filed Mar. 14, 2013, the content of which is hereby incorporated by reference in its entirety.

BACKGROUND

A need exists in the art for an effective treatment of cancer and neoplastic disease.

BRIEF SUMMARY OF THE INVENTION

Provided herein are substituted imidazole-pyridine derivative compounds and pharmaceutical compositions comprising said compounds. The subject compounds and compositions are useful for the inhibition of histone demethylase. Furthermore, the subject compounds and compositions are useful for the treatment of cancer, such as prostate cancer, breast cancer, bladder cancer, lung cancer and/or melanoma and the like. The substituted imidazole-pyridine derivative compounds described herein are based upon a substituted 2-(1H-imidazol-4-yl)pyridine ring system bearing at the 4-position of the pyridine ring a carboxylic acid, carboxylic acid ester, or bioisostere thereof, and additional substituents at the 1-, 2- and 5-position of the imidazole ring. The 1-position substituent, in various embodiments, is selected from a wide variety of groups, such as, but not limited to, alkyl, aryl, carbocyclyl, and the like.

One embodiment provides a compound of Formula (I), or a pharmaceutically acceptable salt thereof:

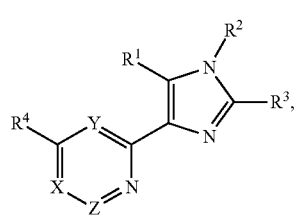

Formula (I)

wherein,
X is CH, Y is CH and Z is CH; or
X is COH, Y is CH and Z is CH; or
X is CH, Y is CH, and Z is N; or
X is N, Y is CH, and Z is CH; or
X is CH, Y is N, and Z is CH;
$R^1$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^2$ is alkyl, carbocyclyl, heterocyclyl, aryl, heteroaryl, carbocyclylalkyl, heterocyclylalkyl, aralkyl, or heteroarylalkyl;
$R^3$ is hydrogen, halogen, —OH, —$NH_2$, —NH(C1-C3alkyl) or C1-C3alkyl;
$R^4$ is —$CO_2H$, —$CO_2R^6$, —C(O)N(H)CN, —C(O)N(H)OH, or tetrazolyl;
each $R^5$ is independently hydrogen, alkyl, carbocyclyl, heterocyclyl, aryl, heteroaryl, carbocyclylalkyl, heterocyclylalkyl, aralkyl, or heteroarylalkyl; and
$R^6$ is alkyl.

Another embodiment provides the compound of Formula (I) having the structure of Formula (II), or a pharmaceutically acceptable salt thereof:

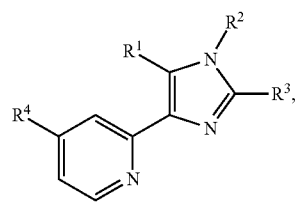

Formula (II)

wherein,
$R^1$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^2$ is alkyl, carbocyclyl, heterocyclyl, aryl, heteroaryl, carbocyclylalkyl, heterocyclylalkyl, aralkyl, or heteroarylalkyl;
$R^3$ is hydrogen, halogen, —OH, —$NH_2$, —NH(C1-C3alkyl) or C1-C3alkyl;
$R^4$ is —$CO_2H$, —$CO_2R^6$, —C(O)N(H)CN, —C(O)N(H)OH, or tetrazolyl;
each $R^5$ is independently hydrogen, alkyl, carbocyclyl, heterocyclyl, aryl, heteroaryl, carbocyclylalkyl, heterocyclylalkyl, aralkyl, or heteroarylalkyl; and
$R^6$ is alkyl.

One embodiment provides a pharmaceutical composition comprising a pharmaceutically acceptable carrier and a compound of Formula (I), or a pharmaceutically acceptable salt thereof, wherein the compound of Formula (I) has the structure:

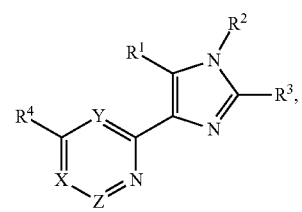

Formula (I)

wherein,
X is CH, Y is CH and Z is CH; or
X is COH, Y is CH and Z is CH; or
X is CH, Y is CH, and Z is N; or
X is N, Y is CH, and Z is CH; or
X is CH, Y is N, and Z is CH;
$R^1$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^2$ is alkyl, carbocyclyl, heterocyclyl, aryl, heteroaryl, carbocyclylalkyl, heterocyclylalkyl, aralkyl, or heteroarylalkyl;
$R^3$ is hydrogen, halogen, —OH, —$NH_2$, —NH(C1-C3alkyl) or C1-C3alkyl;
$R^4$ is —$CO_2H$, —$CO_2R^6$, —C(O)N(H)CN, —C(O)N(H)OH, or tetrazolyl;
each $R^5$ is independently hydrogen, alkyl, carbocyclyl, heterocyclyl, aryl, heteroaryl, carbocyclylalkyl, heterocyclylalkyl, aralkyl, or heteroarylalkyl; and
$R^6$ is alkyl.

One embodiment provides a method for treating cancer in subject comprising administering a composition comprising a compound of Formula (I), or a pharmaceutically acceptable salt thereof, wherein the compound of Formula (I) has the structure:

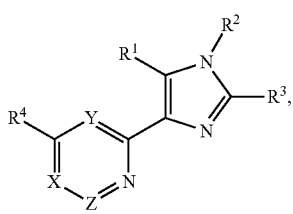

Formula (I)

wherein,

X is CH, Y is CH and Z is CH; or
X is COH, Y is CH and Z is CH; or
X is CH, Y is CH, and Z is N; or
X is N, Y is CH, and Z is CH; or
X is CH, Y is N, and Z is CH;
$R^1$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^2$ is alkyl, carbocyclyl, heterocyclyl, aryl, heteroaryl, carbocyclylalkyl, heterocyclylalkyl, aralkyl, or heteroarylalkyl;
$R^3$ is hydrogen, halogen, —OH, —$NH_2$, —NH(C1-C3alkyl) or C1-C3alkyl;
$R^4$ is —$CO_2H$, —$CO_2R^6$, —C(O)N(H)CN, —C(O)N(H)OH, or tetrazolyl;
each $R^5$ is independently hydrogen, alkyl, carbocyclyl, heterocyclyl, aryl, heteroaryl, carbocyclylalkyl, heterocyclylalkyl, aralkyl, or heteroarylalkyl; and
$R^6$ is alkyl.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

DEFINITIONS

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4- dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

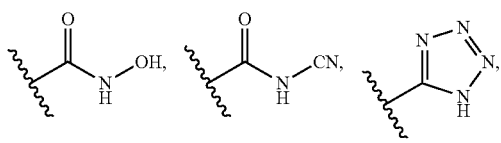

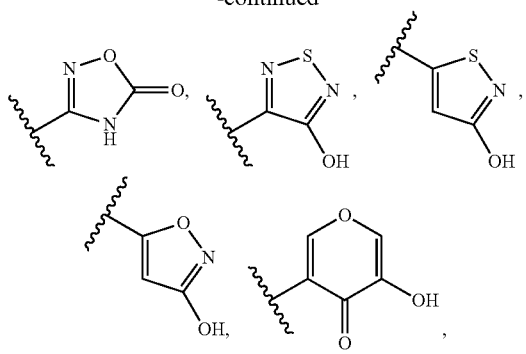

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2), —$R^b$—S(O)$_t R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

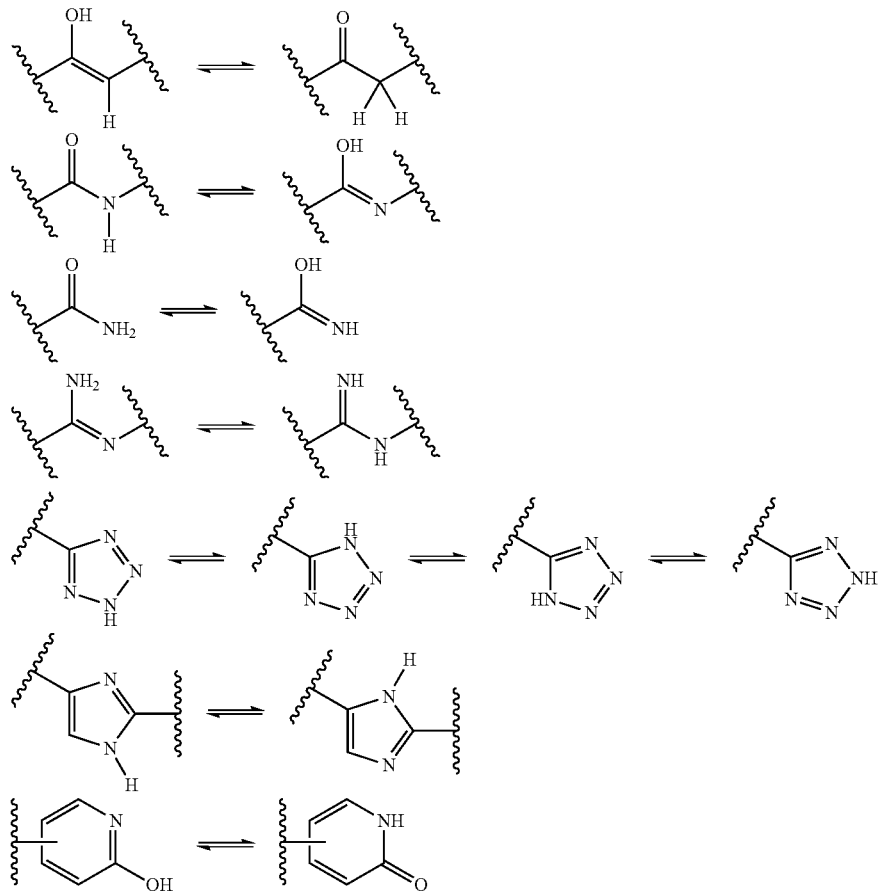

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted imidazole-pyridine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic monoand dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted Imidazole-Pyridine Derivative Compounds

Substituted imidazole-pyridine derivative compounds are described herein that inhibit a histone demethylase enzyme. These compounds, and compositions comprising these compounds, are useful for the treatment of cancer and neoplastic diseases. The compounds described herein may, therefore, be useful for treating prostate cancer, breast cancer, bladder cancer, lung cancer and/or melanoma and the like.

One embodiment provides a compound of Formula (I), or a pharmaceutically acceptable salt thereof:

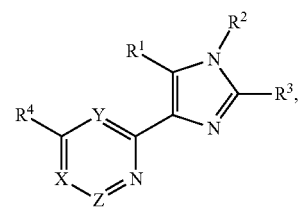

Formula (I)

wherein,

X is CH, Y is CH and Z is CH; or
X is COH, Y is CH and Z is CH; or
X is CH, Y is CH, and Z is N; or
X is N, Y is CH, and Z is CH; or
X is CH, Y is N, and Z is CH;
$R^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;
$R^2$ is alkyl, carbocyclyl, heterocyclyl, aryl, heteroaryl, carbocyclylalkyl, heterocyclylalkyl, aralkyl, or heteroarylalkyl;

$R^3$ is hydrogen, halogen, —OH, —NH$_2$, —NH(C1-C3alkyl) or C1-C3alkyl;

$R^4$ is —CO$_2$H, —CO$_2$R$^6$, —C(O)N(H)CN, —C(O)N(H)OH, or tetrazolyl;

each $R^5$ is independently hydrogen, alkyl, carbocyclyl, heterocyclyl, aryl, heteroaryl, carbocyclylalkyl, heterocyclylalkyl, aralkyl, or heteroarylalkyl; and $R^6$ is alkyl.

Another embodiment provides the compound of Formula (I), wherein X is COH, Y is CH and Z is CH. Another embodiment provides the compound of Formula (I), wherein X is CH, Y is CH, and Z is N. Another embodiment provides the compound of Formula (I), wherein X is N, Y is CH, and Z is CH. Another embodiment provides the compound of Formula (I), wherein X is CH, Y is N, and Z is CH.

Another embodiment provides the compound of Formula (I) having the structure of Formula (II), or a pharmaceutically acceptable salt thereof:

Formula (II)

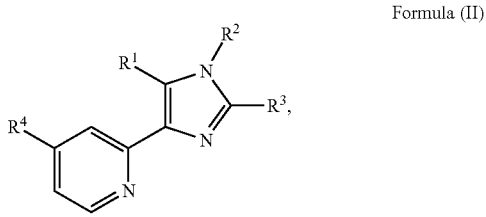

wherein, $R^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^2$ is alkyl, carbocyclyl, heterocyclyl, aryl, heteroaryl, carbocyclylalkyl, heterocyclylalkyl, aralkyl, or heteroarylalkyl;

$R^3$ is hydrogen, halogen, —OH, —NH$_2$, —NH(C1-C3alkyl) or C1-C3alkyl;

$R^4$ is —CO$_2$H, —CO$_2$R$^6$, —C(O)N(H)CN, —C(O)N(H)OH, or tetrazolyl;

each $R^5$ is independently hydrogen, alkyl, carbocyclyl, heterocyclyl, aryl, heteroaryl, carbocyclylalkyl, heterocyclylalkyl, aralkyl, or heteroarylalkyl; and $R^6$ is alkyl.

In another embodiment is a compound of Formula (II) wherein $R^3$ is hydrogen. In another embodiment is a compound of Formula (II) wherein $R^3$ is hydrogen and $R^4$ is —CO$_2$H. In another embodiment is a compound of Formula (II) wherein $R^3$ is hydrogen and $R^4$ is —CO$_2$R$^6$. In another embodiment is a compound of Formula (II) wherein $R^3$ is hydrogen, $R^4$ is —CO$_2$R$^6$, and $R^6$ is methyl. In another embodiment is a compound of Formula (II) wherein $R^3$ is hydrogen, $R^4$ is —CO$_2$R$^6$, and $R^6$ is ethyl. In another embodiment is a compound of Formula (II) wherein $R^3$ is hydrogen, $R^4$ is —C(O)N(H)CN. In another embodiment is a compound of Formula (II) wherein $R^3$ is hydrogen, $R^4$ is tetrazolyl. In another embodiment is a compound of Formula (II) wherein $R^3$ is hydrogen, $R^4$ is —C(O)N(H)OH. In another embodiment is a compound of Formula (II) wherein $R^4$ is tetrazolyl and the tetrazolyl is further substituted with a methyl or —R$^b$—OC(O)—R$^a$ wherein R$^b$ is C$_1$-C$_3$ alkylene and R$^a$ is alkyl.

In another embodiment is a compound of Formula (II) wherein $R^3$ is hydrogen, $R^4$ is —CO$_2$H, and $R^2$ is alkyl. In another embodiment is a compound of Formula (II) wherein $R^3$ is hydrogen, $R^4$ is —CO$_2$H, and $R^2$ is methyl. In another embodiment is a compound of Formula (II) wherein $R^3$ is hydrogen, $R^4$ is —CO$_2$H, $R^2$ is alkyl substituted with alkoxy.

In another embodiment is a compound of Formula (II) wherein $R^3$ is hydrogen, $R^4$ is —CO$_2$H, $R^2$ is alkyl substituted with dialkylamino. In another embodiment is a compound of Formula (II) wherein $R^3$ is hydrogen, $R^4$ is —CO$_2$H, $R^2$ is alkyl substituted with (aryl)(alkyl)amino. In another embodiment is a compound of Formula (II) wherein $R^3$ is hydrogen, $R^4$ is —CO$_2$H, $R^2$ is alkyl substituted with (carbocyclyl)(alkyl)amino. In another embodiment is a compound of Formula (II) wherein $R^3$ is hydrogen, $R^4$ is —CO$_2$H, $R^2$ is alkyl substituted with (heteroaryl)(alkyl)amino. In another embodiment is a compound of Formula (II) wherein $R^3$ is hydrogen, $R^4$ is —CO$_2$H, $R^2$ is alkyl substituted with (heterocyclyl)(alkyl)amino. In another embodiment is a compound of Formula (II) wherein $R^3$ is hydrogen, $R^4$ is —CO$_2$H, $R^2$ is alkyl substituted with (aralkyl)(alkyl)amino. In another embodiment is a compound of Formula (II) wherein $R^3$ is hydrogen, $R^4$ is —CO$_2$H, $R^2$ is alkyl substituted with (carbocyclylalkyl)(alkyl)amino. In another embodiment is a compound of Formula (II) wherein $R^3$ is hydrogen, $R^4$ is —CO$_2$H, $R^2$ is alkyl substituted with (heteroarylalkyl)(alkyl)amino. In another embodiment is a compound of Formula (II) wherein $R^3$ is hydrogen, $R^4$ is —CO$_2$H, $R^2$ is alkyl substituted with (heterocyclylalkyl)(alkyl)amino. In another embodiment is a compound of Formula (II) wherein $R^3$ is hydrogen, $R^4$ is —CO$_2$H, $R^2$ is heterocyclylalkyl. In another embodiment is a compound of Formula (II) wherein $R^3$ is hydrogen, $R^4$ is —CO$_2$H, $R^2$ is heteroaryl. In another embodiment is a compound of Formula (II) wherein $R^3$ is hydrogen, $R^4$ is —CO$_2$H, $R^2$ is heteroarylalkyl. In another embodiment is a compound of Formula (II) wherein $R^3$ is hydrogen, $R^4$ is —CO$_2$H, $R^2$ is aralkyl. In another embodiment is a compound of Formula (II) wherein $R^3$ is hydrogen, $R^4$ is —CO$_2$H, $R^2$ is carbocyclylalkyl. In another embodiment is a compound of Formula (II) wherein $R^3$ is hydrogen, $R^4$ is tetrazolyl, $R^2$ is heterocyclylalkyl. In another embodiment is a compound of Formula (II) wherein $R^3$ is hydrogen, $R^4$ is tetrazolyl, $R^2$ is heteroarylalkyl. In another embodiment is a compound of Formula (II) wherein $R^3$ is hydrogen, $R^4$ is tetrazolyl, $R^2$ is aralkyl. In another embodiment is a compound of Formula (II) wherein $R^3$ is hydrogen, $R^4$ is tetrazolyl, $R^2$ is carbocyclylalkyl.

In another embodiment of the aforementioned embodiments is a compound of Formula (II) wherein $R^1$ is aryl. In a further embodiment of the aforementioned embodiments is a compound of Formula (II) wherein $R^1$ is phenyl optionally substituted with one or more groups selected from halogen, —OH, —OR$^5$, —N(R$^5$)$_2$, —CON(R$^5$)$_2$, alkyl, alkynyl, carbocyclyl, heterocyclyl, aryl, heteroaryl, carbocyclylalkyl, heterocyclylalkyl, aralkyl, and heteroarylalkyl. In yet a further embodiment of the aforementioned embodiments is a compound of Formula (II) wherein $R^1$ is phenyl optionally substituted with one or more groups selected from halogen, —OH, —OR$^5$, alkyl, carbocyclyl, heterocyclyl, and heteroaryl.

In another embodiment is a compound of Formula (II) wherein $R^1$ is hydrogen, $R^3$ is hydrogen, $R^4$ is —CO$_2$H, and $R^2$ is alkyl. In another embodiment is a compound of Formula (II) wherein $R^1$ is hydrogen, $R^3$ is hydrogen, $R^4$ is —CO$_2$H, and $R^2$ is methyl. In another embodiment is a compound of Formula (II) wherein $R^1$ is hydrogen, $R^3$ is hydrogen, $R^4$ is —CO$_2$H, $R^2$ is alkyl substituted with alkoxy. In another embodiment is a compound of Formula (II) wherein $R^1$ is hydrogen, $R^3$ is hydrogen, $R^4$ is —CO$_2$H, $R^2$ is alkyl substituted with dialkylamino. In another embodiment is a compound of Formula (II) wherein $R^1$ is hydrogen, $R^3$ is hydrogen, $R^4$ is —CO$_2$H, $R^2$ is alkyl substituted with (aryl)(alkyl)amino. In another embodiment is a compound of Formula (II)

wherein R¹ is hydrogen, R³ is hydrogen, R⁴ is —CO₂H, R² is alkyl substituted with (carbocyclyl)(alkyl)amino. In another embodiment is a compound of Formula (II) wherein R¹ is hydrogen, R³ is hydrogen, R⁴ is —CO₂H, R² is alkyl substituted with (heteroaryl)(alkyl)amino. In another embodiment is a compound of Formula (II) wherein R¹ is hydrogen, R³ is hydrogen, R⁴ is —CO₂H, R² is alkyl substituted with (heterocyclyl)(alkyl)amino. In another embodiment is a compound of Formula (II) wherein R¹ is hydrogen, R³ is hydrogen, R⁴ is —CO₂H, R² is alkyl substituted with (aralkyl)(alkyl)amino. In another embodiment is a compound of Formula (II) wherein R¹ is hydrogen, R³ is hydrogen, R⁴ is —CO₂H, R² is alkyl substituted with (carbocyclylalkyl)(alkyl)amino. In another embodiment is a compound of Formula (II) wherein R¹ is hydrogen, R³ is hydrogen, R⁴ is —CO₂H, R² is alkyl substituted with (heteroarylalkyl)(alkyl)amino. In another embodiment is a compound of Formula (II) wherein R¹ is hydrogen, R³ is hydrogen, R⁴ is —CO₂H, R² is alkyl substituted with (heterocyclylalkyl)(alkyl)amino. In another embodiment is a compound of Formula (II) wherein R¹ is hydrogen, R³ is hydrogen, R⁴ is —CO₂H, R² is heterocyclylalkyl. In another embodiment is a compound of Formula (II) wherein R¹ is hydrogen, R³ is hydrogen, R⁴ is —CO₂H, R² is heteroaryl. In another embodiment is a compound of Formula (II) wherein R¹ is hydrogen, R³ is hydrogen, R⁴ is —CO₂H, R² is heteroarylalkyl. In another embodiment is a compound of Formula (II) wherein R¹ is hydrogen, R³ is hydrogen, R⁴ is —CO₂H, R² is aralkyl. In another embodiment is a compound of Formula (II) wherein R¹ is hydrogen, R³ is hydrogen, R⁴ is —CO₂H, R² is carbocyclylalkyl. In another embodiment is a compound of Formula (II) wherein R¹ is hydrogen, R³ is hydrogen, R⁴ is tetrazolyl, R² is heterocyclylalkyl. In another embodiment is a compound of Formula (II) wherein R¹ is hydrogen, R³ is hydrogen, R⁴ is tetrazolyl, R² is heteroarylalkyl. In another embodiment is a compound of Formula (II) wherein R¹ is hydrogen, R³ is hydrogen, R⁴ is tetrazolyl, R² is aralkyl. In another embodiment is a compound of Formula (II) wherein R¹ is hydrogen, R³ is hydrogen, R⁴ is tetrazolyl, R² is carbocyclylalkyl.

In another embodiment is a compound of Formula (II) wherein R¹ is phenyl substituted with one or more groups selected from halogen, —OH, —OR⁵, —N(R⁵)₂, —CON(R⁵)₂, alkyl, alkynyl, carbocyclyl, heterocyclyl, aryl, heteroaryl, carbocyclylalkyl, heterocyclylalkyl, aralkyl, and heteroarylalkyl, R³ is hydrogen, R⁴ is —CO₂H, and R² is hydrogen. In another embodiment is a compound of Formula (II) wherein R¹ is phenyl substituted with one or more groups selected from halogen, —OH, —OR⁵, —N(R⁵)₂, —CON(R⁵)₂, alkyl, alkynyl, carbocyclyl, heterocyclyl, aryl, heteroaryl, carbocyclylalkyl, heterocyclylalkyl, aralkyl, and heteroarylalkyl, R³ is hydrogen, R⁴ is —CO₂H, and R² is alkyl. In another embodiment is a compound of Formula (II) wherein R¹ is phenyl substituted with one or more groups selected from halogen, —OH, —OR⁵, —N(R⁵)₂, —CON(R⁵)₂, alkyl, alkynyl, carbocyclyl, heterocyclyl, aryl, heteroaryl, carbocyclylalkyl, heterocyclylalkyl, aralkyl, and heteroarylalkyl, R³ is hydrogen, R⁴ is —CO₂H, and R² is methyl. In another embodiment is a compound of Formula (II) wherein R¹ is phenyl substituted with one or more groups selected from halogen, —OH, —OR⁵, —N(R⁵)₂, —CON(R⁵)₂, alkyl, alkynyl, carbocyclyl, heterocyclyl, aryl, heteroaryl, carbocyclylalkyl, heterocyclylalkyl, aralkyl, and heteroarylalkyl, R³ is hydrogen, R⁴ is —CO₂R⁶, and R² is methyl. In another embodiment is a compound of Formula (II) wherein R¹ is phenyl substituted with one or more groups selected from halogen, —OH, —OR⁵, —N(R⁵)₂, —CON(R⁵)₂, alkyl, alkynyl, carbocyclyl, heterocyclyl, aryl, heteroaryl, carbocyclylalkyl, heterocyclylalkyl, aralkyl, and heteroarylalkyl, R³ is hydrogen, R⁴ is tetrazolyl, and R² is methyl. In another embodiment is a compound of Formula (II) wherein R¹ is phenyl substituted with two halogens, R³ is hydrogen, R⁴ is —CO₂H, and R² is methyl. In another embodiment is a compound of Formula (II) wherein R¹ is phenyl substituted with one halogen, R³ is hydrogen, R⁴ is —CO₂H, and R² is methyl. In another embodiment is a compound of Formula (II) wherein R¹ is phenyl substituted with one alkyl, R³ is hydrogen, R⁴ is —CO₂H, and R² is methyl. In another embodiment is a compound of Formula (II) wherein R¹ is phenyl substituted with one carbocyclyl, R³ is hydrogen, R⁴ is —CO₂H, and R² is methyl. In another embodiment is a compound of Formula (II) wherein R¹ is phenyl substituted with one heterocyclyl, R³ is hydrogen, R⁴ is —CO₂H, and R² is methyl. In another embodiment is a compound of Formula (II) wherein R¹ is phenyl substituted with one heteroaryl, R³ is hydrogen, R⁴ is —CO₂H, and R² is methyl.

Another embodiment provides the compound of Formula (II) having the structure of Formula (IIa), or a pharmaceutically acceptable salt thereof:

Formula (IIa)

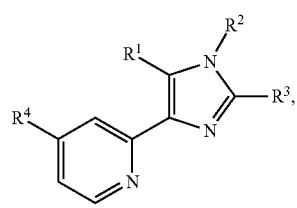

wherein,

R¹ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;

R² is alkyl, carbocyclyl, heterocyclyl, aryl, heteroaryl, carbocyclylalkyl, heterocyclylalkyl, aralkyl, or heteroarylalkyl;

R³ is hydrogen, halogen, —OH, —NH₂, —NH(C1-C3alkyl) or C1-C3alkyl;

R⁴ is a tetrazolyl further substituted with a methyl or —Rᵇ—OC(O)—Rᵃ wherein Rᵇ is C₁-C₃ alkylene and Rᵃ is alkyl; and each R⁵ is independently hydrogen, alkyl, carbocyclyl, heterocyclyl, aryl, heteroaryl, carbocyclylalkyl, heterocyclylalkyl, aralkyl, or heteroarylalkyl.

In another embodiment is a compound of Formula (IIa) wherein R³ is hydrogen, and R² is heterocyclylalkyl. In another embodiment is a compound of Formula (IIa) wherein R³ is hydrogen, and R² is heteroarylalkyl. In another embodiment is a compound of Formula (IIa) wherein R³ is hydrogen, and R² is aralkyl. In another embodiment is a compound of Formula (IIa) wherein R³ is hydrogen, and R² is carbocyclylalkyl. In another embodiment is a compound of Formula (IIa) wherein R¹ is hydrogen, R³ is hydrogen, and R² is heterocyclylalkyl. In another embodiment is a compound of Formula (IIa) wherein R¹ is hydrogen, R³ is hydrogen, and R² is heteroarylalkyl. In another embodiment is a compound of Formula (IIa) wherein R¹ is hydrogen, R³ is hydrogen, and R² is aralkyl. In another embodiment is a compound of Formula (IIa) wherein R¹ is hydrogen, R³ is hydrogen, and R² is carbocyclylalkyl. In another embodiment is a compound of Formula (IIa) wherein R¹ is phenyl substituted with one or more groups selected from halogen, —OH, —OR⁵, —N(R⁵)₂, —CON(R⁵)₂, alkyl, alkynyl, carbocyclyl, heterocyclyl, aryl, heteroaryl, carbocyclylalkyl, heterocyclylalkyl, aralkyl, and heteroarylalkyl, R³ is hydrogen, and R² is methyl. In another embodiment is a compound of Formula (IIa) wherein $R^1$ is an optionally substituted phenyl, $R^3$ is hydrogen, and $R^2$ is heterocyclylalkyl. In another embodiment is a compound of Formula (IIa) wherein $R^1$ is an optionally substituted phenyl, $R^3$ is hydrogen, and $R^2$ is heteroarylalkyl. In another embodiment is a compound of Formula (IIa) wherein $R^1$ is an optionally substituted phenyl, $R^3$ is hydrogen, and $R^2$ is aralkyl. In another embodiment is a compound of Formula (IIa) wherein $R^1$ is an optionally substituted phenyl, $R^3$ is hydrogen, and $R^2$ is carbocyclylalkyl.

One embodiment provides a compound of Formula (III) or a pharmaceutically acceptable salt thereof:

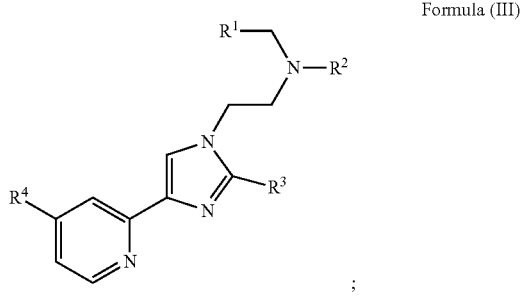

Formula (III)

wherein:

$R^1$ is carbocyclyl, heterocyclyl, aryl, or heteroaryl;

$R^2$ is alkyl, carbocyclyl, heterocyclyl, aryl, heteroaryl, carbocyclylalkyl, heterocyclylalkyl, aralkyl, heteroarylalkyl, —CON($R^5$)$_2$, —CO$_2R^5$, SO$_2$N($R^5$)$_2$, or SO$_2R^5$;

$R^3$ is hydrogen, halogen, —OH, —NH$_2$, —NH(C1-C3alkyl) or C1-C3alkyl;

$R^4$ is —CO$_2$H, —CO$_2R^6$, —C(O)N(H)CN, —C(O)N(H)OH, or tetrazolyl;

each $R^5$ is independently hydrogen, alkyl, carbocyclyl, heterocyclyl, aryl, heteroaryl, carbocyclylalkyl, heterocyclylalkyl, aralkyl, or heteroarylalkyl; and $R^6$ is alkyl.

Another embodiment provides the compound of Formula (III), wherein $R^1$ is aryl. Another embodiment provides the compound of Formula (III), wherein $R^3$ is hydrogen.

In some embodiments, the compound disclosed herein has the structure provided in Table 1.

TABLE 1

| Chemical Synthesis Example | Structure | Name |
|---|---|---|
| 1 | 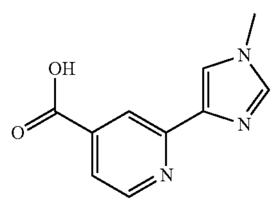 | 2-(1-methyl-1H-imidazol-4-yl)pyridine-4-carboxylic acid |
| 2 | 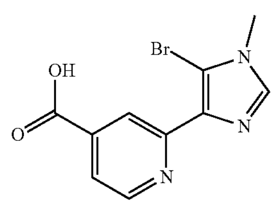 [SMILES: Cn1cnc(-c2cc(C(=O)O)ccn2)c1Br] | 2-(5-bromo-1-methyl-1H-imidazol-4-yl)pyridine-4-carboxylic acid |
| 3 | 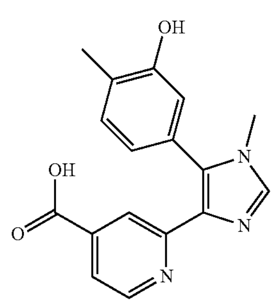 [SMILES: Cc1ccc(-c2c(-c3cc(C(=O)O)ccn3)ncn2C)cc1O] | 2-[5-(3-hydroxy-4-methylphenyl)-1-methyl-1H-imidazol-4-yl]pyridine-4-carboxylic acid |

TABLE 1-continued

| Chemical Synthesis Example | Structure | Name |
|---|---|---|
| 4 | 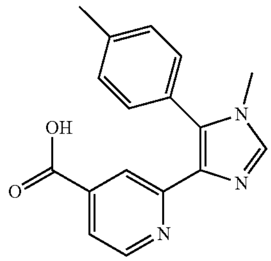 [SMILES: Cc1ccc(-c2c(-c3cc(C(=O)O)ccn3)ncn2C)cc1] | 2-[1-methyl-5-(4-methylphenyl)-1H-imidazol-4-yl]pyridine-4-carboxylic acid |
| 5 | 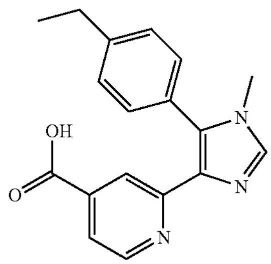 [SMILES: CCc1ccc(-c2c(-c3cc(C(=O)O)ccn3)ncn2C)cc1] | 2-[5-(4-ethylphenyl)-1-methyl-1H-imidazol-4-yl]pyridine-4-carboxylic acid |
| 6 | 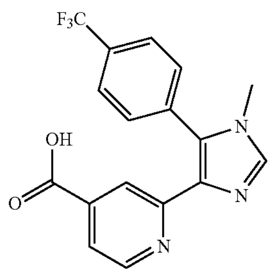 [SMILES: Cn1cnc(-c2cc(C(=O)O)ccn2)c1-c1ccc(C(F)(F)F)cc1] | 2-{1-methyl-5-[4-(trifluoromethyl)phenyl]-1H-imidazol-4-yl}pyridine-4-carboxylic acid |
| 7 | 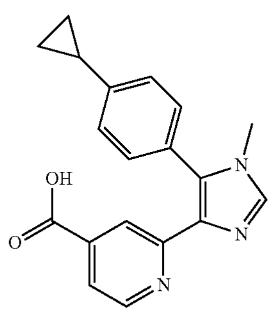 [SMILES: Cn1cnc(-c2cc(C(=O)O)ccn2)c1-c1ccc(C2CC2)cc1] | 2-[5-(4-cyclopropylphenyl)-1-methyl-1H-imidazol-4-yl]pyridine-4-carboxylic acid |
| 8 | 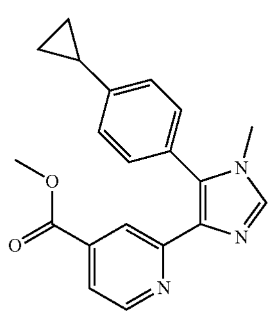 [SMILES: COC(=O)c1ccnc(-c2ncn(C)c2-c2ccc(C3CC3)cc2)c1] | methyl 2-[5-(4-cyclopropylphenyl)-1-methyl-1H-imidazol-4-yl]pyridine-4-carboxylate |

TABLE 1-continued

| Chemical Synthesis Example | Structure | Name |
|---|---|---|
| 9 | 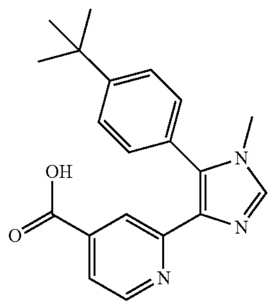 [SMILES: Cn1cnc(-c2cc(C(=O)O)ccn2)c1-c1ccc(C(C)(C)C)cc1] | 2-[5-(4-tert-butylphenyl)-1-methyl-1H-imidazol-4-yl]pyridine-4-carboxylic acid |
| 10 | 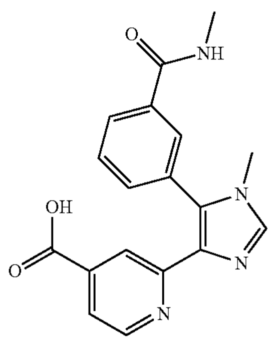 [SMILES: CNC(=O)c1cccc(-c2c(-c3cc(C(=O)O)ccn3)ncn2C)c1] | 2-{1-methyl-5-[3-(methylcarbamoyl)phenyl]-1H-imidazol-4-yl}pyridine-4-carboxylic acid |
| 11 | 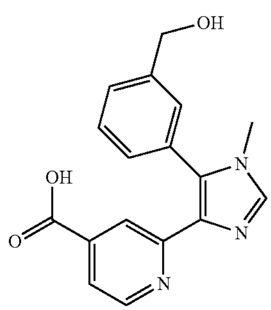 [SMILES: Cn1cnc(-c2cc(C(=O)O)ccn2)c1-c1cccc(CO)c1] | 2-{5-[3-(hydroxymethyl)phenyl]-1-methyl-1H-imidazol-4-yl}pyridine-4-carboxylic acid |
| 12 | 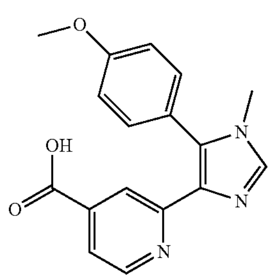 [SMILES: COc1ccc(-c2c(-c3cc(C(=O)O)ccn3)ncn2C)cc1] | 2-[5-(4-methoxyphenyl)-1-methyl-1H-imidazol-4-yl]pyridine-4-carboxylic acid |
| 13 | 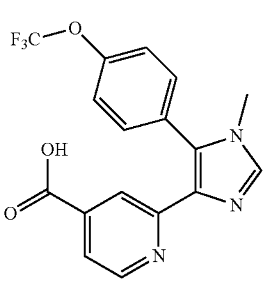 [SMILES: Cn1cnc(-c2cc(C(=O)O)ccn2)c1-c1ccc(OC(F)(F)F)cc1] | 2-{1-methyl-5-[4-(trifluoromethoxy)phenyl]-1H-imidazol-4-yl}pyridine-4-carboxylic acid |

TABLE 1-continued

| Chemical Synthesis Example | Structure | Name |
|---|---|---|
| 14 | 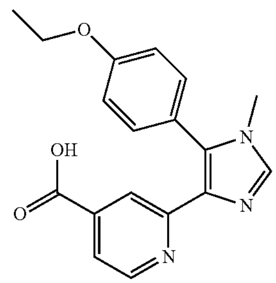 [SMILES: CCOc1ccc(-c2c(-c3cc(C(=O)O)ccn3)ncn2C)cc1] | 2-[5-(4-ethoxyphenyl)-1-methyl-1H-imidazol-4-yl]pyridine-4-carboxylic acid |
| 15 | 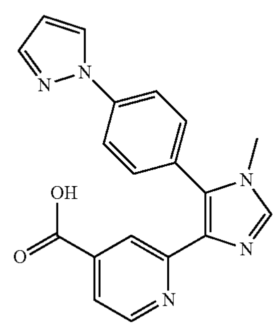 [SMILES: Cn1cnc(-c2cc(C(=O)O)ccn2)c1-c1ccc(-n2cccn2)cc1] | 2-{1-methyl-5-[4-(1H-pyrazol-1-yl)phenyl]-1H-imidazol-4-yl}pyridine-4-carboxylic acid |
| 16 | 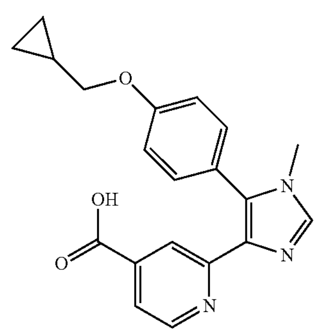 [SMILES: Cn1cnc(-c2cc(C(=O)O)ccn2)c1-c1ccc(OCC2CC2)cc1] | 2-{5-[4-(cyclopropylmethoxy)phenyl]-1-methyl-1H-imidazol-4-yl}pyridine-4-carboxylic acid |
| 17 | 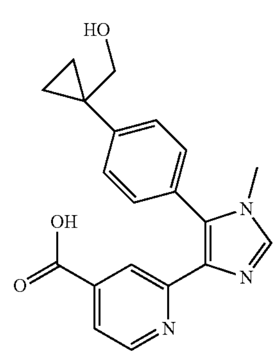 [SMILES: Cn1cnc(-c2cc(C(=O)O)ccn2)c1-c1ccc(C2(CO)CC2)cc1] | 2-(5-{4-[1-(hydroxymethyl)cyclopropyl]phenyl}-1-methyl-1H-imidazol-4-yl)pyridine-4-carboxylic acid |

TABLE 1-continued

| Chemical Synthesis Example | Structure | Name |
|---|---|---|
| 18 | 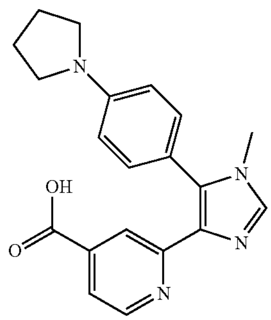 [SMILES: Cn1cnc(-c2cc(C(=O)O)ccn2)c1-c1ccc(N2CCCC2)cc1] | 2-{1-methyl-5-[4-(pyrrolidin-1-yl)phenyl]-1H-imidazol-4-yl}pyridine-4-carboxylic acid |
| 19 | 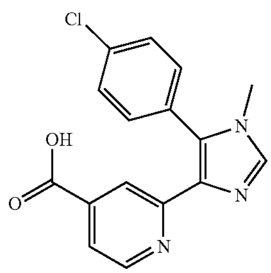 [SMILES: Cn1cnc(-c2cc(C(=O)O)ccn2)c1-c1ccc(Cl)cc1] | 2-[5-(4-chlorophenyl)-1-methyl-1H-imidazol-4-yl]pyridine-4-carboxylic acid |
| 20 | 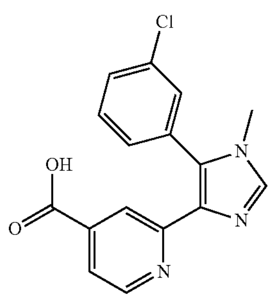 | 2-[5-(3-chlorophenyl)-1-methyl-1H-imidazol-4-yl]pyridine-4-carboxylic acid |
| 21 | 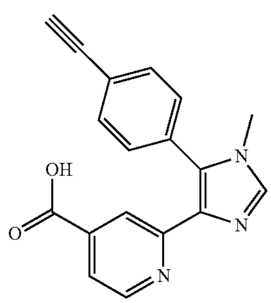 [SMILES: C#Cc1ccc(-c2c(-c3cc(C(=O)O)ccn3)ncn2C)cc1] | 2-[5-(4-ethynylphenyl)-1-methyl-1H-imidazol-4-yl]pyridine-4-carboxylic acid |
| 22 | 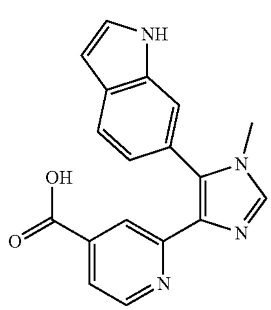 [SMILES: Cn1cnc(-c2cc(C(=O)O)ccn2)c1-c1ccc2cc[nH]c2c1] | 2-[5-(1H-indol-6-yl)-1-methyl-1H-imidazol-4-yl]pyridine-4-carboxylic acid |

TABLE 1-continued

| Chemical Synthesis Example | Structure | Name |
|---|---|---|
| 23 | 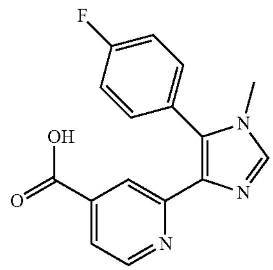 [SMILES: Cn1cnc(-c2cc(C(=O)O)ccn2)c1-c1ccc(F)cc1] | 2-[5-(4-fluorophenyl)-1-methyl-1H-imidazol-4-yl]pyridine-4-carboxylic acid |
| 24 | 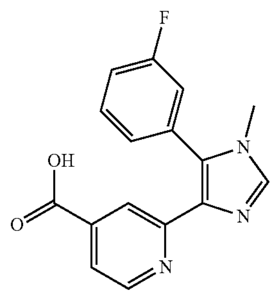 [SMILES: Cn1cnc(-c2cc(C(=O)O)ccn2)c1-c1cccc(F)c1] | 2-[5-(3-fluorophenyl)-1-methyl-1H-imidazol-4-yl]pyridine-4-carboxylic acid |
| 25 | 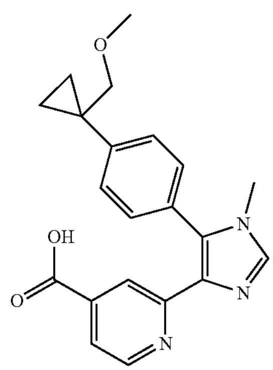 [SMILES: COCC1(c2ccc(-c3c(-c4cc(C(=O)O)ccn4)ncn3C)cc2)CC1] | 2-(5-{4-[1-(methoxymethyl)cyclopropyl]phenyl}-1-methyl-1H-imidazol-4-yl)pyridine-4-carboxylic acid |
| 26 | 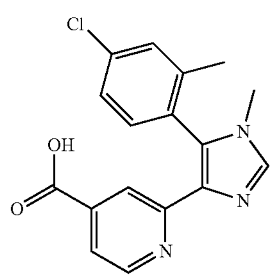 [SMILES: Cc1cc(Cl)ccc1-c1c(-c2cc(C(=O)O)ccn2)ncn1C] | 2-[5-(4-chloro-2-methylphenyl)-1-methyl-1H-imidazol-4-yl]pyridine-4-carboxylic acid |
| 27 | 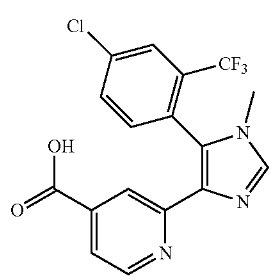 [SMILES: Cn1cnc(-c2cc(C(=O)O)ccn2)c1-c1ccc(Cl)cc1C(F)(F)F] | 2-{5-[4-chloro-2-(trifluoromethyl)phenyl]-1-methyl-1H-imidazol-4-yl}pyridine-4-carboxylic acid |

TABLE 1-continued

| Chemical Synthesis Example | Structure | Name |
|---|---|---|
| 28 | 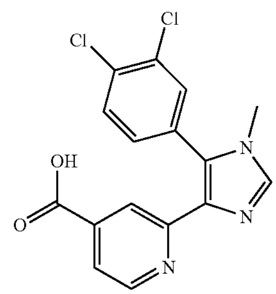 [SMILES: Cn1cnc(-c2cc(C(=O)O)ccn2)c1-c1ccc(Cl)c(Cl)c1] | 2-[5-(3,4-dichlorophenyl)-1-methyl-1H-imidazol-4-yl]pyridine-4-carboxylic acid |
| 29 | 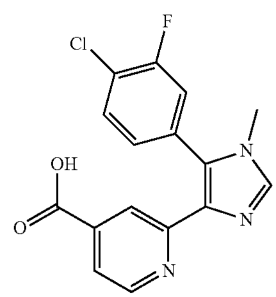 [SMILES: Cn1cnc(-c2cc(C(=O)O)ccn2)c1-c1ccc(Cl)c(F)c1] | 2-[5-(4-chloro-3-fluorophenyl)-1-methyl-1H-imidazol-4-yl]pyridine-4-carboxylic acid |
| 30 | 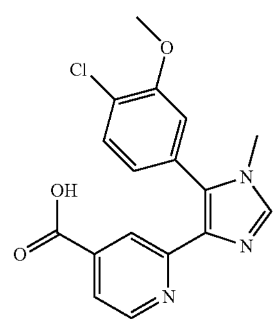 [SMILES: COc1cc(-c2c(-c3cc(C(=O)O)ccn3)ncn2C)ccc1Cl] | 2-[5-(4-chloro-3-methoxyphenyl)-1-methyl-1H-imidazol-4-yl]pyridine-4-carboxylic acid |
| 31 | 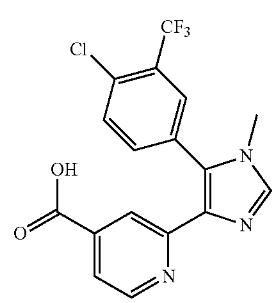 [SMILES: Cn1cnc(-c2cc(C(=O)O)ccn2)c1-c1ccc(Cl)c(C(F)(F)F)c1] | 2-{5-[4-chloro-3-(trifluoromethyl)phenyl]-1-methyl-1H-imidazol-4-yl}pyridine-4-carboxylic acid |
| 32 | 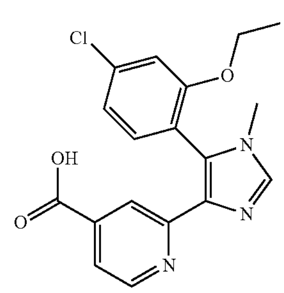 [SMILES: CCOc1cc(Cl)ccc1-c1c(-c2cc(C(=O)O)ccn2)ncn1C] | 2-[5-(4-chloro-2-ethoxyphenyl)-1-methyl-1H-imidazol-4-yl]pyridine-4-carboxylic acid |

TABLE 1-continued

| Chemical Synthesis Example | Structure | Name |
|---|---|---|
| 33 | 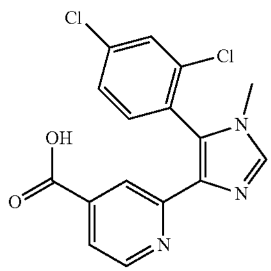 [SMILES: Cn1cnc(-c2cc(C(=O)O)ccn2)c1-c1ccc(Cl)cc1Cl] | 2-[5-(2,4-dichlorophenyl)-1-methyl-1H-imidazol-4-yl]pyridine-4-carboxylic acid |
| 34 | 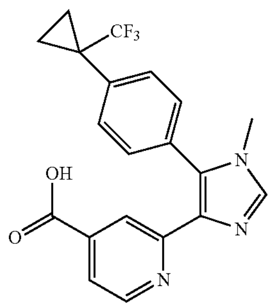 [SMILES: Cn1cnc(-c2cc(C(=O)O)ccn2)c1-c1ccc(C2(C(F)(F)F)CC2)cc1] | 2-(1-methyl-5-{4-[1-(trifluoromethyl)cyclopropyl]phenyl}-1H-imidazol-4-yl)pyridine-4-carboxylic acid |
| 35 | 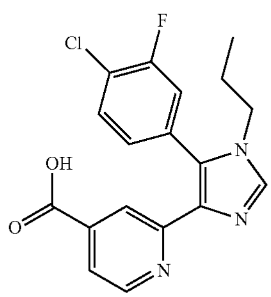 [SMILES: CCCn1cnc(-c2cc(C(=O)O)ccn2)c1-c1ccc(Cl)c(F)c1] | 2-[5-(4-chloro-3-fluorophenyl)-1-propyl-1H-imidazol-4-yl]pyridine-4-carboxylic acid |
| 36 | 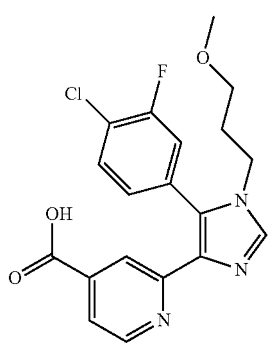 [SMILES: COCCCn1cnc(-c2cc(C(=O)O)ccn2)c1-c1ccc(Cl)c(F)c1] | 2-[5-(4-chloro-3-fluorophenyl)-1-(3-methoxypropyl)-1H-imidazol-4-yl]pyridine-4-carboxylic acid |
| 37 | 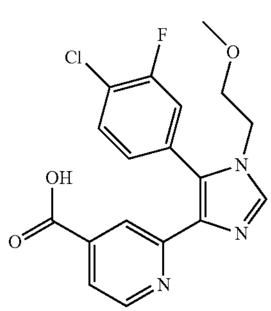 [SMILES: COCCn1cnc(-c2cc(C(=O)O)ccn2)c1-c1ccc(Cl)c(F)c1] | 2-[5-(4-chloro-3-fluorophenyl)-1-(2-methoxyethyl)-1H-imidazol-4-yl]pyridine-4-carboxylic acid |

TABLE 1-continued

| Chemical Synthesis Example | Structure | Name |
|---|---|---|
| 38 | 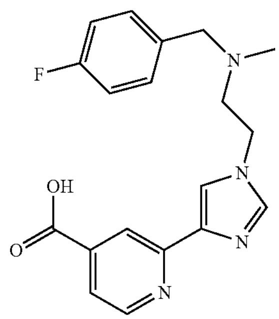 [SMILES: CN(CCn1cnc(-c2cc(C(=O)O)ccn2)c1)Cc1ccc(F)cc1] | 2-[1-[2-[(4-fluorophenyl)methyl-methylamino]ethyl]imidazol-4-yl]pyridine-4-carboxylic acid |
| 39 | 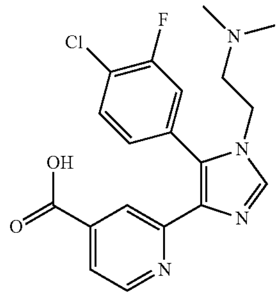 [SMILES: CN(C)CCn1cnc(-c2cc(C(=O)O)ccn2)c1-c1ccc(Cl)c(F)c1] | 2-{5-(4-chloro-3-fluorophenyl)-1-[2-(dimethylamino)ethyl]-1H-imidazol-4-yl)pyridine-4-carboxylic acid |
| 40 | 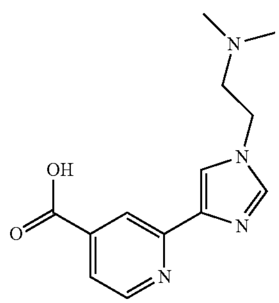 [SMILES: CN(C)CCn1cnc(-c2cc(C(=O)O)ccn2)c1] | 2-{1-[2-(dimethylamino)ethyl]-1H-imidazol-4-yl}pyridine-4-carboxylic acid |
| 41 | 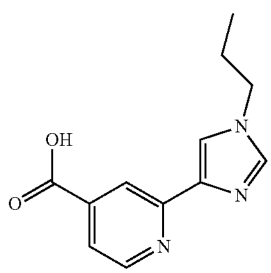 [SMILES: CCCn1cnc(-c2cc(C(=O)O)ccn2)c1] | 2-(1-propyl-1H-imidazol-4-yl)pyridine-4-carboxylic acid |
| 42 | 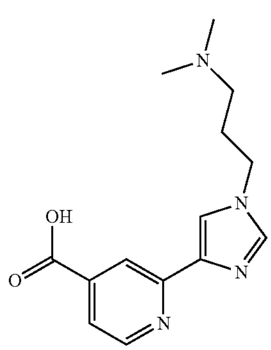 [SMILES: CN(C)CCCn1cnc(-c2cc(C(=O)O)ccn2)c1] | 2-{1-[3-(dimethylamino)propyl]-1H-imidazol-4-yl}pyridine-4-carboxylic acid |

TABLE 1-continued
| Chemical Synthesis Example | Structure | Name |
|---|---|---|
| 43 | 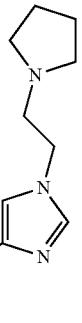 | 2-{1-[2-(pyrrolidin-1-yl)ethyl]-1H-imidazol-4-yl}pyridine-4-carboxylic acid |
| 44 | 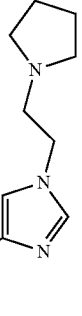 | methyl 2-{1-[2-(pyrrolidin-1-yl)ethyl]-1H-imidazol-4-yl}pyridine-4-carboxylate |
| 45 | 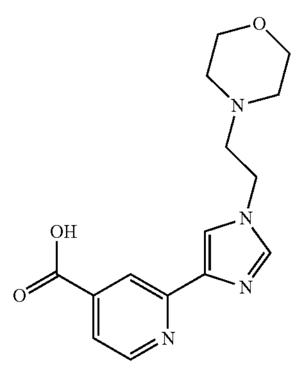 [SMILES: O=C(O)c1ccnc(-c2cn(CCN3CCOCC3)cn2)c1] | 2-{1-[2-(morpholin-4-yl)ethyl]-1H-imidazol-4-yl}pyridine-4-carboxylic acid |
| 46 | 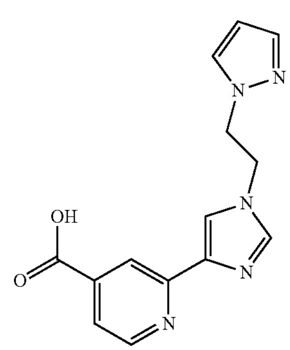 [SMILES: O=C(O)c1ccnc(-c2cn(CCn3cccn3)cn2)c1] | 2-{1-[2-(1H-pyrazol-1-yl)ethyl]-1H-imidazol-4-yl}pyridine-4-carboxylic acid |

TABLE 1-continued

| Chemical Synthesis Example | Structure | Name |
|---|---|---|
| 47 | 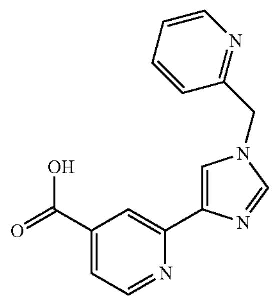 [SMILES: O=C(O)c1ccnc(-c2cn(Cc3ccccn3)cn2)c1] | 2-[1-(pyridin-2-ylmethyl)-1H-imidazol-4-yl]pyridine-4-carboxylic acid |
| 48 | 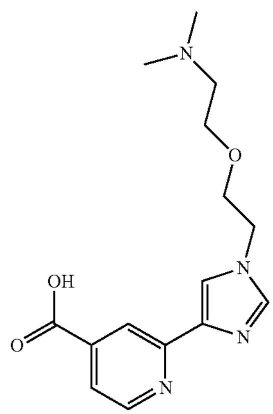 [SMILES: CN(C)CCOCCn1cnc(-c2cc(C(=O)O)ccn2)c1] | 2-(1-{2-[2-(dimethylamino)ethoxy]ethyl}-1H-imidazol-4-yl)pyridine-4-carboxylic acid |
| 49 | 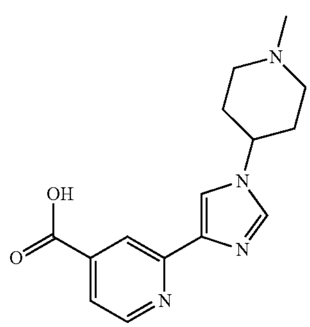 [SMILES: CN1CCC(n2cnc(-c3cc(C(=O)O)ccn3)c2)CC1] | 2-[1-(1-methylpiperidin-4-yl)-1H-imidazol-4-yl]pyridine-4-carboxylic acid |
| 50 | 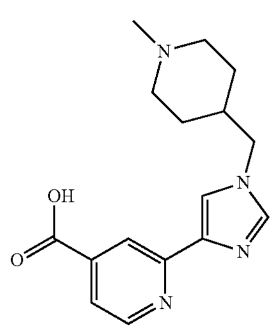 [SMILES: CN1CCC(Cn2cnc(-c3cc(C(=O)O)ccn3)c2)CC1] | 2-{1-[(1-methylpiperidin-4-yl)methyl]-1H-imidazol-4-yl}pyridine-4-carboxylic acid |

TABLE 1-continued

| Chemical Synthesis Example | Structure | Name |
|---|---|---|
| 51 | 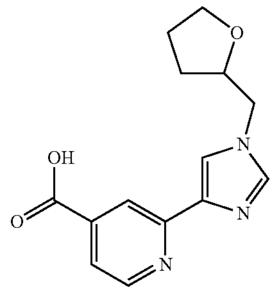 [SMILES: O=C(O)c1ccnc(-c2cn(CC3CCCO3)cn2)c1] | 2-[1-(tetrahydrofuran-2-ylmethyl)-1H-imidazol-4-yl]pyridine-4-carboxylic acid |
| 52 | 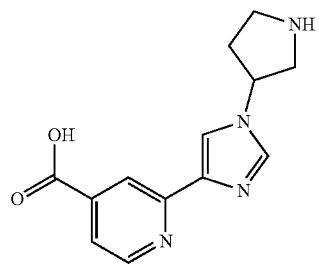 [SMILES: O=C(O)c1ccnc(-c2cn(C3CCNC3)cn2)c1] | 2-[1-(pyrrolidin-3-yl)-1H-imidazol-4-yl]pyridine-4-carboxylic acid |
| 53 | 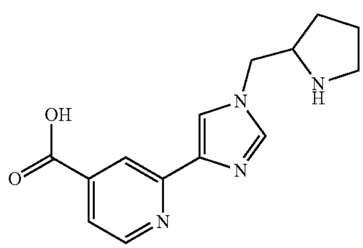 [SMILES: O=C(O)c1ccnc(-c2cn(CC3CCCN3)cn2)c1] | 2-[1-(pyrrolidin-2-ylmethyl)-1H-imidazol-4-yl]pyridine-4-carboxylic acid |
| 54 | 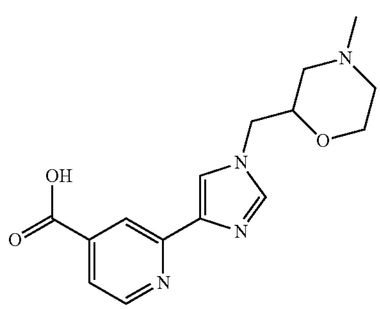 [SMILES: CN1CCOC(Cn2cnc(-c3cc(C(=O)O)ccn3)c2)C1] | 2-(1-[(4-methylmorpholin-2-yl)methyl]-1H-imidazol-4-yl)pyridine-4-carboxylic acid |
| 55 | 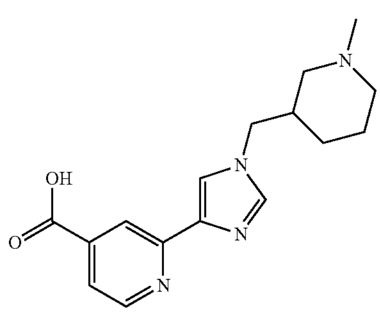 [SMILES: CN1CCCC(Cn2cnc(-c3cc(C(=O)O)ccn3)c2)C1] | 2-{1-[(1-methylpiperidin-3-yl)methyl]-1H-imidazol-4-yl)pyridine-4-carboxylic acid |

TABLE 1-continued
| Chemical Synthesis Example | Structure | Name |
|---|---|---|
| 56 | 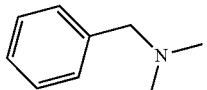 | methyl 2-(1-{2-[benzyl(methyl)amino]ethyl}-1H-imidazol-4-yl)pyridine-4-carboxylate |
| 57 | 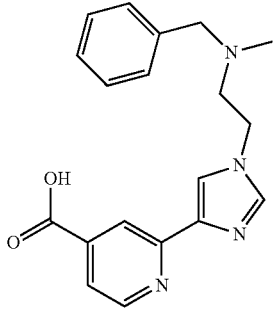 [SMILES: CN(CCn1cnc(-c2cc(C(=O)O)ccn2)c1)Cc1ccccc1] | 2-(1-{2-[benzyl(methyl)amino]ethyl}-1H-imidazol-4-yl)pyridine-4-carboxylic acid |
| 58 | 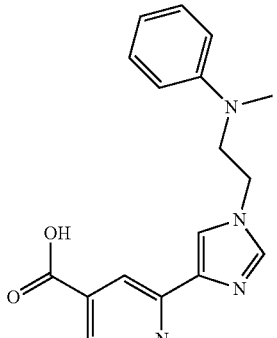 | 2-(1-{2-[methyl(phenyl)amino]ethyl}-1H-imidazol-4-yl)pyridine-4-carboxylic acid |
| 59 | 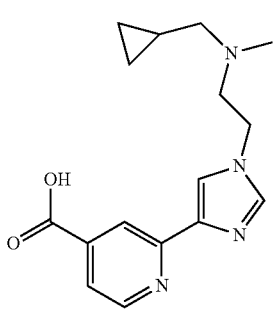 [SMILES: CN(CCn1cnc(-c2cc(C(=O)O)ccn2)c1)CC1CC1] | 2-(1-{2-[(cyclopropylmethyl)(methyl)amino]ethyl}-1H-imidazol-4-yl)pyridine-4-carboxylic acid |

TABLE 1-continued

| Chemical Synthesis Example | Structure | Name |
|---|---|---|
| 60 | 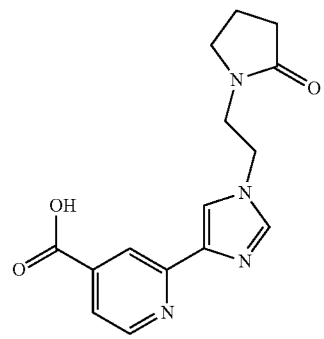 [SMILES: O=C(O)c1ccnc(-c2cn(CCN3CCCC3=O)cn2)c1] | 2-{1-[2-(2-oxopyirolidin-1-yl)ethyl]-1H-imidazol-4-yl}pyridine-4-carboxylic acid |
| 61 | 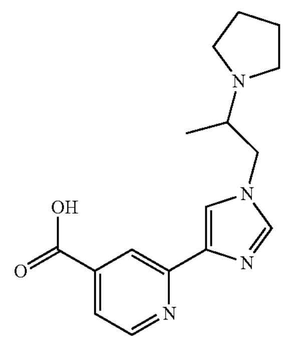 [SMILES: CC(Cn1cnc(-c2cc(C(=O)O)ccn2)c1)N1CCCC1] | 2-{1-[2-(pyrrolidin-1-yl)propyl]-1H-imidazol-4-yl}pyridine-4-carboxylic acid |
| 62 | 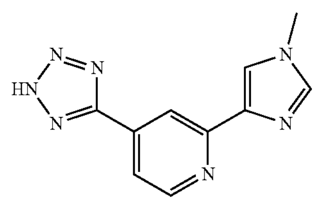 [SMILES: Cn1cnc(-c2cc(-c3nn[nH]n3)ccn2)c1] | 2-(1-methyl-1H-imidazol-4-yl)-4-(2H-tetrazol-5-yl)pyridine |
| 63 | 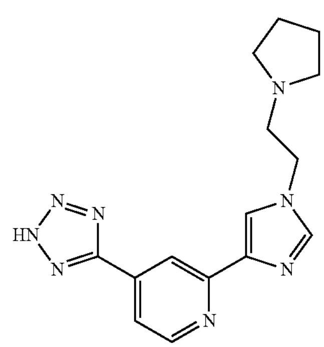 [SMILES: c1cc(-c2nn[nH]n2)cc(-c2cn(CCN3CCCC3)cn2)n1] | 2-{1-[2-(pyrrolidin-1-yl)ethyl]-1H-imidazol-4-yl}-4-(2H-tetrazol-5-yl)pyridine |
| 64 | 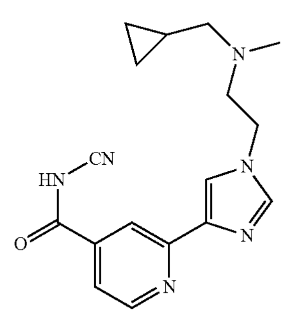 [SMILES: CN(CCn1cnc(-c2cc(C(=O)NC#N)ccn2)c1)CC1CC1] | N-cyano-2-(1-{2-[(cyclopropylmethyl)(methyl)amino]ethyl}-1H-imidazol-4-yl)pyridine-4-carboxamide |

TABLE 1-continued

| Chemical Synthesis Example | Structure | Name |
|---|---|---|
| 65 | 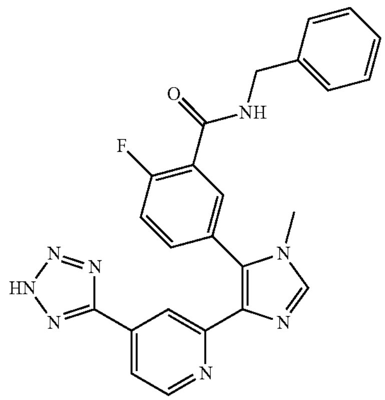 [SMILES: Cn1cnc(-c2cc(-c3nn[nH]n3)ccn2)c1-c1ccc(F)c(C(=O)NCc2ccccc2)c1] | N-benzyl-2-fluoro-5-[3-methyl-5-[4-(2H-tetrazol-5-yl)pyridin-2-yl]imidazol-4-yl]benzamide |
| 66 | 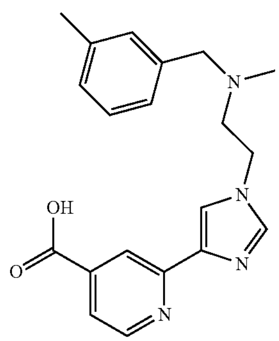 [SMILES: Cc1cccc(CN(C)CCn2cnc(-c3cc(C(=O)O)ccn3)c2)c1] | 2-[1-[2-[methyl-[(3-methylphenyl)methyl]amino]ethyl]imidazol-4-yl]pyridine-4-carboxylic acid |
| 67 | 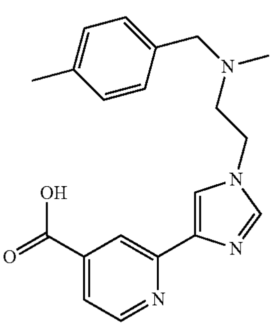 [SMILES: Cc1ccc(CN(C)CCn2cnc(-c3cc(C(=O)O)ccn3)c2)cc1] | 2-[1-[2-[methyl-[(4-methylphenyl)methyl]amino]ethyl]imidazol-4-yl]pyridine-4-carboxylic acid |
| 68 | 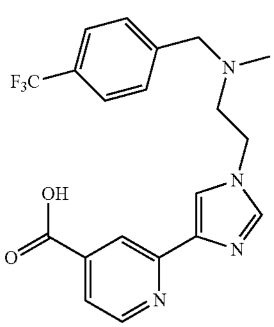 [SMILES: CN(CCn1cnc(-c2cc(C(=O)O)ccn2)c1)Cc1ccc(C(F)(F)F)cc1] | 2-[1-[2-[methyl-[[4-(trifluoromethyl)phenyl]methyl]amino]ethyl]imidazol-4-yl]pyridine-4-carboxylic acid |

TABLE 1-continued

| Chemical Synthesis Example | Structure | Name |
|---|---|---|
| 69 | 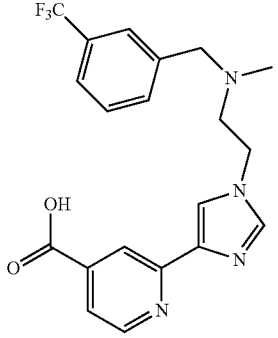 [SMILES: CN(CCn1cnc(-c2cc(C(=O)O)ccn2)c1)Cc1cccc(C(F)(F)F)c1] | 2-[1-[2-[(3-fluorophenyl)methyl-methylamino]ethyl]imidazol-4-yl]pyridine-4-carboxylic acid |
| 70 | 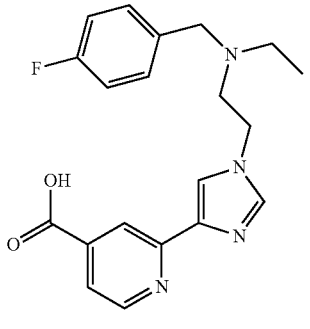 [SMILES: CCN(CCn1cnc(-c2cc(C(=O)O)ccn2)c1)Cc1ccc(F)cc1] | 2-[1-[2-[ethyl-[(4-fluorophenyl)methyl]amino]ethyl]imidazol-4-yl]pyridine-4-carboxylic acid |
| 71 | 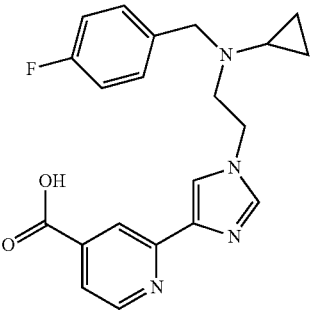 [SMILES: O=C(O)c1ccnc(-c2cn(CCN(Cc3ccc(F)cc3)C3CC3)cn2)c1] | 2-[1-[2-[cyclopropyl-[(4-fluorophenyl)methyl]amino]ethyl]imidazol-4-yl]pyridine-4-carboxylic acid |
| 72 | 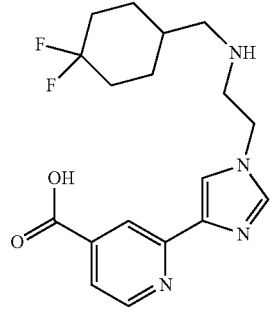 [SMILES: O=C(O)c1ccnc(-c2cn(CCNCC3CCC(F)(F)CC3)cn2)c1] | 2-[1-[2-[(4,4-difluorocyclohexyl)methylamino]ethyl]imidazol-4-yl]pyridine-4-carboxylic acid |

TABLE 1-continued

| Chemical Synthesis Example | Structure | Name |
|---|---|---|
| 73 | 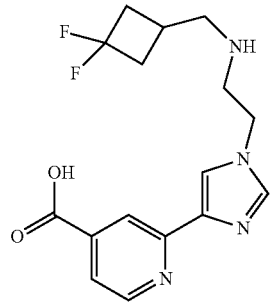 [SMILES: O=C(O)c1ccnc(-c2cn(CCNCC3CC(F)(F)C3)cn2)c1] | 2-[1-[2-[(3,3-difluorocyclobutyl)methylamino]ethyl]imidazol-4-yl]pyridine-4-carboxylic acid |
| 74 | 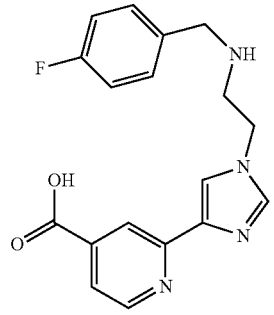 [SMILES: O=C(O)c1ccnc(-c2cn(CCNCc3ccc(F)cc3)cn2)c1] | 2-[1-[2-[(4-fluorophenyl)methylamino]ethyl]imidazol-4-yl]pyridine-4-carboxylic acid |
| 75 | 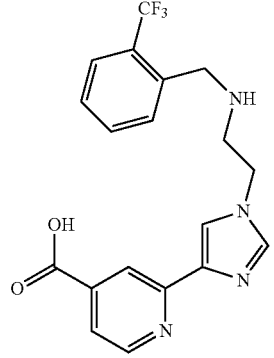 [SMILES: O=C(O)c1ccnc(-c2cn(CCNCc3ccccc3C(F)(F)F)cn2)c1] | 2-[1-[2-[[2-(trifluoromethyl)phenyl]methylamino]ethyl]imidazol-4-yl]pyridine-4-carboxylic acid |
| 76 | 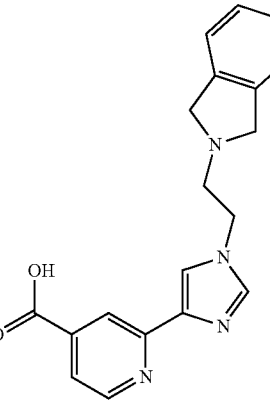 | 2-[1-[2-(1,3-dihydroisoindol-2-yl)ethyl]imidazol-4-yl]pyridine-4-carboxylic acid |

TABLE 1-continued
| Chemical Synthesis Example | Structure | Name |
|---|---|---|
| 77 | 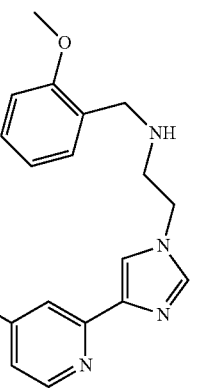 | 2-[1-[2-[(2-methoxyphenyl)methylamino]ethyl]imidazol-4-yl]pyridine-4-carboxylic acid |
| 78 | 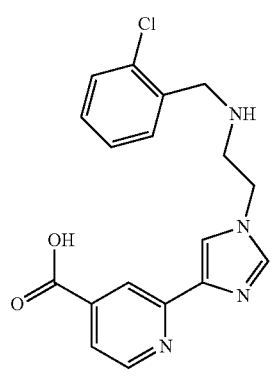 [SMILES: O=C(O)c1ccnc(-c2cn(CCNCc3ccccc3Cl)cn2)c1] | 2-[1-[2-[(2-chlorophenyl)methylamino]ethyl]imidazol-4-yl]pyridine-4-carboxylic acid |
| 79 | 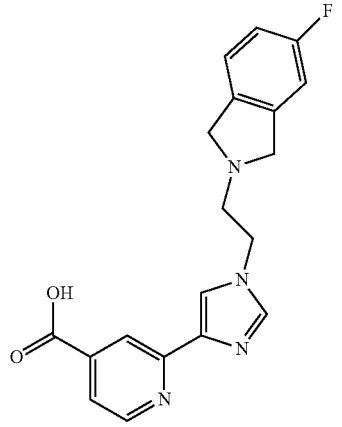 [SMILES: O=C(O)c1ccnc(-c2cn(CCN3Cc4ccc(F)cc4C3)cn2)c1] | 2-[1-[2-(5-fluoro-1,3-dihydroisoindol-2-yl)ethyl]imidazol-4-yl]pyridine-4-carboxylic acid |
| 80 | 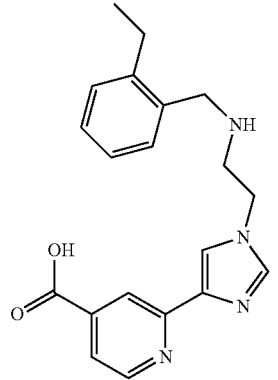 | 2-[1-[2-[(2-ethylphenyl)methylamino]ethyl]imidazol-4-yl]pyridine-4-carboxylic acid |

TABLE 1-continued
| Chemical Synthesis Example | Structure | Name |
|---|---|---|
| 81 | 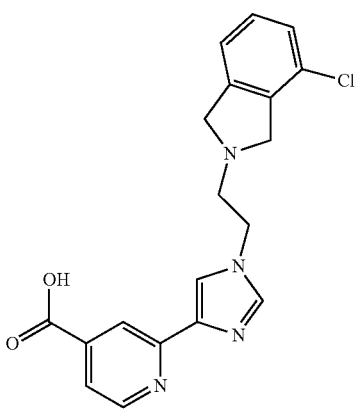 [SMILES: O=C(O)c1ccnc(-c2cn(CCN3Cc4cccc(Cl)c4C3)cn2)c1] | 2-[1-[2-(4-chloro-1,3-dihydroisoindol-2-yl)ethyl]imidazol-4-yl]pyridine-4-carboxylic acid |
| 82 | 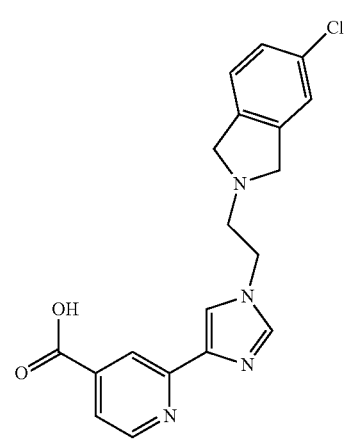 [SMILES: O=C(O)c1ccnc(-c2cn(CCN3Cc4ccc(Cl)cc4C3)cn2)c1] | 2-[1-[2-(5-chloro-1,3-dihydroisoindol-2-yl)ethyl]imidazol-4-yl]pyridine-4-carboxylic acid |
| 83 | 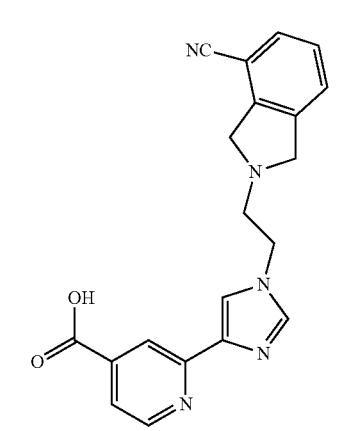 [SMILES: N#Cc1cccc2c1CN(CCn1cnc(-c3cc(C(=O)O)ccn3)c1)C2] | 2-[1-[2-(4-cyano-1,3-dihydroisoindol-2-yl)ethyl]imidazol-4-yl]pyridine-4-carboxylic acid |

TABLE 1-continued

| Chemical Synthesis Example | Structure | Name |
|---|---|---|
| 84 | 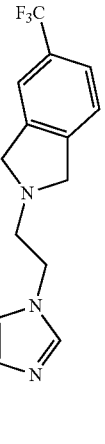 | 2-[1-[2-[5-(trifluoromethyl)-1,3-dihydroisoindol-2-yl]ethyl]imidazol-4-yl]pyridine-4-carboxylic acid |
| 85 | 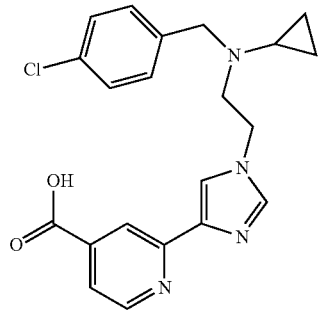 | 2-[1-[2-[(4-chlorophenyl)methyl-cyclopropylamino]ethyl]imidazol-4-yl]pyridine-4-carboxylic acid |
| 86 | 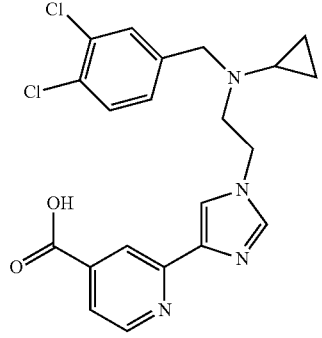 [SMILES: O=C(O)c1ccnc(-c2cn(CCN(Cc3ccc(Cl)c(Cl)c3)C3CC3)cn2)c1] | 2-[1-[2-[cyclopropyl-[(3,4-dichlorophenyl)methyl]amino]ethyl]imidazol-4-yl]pyridine-4-carboxylic acid |
| 87 | 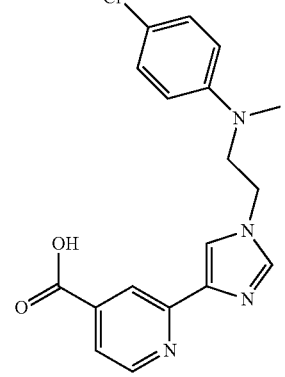 | 2-[1-[2-(4-chloro-N-methylanilino)ethyl]imidazol-4-yl]pyridine-4-carboxylic acid |

TABLE 1-continued

| Chemical Synthesis Example | Structure | Name |
|---|---|---|
| 88 | 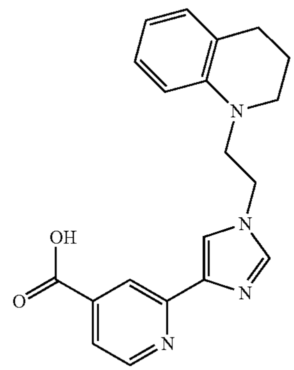 [SMILES: O=C(O)c1ccnc(-c2cn(CCN3CCCc4ccccc43)cn2)c1] | 2-[1-[2-(3,4-dihydro-2H-quinolin-1-yl)ethyl]imidazol-4-yl]pyridine-4-carboxylic acid |
| 89 | 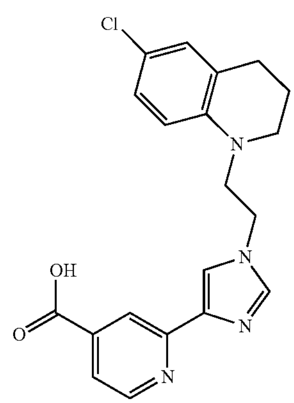 [SMILES: O=C(O)c1ccnc(-c2cn(CCN3CCCc4cc(Cl)ccc43)cn2)c1] | 2-[1-[2-(6-chloro-3,4-dihydro-2H-quinolin-1-yl)ethyl]imidazol-4-yl]pyridine-4-carboxylic acid |
| 90 | 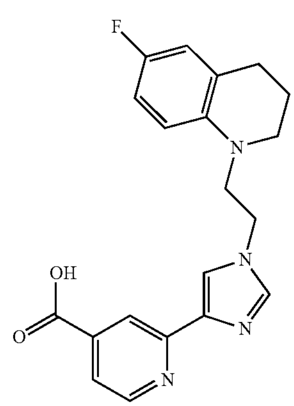 [SMILES: O=C(O)c1ccnc(-c2cn(CCN3CCCc4cc(F)ccc43)cn2)c1] | 2-[1-[2-(6-fluoro-3,4-dihydro-2H-quinolin-1-yl)ethyl]imidazol-4-yl]pyridine-4-carboxylic acid |

TABLE 1-continued
| Chemical Synthesis Example | Structure | Name |
|---|---|---|
| 91 | 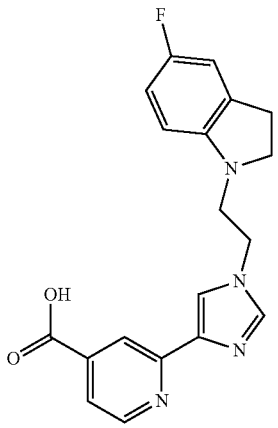 [SMILES: O=C(O)c1ccnc(-c2cn(CCN3CCc4cc(F)ccc43)cn2)c1] | 2-[1-[2-(5-fluoro-2,3-dihydroindol-1-yl)ethyl]imidazol-4-yl]pyridine-4-carboxylic acid |
| 92 | 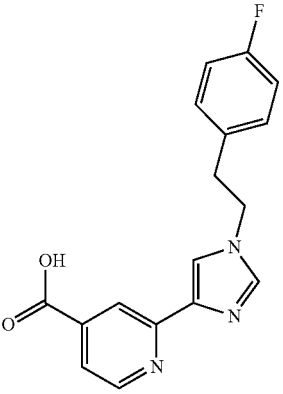 [SMILES: O=C(O)c1ccnc(-c2cn(CCc3ccc(F)cc3)cn2)c1] | 2-[1-[2-(4-fluorophenyl)ethyl]imidazol-4-yl]pyridine-4-carboxylic acid |
| 93 | 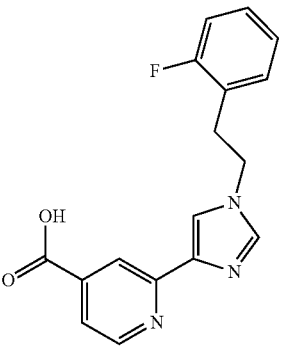 [SMILES: O=C(O)c1ccnc(-c2cn(CCc3ccccc3F)cn2)c1] | 2-[1-[2-(2-fluorophenyl)ethyl]imidazol-4-yl]pyridine-4-carboxylic acid |

TABLE 1-continued
| Chemical Synthesis Example | Structure | Name |
|---|---|---|
| 94 | 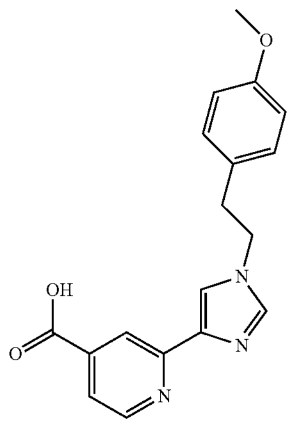 [SMILES: COc1ccc(CCn2cnc(-c3cc(C(=O)O)ccn3)c2)cc1] | 2-[1-[2-(4-methoxyphenyl)ethyl]imidazol-4-yl]pyridine-4-carboxylic acid |
| 95 | 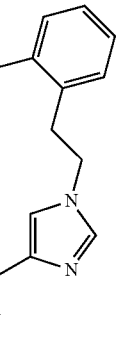 | 2-[1-[2-(2-methoxyphenyl)ethyl]imidazol-4-yl]pyridine-4-carboxylic acid |
| 96 | 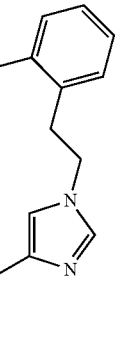 | 2-[1-[2-(2-methylphenyl)ethyl]imidazol-4-yl]pyridine-4-carboxylic acid |
| 97 | 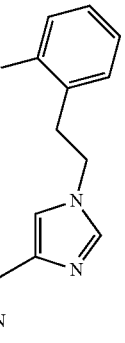 | 2-[1-[2-(2-chlorophenyl)ethyl]imidazol-4-yl]pyridine-4-carboxylic acid |

TABLE 1-continued
| Chemical Synthesis Example | Structure | Name |
|---|---|---|
| 98 | 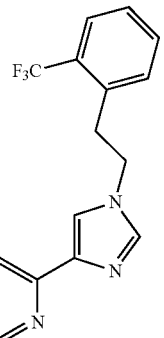 | 2-[1-[2-[2-(trifluoromethyl)phenyl]ethyl]imidazol-4-yl]pyridine-4-carboxylic acid |
| 99 | 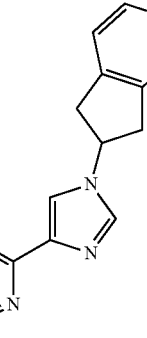 | 2-[1-(2,3-dihydro-1H-inden-2-yl)imidazol-4-yl]pyridine-4-carboxylic acid |
| 100 | 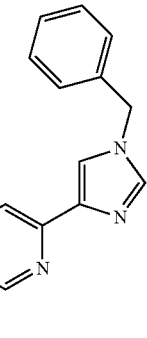 | 2-(1-benzylimidazol-4-yl)pyridine-4-carboxylic acid |
| 101 | 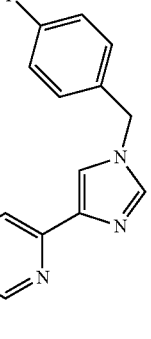 | 2-[1-[(4-fluorophenyl)methyl]imidazol-4-yl]pyridine-4-carboxylic acid |

TABLE 1-continued
| Chemical Synthesis Example | Structure | Name |
|---|---|---|
| 102 | 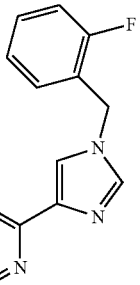 | 2-[1-[(2-fluorophenyl)methyl]imidazol-4-yl]pyridine-4-carboxylic acid |
| 103 | 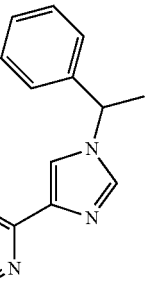 | 2-[1-(1-phenylethyl)imidazol-4-yl]pyridine-4-carboxylic acid |
| 104 | 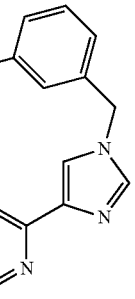 | 2-[1-[(3-fluorophenyl)methyl]imidazol-4-yl]pyridine-4-carboxylic |
| 105 | 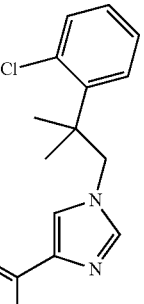 | 2-[1-[2-(2-chlorophenyl)-2-methylpropyl]imidazol-4-yl]pyridine-4-carboxylic acid |

TABLE 1-continued
| Chemical Synthesis Example | Structure | Name |
|---|---|---|
| 106 | 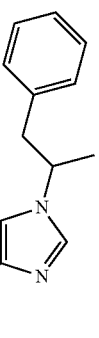 | 2-[1-(1-phenylpropan-2-yl)imidazol-4-yl]pyridine-4-carboxylic acid |
| 107 | 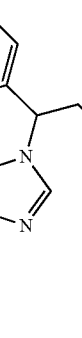 | 2-[1-(1-phenylpropyl)imidazol-4-yl]pyridine-4-carboxylic acid |
| 108 | 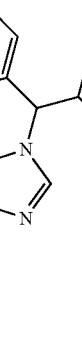 | 2-[1-(2-methyl-1-phenylpropyl)imidazol-4-yl]pyridine-4-carboxylic acid |
| 109 | 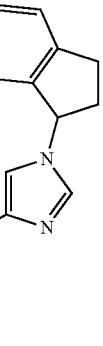 | 2-[1-(6-fluoro-2,3-dihydro-1H-inden-1-yl)imidazol-4-yl]pyridine-4-carboxylic acid |

TABLE 1-continued

| Chemical Synthesis Example | Structure | Name |
|---|---|---|
| 110 | 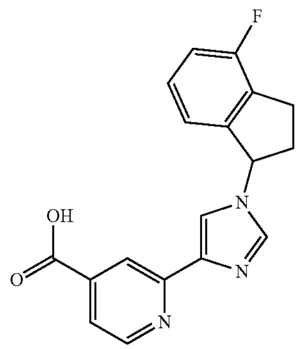 [SMILES: O=C(O)c1ccnc(-c2cn(C3CCc4c(F)cccc43)cn2)c1] | 2-[1-(4-fluoro-2,3-dihydro-1H-inden-1-yl)imidazol-4-yl]pyridine-4-carboxylic acid |
| 111 | 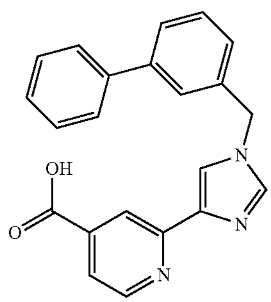 [SMILES: O=C(O)c1ccnc(-c2cn(Cc3cccc(-c4ccccc4)c3)cn2)c1] | 2-[1-[(3-phenylphenyl)methyl]imidazol-4-yl]pyridine-4-carboxylic acid |
| 112 | 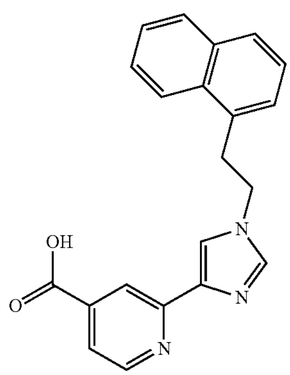 [SMILES: O=C(O)c1ccnc(-c2cn(CCc3cccc4ccccc34)cn2)c1] | 2-[1-(2-naphthalen-1-ylethyl)imidazol-4-yl]pyridine-4-carboxylic acid |
| 113 | 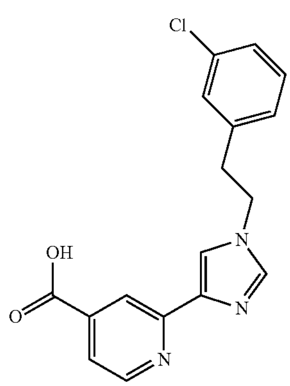 [SMILES: O=C(O)c1ccnc(-c2cn(CCc3cccc(Cl)c3)cn2)c1] | 2-[1-[2-(3-chlorophenyl)ethyl]imidazol-4-yl]pyridine-4-carboxylic acid |

TABLE 1-continued

| Chemical Synthesis Example | Structure | Name |
|---|---|---|
| 114 | 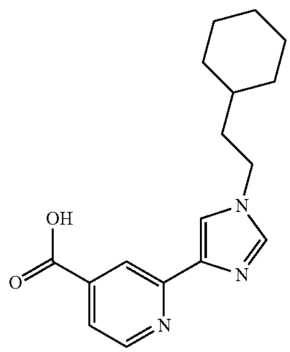 [SMILES: O=C(O)c1ccnc(-c2cn(CCC3CCCCC3)cn2)c1] | 2-[1-(2-cyclohexylethyl)imidazol-4-yl]pyridine-4-carboxylic acid |
| 115 | 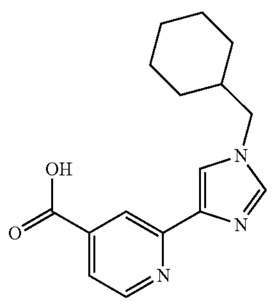 [SMILES: O=C(O)c1ccnc(-c2cn(CC3CCCCC3)cn2)c1] | 2-[1-(cyclohexylmethyl)imidazol-4-yl]pyridine-4-carboxylic acid |
| 116 | 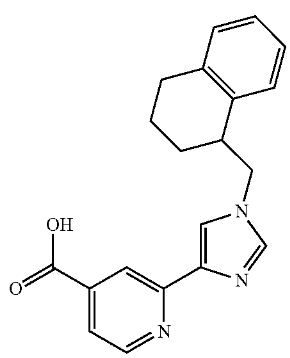 [SMILES: O=C(O)c1ccnc(-c2cn(CC3CCCc4ccccc43)cn2)c1] | 2-[1-(1,2,3,4-tetrahydronaphthalen-1-ylmethyl)imidazol-4-yl]pyridine-4-carboxylic acid |
| 117 | 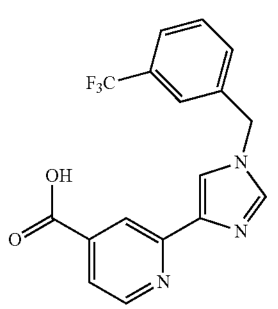 [SMILES: O=C(O)c1ccnc(-c2cn(Cc3cccc(C(F)(F)F)c3)cn2)c1] | 2-[1-[[3-(trifluoromethyl)phenyl]methyl]imidazol-4-yl]pyridine-4-carboxylic acid |

TABLE 1-continued
| Chemical Synthesis Example | Structure | Name |
|---|---|---|
| 118 | 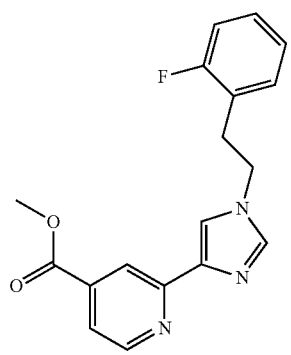 [SMILES: COC(=O)c1ccnc(-c2cn(CCc3ccccc3F)cn2)c1] | methyl 2-[1-[2-(2-fluorophenyl)ethyl]imidazol-4-yl]pyridine-4-carboxylate |
| 119 | 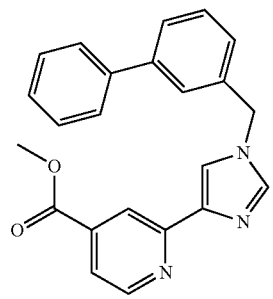 [SMILES: COC(=O)c1ccnc(-c2cn(Cc3cccc(-c4ccccc4)c3)cn2)c1] | methyl 2-[1-[(3-phenylphenyl)methyl]imidazol-4-yl]pyridine-4-carboxylate |
| 120 | 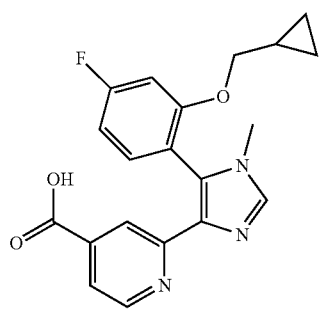 [SMILES: Cn1cnc(-c2cc(C(=O)O)ccn2)c1-c1ccc(F)cc1OCC1CC1] | 2-[5-[2-(cyclopropylmethoxy)-4-fluorophenyl]-1-methylimidazol-4-yl]pyridine-4-carboxylic acid |
| 121 | 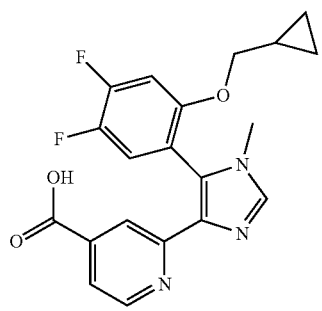 [SMILES: Cn1cnc(-c2cc(C(=O)O)ccn2)c1-c1cc(F)c(F)cc1OCC1CC1] | 2-[5-[2-(cyclopropylmethoxy)-4,5-difluorophenyl]-1-methylimidazol-4-yl]pyridine-4-carboxylic acid |

TABLE 1-continued

| Chemical Synthesis Example | Structure | Name |
|---|---|---|
| 122 | 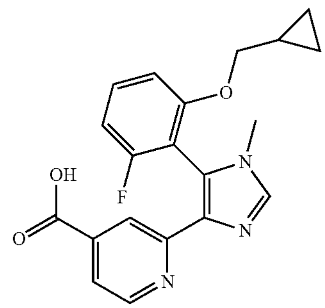 [SMILES: Cn1cnc(-c2cc(C(=O)O)ccn2)c1-c1c(F)cccc1OCC1CC1] | 2-[5-[2-(cyclopropylmethoxy)-6-fluorophenyl]-1-methylimidazol-4-yl]pyridine-4-carboxylic acid |
| 123 | 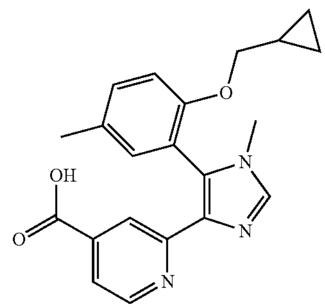 [SMILES: Cc1ccc(OCC2CC2)c(-c2c(-c3cc(C(=O)O)ccn3)ncn2C)c1] | 2-[5-[2-(cyclopropylmethoxy)-5-methylphenyl]-1-methylimidazol-4-yl]pyridine-4-carboxylic acid |
| 124 | 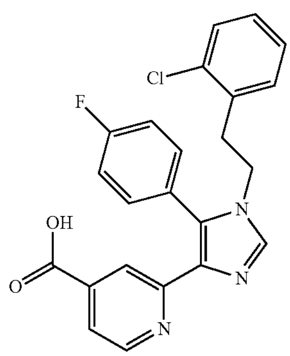 [SMILES: O=C(O)c1ccnc(-c2ncn(CCc3ccccc3Cl)c2-c2ccc(F)cc2)c1] | 2-[1-[2-(2-chlorophenyl)ethyl]-5-(4-fluorophenyl)imidazol-4-yl]pyridine-4-carboxylic acid |
| 125 | 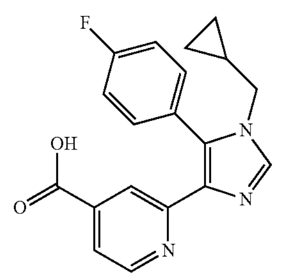 | 2-[1-(cyclopropylmethyl)-5-(4-fluorophenyl)imidazol-4-yl]pyridine-4-carboxylic acid |
| 126 | 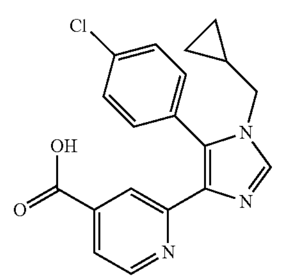 [SMILES: O=C(O)c1ccnc(-c2ncn(CC3CC3)c2-c2ccc(Cl)cc2)c1] | 2-[5-(4-chlorophenyl)-1-(cyclopropylmethyl)imidazol-4-yl]pyridine-4-carboxylic acid |

TABLE 1-continued

| Chemical Synthesis Example | Structure | Name |
|---|---|---|
| 127 | 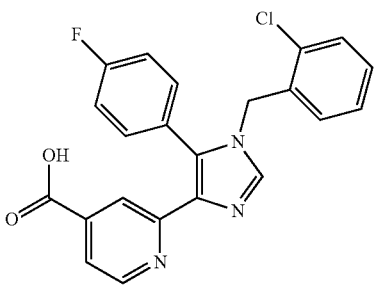 [SMILES: O=C(O)c1ccnc(-c2ncn(Cc3ccccc3Cl)c2-c2ccc(F)cc2)c1] | 2-[1-[(2-chlorophenyl)methyl]-5-(4-fluorophenyl)imidazol-4-yl]pyridine-4-carboxylic acid |
| 128 | 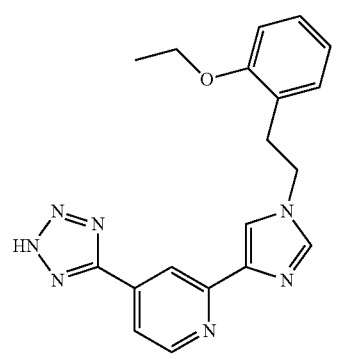 [SMILES: CCOc1ccccc1CCn1cnc(-c2cc(-c3nn[nH]n3)ccn2)c1] | 2-[1-[2-(2-ethoxyphenyl)ethyl]imidazol-4-yl]-4-(2H-tetrazol-5-yl)pyridine |
| 129 | 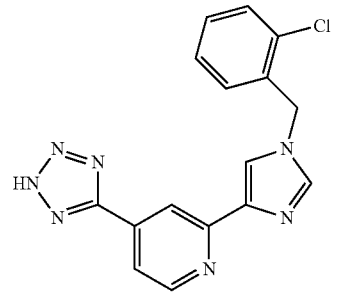 [SMILES: Clc1ccccc1Cn1cnc(-c2cc(-c3nn[nH]n3)ccn2)c1] | 2-[1-[(2-chlorophenyl)methyl]imidazol-4-yl]-4-(2H-tetrazol-5-yl)pyridine |
| 130 | 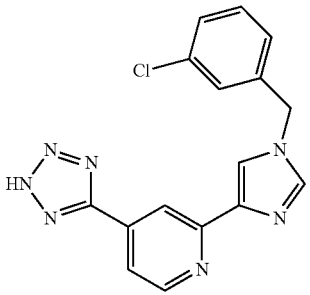 [SMILES: Clc1cccc(Cn2cnc(-c3cc(-c4nn[nH]n4)ccn3)c2)c1] | 2-[1-[(3-chlorophenyl)methyl]imidazol-4-yl]-4-(2H-tetrazol-5-yl)pyridine |
| 131 | 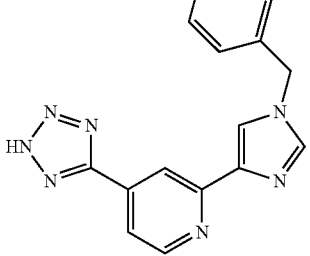 | 2-[1-[(4-chlorophenyl)methyl]imidazol-4-yl]-4-(2H-tetrazol-5-yl)pyridine |

TABLE 1-continued

| Chemical Synthesis Example | Structure | Name |
|---|---|---|
| 132 | 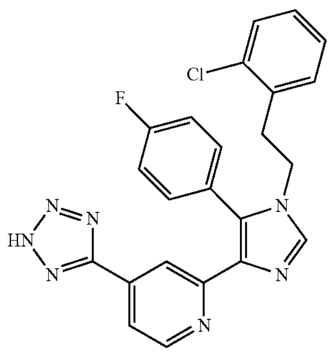 [SMILES: Fc1ccc(-c2c(-c3cc(-c4nn[nH]n4)ccn3)ncn2CCc2ccccc2Cl)cc1] | 2-[1-[2-(2-chlorophenyl)ethyl]-5-(4-fluorophenyl)imidazol-4-yl]-4-(2H-tetrazol-5-yl)pyridine |
| 133 | 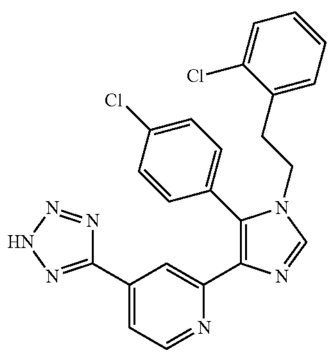 [SMILES: Clc1ccc(-c2c(-c3cc(-c4nn[nH]n4)ccn3)ncn2CCc2ccccc2Cl)cc1] | 2-[5-(4-chlorophenyl)-1-[2-(2-chlorophenyl)ethyl]imidazol-4-yl]-4-(2H-tetrazol-5-yl)pyridine |
| 134 | 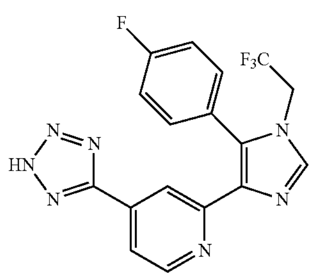 [SMILES: Fc1ccc(-c2c(-c3cc(-c4nn[nH]n4)ccn3)ncn2CC(F)(F)F)cc1] | 2-[5-(4-fluorophenyl)-1-(2,2,2-trifluoroethyl)imidazol-4-yl]-4-(2H-tetrazol-5-yl)pyridine |
| 135 | 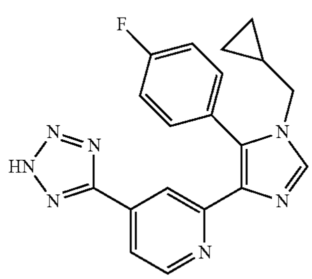 | 2-[1-(cyclopropylmethyl)-5-(4-fluorophenyl)imidazol-4-yl]-4-(2H-tetrazol-5-yl)pyridine |
| 136 | 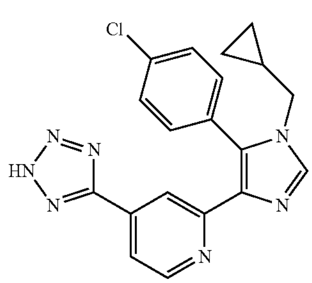 [SMILES: Clc1ccc(-c2c(-c3cc(-c4nn[nH]n4)ccn3)ncn2CC2CC2)cc1] | 2-[5-(4-chlorophenyl)-1-(cyclopropylmethyl)imidazol-4-yl]-4-(2H-tetrazol-5-yl)pyridine |

TABLE 1-continued

| Chemical Synthesis Example | Structure | Name |
|---|---|---|
| 137 | 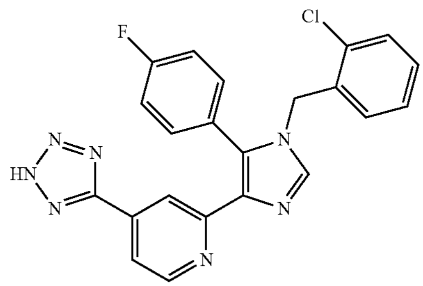 [SMILES: Fc1ccc(-c2c(-c3cc(-c4nn[nH]n4)ccn3)ncn2Cc2ccccc2Cl)cc1] | 2-[1-[(2-chlorophenyl)methyl]-5-(4-fluorophenyl)imidazol-4-yl]-4-(2H-tetrazol-5-yl)pyridine |
| 138 | 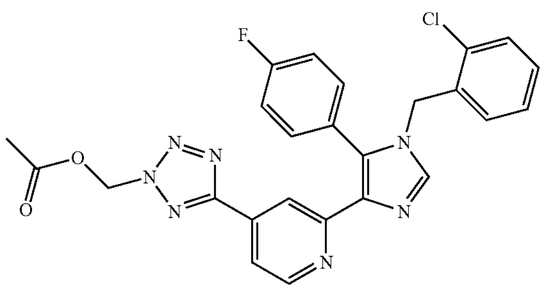 [SMILES: CC(=O)OCn1nnc(-c2ccnc(-c3ncn(Cc4ccccc4Cl)c3-c3ccc(F)cc3)c2)n1] | [5-[2-[1-[(2-chlorophenyl)methyl]-5-(4-fluorophenyl)imidazol-4-yl]pyridin-4-yl]tetrazol-2-yl]methyl acetate |
| 139 | 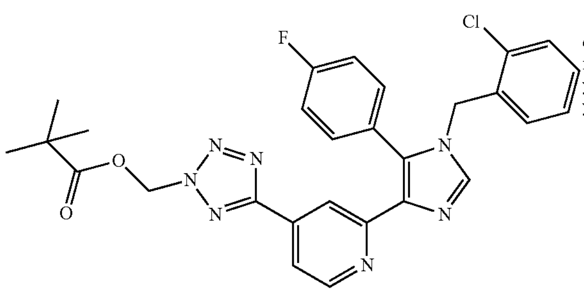 [SMILES: CC(C)(C)C(=O)OCn1nnc(-c2ccnc(-c3ncn(Cc4ccccc4Cl)c3-c3ccc(F)cc3)c2)n1] | [5-[2-[1-[(2-chlorophenyl)methyl]-5-(4-fluorophenyl)imidazol-4-yl]pyridin-4-yl]tetrazol-2-yl]methyl 2,2-dimethylpropanoate |
| 140 | 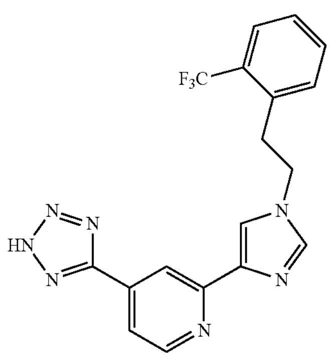 [SMILES: FC(F)(F)c1ccccc1CCn1cnc(-c2cc(-c3nn[nH]n3)ccn2)c1] | 4-(2H-tetrazol-5-yl)-2-[1-[2-[2-(trifluoromethyl)phenyl]ethyl]imidazol-4-yl]pyridine |
| 141 | 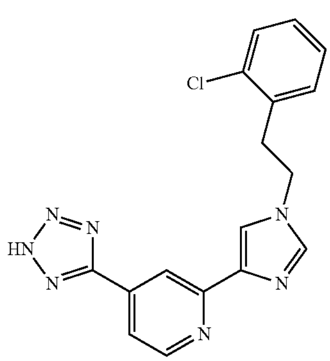 [SMILES: Clc1ccccc1CCn1cnc(-c2cc(-c3nn[nH]n3)ccn2)c1] | 2-[1-[2-(2-chlorophenyl)ethyl]imidazol-4-yl]-4-(2H-tetrazol-5-yl)pyridine |

TABLE 1-continued

| Chemical Synthesis Example | Structure | Name |
|---|---|---|
| 142 | 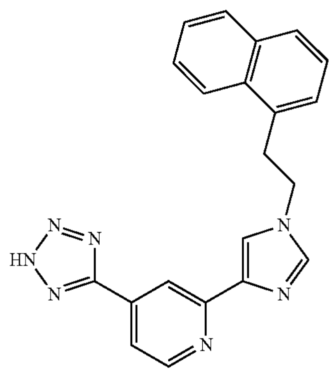 [SMILES: c1ccc2c(CCn3cnc(-c4cc(-c5nn[nH]n5)ccn4)c3)cccc2c1] | 2-[1-(2-naphthalen-1-ylethyl)imidazol-4-yl]-4-(2H-tetrazol-5-yl)pyridine |
| 143 | 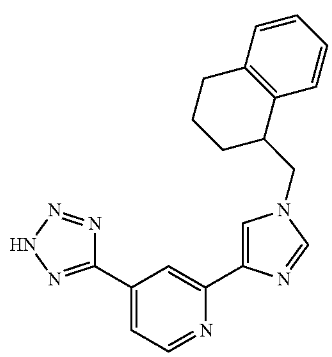 [SMILES: c1ccc2c(c1)CCCC2Cn1cnc(-c2cc(-c3nn[nH]n3)ccn2)c1] | 2-[1-(1,2,3,4-tetrahydronaphthalen-1-ylmethyl)imidazol-4-yl]-4-(2H-tetrazol-5-yl)pyridine |
| 144 | 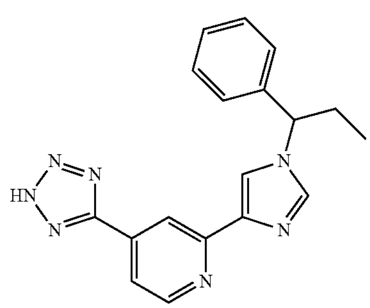 [SMILES: CCC(c1ccccc1)n1cnc(-c2cc(-c3nn[nH]n3)ccn2)c1] | 2-[1-(1-phenylpropyl)imidazol-4-yl]-4-(2H-tetrazol-5-yl)pyridine |
| 145 | 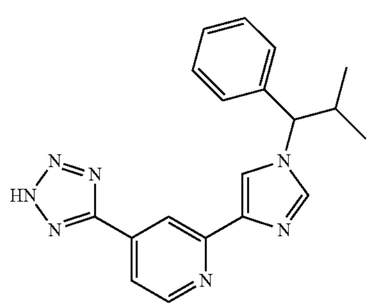 | 2-[1-(2-methyl-1-phenylpropyl)imidazol-4-yl]-4-(2H-tetrazol-5-yl)pyridine |

TABLE 1-continued

| Chemical Synthesis Example | Structure | Name |
|---|---|---|
| 146 | 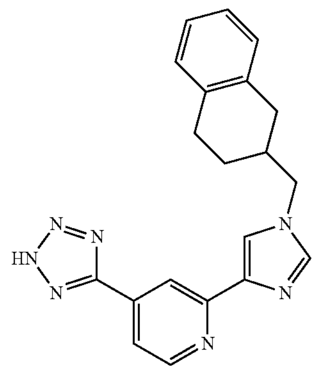 [SMILES: c1ccc2c(c1)CCC(Cn1cnc(-c3cc(-c4nn[nH]n4)ccn3)c1)C2] | 2-[1-(1,2,3,4-tetrahydronaphthalen-2-ylmethyl)imidazol-4-yl]-4-(2H-tetrazol-5-yl)pyridine |
| 147 | 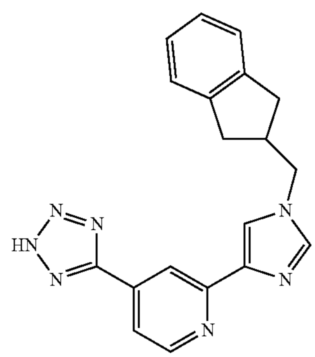 [SMILES: c1ccc2c(c1)CC(Cn1cnc(-c3cc(-c4nn[nH]n4)ccn3)c1)C2] | 2-[1-(2,3-dihydro-1H-inden-2-ylmethyl)imidazol-4-yl]-4-(2H-tetrazol-5-yl)pyridine |
| 148 | 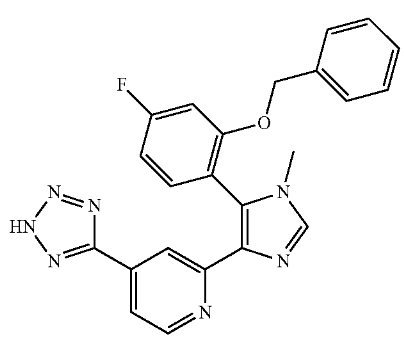 [SMILES: Cn1cnc(-c2cc(-c3nn[nH]n3)ccn2)c1-c1ccc(F)cc1OCc1ccccc1] | 2-[5-(4-fluoro-2-phenylmethoxyphenyl)-1-methylimidazol-4-yl]-4-(2H-tetrazol-5-yl)pyridine |
| 149 | 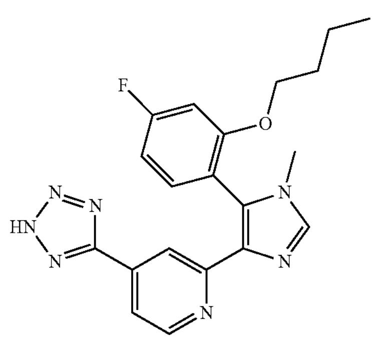 [SMILES: CCCCOc1cc(F)ccc1-c1c(-c2cc(-c3nn[nH]n3)ccn2)ncn1C] | 2-[5-(2-butoxy-4-fluorophenyl)-1-methylimidazol-4-yl]-4-(2H-tetrazol-5-yl)pyridine |

TABLE 1-continued

| Chemical Synthesis Example | Structure | Name |
|---|---|---|
| 150 | 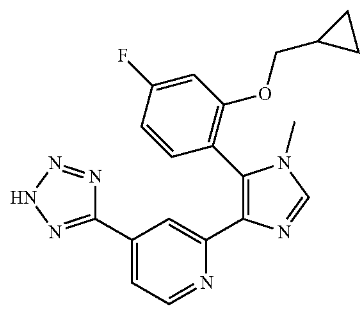 [SMILES: Cn1cnc(-c2cc(-c3nn[nH]n3)ccn2)c1-c1ccc(F)cc1OCC1CC1] | 2-[5-[2-(cyclopropylmethoxy)-4-fluorophenyl]-1-methylimidazol-4-yl]-4-(2H-tetrazol-5-yl)pyridine |
| 151 | 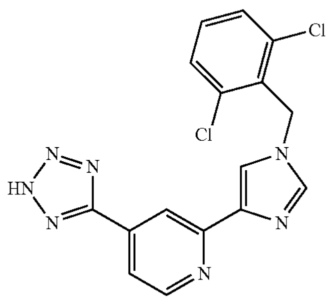 [SMILES: Clc1cccc(Cl)c1Cn1cnc(-c2cc(-c3nn[nH]n3)ccn2)c1] | 2-[1-[(2,6-dichlorophenyl)methyl]imidazol-4-yl]-4-(2H-tetrazol-5-yl)pyridine |
| 152 | 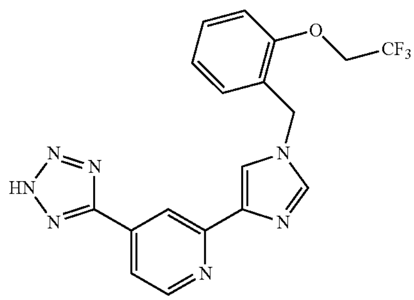 [SMILES: FC(F)(F)COc1ccccc1Cn1cnc(-c2cc(-c3nn[nH]n3)ccn2)c1] | 4-(2H-tetrazol-5-yl)-2-[1-[[2-(2,2,2-trifluoroethoxy)phenyl]methyl]imidazol-4-yl]pyridine |
| 153 | 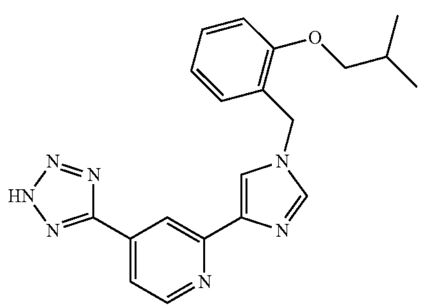 [SMILES: CC(C)COc1ccccc1Cn1cnc(-c2cc(-c3nn[nH]n3)ccn2)c1] | 2-[1-[[2-(2-methylpropoxy)phenyl]methyl]imidazol-4-yl]-4-(2H-tetrazol-5-yl)pyridine |
| 154 | 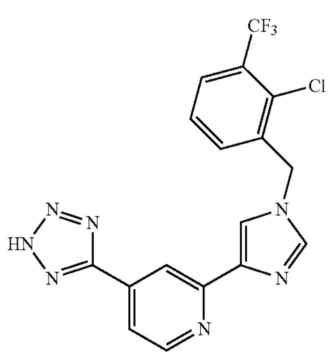 | 2-[1-[[2-chloro-3-(trifluoromethyl)phenyl]methyl]imidazol-4-yl]-4-(2H-tetrazol-5-yl)pyridine |

TABLE 1-continued

| Chemical Synthesis Example | Structure | Name |
|---|---|---|
| 155 | 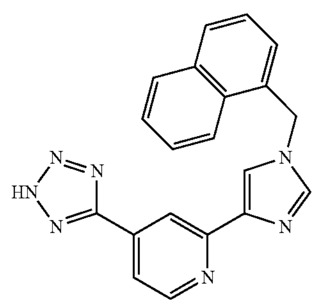 [SMILES: c1ccc2c(Cn3cnc(-c4cc(-c5nn[nH]n5)ccn4)c3)cccc2c1] | 2-[1-(naphthalen-1-ylmethyl)imidazol-4-yl]-4-(2H-tetrazol-5-yl)pyridine |
| 156 | 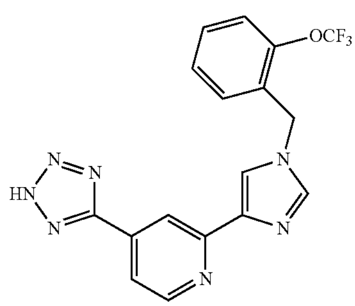 [SMILES: FC(F)(F)Oc1ccccc1Cn1cnc(-c2cc(-c3nn[nH]n3)ccn2)c1] | 4-(2H-tetrazol-5-yl)-2-[1-[[2-(trifluoromethoxy)phenyl]methyl]imidazol-4-yl]pyridine |
| 157 | 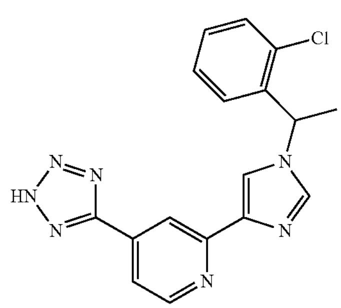 [SMILES: CC(c1ccccc1Cl)n1cnc(-c2cc(-c3nn[nH]n3)ccn2)c1] | 2-[1-[1-(2-chlorophenyl)ethyl]imidazol-4-yl]-4-(2H-tetrazol-5-yl)pyridine |
| 158 | 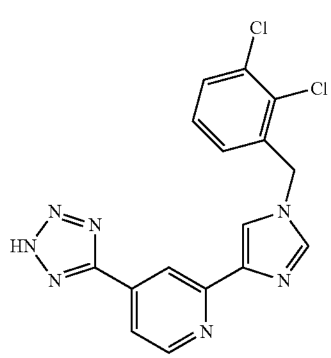 [SMILES: Clc1cccc(Cn2cnc(-c3cc(-c4nn[nH]n4)ccn3)c2)c1Cl] | 2-[1-[(2,3-dichlorophenyl)methyl]imidazol-4-yl]-4-(2H-tetrazol-5-yl)pyridine |

TABLE 1-continued

| Chemical Synthesis Example | Structure | Name |
|---|---|---|
| 159 | 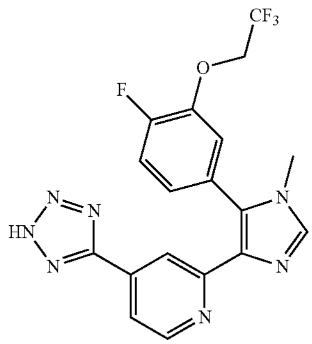 [SMILES: Cn1cnc(-c2cc(-c3nn[nH]n3)ccn2)c1-c1ccc(F)c(OCC(F)(F)F)c1] | 2-[5-[4-fluoro-3-(2,2,2-trifluoroethoxy)phenyl]-1-methylimidazol-4-yl]-4-(2H-tetrazol-5-yl)pyridine |
| 160 | 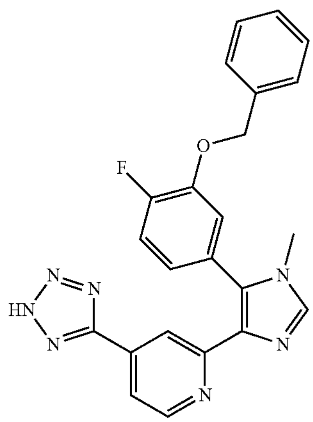 | 2-[5-(4-fluoro-3-phenylmethoxyphenyl)-1-methylimidazol-4-yl]-4-(2H-tetrazol-5-yl)pyridine |
| 161 | 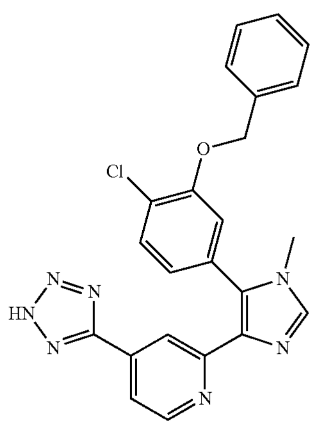 [SMILES: Cn1cnc(-c2cc(-c3nn[nH]n3)ccn2)c1-c1ccc(Cl)c(OCc2ccccc2)c1] | 2-[5-(4-chloro-3-phenylmethoxyphenyl)-1-methylimidazol-4-yl]pyridine-4-carbonitrile |
| 162 | 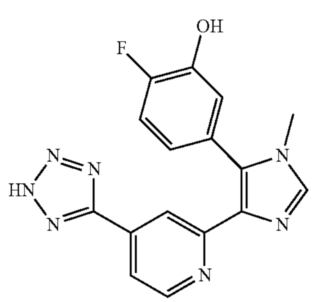 [SMILES: Cn1cnc(-c2cc(-c3nn[nH]n3)ccn2)c1-c1ccc(F)c(O)c1] | 2-fluoro-5-[3-methyl-5-[4-(2H-tetrazol-5-yl)pyridin-2-yl]imidazol-4-yl]phenol |

TABLE 1-continued

| Chemical Synthesis Example | Structure | Name |
|---|---|---|
| 163 | 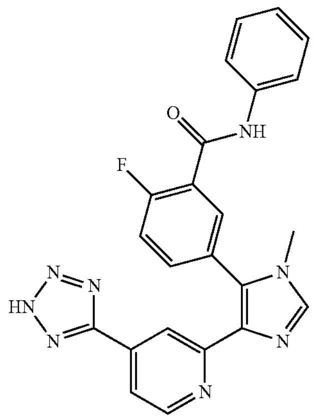 [SMILES: Cn1cnc(-c2cc(-c3nn[nH]n3)ccn2)c1-c1ccc(F)c(C(=O)Nc2ccccc2)c1] | 2-fluoro-5-[3-methyl-5-[4-(2H-tetrazol-5-yl)pyridin-2-yl]imidazol-4-yl]-N-phenylbenzamide |
| 164 | 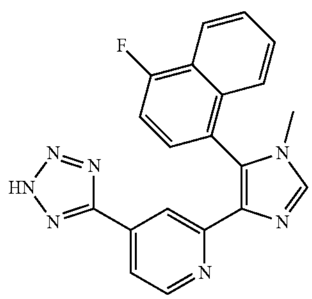 [SMILES: Cn1cnc(-c2cc(-c3nn[nH]n3)ccn2)c1-c1ccc(F)c2ccccc12] | 2-[5-(4-fluoronaphthalen-1-yl)-1-methylimidazol-4-yl]-4-(2H-tetrazol-5-yl)pyridine |
| 165 | 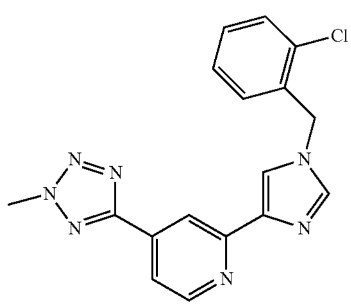 [SMILES: Cn1nnc(-c2ccnc(-c3cn(Cc4ccccc4Cl)cn3)c2)n1] | 2-(1-(2-chlorobenzyl)-1H-imidazol-4-yl)-4-(2-methyl-2H-tetrazol-5-yl)pyridine |
| 166 | 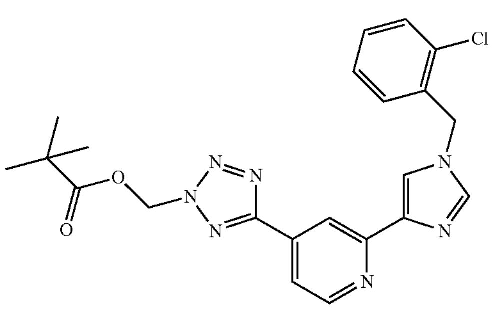 [SMILES: CC(C)(C)C(=O)OCn1nnc(-c2ccnc(-c3cn(Cc4ccccc4Cl)cn3)c2)n1] | (5-(2-(1-(2-chlorobenzyl)-1H-imidazol-4-yl)pyridin-4-yl)-2H-tetrazol-2-yl)methyl pivalate |

TABLE 1-continued

| Chemical Synthesis Example | Structure | Name |
|---|---|---|
| 167 | 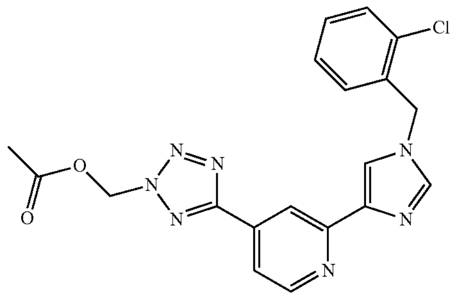 [SMILES: CC(=O)OCn1nnc(-c2ccnc(-c3cn(Cc4ccccc4Cl)cn3)c2)n1] | (5-(2-(1-(2-chlorobenzyl)-1H-imidazol-4-yl)pyridin-4-yl)-2H-tetrazol-2-yl)methyl acetate |
| 168 | 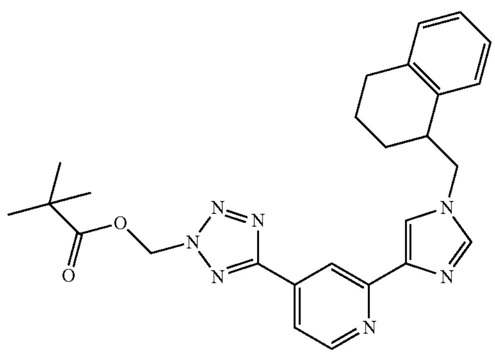 [SMILES: CC(C)(C)C(=O)OCn1nnc(-c2ccnc(-c3cn(CC4CCCc5ccccc54)cn3)c2)n1] | (5-(2-(1-((1,2,3,4-tetrahydronaphthalen-1-yl)methyl)-1H-imidazol-4-yl)pyridin-4-yl)-2H-tetrazol-2-yl)methyl pivalate |
| 169 | 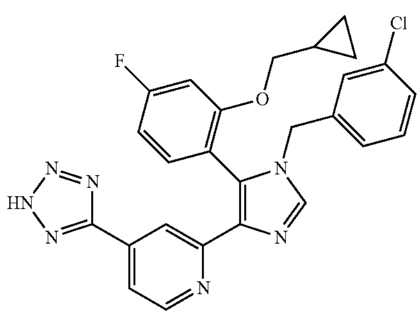 [SMILES: Fc1ccc(-c2c(-c3cc(-c4nn[nH]n4)ccn3)ncn2Cc2cccc(Cl)c2)c(OCC2CC2)c1] | 2-(1-(3-chlorobenzyl)-5-(2-(cyclopropylmethoxy)-4-fluorophenyl)-1H-imidazol-4-yl)-4-(2H-tetrazol-5-yl)pyridine |

In some embodiments, the compound disclosed herein has the structure provided in Table 2.

TABLE 2

2-[1-[2-[cyclobutylmethyl(methyl)amino]ethyl]imidazol-4-yl]pyridine-4-carboxylic acid TABLE 2-continued 2-[1-[2-[cyclohexylmethyl(methyl)amino]ethyl]imidazol-4-yl]pyridine-4-carboxylic acid TABLE 2-continued

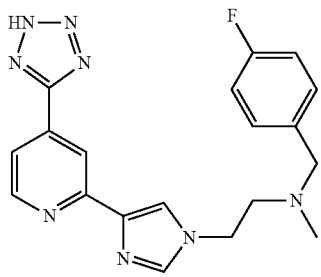

N-[(4-fluorophenyl)methyl]-N-methyl-
2-[4-[4-(2H-tetrazol-5-yl)pyridin-2-
yl]imidazol-1-yl]ethanamine

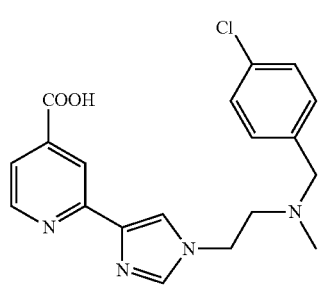

2-[1-[2-[(4-chlorophenyl)methyl-
methylamino]ethyl]imidazol-4-
yl]pyridine-4-carboxylic acid

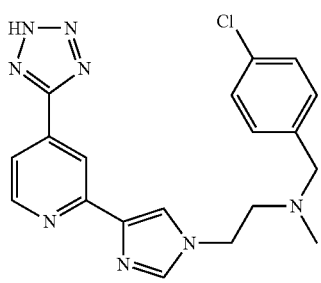

N-[(4-chlorophenyl)methyl]-N-methyl-
2-[4-[4-(2H-tetrazol-5-yl)pyridin-2-
yl]imidazol-1-yl]ethanamine

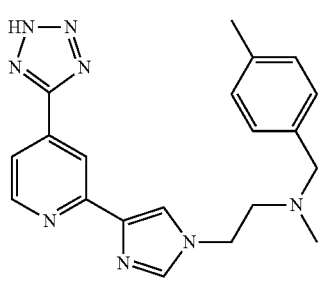

N-methyl-N-[(4-methylphenyl)methyl]-
2-[4-[4-(2H-tetrazol-5-yl)pyridin-2-
yl]imidazol-1-yl]ethanamine TABLE 2-continued

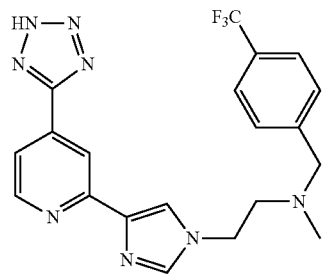

N-methyl-2-[4-[4-(2H-tetrazol-5-
yl)pyridin-
2-yl]imidazol-1-yl]-N-[[4-
(trifluoromethyl)phenyl]methyl]eth-
anamine

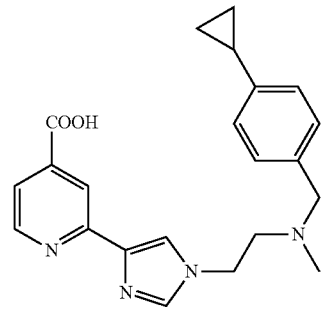

2-[1-[2-[(4-cyclopropylphenyl)methyl-
methylamino]ethyl]imidazol-4-
yl]pyridine-4-carboxylic acid

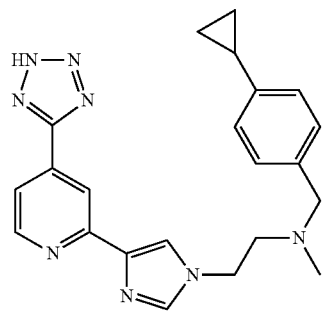

N-[(4-cyclopropylphenyl)methyl]-
N-methyl-
2-[4-[4-(2H-tetrazol-5-yl)pyridin-2-
yl]imidazol-1-yl]ethanamine

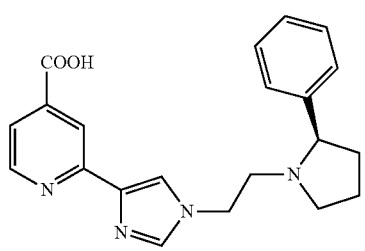

2-[1-[2-[(2R)-2-phenylpyrrolidin-1-
yl]ethyl]imidazol-4-yl]pyridine-4-
carboxylic acid TABLE 2-continued

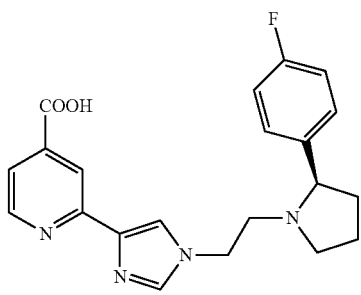

2-[1-[2-[(2R)-2-(4-fluorophenyl)pyrrolidin-1-yl]ethyl]imidazol-4-yl]pyridine-4-carboxylic acid

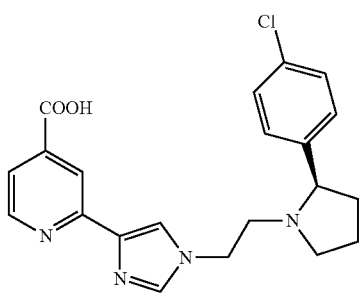

2-[1-[2-[(2R)-2-(4-chlorophenyl)pyrrolidin-1-yl]ethyl]imidazol-4-yl]pyridine-4-carboxylic acid

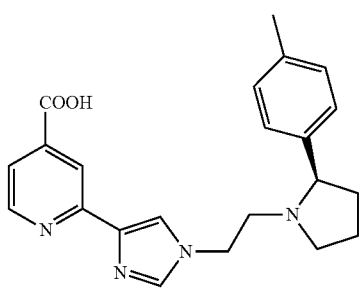

2-[1-[2-[(2R)-2-(4-methylphenyl)pyrrolidin-1-yl]ethyl]imidazol-4-yl]pyridine-4-carboxylic acid

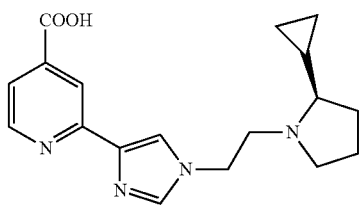

2-[1-[2-[(2R)-2-cyclopropylpyrrolidin-1-yl]ethyl]imidazol-4-yl]pyridine-4-carboxylic acid TABLE 2-continued

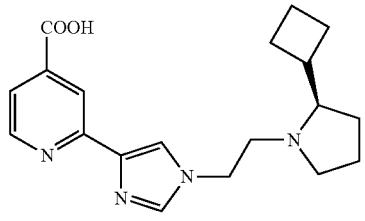

2-[1-[2-[(2R)-2-cyclobutylpyrrolidin-1-yl]ethyl]imidazol-4-yl]pyridine-4-carboxylic acid

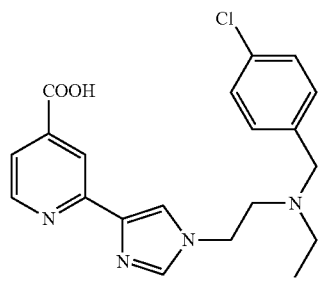

2-[1-[2-[(4-chlorophenyl)methyl-ethylamino]ethyl]imidazol-4-yl]pyridine-4-carboxylic acid

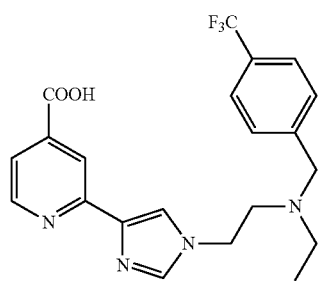

2-[1-[2-[(4-trifluoromethylphenyl)methyl-ethylamino]ethyl]imidazol-4-yl]pyridine-4-carboxylic acid

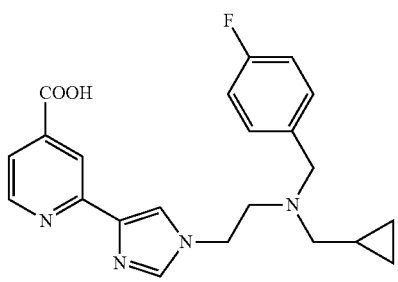

2-[1-[2-[(4-fluorophenyl)methyl-cyclopropylmethylamino]ethyl]imidazol-4-yl]pyridine-4-carboxylic acid TABLE 2-continued

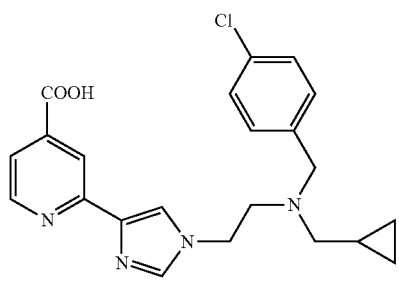

2-[1-[2-[(4-chlorophenyl)methyl-
cyclopropylmethylamino]eth-
yl]imidazol-4-yl]pyridine-4-
carboxylic acid

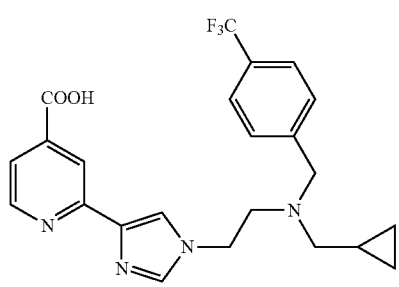

2-[1-[2-[(4-trifluoromethylphenyl)methyl-
cyclopropylmethylamino]eth-
yl]imidazol-4-yl]pyridine-4-
carboxylic acid

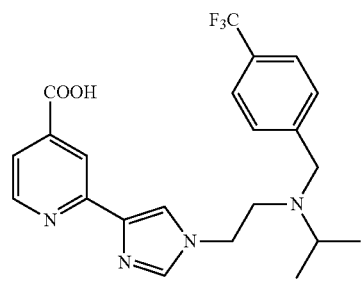

2-[1-[2-[(4-trifluoromethylphenyl)methyl-
isopropylamino]ethyl]imidazol-4-
yl]pyridine-4-carboxylic acid

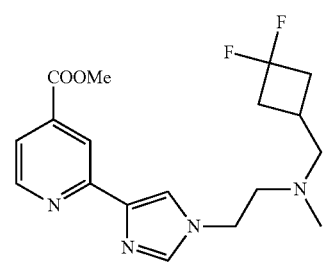

methyl 2-[1-[2-[(3,3-
difluorocyclobutyl)methyl-
methylamino]ethyl]imidazol-4-
yl]pyridine-4-carboxylate TABLE 2-continued

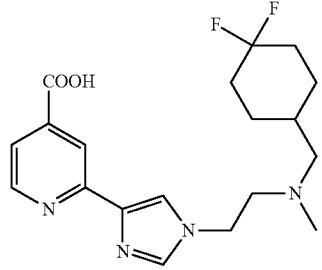

2-[1-[2-[(4,4-difluorocyclo-
hexyl)methyl-
methylamino]ethyl]imidazol-4-
yl]pyridine-1-carboxylic acid

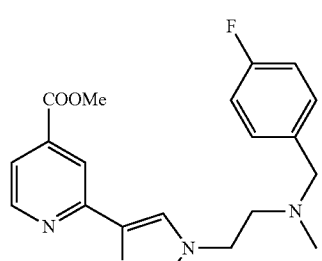

methyl 2-[1-[2-[(4-fluorophenyl)methyl-
methylamino]ethyl]imidazol-4-
yl]pyridine-4-carboxylate

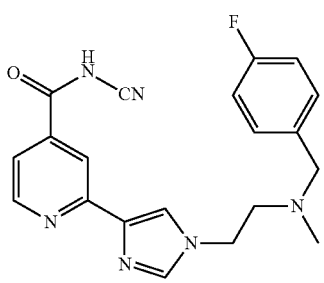

N-cyano-2-[1-[2-[(4-
fluorophenyl)methyl-
methylamino]ethyl]imidazol-4-
yl]pyridine-4-carboxamide

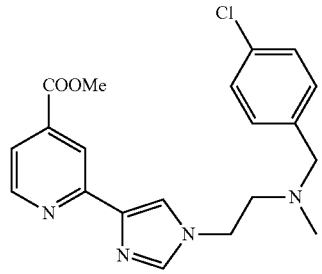

methyl 2-[1-[2-[(4-chlorophenyl)methyl-
methylamino]ethyl]imidazol-4-
yl]pyridine-4-carboxylate TABLE 2-continued

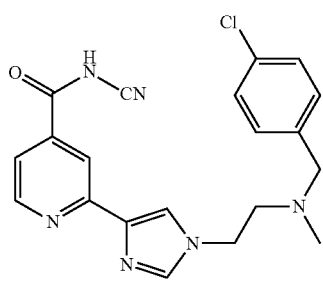

2-[1-[2-[(4-chlorophenyl)methyl-
methylamino]ethyl]imidazol-4-yl]-
N-cyanopyridine-4-carboxamide

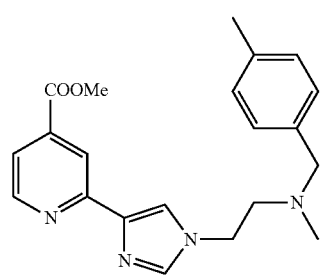

methyl 2-[1-[2-[methyl-[(4-
methylphenyl)methyl]amino]eth-
yl]imidazol-4-yl]pyridine-4-carboxylate

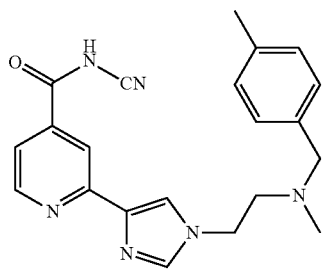

N-cyano-2-[1-[2-[methyl-[(4-
methylphenyl)methyl]amino]eth-
yl]imidazol-4-yl]pyridine-4-
carboxamide

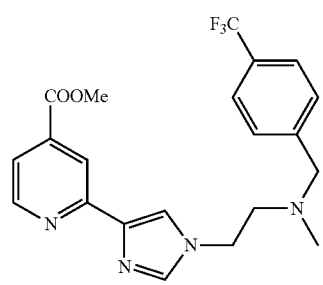

methyl 2-[1-[2-[methyl-[[4-
(trifluoromethyl)phenyl]methyl]a-
mino]ethyl]imidazol-4-yl]pyridine-4-
carboxylate TABLE 2-continued

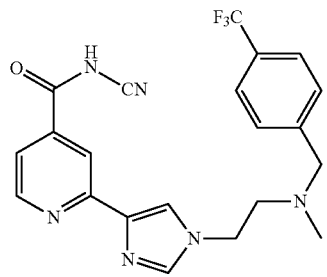

N-cyano-2-[1-[2-[methyl-[[4-
(trifluoromethyl)phenyl]methyl]a-
mino]ethyl]imidazol-4-yl]pyridine-4-
carboxamide

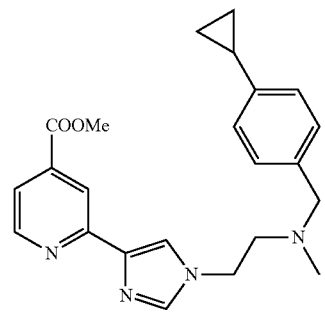

methyl 2-[1-[2-[(4-
cyclopropylphenyl)methyl-
methylamino]ethyl]imidazol-4-
yl]pyridine-4-carboxylate

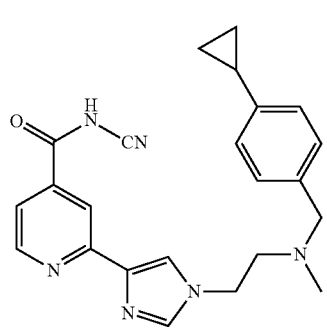

N-cyano-2-[1-[2-[(4-
cyclopropylphenyl)methyl-
methylamino]ethyl]imidazol-4-
yl]pyridine-4-carboxamide

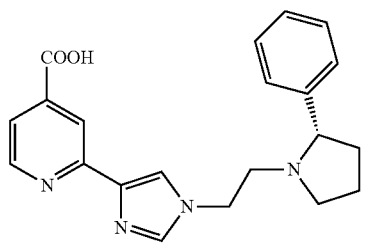

2-[1-[2-[(2S)-2-phenylpyrrolidin-1-
yl]ethyl]imidazol-4-yl]pyridine-4-
carboxylic acid TABLE 2-continued

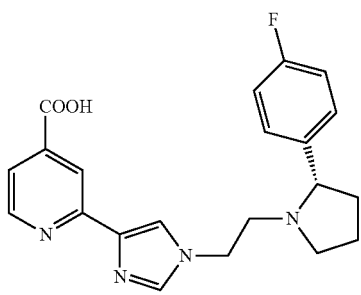

2-[1-[2-[(2S)-2-(4-fluorophenyl)pyrrolidin-1-yl]ethyl]imidazol-4-yl]pyridine-4-carboxylic acid

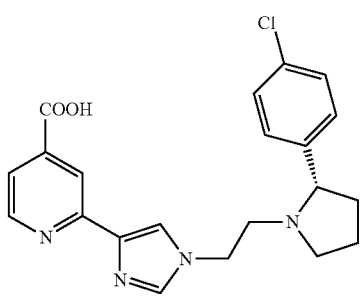

2-[1-[2-[(2S)-2-(4-chlorophenyl)pyrrolidin-1-yl]ethyl]imidazol-4-yl]pyridine-4-carboxylic acid

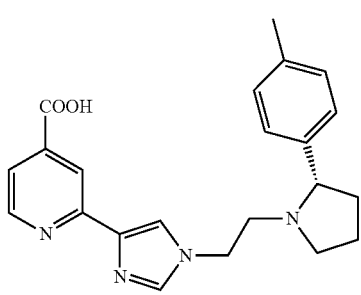

2-[1-[2-[(2S)-2-(4-methylphenyl)pyrrolidin-1-yl]ethyl]imidazol-4-yl]pyridine-4-carboxylic acid

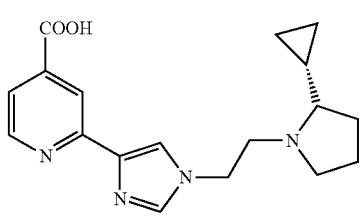

2-[1-[2-(2-cyclopropylpyrrolidin-1-yl)ethyl]imidazol-4-yl]pyridine-4-carboxylic acid TABLE 2-continued

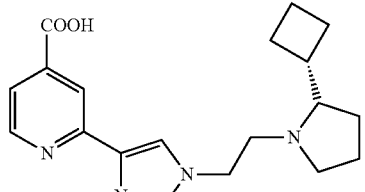

2-[1-[2-(2-cyclobutylpyrrolidin-1-yl)ethyl]imidazol-4-yl]pyridine-4-carboxylic acid

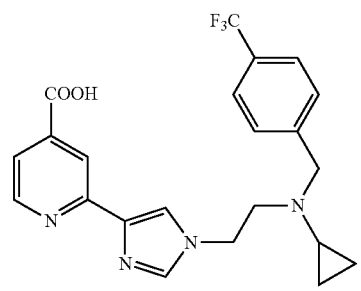

2-[1-[2-[(4-trifluoromethylpheny)methyl-cyclopropylamino]ethyl]imidazol-4-yl]pyridine-4-carboxylic acid

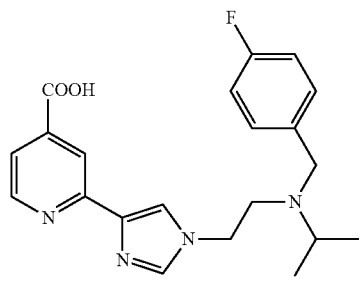

2-[1-[2-[(4-fluorophenyl)methyl-isopropylamino]ethyl]imidazol-4-yl]pyridine-4-carboxylic acid

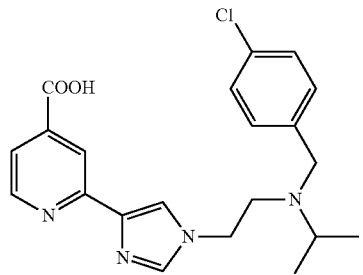

2-[1-[2-[(4-chlorophenyl)methyl-isopropylamio]ethyl]imidazol-4-yl]pyridine-4-carboxylic acid Preparation of the Substituted Imidazole-Pyridine Derivative Compounds The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd.

(Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted imidazole-pyridine derivative compounds described herein is P. H. Stahl & C. G. Wermuth "Handbook of Pharmaceutical Salts", Verlag Helvetica Chimica Acta, Zurich, 2002.

The substituted imidazole-pyridine derivative compounds are prepared by the general synthetic routes described below in Schemes 1-5.

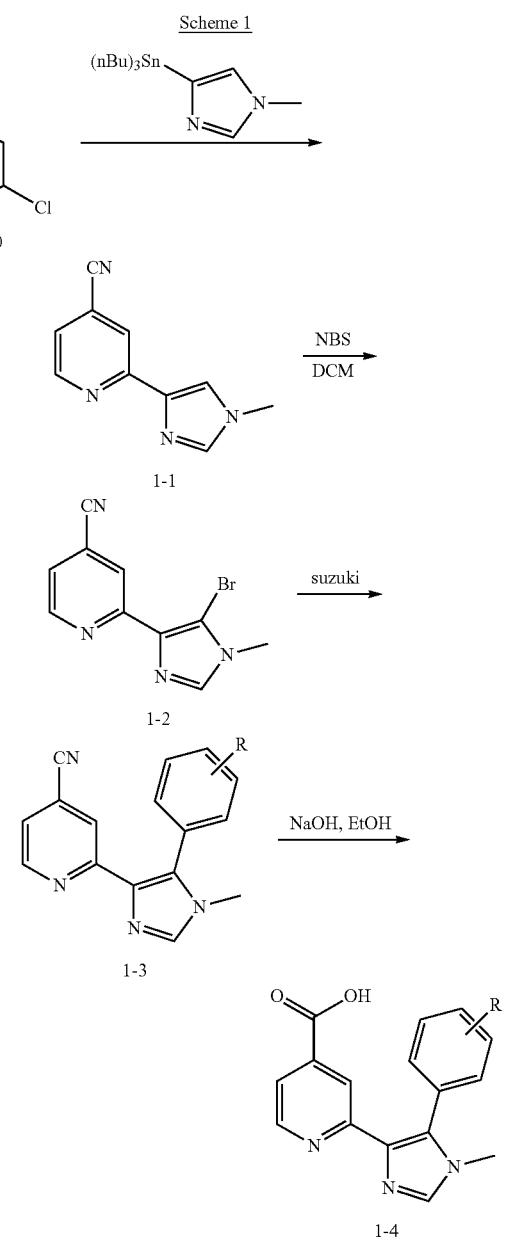

A method for preparing compounds of formula 1-4 is provided in Scheme 1. Via Stille coupling, 2-chloro-4-pyridinenitrile is treated with N-methyl-4-(tributylstannyl)imidazole in an organic solvent, such as toluene, under microwave heating (e.g., about 120° C.), in presence of a Pd catalyst (e.g. tetrakistriphenylphosphine palladium (0)) to give intermediate 1-1. Subsequent reaction with stoichiometric amount of NBS provides a single brominated product 1-2. Using Suzuki condition, substituted phenyl imidazole intermediates 1-3 are obtained, which upon heating using NaOH aqueous solution (5-10N) in an alcoholic solvent such as EtOH afford the carboxylic acid compounds of formula 1-4.

ethanol is first treated with trityl chloride in presence of a base, such as TEA, in an anhydrous organic solvent, such as DCM, to give 3-1. Alkylation of bromoimidazole (obtained by bromination on imidazole using bromine) using 3-1, under treatment with sodium hydride gives 3-2. It is then converted to tin reagent using bis(tributyltin), triphenyl phosphine, palladium acetate and a base (e.g sodium carbonate) under heating

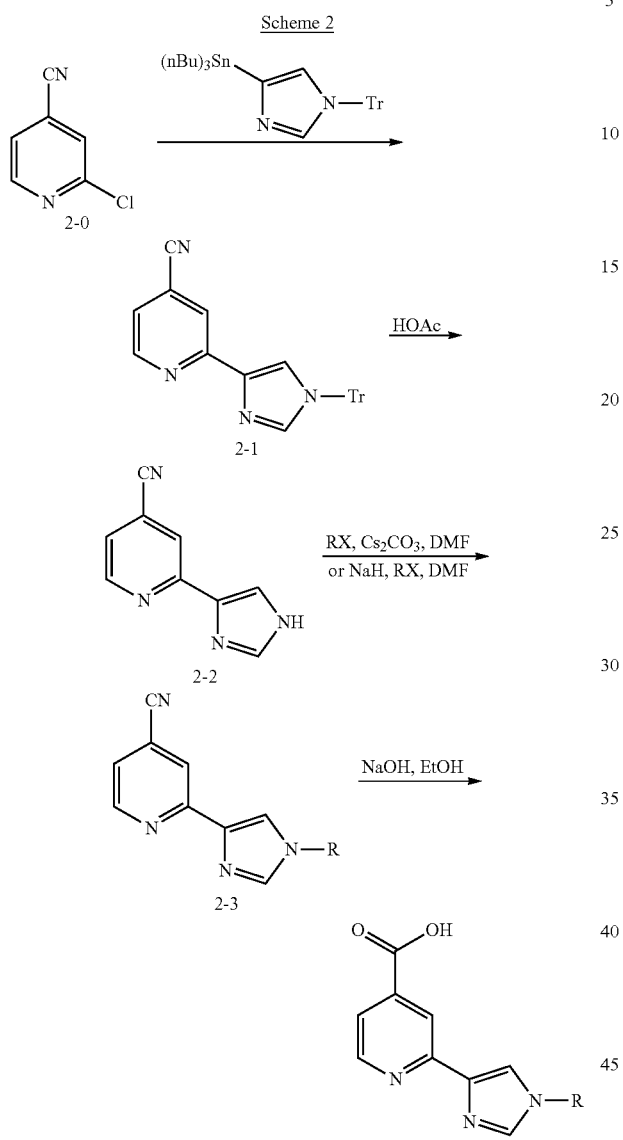

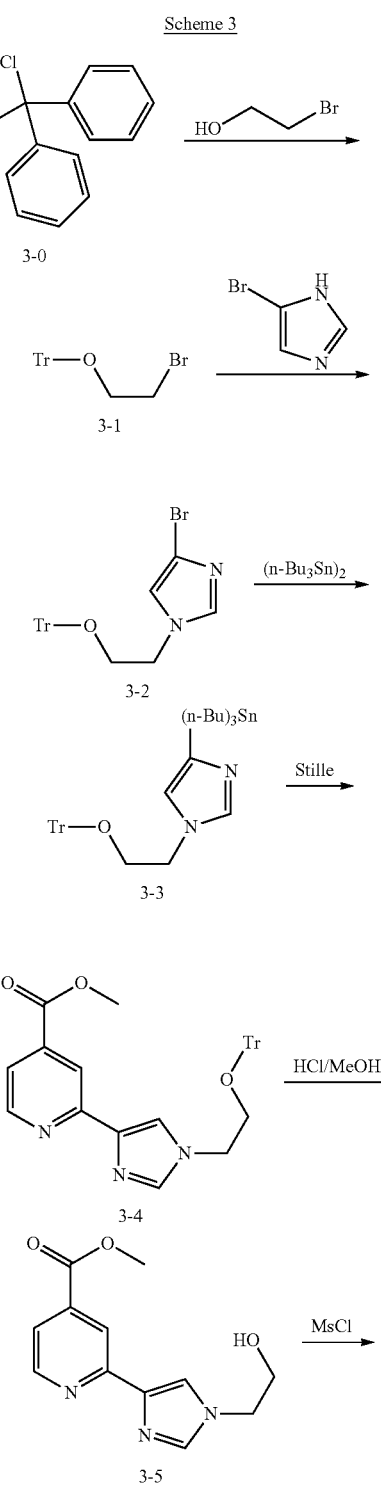

A method for preparing compounds of formula 2-4 is provided in Scheme 2. 2-Chloro-4-pyridinenitrile is treated with 4-(tributylstannyl)-1-tritylimidazole using a similar Stille coupling condition as described in scheme 1 to give trityl protected imidazole intermediate 2-1. It is then treated with acetic acid at elevated temperature (e.g. 90° C.) to deprotect the trityl group. Intermediate 2-2 is then alkylated with alkyl halide (alkyl chloro or alkyl bromo) using a base, such as sodium hydride or cesium carbonate, in an organic solvent, such as DMF, at room temperature (when using NaH) or under heating condition (e.g 90-120° C., when using cesium carbonate) to give 2-3. Hydrolysis using concentrated sodium hydroxide solution (e.g. 5-10 N) in ethanol upon heating (e.g. 90° C.) provides the carboxylic acid compounds of formula 2-4.

A method to prepare N-ethylamino substituted imidazole-pyridines of formula 3-7 is provided in Scheme 3. 2-Bromo-

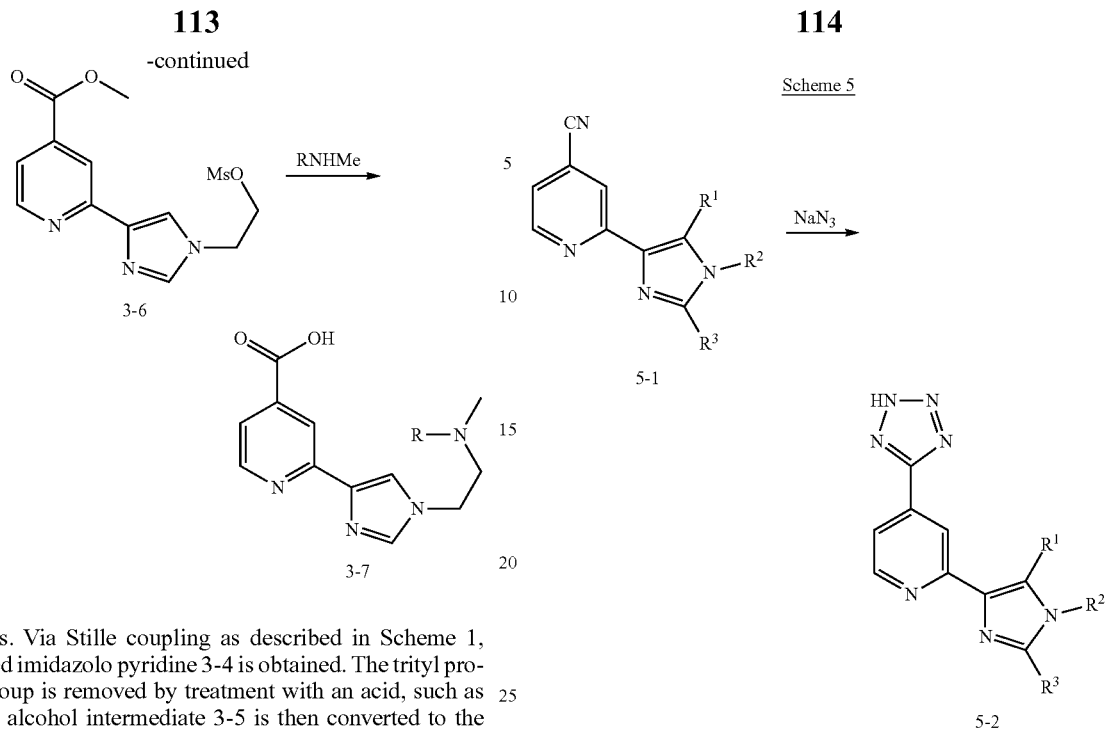

conditions. Via Stille coupling as described in Scheme 1, substituted imidazolo pyridine 3-4 is obtained. The trityl protective group is removed by treatment with an acid, such as HCl. The alcohol intermediate 3-5 is then converted to the mesylate, followed by displacement with N-methyl substituted amines under heating condition (e.g. 110° C.) in an organic solvent, such as toluene. Upon hydrolysis using sodium hydroxide solution (5-10N), the carboxylic acid compounds of formula 3-7 are obtained.

In each of the above reaction procedures or schemes, the various substituents may be selected from among the various substituents otherwise taught herein.

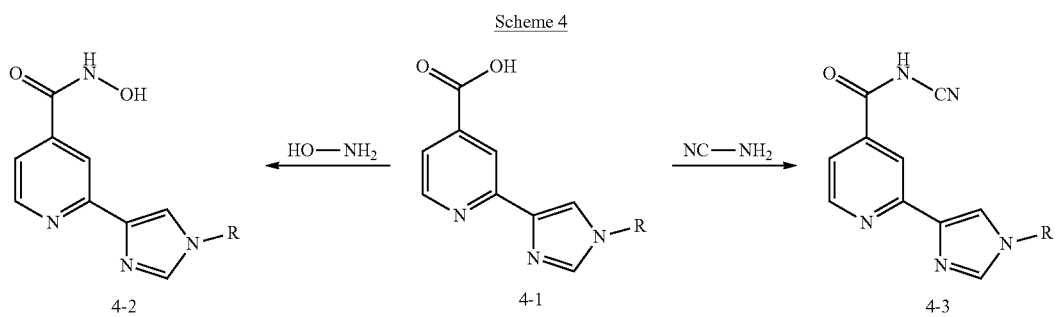

Methods for preparing compounds of formula 4-2 and 4-3 are provided in Scheme 4. Treatment of acid 4-1 with hydroxylamine hydrochloride in the presence of a coupling reagent, such as HATU, in a solvent, such as DMF, at room temperature for 1 to 24 hours provides compounds 4-2. Compound 4-1 can also be used to prepare N-acylcyanamides such as compound 4-3. Treatment of 4-1 with cyanamide in the presence of an acid coupling reagent, such as HATU, in a solvent, such as DMF, at room temperature for 1 to 24 hours provides compounds 4-3.

A method for preparing compounds of formula 5-2 is provided in Scheme 5. Treatment of the nitrile intermediate 5-1 with sodium azide and ammonium chloride in DMF followed by heating to 90° C. for 2 to 24 hours provides the desired tetrazole derivative 5-2.

Pharmaceutical Compositions

In certain embodiments, the substituted imidazole-pyridine derivative compound as described herein is administered as a pure chemical. In other embodiments, the substituted imidazole-pyridine derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)), the disclosure of which is hereby incorporated herein by reference in its entirety.

Accordingly, provided herein is a pharmaceutical composition comprising at least one substituted imidazole-pyridine derivative compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof.

One embodiment provides a pharmaceutical composition comprising a pharmaceutically acceptable carrier and a compound of Formula (III), or a pharmaceutically acceptable salt thereof.

In certain embodiments, the substituted imidazole-pyridine derivative compound as described by Formula (I) or (III) is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The dose of the composition comprising at least one substituted imidazole-pyridine derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses can typically range from about 1.0 mg to about 1000 mg, one to four times, or more, per day.

Histone Demethylase

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which can covalently modify histones at various sites.

Proteins can be post-translationally modified by methylation on amino groups of lysines and guanidino groups of arginines or carboxymethylated on aspartate, glutamate, or on the C-terminus of the protein. Post-translational protein methylation has been implicated in a variety of cellular processes such as RNA processing, receptor mediated signaling, and cellular differentiation. Post-translational protein methylation is widely known to occur on histones, such reactions known to be catalyzed by histone methyltransferases, which transfer methyl groups from S-adenyosyl methionine (SAM) to histones. Histone methylation is known to participate in a diverse range of biological processes including heterochromatin formation, X-chromosome inactivation, and transcriptional regulation (Lachner et al., (2003) J. Cell Sci. 116:2117-2124; Margueron et al., (2005) Curr. Opin. Genet. Dev. 15:163-176).

Unlike acetylation, which generally correlates with transcriptional activation, whether histone methylation leads to transcription activation or repression depends on the particular site of methylation and the degree of methylation (e.g., whether a particular histone lysine residue is mono-, di-, or tri-methylated). However, generally, methylation on H3K9, H3K27 and H4K20 is linked to gene silencing, while methylation on H3K4, H3K36, and H3K79 is generally associated with active gene expression. In addition, tri- and di-methylation of H3K4 generally marks the transcriptional start sites of actively transcribed genes, whereas mono-methylation of H3K4 is associated with enhancer sequences.

A "demethylase" or "protein demethylase," as referred to herein, refers to an enzyme that removes at least one methyl group from an amino acid side chain. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found using a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.

JMJD2 Family

The JMJD2 family of proteins are a family of histone-demethylases known to demethylate tri- and di-methylated H3-K9, and were the first identified histone tri-methyl demethylases. In particular, ectopic expression of JMJD2 family members was found to dramatically decrease levels of tri- and di-methylated H3-K9, while increasing levels of mono-methylated H3-K9, which delocalized Heterochromatin Protein 1 (HP1) and reduced overall levels of heterochromatin in vivo. Members of the JMJD2 subfamily of jumonji proteins include JMJD2C and its homologues JMJD2A, JMJD2B, JMJD2D and JMJD2E. Common structural features found in the JMJD2 subfamily of Jumonji proteins include the JmjN, JmjC, PHD and Tdr sequences.

JMJD2C, also known as GASC1 and KDM4C, is known to demethylate tri-methylated H3K9 and H3K36. Histone demethylation by JMJD2C occurs via a hydroxylation reaction dependent on iron and α-ketoglutarate, wherein oxidative decarboxylation of α-ketoglutarate by JMJD2C produces carbon dioxide, succinate, and ferryl and ferryl subsequently hydroxylates a methyl group of lysine H3K9, releasing formaldehyde. JMJD2C is known to modulate regulation of adipogenesis by the nuclear receptor PPARγ and is known to be involved in regulation of self-renewal in embryonic stem cells.

JARID Family

As used herein, a "JARID protein" includes proteins in the JARID1 subfamily (e.g., JARID1A, JARID1B, JARID1C and JARID1D proteins) and the JARID2 subfamily, as well as homologues thereof. A further description and listing of JARID proteins can be found in Klose et al. (2006) Nature Reviews/Genetics 7:715-727. The JARID1 family contains several conserved domains: JmjN, ARID, JmjC, PHD and a C5HC2 zing finger.

JARID1A, also called KDM5A or RBP2, was initially found as a binding partner of retinoblastoma (Rb) protein. JARID1A was subsequently found to function as a demethylase of tri- and di-methylated H3K4, and has been found to promote cell growth, while inhibiting senescence and differentiation. For instance, abrogation of JARID1A from mouse cells inhibits cell growth, induces senescence and differentiation, and causes loss of pluripotency of embryonic stem cells in vitro. JARID1A has been found to be overexpressed in gastric cancer and the loss of JARID1A has been found to reduce tumorigenesis in a mouse cancer model. Additionally, studies have demonstrated that loss of the retinoblastome binding protein 2 (RBP2) histone demethylase suppresses tumorigenesis in mice lacking Rb1 or Men1 (Lin et al. Proc. Natl. Acad. Sci. USA, Aug. 16, 2011, 108(33), 13379-86; doi: 10.1073/pnas.1110104108) and lead to the conclusion that RBP2-inhibitory drugs would have anti-cancer activity.

JARID1B, also referred to as KDM5B and PLU1, was originally found in experiments to discover genes regulated by the HER2 tyrosine kinase. JARID1B has consistently been found to be expressed in breast cancer cell lines, although restriction of JARID1B has been found in normal adult tissues, with the exception of the testis. In addition, 90% of invasive ductal carcinomas have been found to express JARID1B. In addition, JARID1B has been found to be up-regulated in prostate cancers, while having more limited expression in benign prostate, and has also been found to be up-regulated in bladder cancer and lung cancer (both SCLC and NSCLC). JARID1B has also been found to repress tumor suppressor genes such as BRCA1, CAV1 and 14-3-3σ, and knockdown of JARID1B was found to increase the levels of tri-methylated H3K4 at these genes.

FBXL10 and FBXL11

F-box and leucine-rich repeat protein 10 (FBXL10) and F-box and leucine-rich repeat protein 11 (FBXL11) are multifunctional F-box family proteins that demethylate histone H3 through a hydroxylation based mechanism. FBXL10, also known as lysine (K)-specific demethylase 2B (KDM2B) or Jumonji C domain-containing histone demethylase 1B (JHDM1B), preferentially demethylates trimethylated K4 and dimethylated K36 of histone H3, but contains weak or no activity for mono- and tri-methylated H3-K36. FBXL10 contains three domains, a catalytic JMJC domain, an F-box domain and a CXXC DNA-binding domain. The N-terminal JMJC domain coordinates iron and α-ketoglutarate to catalyze demethylation through the hydroxylation based mechanism. The CXXC DNA-binding domain allows FBXL10 to preferentially bind to transcribed region of the ribosomal RNA, leading to repression of the ribosomal RNA gene transcription and ultimately leading to inhibition of cell growth and proliferation. FBXL10 has been found to be overexpressed in acute myeloid leukemia, bladder carcinoma and pancreatic ductal adenocarcinoma. Recently, it has been demonstrated that FBXL10 regulates the expression of Polycomb target genes, those proteins are epigenetic regulators essential for stem cell differentiation. This regulation implicates FBXL10's involvement in tumorigenesis through the regulation of these Polycomb target genes. FBXL11, also known as KDM2A or JHDM1A, demethylates mono- and di-methylated K36 of histone H3. The CXXC DNA-binding domain recognizes non-methylated DNA and targets CpG island regions where it specifically removes H3K3 methylation. Further, FBXL11 is required to maintain a heterochromatic state, sustain centromeric integrity and genomic stability during mitosis. In addition, FBXL11 is a key negative regulator of NF-KB. Overexpression of FBXL11 has been observed in non-small cell lung cancer (NSCLC) where FBXL11 upregulates phosphor-ERK1/2 by repressing DUSP3 expression in NSCLC cell lines. Negative regulation of gluconeogenic gene expression by FBXL11 results in suppression of two rate-limiting gluconeogenic enzymes, critical for maintaining blood glucose homeostasis.

In an additional embodiment is a method for inhibiting a histone-demethylase enzyme comprising contacting a histone demethylase enzyme with a compound of Formula (I) or (II), or a pharmaceutically acceptable salt thereof.

In an additional embodiment is the method for inhibiting a histone-demethylase enzyme, wherein the histone-demethylase enzyme comprises a JmjC domain. In an additional embodiment is the method for inhibiting a histone-demethylase enzyme, wherein the histone-demethylase enzyme is selected from JARID1A, JARID1B, JMJD2C, JMJD2A or FBXL10.

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation. For example, in particular embodiments, the invention provides a method of treating a disease regulated by histone methylation and/or demethylation in a subject in need thereof by modulating the activity of a demethylase comprising a JmjC domain (e.g., a histone demethylase such as a JHDM protein(s)).

In an additional embodiment is a method for treating cancer in subject comprising administering a composition comprising a compound of Formula (I) or (III), or a pharmaceutically acceptable salt thereof.

In a further embodiment is the method for treating cancer in a subject wherein the cancer is selected from prostate cancer, breast cancer, bladder cancer, lung cancer or melanoma.

In an additional embodiment is a method for inhibiting the growth of a tumor comprising administering a composition comprising a compound of Formula (I) or (III), or a pharmaceutically acceptable salt thereof, wherein the tumor is characterized by a loss of retinoblastoma gene (RB1) function.

In an additional embodiment is a method for inhibiting the growth of a tumor comprising administering a composition comprising a compound of Formula (I) or (III), or a pharmaceutically acceptable salt thereof, wherein the tumor is characterized by a loss of multiple endocrine neoplasia type 1 gene (Men1) function.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Example 1

2-(1-methyl-1H-imidazol-4-yl)pyridine-4-carboxylic acid

A: 2-(1-methyl-1H-imidazol-4-yl)pyridine-4-carbonitrile

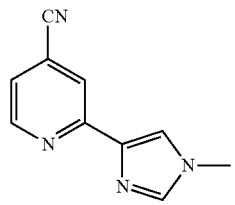

To a solution of 2-chloro-4-pyridinenitrile (300 mg, 2.16 mmol) in toluene (10 mL) was added N-methyl-4-(tributylstannyl)imidazole (964 mg, 2.6 mmol), followed by tetrakistriphenylphosphine palladium (0) (150 mg, 0.13 mmol). The reaction mixture was heated at 120° C. in a microwave initiator for 1 hr. The mixture was cooled down to r.t, solid filtered and dried to give 250 mg of 2-(1-methyl-1H-imidazol-4-yl)pyridine-4-carbonitrile as a white solid. Filtrate was purified by flash column chromatography ($CH_2Cl_2$/MeOH=20/1) to give additional 100 mg of the product (total 350 mg, 88%). $^1$H NMR (400 MHz, DMSO-$d_6$): δ 3.73 (3H, s), 7.59 (1H, d, J=4.8 Hz), 7.82 (1H, s), 8.09 (1H, s), 8.72 (1H, d, J=5 Hz). [M+H] Calc'd for $C_{10}H_8N_4$, 185. Found, 185.

B: 2-(1-methyl-1H-imidazol-4-yl)pyridine-4-carboxylic acid

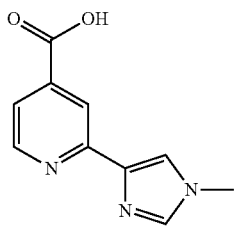

A solution of 2-(1-methyl-1H-imidazol-4-yl)pyridine-4-carbonitrile (50 mg, 0.3 mmol) in EtOH (2 mL) was treated with 10N NaOH (0.5 ml) and stirred at 90° C. for 2 hrs. The reaction mixture was purified by prep-HPLC to afford the title compound (22 mg, 40%) as light pink solid. $^1$H NMR (400 MHz, DMSO-$d_6$): δ 3.72 (3H, s), 7.57 (1H, d, J=5 Hz), 7.72 (1H, s), 7.76 (1H, s), 8.28 (1H, s), 8.63 (1H, d, J=4.9 Hz). [M+H] Calc'd for $C_{10}H_9N_3O_2$, 204. Found, 204.

Example 2

2-(5-bromo-1-methyl-1H-imidazol-4-yl)pyridine-4-carboxylic acid

A: 2-(5-bromo-1-methyl-1H-imidazol-4-yl)pyridine-4-carbonitrile

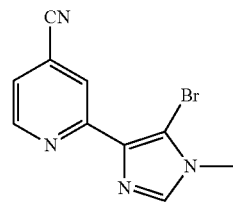

To a solution of 2-(1-methyl-1H-imidazol-4-yl)pyridine-4-carbonitrile (100 mg, 0.54 mmol) in dichloromethane (5 mL) was added N-bromosuccinimide (102 mg, 0.57 mmol). The reaction mixture was stirred at r.t. for 3 hrs. It was then purified by flash column chromatography (EtOAc/Hexane) to afford 2-(5-bromo-1-methyl-1H-imidazol-4-yl)pyridine-4-carbonitrile (140 mg, quantitative yield) as a white solid. $^1$H NMR (400 MHz, DMSO-$d_6$): δ 3.67 (3H, s), 7.70 (1H, d, J=4.8 Hz), 8.04 (1H, s), 8.19 (1H, s), 8.81 (1H, d, J=4.2 Hz). [M+H] Calc'd for $C_{10}H_7BrN_4$, 264. Found, 263, 265.

B. 2-(5-bromo-1-methyl-1H-imidazol-4-yl)pyridine-4-carboxylic acid

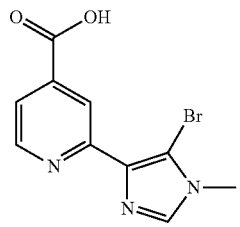 [SMILES: Cn1cnc(-c2cc(C(=O)O)ccn2)c1Br]

The title compound was prepared in 28% yield from 2-(5-bromo-1-methyl-1H-imidazol-4-yl)pyridine-4-carbonitrile according to the procedure for the preparation of Example 1. $^1$H NMR (400 MHz, DMSO-$d_6$): δ 3.66 (3H, s), 7.65 (1H, dd, J=1.4 Hz and 4.9 Hz), 8.01 (1H, s), 8.37 (1H, s), 8.72 (1H, d, J=4.9 Hz). [M+H] Calc'd for $C_{10}H_8BrN_3O_2$, 283. Found, 282, 284.

Example 3

2-[5-(3-hydroxy-4-methylphenyl)-1-methyl-1H-imidazol-4-yl]pyridine-4-carboxylic acid A. 2-[5-(3-hydroxy-4-methylphenyl)-1-methyl-1H-imidazol-4-yl]pyridine-4-carbonitrile

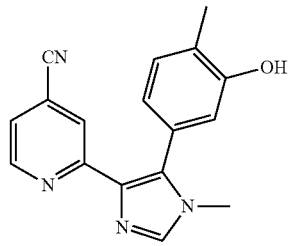 [SMILES: Cc1ccc(-c2c(-c3cc(C#N)ccn3)ncn2C)cc1O]

To a microwave vessel was added 2-(5-bromo-1-methyl-1H-imidazol-4-yl)pyridine-4-carbonitrile (79 mg, 0.3 mmol), 3-hydroxy-4-methylphenyl boronic acid (55 mg, 0.36 mmol), PdCl$_2$(dppf) (22 mg, 0.03 mmol), 2M Na$_2$CO$_3$ (0.3 mL, 0.6 mmol) in 2 mL dioxane. The reaction mixture was heated in a microwave oven at 120° C. for 1 hr. It was then purified by ISCO flash column (MeOH/DCM=0-5%) to give 60 mg product (69%). $^1$H NMR (400 MHz, DMSO-d$_6$): δ 2.11 (3H, s), 3.46 (3H, s), 6.71 (1H, d, J=7.6 Hz), 6.75 (1H, s), 7.12 (1H, d, J=7.7 Hz), 7.52 (1H, d, J=4.9 Hz), 7.85 (1H, s), 8.06 (1H, s), 8.50 (1H, d, J=5 Hz), 9.36 (1H, s). [M+H] Calc'd for C$_{17}$H$_{14}$N$_4$O, 291. Found, 291.

B. 2-[5-(3-hydroxy-4-methylphenyl)-1-methyl-1H-imidazol-4-yl]pyridine-4-carboxylic acid

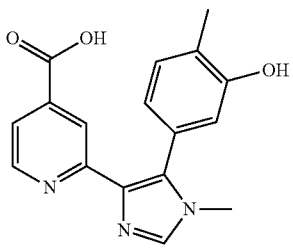 [SMILES: Cc1ccc(-c2c(-c3cc(C(=O)O)ccn3)ncn2C)cc1O]

The title compound was prepared in 28% yield from 2-[5-(3-hydroxy-4-methylphenyl)-1-methyl-1H-imidazol-4-yl]pyridine-4-carbonitrile according to the procedure for the preparation of Example 1. $^1$H NMR (400 MHz, DMSO-d$_6$): δ 2.11 (3H, s), 3.44 (3H, s), 6.67 (1H, d, J=7.4 Hz), 6.71 (1H, s), 7.07 (1H, d, J=7.7 Hz), 7.48 (1H, s), 8.06 (1H, s), 8.11 (1H, s), 8.43 (1H, d, J=3.3 Hz), 9.33 (1H, s). [M+H] Calc'd for C$_{17}$H$_{15}$N$_3$O$_3$, 310. Found, 310.

Example 4

2-[1-methyl-5-(4-methylphenyl)-1H-imidazol-4-yl]pyridine-4-carboxylic acid

A. 2-[1-methyl-5-(4-methylphenyl)-1H-imidazol-4-yl]pyridine-4-carbonitrile

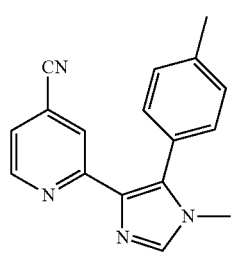 [SMILES: Cc1ccc(-c2c(-c3cc(C#N)ccn3)ncn2C)cc1]

The title compound was prepared in 54% yield from 2-(5-bromo-1-methyl-1H-imidazol-4-yl)pyridine-4-carbonitrile and p-tolylboronic acid according to the procedure for the preparation of Example 3, part A. [M+H] Calc'd for C$_{17}$H$_{14}$N$_4$, 275. Found, 275.

B. 2-[1-methyl-5-(4-methylphenyl)-1H-imidazol-4-yl]pyridine-4-carboxylic acid

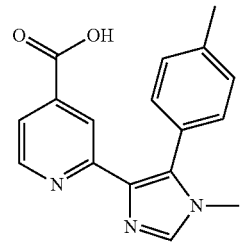 [SMILES: Cc1ccc(-c2c(-c3cc(C(=O)O)ccn3)ncn2C)cc1]

The title compound was prepared in 13% yield (two steps) from 2-[1-methyl-5-(4-methylphenyl)-1H-imidazol-4-yl]pyridine-4-carbonitrile according to the procedure for the preparation of Example 1. $^1$H NMR (400 MHz, DMSO-d$_6$): δ 2.30 (3H, s), 3.40 (3H, s), 7.16-7.24 (4H, m), 7.41 (1H, d, J=4.9 Hz), 7.76 (1H, s), 8.21 (1H, s), 8.28 (1H, d, J=4.8 Hz). [M+H] Calc'd for C$_{17}$H$_{15}$N$_3$O$_2$, 294. Found, 294.

Example 5

2-[5-(4-ethylphenyl)-1-methyl-1H-imidazol-4-yl]pyridine-4-carboxylic acid

A. 2-[5-(4-ethylphenyl)-1-methyl-1H-imidazol-4-yl]pyridine-4-carbonitrile

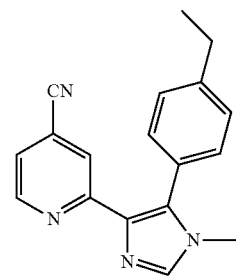 [SMILES: CCc1ccc(-c2c(-c3cc(C#N)ccn3)ncn2C)cc1]

The title compound was prepared in 90% yield from 2-(5-bromo-1-methyl-1H-imidazol-4-yl)pyridine-4-carbonitrile and 4-ethylphenylboronic acid according to the procedure for the preparation of Example 3, part A. [M+H] Calc'd for C$_{18}$H$_{16}$N$_4$, 289. Found, 289.

B. 2-[5-(4-ethylphenyl)-1-methyl-1H-imidazol-4-yl]pyridine-4-carboxylic acid

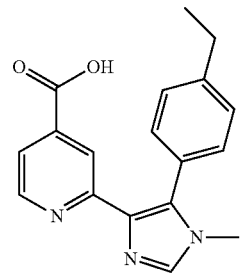 [SMILES: CCc1ccc(-c2c(-c3cc(C(=O)O)ccn3)ncn2C)cc1]

The title compound was prepared in 25% yield (two steps) from 2-[5-(4-ethylphenyl)-1-methyl-1H-imidazol-4-yl]pyridine-4-carbonitrile according to the procedure for the preparation of Example 1. $^1$H NMR (400 MHz, DMSO-d$_6$): δ 1.17 (3H, t, J=7.6 Hz), 2.62 (2H, q, J=7.6 Hz), 3.41 (3H, s), 7.19-7.27 (4H, m), 7.41 (1H, d, J=4.9 Hz), 7.77 (1H, s), 8.21 (1H, s), 8.31 (1H, d, J=4.9 Hz). [M+H] Calc'd for C$_{18}$H$_{17}$N$_3$O$_2$, 308. Found, 308.

Example 6

2-{1-methyl-5-[4-(trifluoromethyl)phenyl]-1H-imidazol-4-yl}pyridine-4-carboxylic acid A. 2-{1-methyl-5-[4-(trifluoromethyl)phenyl]-1H-imidazol-4-yl}pyridine-4-carbonitrile

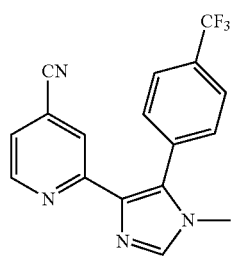 [SMILES: Cn1cnc(-c2cc(C#N)ccn2)c1-c1ccc(C(F)(F)F)cc1]

The title compound was prepared in 93% yield from 2-(5-bromo-1-methyl-1H-imidazol-4-yl)pyridine-4-carbonitrile and 4-(trifluoromethyl)phenylboronic acid according to the procedure for the preparation of Example 3, part A. [M+H] Calc'd for C$_{17}$H$_{11}$F$_3$N$_4$, 329. Found, 329.

B. 2-{1-methyl-5-[4-(trifluoromethyl)phenyl]-1H-imidazol-4-yl}pyridine-4-carboxylic acid

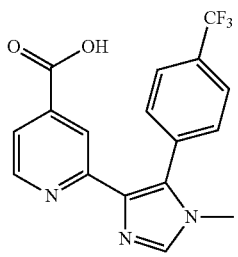 [SMILES: Cn1cnc(-c2cc(C(=O)O)ccn2)c1-c1ccc(C(F)(F)F)cc1]

The title compound was prepared in 20% yield (two steps) from 2-{1-methyl-5-[4-(trifluoromethyl)phenyl]-1H-imidazol-4-yl}pyridine-4-carbonitrile according to the procedure for the preparation of Example 1. $^1$H NMR (400 MHz, DMSO-d$_6$): δ 3.46 (3H, s), 7.60 (2H, d&s, J=8 Hz), 7.72 (2H, d&s, J=8.2 Hz), 7.86 (1H, s), 8.29 (1H, s), 8.31 (1H, d, J=5.0 Hz). [M+H] Calc'd for C$_{17}$H$_{12}$N$_3$F$_3$O$_2$, 348. Found, 348.

Example 7

2-[5-(4-cyclopropylphenyl)-1-methyl-1H-imidazol-4-yl]pyridine-4-carboxylic acid

A. 2-[5-(4-cyclopropylphenyl)-1-methyl-1H-imidazol-4-yl]pyridine-4-carbonitrile

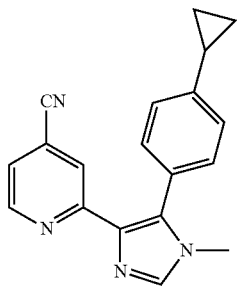 [SMILES: Cn1cnc(-c2cc(C#N)ccn2)c1-c1ccc(C2CC2)cc1]

The title compound was prepared from 2-(5-bromo-1-methyl-1H-imidazol-4-yl)pyridine-4-carbonitrile and 4-cyclopropylphenylboronic acid according to the procedure for the preparation of Example 3, part A. [M+H] Calc'd for C$_{19}$H$_{16}$N$_4$, 301. Found, 301.

B. 2-[5-(4-cyclopropylphenyl)-1-methyl-1H-imidazol-4-yl]pyridine-4-carboxylic acid

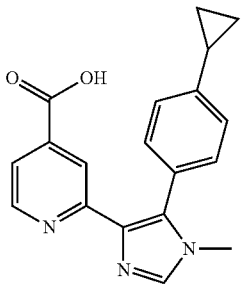 [SMILES: Cn1cnc(-c2cc(C(=O)O)ccn2)c1-c1ccc(C2CC2)cc1]

The title compound was prepared in 24% yield (two steps) from 2-[5-(4-cyclopropylphenyl)-1-methyl-1H-imidazol-4-yl]pyridine-4-carbonitrile according to the procedure for the preparation of Example 1. $^1$H NMR (400 MHz, DMSO-d$_6$): δ 0.75 (2H, m), 1.02 (2H, m), 1.99 (1H, m), 3.52 (3H, s), 7.17 (2H, d&s, J=7.8 Hz), 7.31 (2H, d&s, J=8.1 Hz), 7.55 (1H, d, J=3.8 Hz), 8.13 (2H, s), 8.50 (1H, s). [M+H] Calc'd for C$_{19}$H$_{17}$N$_3$O$_2$, 320. Found, 320.

Example 8 methyl 2-[5-(4-cyclopropylphenyl)-1-methyl-1H-imidazol-4-yl]pyridine-4-carboxylate

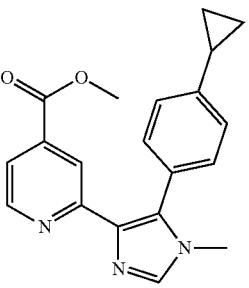 [SMILES: COC(=O)c1ccnc(-c2ncn(C)c2-c2ccc(C3CC3)cc2)c1]

To a mixture of 2-[5-(4-cyclopropylphenyl)-1-methyl-1H-imidazol-4-yl]pyridine-4-carboxylic acid (26 mg, 0.08 mmol, Example 7) in MeOH (5 mL) was added 3 drops of concentrated sulfuric acid. The reaction mixture was heated to reflux for 1 hr. It was then concentrated, separated between water and ethyl acetate. Organic layer dried and concentrated to give the title compound as light pink solid (25 mg, 94%). $^1$H NMR (400 MHz, DMSO-$d_6$): δ 0.77 (2H, m), 1.02 (2H, m), 2.02 (1H, m), 3.54 (3H, s), 3.85 (3H, s), 7.22 (2H, d&s, J=7.8 Hz), 7.36 (2H, d&s, J=8.1 Hz), 7.64 (1H, d, J=4.4 Hz), 7.98 (1H, s), 8.51 (1H, s), 8.63 (1H, s). [M+H] Calc'd for $C_{20}H_{19}N_3O_2$, 334. Found, 334.

Example 9

2-[5-(4-tert-butylphenyl)-1-methyl-1H-imidazol-4-yl]pyridine-4-carboxylic acid

A. 2-[5-(4-tert-butylphenyl)-1-methyl-1H-imidazol-4-yl]pyridine-4-carbonitrile

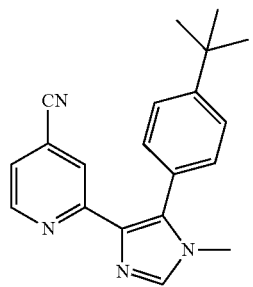 [SMILES: Cn1cnc(-c2cc(C#N)ccn2)c1-c1ccc(C(C)(C)C)cc1]

The title compound was prepared from 2-(5-bromo-1-methyl-1H-imidazol-4-yl)pyridine-4-carbonitrile and 4-tert-butylphenylboronic acid according to the procedure for the preparation of Example 3, part A. [M+H] Calc'd for $C_{20}H_{20}N_4$, 317. Found, 317.

B. 2-[5-(4-tert-butylphenyl)-1-methyl-1H-imidazol-4-yl]pyridine-4-carboxylic acid

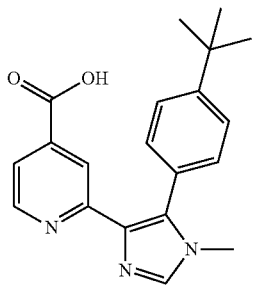 [SMILES: Cn1cnc(-c2cc(C(=O)O)ccn2)c1-c1ccc(C(C)(C)C)cc1]

The title compound was prepared in 13% yield (two steps) from 2-[5-(4-tert-butylphenyl)-1-methyl-1H-imidazol-4-yl]pyridine-4-carbonitrile according to the procedure for the preparation of Example 1. $^1$H NMR (400 MHz, DMSO-$d_6$): δ 1.33 (9H, s), 3.48 (3H, s), 7.34 (2H, d&s, J=8.1 Hz), 7.44 (2H, d&s, J=8.1 Hz), 7.48 (1H, d, J=5.2 Hz), 7.82 (1H, s), 8.26 (2H, s). [M+H] Calc'd for $C_{20}H_{21}N_3O_2$, 336. Found, 336.

Example 10

2-{1-methyl-5-[3-(methylcarbamoyl)phenyl]-1H-imidazol-4-yl}pyridine-4-carboxylic acid A. 3-[4-(4-cyanopyridin-2-yl)-1-methyl-1H-imidazol-5-yl]-N-methylbenzamide

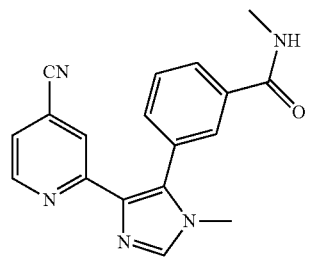 [SMILES: CNC(=O)c1cccc(-c2c(-c3cc(C#N)ccn3)ncn2C)c1]

The title compound was prepared from 2-(5-bromo-1-methyl-1H-imidazol-4-yl)pyridine-4-carbonitrile and 3-(N-methylaminocarbonyl)phenylboronic acid according to the procedure for the preparation of Example 3, part A. [M+H] Calc'd for $C_{18}H_{15}N_5O$, 318. Found, 318.

B. 2-{1-methyl-5-[3-(methylcarbamoyl)phenyl]-1H-imidazol-4-yl}pyridine-4-carboxylic acid

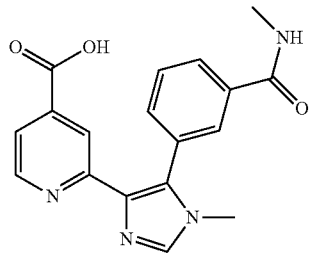 [SMILES: CNC(=O)c1cccc(-c2c(-c3cc(C(=O)O)ccn3)ncn2C)c1]

The title compound was prepared in 26% yield (two steps) from 3-[4-(4-cyanopyridin-2-yl)-1-methyl-1H-imidazol-5-yl]-N-methylbenzamide according to the procedure for the preparation of Example 1. $^1$H NMR (400 MHz, DMSO-$d_6$): δ 2.78 (3H, d, J=4.5 Hz), 3.67 (3H, s), 7.66 (3H, m), 7.86 (1H, s), 7.99 (1H, s), 8.04 (1H, d, J=7.1 Hz), 8.60 (1H, s), 8.66 (1H, s). [M+H] Calc'd for $C_{18}H_{16}N_4O_3$, 337. Found, 337.

Example 11

2-{5-[3-(hydroxymethyl)phenyl]-1-methyl-1H-imidazol-4-yl}pyridine-4-carboxylic acid A. 2-{5-[3-(hydroxymethyl)phenyl]-1-methyl-1H-imidazol-4-yl}pyridine-4-carbonitrile

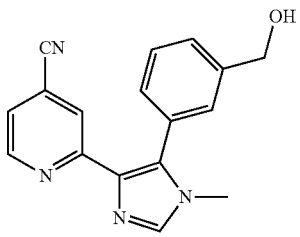 [SMILES: Cn1cnc(-c2cc(C#N)ccn2)c1-c1cccc(CO)c1]

The title compound was prepared from 2-(5-bromo-1-methyl-1H-imidazol-4-yl)pyridine-4-carbonitrile and 3-hydroxymethylphenylboronic acid according to the procedure for the preparation of Example 3, part A. [M+H] Calc'd for C₁₇H₁₄N₄O, 291. Found, 291.

B. 2-{5-[3-(hydroxymethyl)phenyl]-1-methyl-1H-imidazol-4-yl}pyridine-4-carboxylic acid

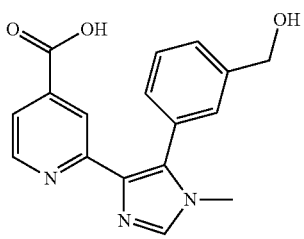 [SMILES: Cn1cnc(-c2cc(C(=O)O)ccn2)c1-c1cccc(CO)c1]

The title compound was prepared in 32% yield (two steps) from 2-{5-[3-(hydroxymethyl)phenyl]-1-methyl-1H-imidazol-4-yl}pyridine-4-carbonitrile according to the procedure for the preparation of Example 1. ¹H NMR (400 MHz, DMSO-d₆): δ 3.70 (3H, s), 4.58 (2H, s), 7.14-7.51 (4H, m), 7.72 (1H, s), 7.76 (1H, d, J=4.4 Hz), 8.77 (1H, d, J=4.1 Hz), 9.17 (1H, s). [M+H] Calc'd for C₁₇H₁₅N₃O₃, 310. Found, 310.

Example 12

2-[5-(4-methoxyphenyl)-1-methyl-1H-imidazol-4-yl]pyridine-4-carboxylic acid

A. 2-[5-(4-methoxyphenyl)-1-methyl-1H-imidazol-4-yl]pyridine-4-carbonitrile

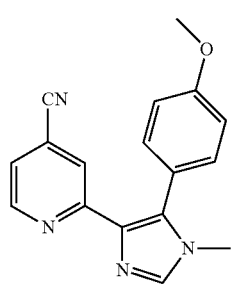 [SMILES: COc1ccc(-c2c(-c3cc(C#N)ccn3)ncn2C)cc1]

The title compound was prepared from 2-(5-bromo-1-methyl-1H-imidazol-4-yl)pyridine-4-carbonitrile and 4-methoxyphenylboronic acid according to the procedure for the preparation of Example 3, part A. [M+H] Calc'd for C₁₇H₁₄N₄O, 291. Found, 291.

B. 2-[5-(4-methoxyphenyl)-1-methyl-1H-imidazol-4-yl]pyridine-4-carboxylic acid

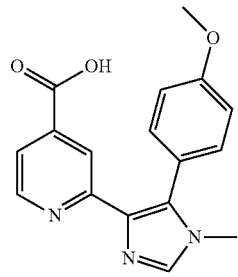 [SMILES: COc1ccc(-c2c(-c3cc(C(=O)O)ccn3)ncn2C)cc1]

The title compound was prepared in 24% yield (two steps) from 2-[5-(4-methoxyphenyl)-1-methyl-1H-imidazol-4-yl]pyridine-4-carbonitrile according to the procedure for the preparation of Example 1. ¹H NMR (400 MHz, DMSO-d₆): δ 3.59 (3H, s), 3.90 (3H, s), 7.15 (2H, d&s, J=8.5 Hz), 7.49 (2H, d&s, J=8.6 Hz), 7.74 (2H, d, J=4.1 Hz), 8.77 (1H, s),

Example 13

2-{1-methyl-5-[4-(trifluoromethoxy)phenyl]-1H-imidazol-4-yl}pyridine-4-carboxylic acid

A. 2-{1-methyl-5-[4-(trifluoromethoxy)phenyl]-1H-imidazol-4-yl}pyridine-4-carbonitrile

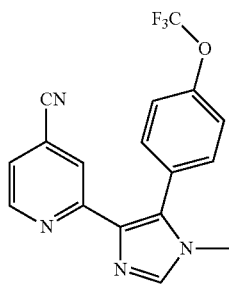 [SMILES: Cn1cnc(-c2cc(C#N)ccn2)c1-c1ccc(OC(F)(F)F)cc1]

The title compound was prepared from 2-(5-bromo-1-methyl-1H-imidazol-4-yl)pyridine-4-carbonitrile and 4-(trifluoromethoxy)phenylboronic acid according to the procedure for the preparation of Example 3, part A. [M+H] Calc'd for C₁₇H₁₁F₃N₄O, 345. Found, 345.

B. 2-{1-methyl-5-[4-(trifluoromethoxy)phenyl]-1H-imidazol-4-yl}pyridine-4-carboxylic acid

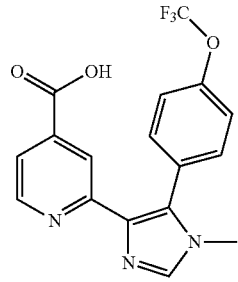 [SMILES: Cn1cnc(-c2cc(C(=O)O)ccn2)c1-c1ccc(OC(F)(F)F)cc1]

The title compound was prepared in 24% yield (two steps) from 2-{1-methyl-5-[4-(trifluoromethoxy)phenyl]-1H-imidazol-4-yl}pyridine-4-carbonitrile according to the procedure for the preparation of Example 1. $^1$H NMR (400 MHz, DMSO-d$_6$): δ 3.51 (3H, s), 7.42 (2H, d&s, J=8.5 Hz), 7.51 (1H, d, J=3.9 Hz), 7.58 (2H, d &s, J=8.4 Hz), 7.90 (1H, s), 8.33 (1H, s), 8.38 (1H, d, J=4.5 Hz). [M+H] Calc'd for C$_{17}$H$_{12}$F$_3$N$_3$O$_3$, 364. Found, 364.

Example 14

2-[5-(4-ethoxyphenyl)-1-methyl-1H-imidazol-4-yl]pyridine-4-carboxylic acid

A. 2-[5-(4-ethoxyphenyl)-1-methyl-1H-imidazol-4-yl]pyridine-4-carbonitrile

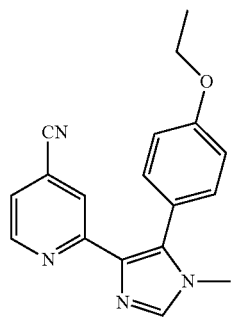 [SMILES: CCOc1ccc(-c2c(-c3cc(C#N)ccn3)ncn2C)cc1]

The title compound was prepared from 2-(5-bromo-1-methyl-1H-imidazol-4-yl)pyridine-4-carbonitrile and 4-ethoxyphenylboronic acid according to the procedure for the preparation of Example 3, part A. [M+H] Calc'd for C$_{18}$H$_{16}$N$_4$O, 305. Found, 305.

B. 2-[5-(4-ethoxyphenyl)-1-methyl-1H-imidazol-4-yl]pyridine-4-carboxylic acid

The title compound was prepared in 34% yield (two steps) from 2-[5-(4-ethoxyphenyl)-1-methyl-1H-imidazol-4-yl]pyridine-4-carbonitrile according to the procedure for the preparation of Example 1. $^1$H NMR (400 MHz, DMSO-d$_6$): δ 1.38 (3H, t, J=6.9 Hz), 3.59 (3H, s), 4.12 (2H, q, J=6.9 Hz), 7.12 (2H, d&s, J=8.3 Hz), 7.47 (2H, d&s, J=8.2 Hz), 7.73 (2H, d, J=4.3 Hz), 8.76 (1H, s), 9.01 (1H, s). [M+H] Calc'd for C$_{18}$H$_{17}$N$_3$O$_3$, 324. Found, 324.

Example 15

2-{1-methyl-5-[4-(1H-pyrazol-1-yl)phenyl]-1H-imidazol-4-yl}pyridine-4-carboxylic acid A. 2-{1-methyl-5-[4-(1H-pyrazol-1-yl)phenyl]-1H-imidazol-4-yl}pyridine-4-carbonitrile

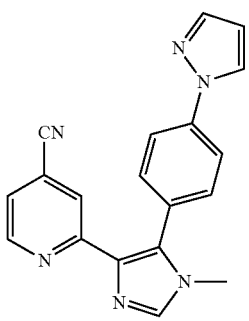 [SMILES: Cn1cnc(-c2cc(C#N)ccn2)c1-c1ccc(-n2cccn2)cc1]

The title compound was prepared from 2-(5-bromo-1-methyl-1H-imidazol-4-yl)pyridine-4-carbonitrile and 4-pyrazol-1-yl-phenylboronic acid according to the procedure for the preparation of Example 3, part A. [M+H] Calc'd for C$_{19}$H$_{14}$N$_6$, 327. Found, 327.

B. 2-{1-methyl-5-[4-(1H-pyrazol-1-yl)phenyl]-1H-imidazol-4-yl}pyridine-4-carboxylic acid

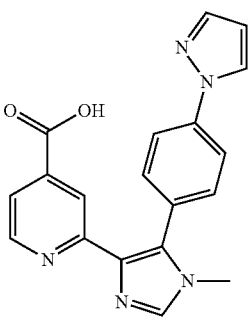 [SMILES: Cn1cnc(-c2cc(C(=O)O)ccn2)c1-c1ccc(-n2cccn2)cc1]

The title compound was prepared in 31% yield (two steps) from 2-{1-methyl-5-[4-(1H-pyrazol-1-yl)phenyl]-1H-imidazol-4-yl}pyridine-4-carbonitrile according to the procedure for the preparation of Example 1. $^1$H NMR (400 MHz, DMSO-d$_6$): δ 3.53 (3H, s), 6.58 (1H, t, J=2.3 Hz), 7.46 (1H, d, J=1.5 Hz), 7.53 (2H, d&s, J=8.6 Hz), 7.78 (1H, s), 7.86

(1H, s), 7.89 (2H, d&s, J=8.6 Hz), 8.30 (2H, s), 8.58 (1H, d, J=2.4 Hz). [M+H] Calc'd for $C_{19}H_{15}N_5O_2$, 346. Found, 346.

Example 16

2-{5-[4-(cyclopropylmethoxy)phenyl]-1-methyl-1H-imidazol-4-yl}pyridine-4-carboxylic acid A. 2-{5-[4-(cyclopropylmethoxy)phenyl]-1-methyl-1H-imidazol-4-yl}pyridine-4-carbonitrile

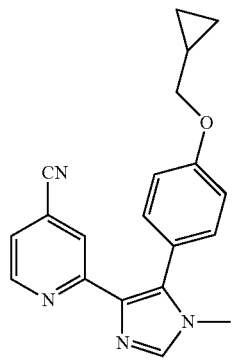 [SMILES: Cn1cnc(-c2cc(C#N)ccn2)c1-c1ccc(OCC2CC2)cc1]

The title compound was prepared from 2-(5-bromo-1-methyl-1H-imidazol-4-yl)pyridine-4-carbonitrile and 4-(cyclopropylmethoxy)phenylboronic acid according to the procedure for the preparation of Example 3, part A. [M+H] Calc'd for $C_{20}H_{18}N_4O$, 331. Found, 331.

B. 2-{5-[4-(cyclopropylmethoxy)phenyl]-1-methyl-1H-imidazol-4-yl}pyridine-4-carboxylic acid

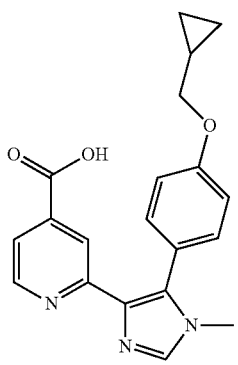 [SMILES: Cn1cnc(-c2cc(C(=O)O)ccn2)c1-c1ccc(OCC2CC2)cc1]

The title compound was prepared in 31% yield (two steps) from 2-{5-[4-(cyclopropylmethoxy)phenyl]-1-methyl-1H-imidazol-4-yl}pyridine-4-carbonitrile according to the procedure for the preparation of Example 1. $^1$H NMR (400 MHz, DMSO-$d_6$): δ 0.34 (2H, d, J=5.0 Hz), 0.58 (2H, d, J=5.8 Hz), 1.22 (1H, m), 3.46 (3H, s), 3.86 (2H, d, J=7.0 Hz), 6.95 (2H, d&s, J=8.6 Hz), 7.30 (2H, d&s, J=8.7 Hz), 7.45 (1H, s), 7.80 (1H, s), 8.25 (1H, s), 8.31 (1H, s). [M+H] Calc'd for $C_{20}H_{19}N_3O_3$, 350. Found, 350.

Example 17

2-(5-{4-[1-(hydroxymethyl)cyclopropyl]phenyl}-1-methyl-1H-imidazol-4-yl)pyridine-4-carboxylic acid A. 2-(5-{4-[1-(hydroxymethyl)cyclopropyl]phenyl}-1-methyl-1H-imidazol-4-yl)pyridine-4-carbonitrile

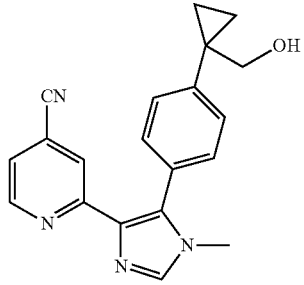 [SMILES: Cn1cnc(-c2cc(C#N)ccn2)c1-c1ccc(C2(CO)CC2)cc1]

The title compound was prepared from 2-(5-bromo-1-methyl-1H-imidazol-4-yl)pyridine-4-carbonitrile and 4-(1-(hydroxymethyl)cyclopropyl)phenylboronic acid according to the procedure for the preparation of Example 3, part A. [M+H] Calc'd for $C_{20}H_{18}N_4O$, 331. Found, 331.

B. 2-(5-{4-[1-(hydroxymethyl)cyclopropyl]phenyl}-1-methyl-1H-imidazol-4-yl)pyridine-4-carboxylic acid

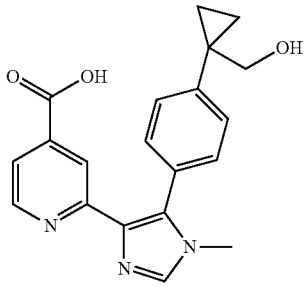 [SMILES: Cn1cnc(-c2cc(C(=O)O)ccn2)c1-c1ccc(C2(CO)CC2)cc1]

The title compound was prepared in 27% yield (two steps) from 2-(5-{4-[1-(hydroxymethyl)cyclopropyl]phenyl}-1-methyl-1H-imidazol-4-yl)pyridine-4-carbonitrile according to the procedure for the preparation of Example 1. $^1$H NMR (400 MHz, DMSO-$d_6$): δ 0.80 (2H, m), 0.88 (2H, m), 3.42 (3H, s), 3.55 (2H, s), 7.31 (4H, m), 7.44 (1H, d&d, J=1.2 Hz and 4.9 Hz), 7.81 (1H, s), 8.24 (1H, s), 8.28 (1H, d, J=5.0 Hz). [M+H] Calc'd for $C_{20}H_{19}N_3O_3$, 350. Found, 350.

Example 18

2-{1-methyl-5-[4-(pyrrolidin-1-yl)phenyl]-1H-imidazol-4-yl}pyridine-4-carboxylic acid A. 2-{1-methyl-5-[4-(pyrrolidin-1-yl)phenyl]-1H-imidazol-4-yl}pyridine-4-carbonitrile

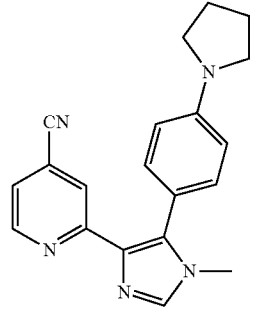 [SMILES: Cn1cnc(-c2cc(C#N)ccn2)c1-c1ccc(N2CCCC2)cc1]

The title compound was prepared from 2-(5-bromo-1-methyl-1H-imidazol-4-yl)pyridine-4-carbonitrile and 4-pyrrolidinophenylboronic acid according to the procedure for the preparation of Example 3, part A. [M+H] Calc'd for $C_{20}H_{19}N_5$, 330. Found, 330.

B. 2-{1-methyl-5-[4-(pyrrolidin-1-yl)phenyl]-1H-imidazol-4-yl}pyridine-4-carboxylic acid

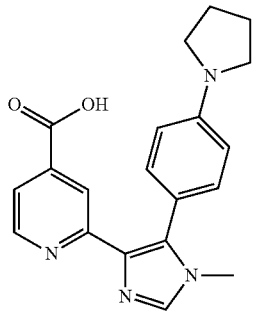 [SMILES: Cn1cnc(-c2cc(C(=O)O)ccn2)c1-c1ccc(N2CCCC2)cc1]

The title compound was prepared in 50% yield (two steps) from 2-{1-methyl-5-[4-(pyrrolidin-1-yl)phenyl]-1H-imidazol-4-yl}pyridine-4-carbonitrile according to the procedure for the preparation of Example 1. $^1$H NMR (400 MHz, DMSO-d$_6$): δ 1.97 (4H, m), 3.29 (4H, m), 3.45 (3H, s), 6.56 (2H, d&s, J=8.5 Hz), 7.18 (2H, d&s, J=8.5 Hz), 7.44 (1H, d, J=4.9 Hz), 7.77 (1H, s), 8.22 (1H, s), 8.34 (1H, d, J=4.9 Hz). [M+H] Calc'd for $C_{20}H_{20}N_4O_2$, 349. Found, 349.

Example 19

2-[5-(4-chlorophenyl)-1-methyl-1H-imidazol-4-yl]pyridine-4-carboxylic acid

A. 2-[5-(4-chlorophenyl)-1-methyl-1H-imidazol-4-yl]pyridine-4-carbonitrile

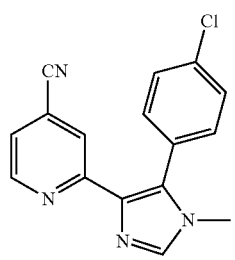 [SMILES: Cn1cnc(-c2cc(C#N)ccn2)c1-c1ccc(Cl)cc1]

The title compound was prepared from 2-(5-bromo-1-methyl-1H-imidazol-4-yl)pyridine-4-carbonitrile and 4-chlorophenylboronic acid according to the procedure for the preparation of Example 3, part A. [M+H] Calc'd for $C_{16}H_{11}ClN_4$, 296. Found, 295, 297.

B. 2-[5-(4-chlorophenyl)-1-methyl-1H-imidazol-4-yl]pyridine-4-carboxylic acid

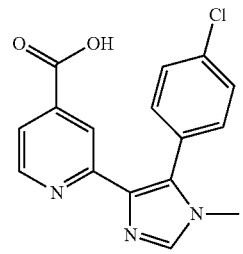 [SMILES: Cn1cnc(-c2cc(C(=O)O)ccn2)c1-c1ccc(Cl)cc1]

The title compound was prepared in 30% yield (two steps) from 2-[5-(4-chlorophenyl)-1-methyl-1H-imidazol-4-yl]pyridine-4-carbonitrile according to the procedure for the preparation of Example 1. $^1$H NMR (400 MHz, DMSO-d$_6$): δ 3.49 (3H, s), 7.45 (5H, m), 7.85 (1H, s), 8.25 (1H, d, J=4.8 Hz), 8.27 (1H, s). [M+H] Calc'd for $C_{16}H_{12}ClN_3O_2$, 315. Found, 314, 316.

Example 20

2-[5-(3-chlorophenyl)-1-methyl-1H-imidazol-4-yl]pyridine-4-carboxylic acid

A. 2-[5-(3-chlorophenyl)-1-methyl-1H-imidazol-4-yl]pyridine-4-carbonitrile

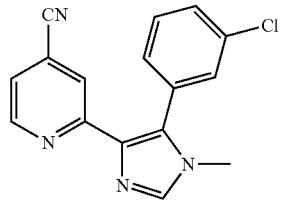 [SMILES: Cn1cnc(-c2cc(C#N)ccn2)c1-c1cccc(Cl)c1]

The title compound was prepared from 2-(5-bromo-1-methyl-1H-imidazol-4-yl)pyridine-4-carbonitrile and 3-chlorophenylboronic acid according to the procedure for the preparation of Example 3, part A. [M+H] Calc'd for $C_{16}H_{11}ClN_4$, 296. Found, 295, 297.

B. 2-[5-(3-chlorophenyl)-1-methyl-1H-imidazol-4-yl]pyridine-4-carboxylic acid

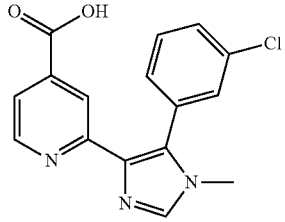 [SMILES: Cn1cnc(-c2cc(C(=O)O)ccn2)c1-c1cccc(Cl)c1]

The title compound was prepared in 26% yield (two steps) from 2-[5-(3-chlorophenyl)-1-methyl-1H-imidazol-4-yl]pyridine-4-carbonitrile according to the procedure for the preparation of Example 1. $^1$H NMR (400 MHz, DMSO-d$_6$): δ 3.51 (3H, s), 7.37 (1H, m), 7.44 (3H, m), 7.51 (1H, s), 7.86

(1H, s), 8.24 (1H, d, J=4.8 Hz), 8.28 (1H, s). [M+H] Calc'd for $C_{16}H_{12}ClN_3O_2$, 315. Found, 314, 316.

Example 21

2-[5-(4-ethynylphenyl)-1-methyl-1H-imidazol-4-yl]pyridine-4-carboxylic acid

A. 2-[5-(4-ethynylphenyl)-1-methyl-1H-imidazol-4-yl]pyridine-4-carbonitrile

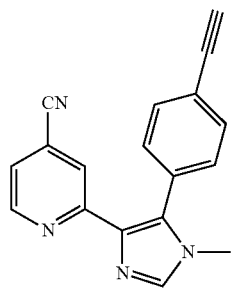 [SMILES: C#Cc1ccc(-c2c(-c3cc(C#N)ccn3)ncn2C)cc1]

The title compound was prepared from 2-(5-bromo-1-methyl-1H-imidazol-4-yl)pyridine-4-carbonitrile and 4-(dihydroxyborophenyl)acetylene according to the procedure for the preparation of Example 3, part A. [M+H] Calc'd for $C_{18}H_{12}N_4$, 285. Found, 285.

B. 2-[5-(4-ethynylphenyl)-1-methyl-1H-imidazol-4-yl]pyridine-4-carboxylic acid

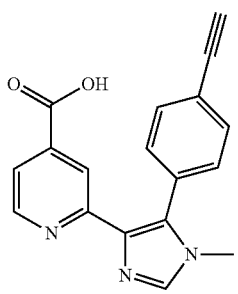 [SMILES: C#Cc1ccc(-c2c(-c3cc(C(=O)O)ccn3)ncn2C)cc1]

The title compound was prepared in 6% yield (two steps) from 2-[5-(4-ethynylphenyl)-1-methyl-1H-imidazol-4-yl]pyridine-4-carboxylic acid according to the procedure for the preparation of Example 1. $^1$H NMR (400 MHz, DMSO-d$_6$): δ 3.42 (3H, s), 3.70 (1H, s), 4.25 (1H, s), 7.41 (2H, d&s, J=8.3 Hz), 7.50 (2H, d&s, J=8.0 Hz), 7.65 (1H, m), 7.83 (1H, s), 8.21 (2H, s). [M+H] Calc'd for $C_{18}H_{13}N_3O_2$, 304. Found, 304.

Example 22

2-[5-(1H-indol-6-yl)-1-methyl-1H-imidazol-4-yl]pyridine-4-carboxylic acid

A. 2-[5-(1H-indol-6-yl)-1-methyl-1H-imidazol-4-yl]pyridine-4-carbonitrile

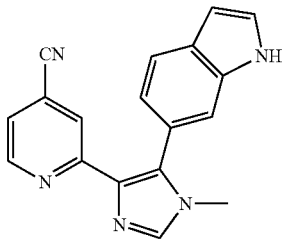 [SMILES: Cn1cnc(-c2cc(C#N)ccn2)c1-c1ccc2cc[nH]c2c1]

The title compound was prepared from 2-(5-bromo-1-methyl-1H-imidazol-4-yl)pyridine-4-carbonitrile and 6-indolylboronic acid according to the procedure for the preparation of Example 3, part A. [M+H] Calc'd for $C_{18}H_{13}N_5$, 300. Found, 300.

B. 2-[5-(1H-indol-6-yl)-1-methyl-1H-imidazol-4-yl]pyridine-4-carboxylic acid

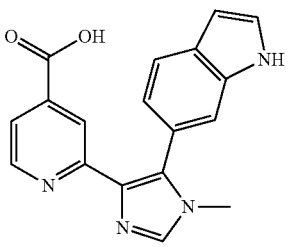 [SMILES: Cn1cnc(-c2cc(C(=O)O)ccn2)c1-c1ccc2cc[nH]c2c1]

The title compound was prepared in 20% yield (two steps) from 2-[5-(1H-indol-6-yl)-1-methyl-1H-imidazol-4-yl]pyridine-4-carbonitrile according to the procedure for the preparation of Example 1. $^1$H NMR (400 MHz, DMSO-d$_6$): δ 3.42 (3H, s), 6.47 (1H, s), 6.97 (1H, dd, J=1.3 Hz and 8.2 Hz), 7.41 (3H, m), 7.56 (1H, d, J=8.1 Hz), 7.81 (1H, s), 8.21 (1H, s), 8.24 (1H, d, J=4.4 Hz). [M+H] Calc'd for $C_{18}H_{14}N_4O_2$, 319. Found, 319.

Example 23

2-[5-(4-fluorophenyl)-1-methyl-1H-imidazol-4-yl]pyridine-4-carboxylic acid

A. 2-[5-(4-fluorophenyl)-1-methyl-1H-imidazol-4-yl]pyridine-4-carbonitrile

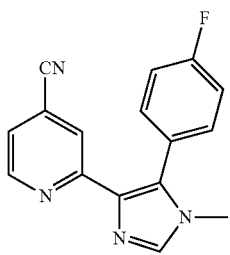 [SMILES: Cn1cnc(-c2cc(C#N)ccn2)c1-c1ccc(F)cc1]

The title compound was prepared from 2-(5-bromo-1-methyl-1H-imidazol-4-yl)pyridine-4-carbonitrile and 4-fluorophenylboronic acid according to the procedure for the preparation of Example 3, part A. [M+H] Calc'd for C$_{16}$H$_{11}$FN$_4$, 279. Found, 279.

B. 2-[5-(4-fluorophenyl)-1-methyl-1H-imidazol-4-yl]pyridine-4-carboxylic acid

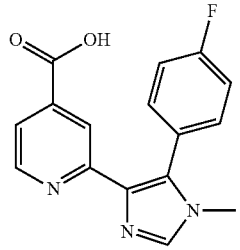 [SMILES: Cn1cnc(-c2cc(C(=O)O)ccn2)c1-c1ccc(F)cc1]

The title compound was prepared in 23% yield (two steps) from 2-[5-(4-fluorophenyl)-1-methyl-1H-imidazol-4-yl]pyridine-4-carbonitrile according to the procedure for the preparation of Example 1. $^1$H NMR (400 MHz, DMSO-d$_6$): δ 3.48 (3H, s), 7.25 (2H, m), 7.47 (3H, m), 7.84 (1H, s), 8.26 (2H, m). [M+H] Calc'd for C$_{16}$H$_{12}$FN$_3$O$_2$, 298. Found, 298.

Example 24

2-[5-(3-fluorophenyl)-1-methyl-1H-imidazol-4-yl]pyridine-4-carboxylic acid

A. 2-[5-(3-fluorophenyl)-1-methyl-1H-imidazol-4-yl]pyridine-4-carbonitrile

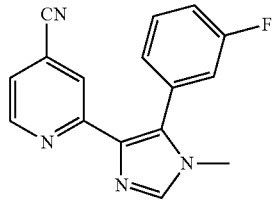 [SMILES: Cn1cnc(-c2cc(C#N)ccn2)c1-c1cccc(F)c1]

The title compound was prepared from 2-(5-bromo-1-methyl-1H-imidazol-4-yl)pyridine-4-carbonitrile and 3-fluorophenylboronic acid according to the procedure for the preparation of Example 3, part A. [M+H] Calc'd for C$_{16}$H$_{11}$FN$_4$, 279. Found, 279.

B. 2-[5-(3-fluorophenyl)-1-methyl-1H-imidazol-4-yl]pyridine-4-carboxylic acid

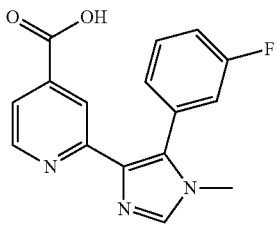 [SMILES: Cn1cnc(-c2cc(C(=O)O)ccn2)c1-c1cccc(F)c1]

The title compound was prepared in 34% yield (two steps) from 2-[5-(4-fluorophenyl)-1-methyl-1H-imidazol-4-yl]pyridine-4-carbonitrile according to the procedure for the preparation of Example 1. $^1$H NMR (400 MHz, DMSO-d$_6$): δ 3.51 (3H, s), 7.23-7.31 (3H, m), 7.46-7.49 (2H, m), 7.87 (1H, s), 8.29-8.32 (2H, m). [M+H] Calc'd for C$_{16}$H$_{12}$FN$_3$O$_2$, 298. Found, 298.

Example 25

2-(5-{4-[1-(methoxymethyl)cyclopropyl]phenyl}-1-methyl-1H-imidazol-4-yl)pyridine-4-carboxylic acid A. 2-(5-{4-[1-(methoxymethyl)cyclopropyl]phenyl}-1-methyl-1H-imidazol-4-yl)pyridine-4-carbonitrile

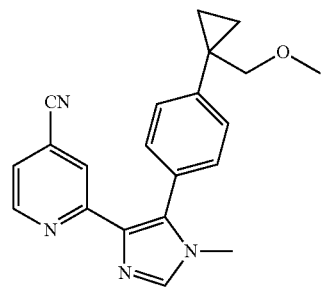 [SMILES: COCC1(c2ccc(-c3c(-c4cc(C#N)ccn4)ncn3C)cc2)CC1]

To a solution of 2-(5-{4-[1-(hydroxymethyl)cyclopropyl]phenyl}-1-methyl-1H-imidazol-4-yl)pyridine-4-carbonitrile (30 mg, 0.09 mmol; Example 17, part A) in anhydrous DMF (2 mL) at 0° C. was added 60% NaH (6 mg, 0.136 mmol). After stirring for 10 minutes, MeI (10 μL, 0.136 mml) was added. The reaction mixture was warmed up to r.t. and stirred for 3 hr. It was then purified by ISCO flash column chromatography (MeOH/DCM=0-5%) to give the title product which was used for next step. [M+H] Calc'd for C$_{21}$H$_{20}$N$_4$O, 345. Found, 345.

B. 2-(5-{4-[1-(methoxymethyl)cyclopropyl]phenyl}-1-methyl-1H-imidazol-4-yl)pyridine-4-carboxylic acid

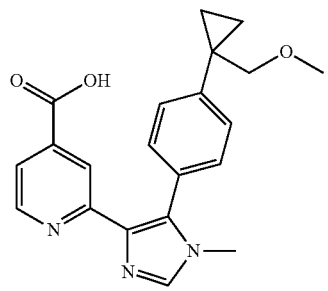 [SMILES: COCC1(c2ccc(-c3c(-c4cc(C(=O)O)ccn4)ncn3C)cc2)CC1]

The title compound was prepared in 15% yield (two steps) from 2-(5-{4-[1-(methoxymethyl)cyclopropyl]phenyl}-1-methyl-1H-imidazol-4-yl)pyridine-4-carbonitrile according to the procedure for the preparation of Example 1. $^1$H NMR (400 MHz, DMSO-d$_6$): δ 0.90 (4H, s), 3.26 (3H, s), 3.42 (3H, s), 3.52 (2H, s), 7.29 (4H, m), 7.41 (1H, d, J=5.2 Hz), 7.78 (1H, s), 8.18 (2H, d&s, J=5.9 Hz), 8.38 (1H, s). [M+H] Calc'd for C$_{21}$H$_{21}$N$_3$O$_3$, 364. Found, 364.

Example 26

2-[5-(4-chloro-2-methylphenyl)-1-methyl-1H-imidazol-4-yl]pyridine-4-carboxylic acid

A. 2-[5-(4-chloro-2-methylphenyl)-1-methyl-1H-imidazol-4-yl]pyridine-4-carbonitrile

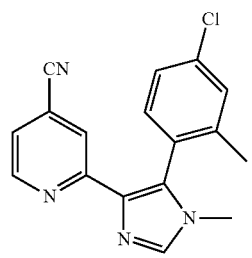 [SMILES: Cc1cc(Cl)ccc1-c1c(-c2cc(C#N)ccn2)ncn1C]

The title compound was prepared from 2-(5-bromo-1-methyl-1H-imidazol-4-yl)pyridine-4-carbonitrile and 4-chloro-2-methylphenylboronic acid according to the procedure for the preparation of Example 3, part A. [M+H] Calc'd for $C_{17}H_{13}ClN_4$, 310. Found, 309, 311.

B. 2-[5-(4-chloro-2-methylphenyl)-1-methyl-1H-imidazol-4-yl]pyridine-4-carboxylic acid

The title compound was prepared in 3% yield (two steps) from 2-[5-(4-chloro-2-methylphenyl)-1-methyl-1H-imidazol-4-yl]pyridine-4-carbonitrile according to the procedure for the preparation of Example 1. [M+H] Calc'd for $C_{17}H_{14}ClN_3O_2$, 329. Found, 328, 330.

Example 27

2-{5-[4-chloro-2-(trifluoromethyl)phenyl]-1-methyl-1H-imidazol-4-yl}pyridine-4-carboxylic acid

A. 2-{5-[4-chloro-2-(trifluoromethyl)phenyl]-1-methyl-1H-imidazol-4-yl}pyridine-4-carbonitrile

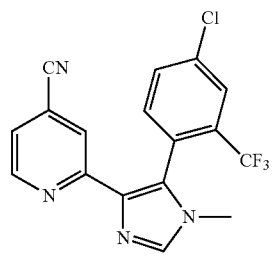 [SMILES: Cn1cnc(-c2cc(C#N)ccn2)c1-c1ccc(Cl)cc1C(F)(F)F]

The title compound was prepared from 2-(5-bromo-1-methyl-1H-imidazol-4-yl)pyridine-4-carbonitrile and 4-chloro-2-trifluoromethylphenylboronic acid according to the procedure for the preparation of Example 3, part A. [M+H] Calc'd for $C_{17}H_{10}ClF_3N_4$, 364. Found, 363, 365.

B. 2-{5-[4-chloro-2-(trifluoromethyl)phenyl]-1-methyl-1H-imidazol-4-yl}pyridine-4-carboxylic acid

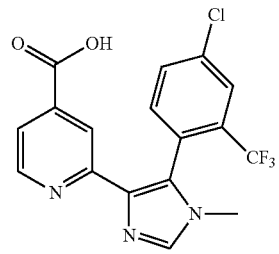 [SMILES: Cn1cnc(-c2cc(C(=O)O)ccn2)c1-c1ccc(Cl)cc1C(F)(F)F]

The title compound was prepared in 2% yield (two steps) from 2-{5-[4-chloro-2-(trifluoromethyl)phenyl]-1-methyl-1H-imidazol-4-yl}pyridine-4-carbonitrile according to the procedure for the preparation of Example 1. [M+H] Calc'd for $C_{17}H_{11}ClF_3N_3O_2$, 383. Found, 382, 384.

Example 28

2-[5-(3,4-dichlorophenyl)-1-methyl-1H-imidazol-4-yl]pyridine-4-carboxylic acid

A. 2-[5-(3,4-dichlorophenyl)-1-methyl-1H-imidazol-4-yl]pyridine-4-carbonitrile

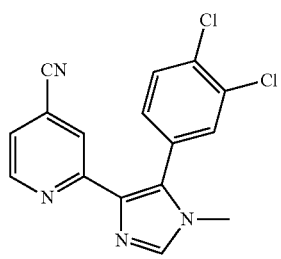 [SMILES: Cn1cnc(-c2cc(C#N)ccn2)c1-c1ccc(Cl)c(Cl)c1]

The title compound was prepared from 2-(5-bromo-1-methyl-1H-imidazol-4-yl)pyridine-4-carbonitrile and 3,4-dichlorophenylboronic acid according to the procedure for the preparation of Example 3, part A. [M+H] Calc'd for $C_{16}H_{10}Cl_2N_4$, 330. Found, 329, 331.

B. 2-[5-(3,4-dichlorophenyl)-1-methyl-1H-imidazol-4-yl]pyridine-4-carboxylic acid

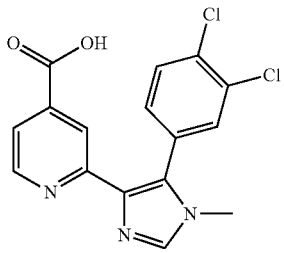 [SMILES: Cn1cnc(-c2cc(C(=O)O)ccn2)c1-c1ccc(Cl)c(Cl)c1]

The title compound was prepared in 12% yield (two steps) from 2-[5-(3,4-dichlorophenyl)-1-methyl-1H-imidazol-4-yl]pyridine-4-carbonitrile according to the procedure for the preparation of Example 1. $^1$H NMR (400 MHz, DMSO-d$_6$): δ 3.53 (3H, s), 7.43 (1H, dd, J=2.0 Hz and 8.3 Hz), 7.52 (1H, dd, J=1.8 Hz and 5.0 Hz), 7.69 (1H, d, J=8.3 Hz), 7.76 (1H, d, J=2.0 Hz), 7.90 (1H, s), 8.35 (1H, s), 8.38 (1H, d, J=5.0 Hz). [M+H] Calc'd for $C_{16}H_{11}Cl_2N_3O_2$, 349. Found, 348, 350.

Example 29

2-[5-(4-chloro-3-fluorophenyl)-1-methyl-1H-imidazol-4-yl]pyridine-4-carboxylic acid A. 2-[5-(4-chloro-3-fluorophenyl)-1-methyl-1H-imidazol-4-yl]pyridine-4-carbonitrile

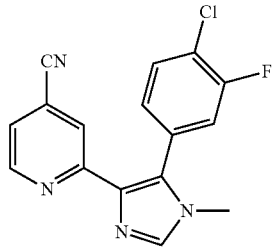 [SMILES: Cn1cnc(-c2cc(C#N)ccn2)c1-c1ccc(Cl)c(F)c1]

The title compound was prepared from 2-(5-bromo-1-methyl-1H-imidazol-4-yl)pyridine-4-carbonitrile and 4-chloro-3-fluorophenylboronic acid according to the procedure for the preparation of Example 3, part A. [M+H] Calc'd for $C_{16}H_{10}ClFN_4$, 314. Found, 313, 315.

B. 2-[5-(4-chloro-3-fluorophenyl)-1-methyl-1H-imidazol-4-yl]pyridine-4-carboxylic acid

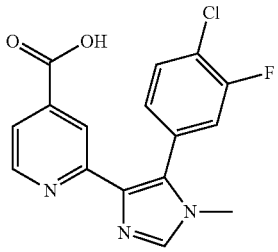 [SMILES: Cn1cnc(-c2cc(C(=O)O)ccn2)c1-c1ccc(Cl)c(F)c1]

The title compound was prepared in 3% yield (two steps) from 2-[5-(4-chloro-3-fluorophenyl)-1-methyl-1H-imidazol-4-yl]pyridine-4-carbonitrile according to the procedure for the preparation of Example 1. $^1$H NMR (400 MHz, DMSO-d$_6$): δ 3.57 (3H, s), 7.27 (1H, dd, J=8.7 Hz), 7.42 (1H, dd, J=4.2 Hz), 7.53 (1H, dd, J=8.8 Hz), 7.59 (1H, d, J=8.2 Hz), 7.85 (1H, s), 8.20 (1H, m), 8.28 (1H, s). [M+H] Calc'd for $C_{16}H_{11}ClFN_3O_2$, 333. Found, 332, 334.

Example 30

2-[5-(4-chloro-3-methoxyphenyl)-1-methyl-1H-imidazol-4-yl]pyridine-4-carboxylic acid A. 2-[5-(4-chloro-3-methoxyphenyl)-1-methyl-1H-imidazol-4-yl]pyridine-4-carbonitrile

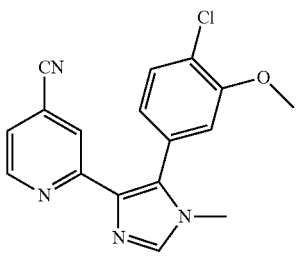 [SMILES: COc1cc(-c2c(-c3cc(C#N)ccn3)ncn2C)ccc1Cl]

The title compound was prepared from 2-(5-bromo-1-methyl-1H-imidazol-4-yl)pyridine-4-carbonitrile and 4-chloro-3-methoxyphenylboronic acid according to the procedure for the preparation of Example 3, part A. [M+H] Calc'd for $C_{17}H_{13}ClN_4O$, 326. Found, 325, 327.

B. 2-[5-(4-chloro-3-methoxyphenyl)-1-methyl-1H-imidazol-4-yl]pyridine-4-carboxylic acid

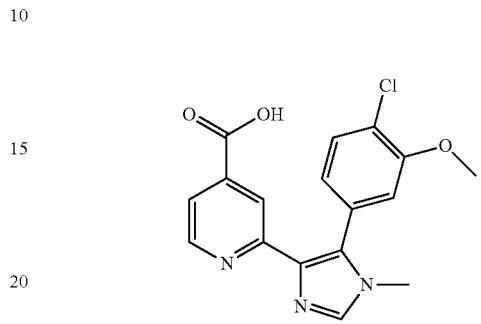

The title compound was prepared in 8% yield (two steps) from 2-[5-(4-chloro-3-methoxyphenyl)-1-methyl-1H-imidazol-4-yl]pyridine-4-carbonitrile according to the procedure for the preparation of Example 1. $^1$H NMR (400 MHz, DMSO-d$_6$): δ 3.53 (3H, s), 3.82 (3H, s), 7.00 (1H, dd, J=1.7 Hz and 8.3 Hz), 7.25 (1H, dd, J=1.8 Hz), 7.45 (1H, d, J=8.2 Hz), 7.50 (1H, d, J=4.1 Hz), 7.87 (1H, s), 8.32 (1H, s), 8.39 (1H, d, J=4.4 Hz). [M+H] Calc'd for $C_{17}H_{14}ClN_3O_3$, 345. Found, 344, 346.

Example 31

2-{5-[4-chloro-3-(trifluoromethyl)phenyl]-1-methyl-1H-imidazol-4-yl}pyridine-4-carboxylic acid A. 2-{5-[4-chloro-3-(trifluoromethyl)phenyl]-1-methyl-1H-imidazol-4-yl}pyridine-4-carbonitrile

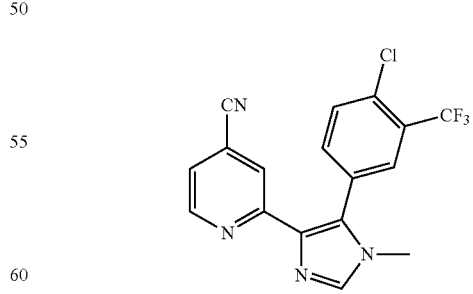

The title compound was prepared from 2-(5-bromo-1-methyl-1H-imidazol-4-yl)pyridine-4-carbonitrile and 4-chloro-3-trifluoromethylphenylboronic acid according to the procedure for the preparation of Example 3, part A. [M+H] Calc'd for $C_{17}H_{10}ClF_3N_4$, 364. Found, 363, 365.

B. 2-{5-[4-chloro-3-(trifluoromethyl)phenyl]-1-methyl-1H-imidazol-4-yl}pyridine-4-carboxylic acid

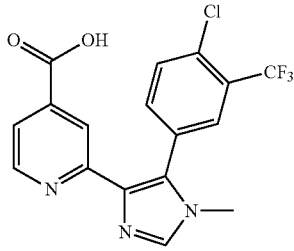 [SMILES: Cn1cnc(-c2cc(C(=O)O)ccn2)c1-c1ccc(Cl)c(C(F)(F)F)c1]

The title compound was prepared in 5% yield (two steps) from 2-{5-[4-chloro-3-(trifluoromethyl)phenyl]-1-methyl-1H-imidazol-4-yl}pyridine-4-carbonitrile according to the procedure for the preparation of Example 1. $^1$H NMR (400 MHz, DMSO-$d_6$): δ 3.55 (3H, s), 7.49 (1H, d, J=4.3 Hz), 7.78 (2H, s), 7.91 (1H, s), 7.96 (1H, s), 8.26 (1H, d, J=4.7 Hz), 8.35 (1H, s). [M+H] Calc'd for $C_{17}H_{11}ClF_3N_3O_2$, 383. Found, 382, 384.

Example 32

2-[5-(4-chloro-2-ethoxyphenyl)-1-methyl-1H-imidazol-4-yl]pyridine-4-carboxylic acid A. 2-[5-(4-chloro-2-ethoxyphenyl)-1-methyl-1H-imidazol-4-yl]pyridine-4-carbonitrile

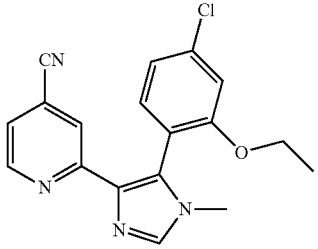 [SMILES: CCOc1cc(Cl)ccc1-c1c(-c2cc(C#N)ccn2)ncn1C]

The title compound was prepared from 2-(5-bromo-1-methyl-1H-imidazol-4-yl)pyridine-4-carbonitrile and 4-chloro-2-ethoxyphenylboronic acid according to the procedure for the preparation of Example 3, part A. [M+H] Calc'd for $C_{18}H_{15}ClN_4O$, 340. Found, 339, 341.

B. 2-[5-(4-chloro-2-ethoxyphenyl)-1-methyl-1H-imidazol-4-yl]pyridine-4-carboxylic acid

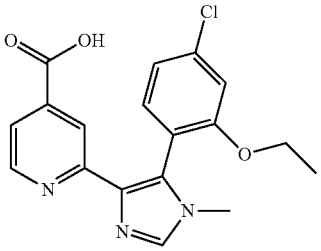 [SMILES: CCOc1cc(Cl)ccc1-c1c(-c2cc(C(=O)O)ccn2)ncn1C]

The title compound was prepared in 2% yield (two steps) from 2-[5-(4-chloro-2-ethoxyphenyl)-1-methyl-1H-imidazol-4-yl]pyridine-4-carbonitrile according to the procedure for the preparation of Example 1. $^1$H NMR (400 MHz, DMSO-$d_6$): δ 0.96 (3H, t, J=6.9 Hz), 3.48 (3H, s), 3.86 (1H, m), 4.02 (1H, m), 7.04 (1H, dd, J=2.0 Hz and 8.1 Hz), 7.14 (1H, d, J=1.8 Hz), 7.27 (1H, d, J=8.2 Hz), 7.44 (1H, d, J=5.6 Hz), 7.84 (1H, s), 8.28 (2H, s). [M+H] Calc'd for $C_{18}H_{16}ClN_3O_3$, 359. Found, 358, 360.

Example 33

2-[5-(2,4-dichlorophenyl)-1-methyl-1H-imidazol-4-yl]pyridine-4-carboxylic acid

A. 2-[5-(2,4-dichlorophenyl)-1-methyl-1H-imidazol-4-yl]pyridine-4-carbonitrile

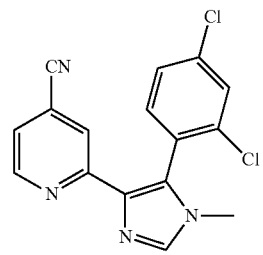 [SMILES: Cn1cnc(-c2cc(C#N)ccn2)c1-c1ccc(Cl)cc1Cl]

The title compound was prepared from 2-(5-bromo-1-methyl-1H-imidazol-4-yl)pyridine-4-carbonitrile and 2,4-dichlorophenylboronic acid according to the procedure for the preparation of Example 3, part A. [M+H] Calc'd for $C_{16}H_{10}Cl_2N_4$, 330. Found, 329, 331.

B. 2-[5-(2,4-dichlorophenyl)-1-methyl-1H-imidazol-4-yl]pyridine-4-carboxylic acid

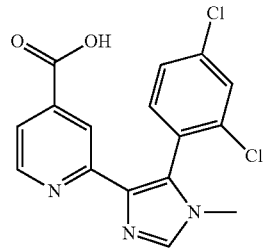 [SMILES: Cn1cnc(-c2cc(C(=O)O)ccn2)c1-c1ccc(Cl)cc1Cl]

The title compound was prepared in 2% yield (two steps) from 2-[5-(2,4-dichlorophenyl)-1-methyl-1H-imidazol-4-yl]pyridine-4-carbonitrile according to the procedure for the preparation of Example 1. $^1$H NMR (400 MHz, DMSO-$d_6$): δ 3.41 (3H, s), 7.44 (1H, m), 7.49 (1H, d, J=7.7 Hz), 7.51 (1H, dd, J=1.8 Hz and 8.0 Hz), 7.76 (1H, d, J=1.6 Hz), 7.90 (1H, s), 8.26 (1H, m), 8.33 (1H, s). [M+H] Calc'd for $C_{16}H_{11}Cl_2N_3O_2$, 349. Found, 348, 350.

Example 34

2-(1-methyl-5-{4-[1-(trifluoromethyl)cyclopropyl]phenyl}-1H-imidazol-4-yl)pyridine-4-carboxylic acid 4,4,5,5-tetramethyl-2-[4-[1-(trifluoromethyl)cyclopropyl]phenyl]-1,3,2-dioxaborolane

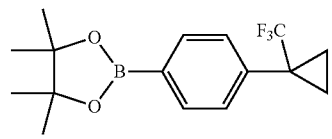 [SMILES: CC1(C)OB(c2ccc(C3(C(F)(F)F)CC3)cc2)OC1(C)C]

To a solution of 1-bromo-4-(1-trifluoromethyl-cyclopropyl)benzene (265 mg, 1 mmol) in 10 mL of dioxane, was added bis(pinacolato)diboron (305 mg, 1.2 mmol), PdCl₂(dppf) (40 mg, 0.05 mmol) and potassium acetate (294 mg, 3 mmol). The reaction mixture was degassed and heated at 90° C. under nitrogen for 18 hrs. The crude mixture was purified by ISCO flash column chromatography (EtOAc/Hexane=0-50%) to give the title compound as white solid (250 mg, 80%). ¹H NMR (400 MHz, DMSO-d₆): δ 1.03 (4H, m), 1.31 (12H, s), 7.48 (2H, d, J=8.0 Hz), 7.79 (2H, d, J=8.1 Hz).

A. 2-(1-methyl-5-{4-[1-(trifluoromethyl)cyclopropyl]phenyl}-1H-imidazol-4-yl)pyridine-4-carbonitrile

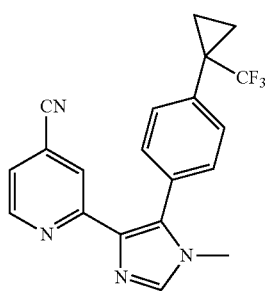 [SMILES: Cn1cnc(-c2cc(C#N)ccn2)c1-c1ccc(C2(C(F)(F)F)CC2)cc1]

The title compound was prepared from 2-(5-bromo-1-methyl-1H-imidazol-4-yl)pyridine-4-carbonitrile and 4,4,5,5-tetramethyl-2-[4-[1-(trifluoromethyl)cyclopropyl]phenyl]-1,3,2-dioxaborolane according to the procedure for the preparation of Example 3, part A. [M+H] Calc'd for C₂₀H₁₅F₃N₄, 369. Found, 369.

B. 2-(1-methyl-5-{4-[1-(trifluoromethyl)cyclopropyl]phenyl}-1H-imidazol-4-yl)pyridine-4-carboxylic acid

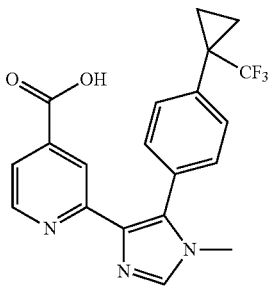 [SMILES: Cn1cnc(-c2cc(C(=O)O)ccn2)c1-c1ccc(C2(C(F)(F)F)CC2)cc1]

The title compound was prepared in 34% yield (two steps) from 2-(1-methyl-5-{4-[1-(trifluoromethyl)cyclopropyl]phenyl}-1H-imidazol-4-yl)pyridine-4-carbonitrile according to the procedure for the preparation of Example 1. ¹H NMR (400 MHz, DMSO-d₆): δ 1.19 (2H, m), 1.38 (2H, m), 3.51 (3H, s), 7.44-7.51 (5H, m), 7.85 (1H, s), 8.25 (1H, s), 8.27 (1H, s). [M+H] Calc'd for C₂₀H₁₆F₃N₃O₂, 388. Found, 388.

Example 35

2-[5-(4-chloro-3-fluorophenyl)-1-propyl-1H-imidazol-4-yl]pyridine-4-carboxylic acid

2-(1H-imidazol-4-yl)pyridine-4-carbonitrile

Step 1: 2-[1-(triphenylmethyl)-1H-imidazol-4-yl]pyridine-4-carbonitrile

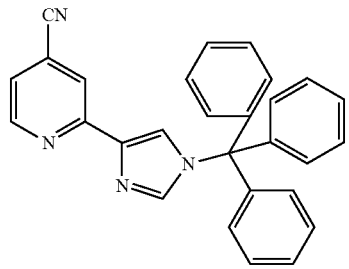 [SMILES: N#Cc1ccnc(-c2cn(C(c3ccccc3)(c3ccccc3)c3ccccc3)cn2)c1]

The title compound was prepared in 77% yield from 2-chloro-4-pyridinenitrile and 4-(tributylstannyl)-1-tritylimidazole according to the procedure for Example 1, part A. ¹H NMR (400 MHz, DMSO-d₆): δ 7.17 (5H, m), 7.40-7.47 (10H, m), 7.49 (1H, d, J=1.2 Hz), 7.62 (1H, d, J=1.3 Hz), 7.65 (1H, dd, J=1.5 Hz and 5.0 Hz), 8.13 (1H, s), 8.67 (1H, d, 5.0 Hz).

Step 2: 2-(1H-imidazol-4-yl)pyridine-4-carbonitrile

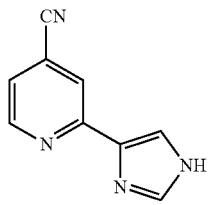 [SMILES: N#Cc1ccnc(-c2c[nH]cn2)c1]

A solution of 2-[1-(triphenylmethyl)-1H-imidazol-4-yl]pyridine-4-carbonitrile (510 mg, 1.2 mmol) in acetic acid (10 ml) was heated at 90° C. for 18 hr. Reaction mixture was purified by ISCO flash column chromatography (EtOAc/Hexane=0-100%) to get 130 mg of product. Some starting material was recovered and heated in acetic acid again overnight at 90° C. Additional product was obtained to give total 160 mg product as light yellow solid (78%). ¹H NMR (400 MHz, DMSO-d₆): δ 7.62 (1H, dd, J=1.2 Hz and 4.9 Hz), 7.81 (2H, s), 8.13 (1H, s), 8.73 (1H, d, J=4.8 Hz). [M+H] Calc'd for C₉H₆N₄, 171. Found, 171.

A. 2-(1-propyl-1H-imidazol-4-yl)pyridine-4-carbonitrile

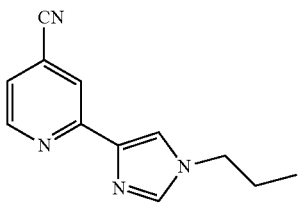 [SMILES: CCCn1cnc(-c2cc(C#N)ccn2)c1]

A solution of 2-(1H-imidazol-4-yl)pyridine-4-carbonitrile (90 mg, 0.53 mmol) in anhydrous DMF (2 mL) was cooled in an ice-water bath. Sodium hydride (60%, 32 mg, 0.8 mmol) was added carefully at 0° C. The reaction mixture was stirred for 10 minutes, after which 1-bromopropane (73 µL, 0.8 mmol) was added. The reaction mixture was warmed up to r.t. and stirred for 1 hr and it was then purified by ISCO flash column (MeOH/DCM=0-5%). 80 mg title compound was obtained as white solid (71%). [M+H] Calc'd for $C_{12}H_{12}N_4$, 213. Found, 213.

B. 2-(5-bromo-1-propyl-1H-imidazol-4-yl)pyridine-4-carbonitrile

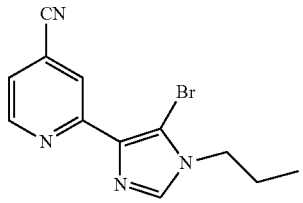 [SMILES: CCCn1cnc(-c2cc(C#N)ccn2)c1Br]

The title compound was prepared in 62% yield from 2-(1-propyl-1H-imidazol-4-yl)pyridine-4-carbonitrile according to the procedure in Example 2. $^1$H NMR (400 MHz, DMSO-$d_6$): δ 0.88 (3H, t, J=7.4 Hz), 1.76 (2H, q, J=7.3 Hz and 7.2 Hz), 4.02 (2H, t, J=7.1 Hz), 7.71 (1H, dd, J=1.4 Hz and 5.0 Hz), 8.08 (1H, s), 8.20 (1H, s), 8.81 (1H, d, J=5.0 Hz). [M+H] Calc'd for $C_{12}H_{11}BrN_4$, 292. Found, 291, 293.

C. 2-[5-(4-chloro-3-fluorophenyl)-1-propyl-1H-imidazol-4-yl]pyridine-4-carbonitrile

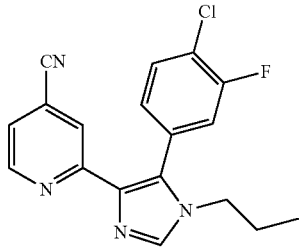 [SMILES: CCCn1cnc(-c2cc(C#N)ccn2)c1-c1ccc(Cl)c(F)c1]

The title compound was prepared from 2-(5-bromo-1-propyl-1H-imidazol-4-yl)pyridine-4-carbonitrile and 4-chloro3-fluorophenylboronic acid according to the procedure for the preparation of Example 3, part A. [M+H] Calc'd for $C_{18}H_{14}ClFN_4$, 342. Found, 341, 343.

D. 2-[5-(4-chloro-3-fluorophenyl)-1-propyl-1H-imidazol-4-yl]pyridine-4-carboxylic acid

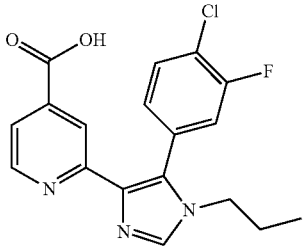 [SMILES: CCCn1cnc(-c2cc(C(=O)O)ccn2)c1-c1ccc(Cl)c(F)c1]

The title compound was prepared in 37% yield (two steps) from 2-[5-(4-chloro-3-fluorophenyl)-1-propyl-1H-imidazol-4-yl]pyridine-4-carbonitrile according to the procedure for the preparation of Example 1. $^1$H NMR (400 MHz, DMSO-$d_6$): δ 0.72 (3H, t, J=7.3 Hz), 1.48 (2H, q, J=7.4 Hz and 7.2 Hz), 3.85 (2H, t, J=7.1 Hz), 7.26 (1H, dd, J=1.3 Hz and 8.2 Hz), 7.46 (1H, dd, J=1.2 Hz and 6.2 Hz), 7.52 (1H, dd, J=1.7 Hz and 10.2 Hz), 7.64 (1H, t, J=8.1 Hz), 7.92 (1H, s), 8.24 (1H, d, J=4.8 Hz), 8.31 (1H, s). [M+H] Calc'd for $C_{18}H_{15}ClFN_3O_2$, 361. Found, 360, 362.

Example 36

2-[5-(4-chloro-3-fluorophenyl)-1-(3-methoxypropyl)-1H-imidazol-4-yl]pyridine-4-carboxylic acid A. 2-[1-(3-methoxypropyl)-1H-imidazol-4-yl]pyridine-4-carbonitrile

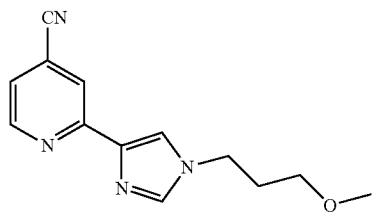 [SMILES: COCCCn1cnc(-c2cc(C#N)ccn2)c1]

The title compound was prepared from 2-(1H-imidazol-4-yl)pyridine-4-carbonitrile and 1-bromo-3-methoxypropane according to the procedure for the preparation of Example 35, part A. [M+H] Calc'd for $C_{13}H_{14}N_4O$, 243. Found, 243.

B. 2-[5-bromo-1-(3-methoxypropyl)-1H-imidazol-4-yl]pyridine-4-carbonitrile

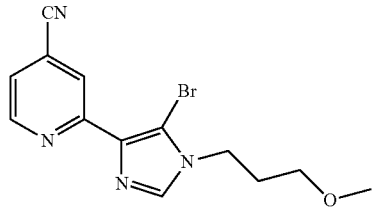 [SMILES: COCCCn1cnc(-c2cc(C#N)ccn2)c1Br]

The title compound was prepared in 83% yield (two steps) from 2-[1-(3-methoxypropyl)-1H-imidazol-4-yl]pyridine-4-carbonitrile according to the procedure in Example 2. [M+H] Calc'd for $C_{13}H_{13}BrN_4O$, 322. Found, 321, 323.

C. 2-[5-(4-chloro-3-fluorophenyl)-1-(3-methoxypropyl)-1H-imidazol-4-yl]pyridine-4-carbonitrile

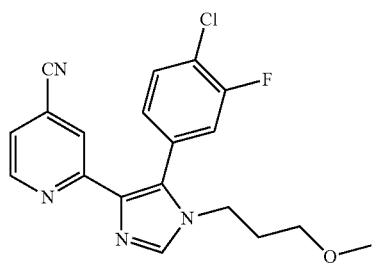 [SMILES: COCCCn1cnc(-c2cc(C#N)ccn2)c1-c1ccc(Cl)c(F)c1]

The title compound was prepared from 2-[5-bromo-1-(3-methoxypropyl)-1H-imidazol-4-yl]pyridine-4-carbonitrile and 4-chloro3-fluorophenylboronic acid according to the procedure for the preparation of Example 3, part A. [M+H] Calc'd for $C_{19}H_{16}ClFN_4O$, 372. Found, 371, 373.

D. 2-[5-(4-chloro-3-fluorophenyl)-1-(3-methoxypropyl)-1H-imidazol-4-yl]pyridine-4-carboxylic acid

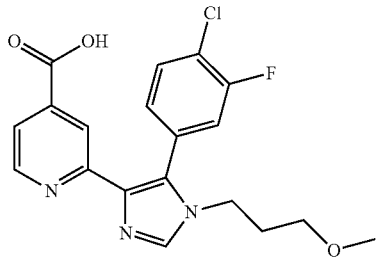 [SMILES: COCCCn1cnc(-c2cc(C(=O)O)ccn2)c1-c1ccc(Cl)c(F)c1]

The title compound was prepared in 15% yield (two steps) from 2-[5-(4-chloro-3-fluorophenyl)-1-(3-methoxypropyl)-1H-imidazol-4-yl]pyridine-4-carbonitrile according to the procedure for the preparation of Example 1. $^1$H NMR (400 MHz, DMSO-$d_6$): δ 1.73 (2H, t, J=7.0 Hz), 3.16 (3H, s), 3.21 (2H, t, J=7.2 Hz), 3.93 (2H, t, J=7.2 Hz), 7.25 (1H, dd, J=8.2 Hz), 7.44 (1H, d, J=4.4 Hz), 7.50 (1H, dd, J=1.4 Hz and 9.0 Hz), 7.63 (1H, t, J=8.1 Hz), 7.89 (1H, s), 8.18 (1H, d, J=4.9 Hz), 8.28 (1H, s). [M+H] Calc'd for $C_{19}H_{17}ClFN_3O_3$, 391. Found, 390, 392.

Example 37

2-[5-(4-chloro-3-fluorophenyl)-1-(2-methoxyethyl)-1H-imidazol-4-yl]pyridine-4-carboxylic acid A. 2-[1-(2-methoxyethyl)-1H-imidazol-4-yl]pyridine-4-carbonitrile

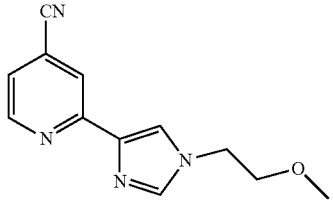 [SMILES: COCCn1cnc(-c2cc(C#N)ccn2)c1]

The title compound was prepared 2-(1H-imidazol-4-yl)pyridine-4-carbonitrile and 2-bromo-ethylmethylether according to the procedure for the preparation of Example 35, part A. [M+H] Calc'd for $C_{12}H_{12}N_4O$, 229. Found, 229.

B. 2-[5-bromo-1-(2-methoxyethyl)-1H-imidazol-4-yl]pyridine-4-carbonitrile

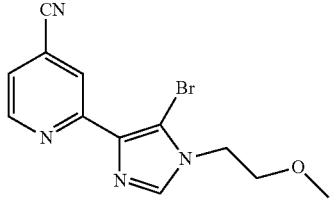 [SMILES: COCCn1cnc(-c2cc(C#N)ccn2)c1Br]

The title compound was prepared in 54% yield (two steps) from 2-[1-(2-methoxyethyl)-1H-imidazol-4-yl]pyridine-4-carbonitrile according to the procedure in Example 2. [M+H] Calc'd for $C_{12}H_{11}BrN_4O$, 308. Found, 307, 309.

C. 2-[5-(4-chloro-3-fluorophenyl)-1-(2-methoxyethyl)-1H-imidazol-4-yl]pyridine-4-carbonitrile

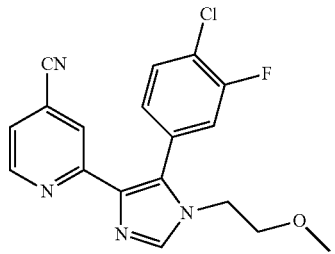 [SMILES: COCCn1cnc(-c2cc(C#N)ccn2)c1-c1ccc(Cl)c(F)c1]

The title compound was prepared from 2-[5-bromo-1-(2-methoxyethyl)-1H-imidazol-4-yl]pyridine-4-carbonitrile and 4-chloro-3-fluorophenylboronic acid according to the procedure for the preparation of Example 3, part A. [M+H] Calc'd for $C_{18}H_{14}ClFN_4O$, 358. Found, 357, 359.

D. 2-[5-(4-chloro-3-fluorophenyl)-1-(2-methoxyethyl)-1H-imidazol-4-yl]pyridine-4-carboxylic acid

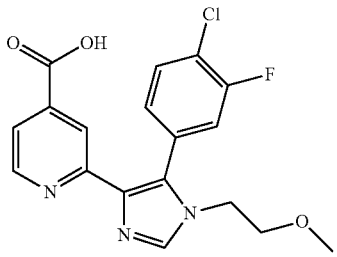 [SMILES: COCCn1cnc(-c2cc(C(=O)O)ccn2)c1-c1ccc(Cl)c(F)c1]

The title compound was prepared in 42% yield (two steps) from 2-[5-(4-chloro-3-fluorophenyl)-1-(2-methoxyethyl)-1H-imidazol-4-yl]pyridine-4-carbonitrile according to the procedure for the preparation of Example 1. $^1$H NMR (400 MHz, DMSO-$d_6$): δ 3.19 (3H, s), 3.43 (2H, t, J=5.2 Hz), 4.01 (2H, t, J=5.2 Hz), 7.24 (1H, dd, J=8.0 Hz), 7.41 (1H, d, J=4.2 Hz), 7.50 (1H, dd, J=1.6 Hz and 10.3 Hz), 7.62 (1H, t, J=8.2 Hz), 7.88 (1H, s), 8.15 (1H, d, J=4.8 Hz), 8.24 (1H, s). [M+H] Calc'd for $C_{18}H_{15}ClFN_3O_3$, 377. Found, 376, 378.

Example 38

2-[1-[2-[(4-fluorophenyl)methyl-methylamino]ethyl]imidazol-4-yl]pyridine-4-carboxylic acid

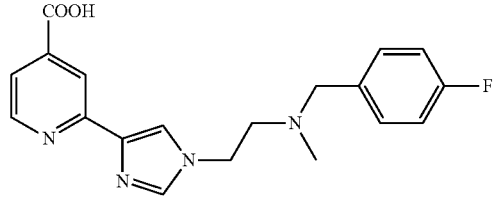 [SMILES: CN(CCn1cnc(-c2cc(C(=O)O)ccn2)c1)Cc1ccc(F)cc1]

The title compound was prepared in 23% yield from methyl 2-(1-{2-[(methylsulfonyl)oxy]ethyl}-1H-imidazol-4-yl)pyridine-4-carboxylate and 4-fluoro-N-methylbenzylamine according to the procedure for the preparation of Example 58. $^1$H NMR (400 MHz, DMSO): δ 2.18 (3H, s), 2.69 (2H, t, J=6 Hz), 3.51 (2H, s), 4.00 (1H, t, J=5.7 Hz), 4.15 (1H, t, J=5.9 Hz), 7.03 (2H, t, J=8.9 Hz), 7.20 (2H, dd, J=8.7

Hz and 2.8 Hz), 7.52 (1H, s), 7.72 (1H, d, J=1.7 Hz), 7.78 (1H, s), 8.26 (1H, s), 8.46 (1H, d, J=4.3 Hz). [M+H] Calc'd for $C_{19}H_{19}FN_4O_2$, 355. Found, 355.

Example 39

2-{5-(4-chloro-3-fluorophenyl)-1-[2-(dimethylamino)ethyl]-1H-imidazol-4-yl}pyridine-4-carboxylic acid A. 2-(5-bromo-1H-imidazol-4-yl)pyridine-4-carbonitrile

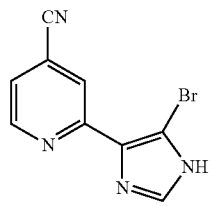 [SMILES: N#Cc1ccnc(-c2nc[nH]c2Br)c1]

The title compound was prepared in 91% yield from 2-(1H-imidazol-4-yl)pyridine-4-carbonitrile according to the procedure in Example 2. [M+H] Calc'd for $C_9H_5BrN_4$, 250. Found, 249, 251.

B. 2-[5-(4-chloro-3-fluorophenyl)-1H-imidazol-4-yl]pyridine-4-carbonitrile

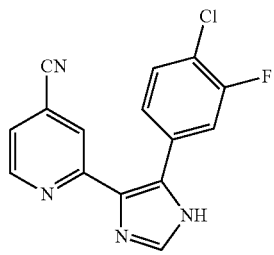 [SMILES: N#Cc1ccnc(-c2nc[nH]c2-c2ccc(Cl)c(F)c2)c1]

The title compound was prepared from 2-(5-bromo-1H-imidazol-4-yl)pyridine-4-carbonitrile and 4-chloro-3-fluorophenylboronic acid according to the procedure for the preparation of Example 3, part A. [M+H] Calc'd for $C_{15}H_8ClFN_4$, 300. Found, 299, 301.

C. 2-{5-(4-chloro-3-fluorophenyl)-1-[2-(dimethylamino)ethyl]-1H-imidazol-4-yl}pyridine-4-carbonitrile

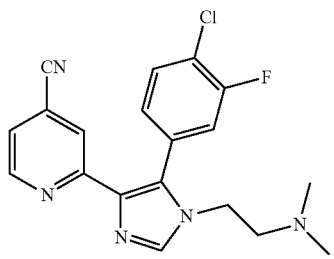 [SMILES: CN(C)CCn1cnc(-c2cc(C#N)ccn2)c1-c1ccc(Cl)c(F)c1]

The title compound was prepared from 2-[5-(4-chloro-3-fluorophenyl)-1H-imidazol-4-yl]pyridine-4-carbonitrile (see above) and dimethylaminomethyl bromide hydrogen bromide salt according to the procedure for the preparation of Example 35, part A. [M+H] Calc'd for $C_{19}H_{17}ClFN_5$, 371. Found, 370, 372.

D. 2-{5-(4-chloro-3-fluorophenyl)-1-[2-(dimethylamino)ethyl]-1H-imidazol-4-yl}pyridine-4-carboxylic acid

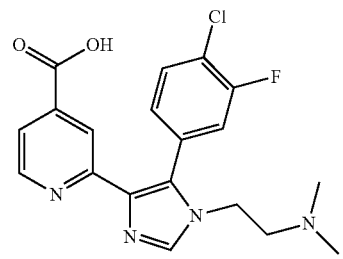 [SMILES: CN(C)CCn1cnc(-c2cc(C(=O)O)ccn2)c1-c1ccc(Cl)c(F)c1]

The title compound was prepared in 6% yield (two steps) from 2-{5-(4-chloro-3-fluorophenyl)-1-[2-(dimethylamino)ethyl]-1H-imidazol-4-yl}pyridine-4-carbonitrile according to the procedure for the preparation of Example 1. $^1$H NMR (400 MHz, DMSO-d$_6$): δ 2.03 (6H, s), 2.33 (2H, t, J=6.0 Hz), 3.93 (2H, t, J=6.3 Hz), 7.24 (1H, dd, J=10.2 Hz), 7.37 (1H, dd, J=1.5 Hz and 5.02 Hz), 7.51 (1H, dd, J=1.9 Hz and 10.6 Hz), 7.62 (1H, t, J=8.1 Hz), 7.89 (1H, s), 8.11 (1H, d, J=4.9 Hz), 8.21 (1H, s). [M+H] Calc'd for $C_{19}H_{18}ClFN_4O_2$, 390. Found, 389, 391.

Example 40

2-{1-[2-(dimethylamino)ethyl]-1H-imidazol-4-yl}pyridine-4-carboxylic acid

A. 2-{1-[2-(dimethylamino)ethyl]-1H-imidazol-4-yl}pyridine-4-carbonitrile

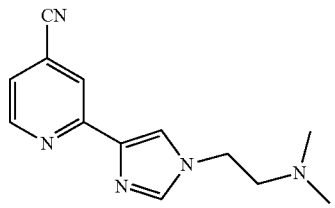 [SMILES: CN(C)CCn1cnc(-c2cc(C#N)ccn2)c1]

The title compound was prepared from 2-(1H-imidazol-4-yl)pyridine-4-carbonitrile and dimethylaminomethyl bromide hydrogen bromide salt according to the procedure for the preparation of Example 35, part A. [M+H] Calc'd for $C_{13}H_{15}N_5$, 242. Found, 242.

B. 2-{1-[2-(dimethylamino)ethyl]-1H-imidazol-4-yl}pyridine-4-carboxylic acid

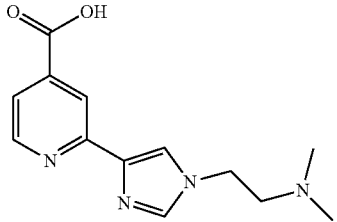 [SMILES: CN(C)CCn1cnc(-c2cc(C(=O)O)ccn2)c1]

The title compound was prepared in 45% yield (two steps) from 2-{1-[2-(dimethylamino)ethyl]-1H-imidazol-4- yl}pyridine-4-carbonitrile according to the procedure for the preparation of Example 1. $^1$H NMR (400 MHz, DMSO-$d_6$): δ 2.20 (6H, s), 2.58 (2H, t, J=6.2 Hz), 4.08 (2H, t, J=6.2 Hz), 7.44 (1H, dd, J=1.4 Hz and 4.8 Hz), 7.69 (2H, 2s), 8.20 (1H, s), 8.36 (1H, d, J=4.9 Hz). [M+H] Calc'd for $C_{13}H_{16}N_4O_2$, 261. Found, 261.

Example 41

2-(1-propyl-1H-imidazol-4-yl)pyridine-4-carboxylic acid

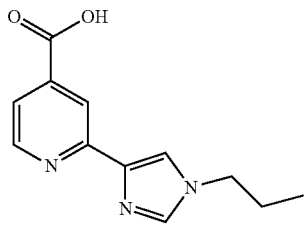 [SMILES: CCCn1cnc(-c2cc(C(=O)O)ccn2)c1]

The title compound was prepared from 2-(1-propyl-1H-imidazol-4-yl)pyridine-4-carbonitrile (Example 35A) according to the procedure for the preparation of Example 1. $^1$H NMR (400 MHz, DMSO-$d_6$): δ 0.85 (3H, t, J=7.3 Hz), 1.77 (2H, q, J=7.2 Hz), 3.97 (2H, t, J=7.0 Hz), 7.53 (1H, d, J=4.6 Hz), 7.73 (2H, 2s), 8.27 (1H, s), 8.47 (1H, d, J=4.4 Hz). [M+H] Calc'd for $C_{12}H_{13}N_3O_2$, 232. Found, 232.

Example 42

2-{1-[3-(dimethylamino)propyl]-1H-imidazol-4-yl}pyridine-4-carboxylic acid

A. 2-{1-[3-(dimethylamino)propyl]-1H-imidazol-4-yl}pyridine-4-carbonitrile

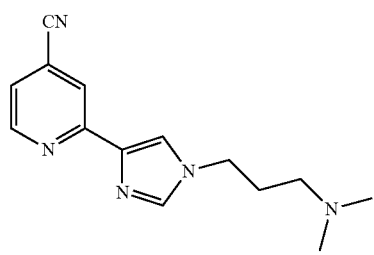 [SMILES: CN(C)CCCn1cnc(-c2cc(C#N)ccn2)c1]

The title compound was prepared from 2-(1H-imidazol-4-yl)pyridine-4-carbonitrile and (3-bromopropyl)dimethylamine hydrogen bromide according to the procedure for the preparation of Example 35, part A. [M+H] Calc'd for $C_{14}H_{17}N_5$, 256. Found, 256.

B. 2-{1-[3-(dimethylamino)propyl]-1H-imidazol-4-yl}pyridine-4-carboxylic acid

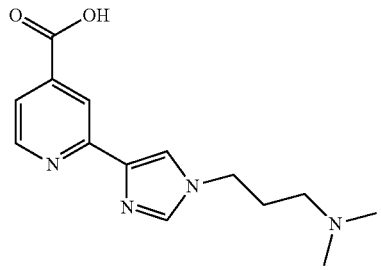 [SMILES: CN(C)CCCn1cnc(-c2cc(C(=O)O)ccn2)c1]

The title compound was prepared in 21% yield (two steps) from 2-{1-[3-(dimethylamino)propyl]-1H-imidazol-4-yl}pyridine-4-carbonitrile according to the procedure for the preparation of Example 1. $^1$H NMR (400 MHz, DMSO-$d_6$): δ 1.90 (2H, m), 2.12 (6H, s), 2.16 (2H, t, J=6.9 Hz), 4.02 (2H, t, J=7.0 Hz), 7.45 (1H, dd, J=1.6 Hz and 4.9 Hz), 7.68 (2H, s), 8.21 (1H, s), 8.37 (1H, d, J=4.8 Hz). [M+H] Calc'd for $C_{14}H_{18}N_4O_2$, 275. Found, 275.

Example 43

2-{1-[2-(pyrrolidin-1-yl)ethyl]-1H-imidazol-4-yl}pyridine-4-carboxylic acid

A. 2-{1-[2-(pyrrolidin-1-yl)ethyl]-1H-imidazol-4-yl}pyridine-4-carbonitrile

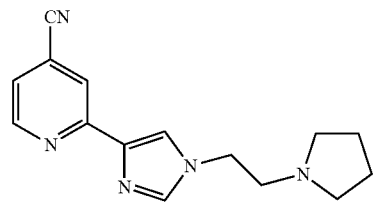 [SMILES: N#Cc1ccnc(-c2cn(CCN3CCCC3)cn2)c1]

A mixture of 2-(1H-imidazol-4-yl)pyridine-4-carbonitrile (20 mg, 0.12 mmol), 1-(2-chloroethyl)pyrrolidine hydrogen chloride (34 mg, 0.2 mmol) and cesium carbonate (130 mg, 0.4 mmol) in 2 mL DMF was heated at 90° C. for 2 hr. The reaction mixture was purified by ISCO flash column chromatography (MeOH/DCM=0-100%). [M+H] Calc'd for $C_{15}H_{17}N_5$, 268. Found, 268.

B. 2-{1-[2-(pyrrolidin-1-yl)ethyl]-1H-imidazol-4-yl}pyridine-4-carboxylic acid

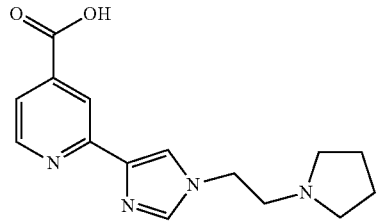 [SMILES: O=C(O)c1ccnc(-c2cn(CCN3CCCC3)cn2)c1]

The title compound was prepared in 30% yield (two steps) from 2-{1-[2-(pyrrolidin-1-yl)ethyl]-1H-imidazol-4-yl}pyridine-4-carbonitrile according to the procedure for the preparation of Example 1. ¹H NMR (400 MHz, DMSO-d₆): δ 1.66 (4H, m), 2.50 (4H, m), 2.78 (2H, t, J=6.3 Hz), 4.11 (2H, t, J=6.3 Hz), 7.45 (1H, dd, J=1.4 Hz and 4.9 Hz), 7.70 (2H, s), 8.21 (1H, s), 8.37 (1H, d, J=4.9 Hz). [M+H] Calc'd for $C_{15}H_{18}N_4O_2$, 287. Found, 287.

Example 44 methyl 2-{1-[2-(pyrrolidin-1-yl)ethyl]-1H-imidazol-4-yl}pyridine-4-carboxylate methyl 2-(1H-imidazol-4-yl)pyridine-4-carboxylate A. methyl 2-[1-(triphenylmethyl)-1H-imidazol-4-yl]pyridine-4-carboxylate

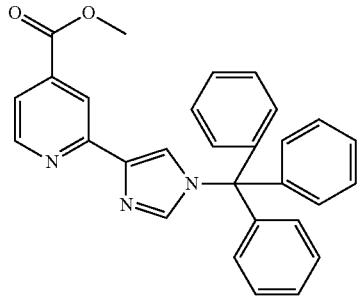 [SMILES: COC(=O)c1ccnc(-c2cn(C(c3ccccc3)(c3ccccc3)c3ccccc3)cn2)c1]

The title compound was prepared from methyl 2-chloropyridine-4-carboxylate and 4-(tributylstannyl)-1-tritylimidazole according to the procedure for Example 1. ¹H NMR (400 MHz, DMSO-d₆): δ 3.92 (3H, s), 7.16 (5H, m), 7.38-7.46 (11H, m), 7.60 (1H, d, J=1.3 Hz), 7.64 (1H, dd, J=1.6 Hz and 5.0 Hz), 8.32 (1H, s), 8.64 (1H, d, 5.0 Hz).

B. methyl 2-(1H-imidazol-4-yl)pyridine-4-carboxylate

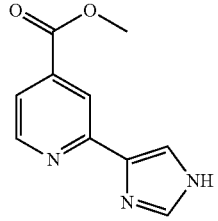

The title compound was prepared in 44% yield (two steps) from methyl 2-[1-(triphenylmethyl)-1H-imidazol-4-yl]pyridine-4-carboxylate according to the procedure for 2-(1H-imidazol-4-yl)pyridine-4-carbonitrile in Example 35. [M+H] Calc'd for $C_{10}H_9N_3O_2$, 204. Found, 204.

C. methyl 2-{1-[2-(pyrrolidin-1-yl)ethyl]-1H-imidazol-4-yl}pyridine-4-carboxylate

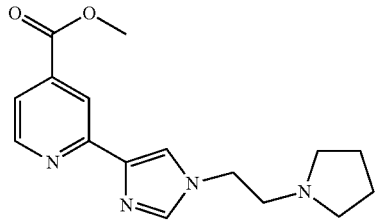 [SMILES: COC(=O)c1ccnc(-c2cn(CCN3CCCC3)cn2)c1]

A mixture of methyl 2-(1H-imidazol-4-yl)pyridine-4-carboxylate (20 mg, 0.10 mmol), 1-(2-chloroethyl)pyrrolidine hydrogen chloride (34 mg, 0.2 mmol) and cesium carbonate (130 mg, 0.4 mmol) in 2 mL DMF was heated at 120° C. for 2 hr. The reaction mixture was purified by ISCO flash column chromatography (MeOH/DCM=0-100%). ¹H NMR (400 MHz, DMSO-d₆): δ 1.77 (4H, m), 2.67 (4H, m), 2.74 (2H, t, J=6.2 Hz), 3.92 (3H, s), 4.17 (2H, t, J=6.2 Hz), 7.62 (1H, dd, J=1.3 Hz and 5.0 Hz), 7.79 (1H, s), 7.87 (1H, s), 8.30 (1H, s), 8.69 (1H, d, J=4.9 Hz). [M+H] Calc'd for $C_{16}H_{20}N_4O_2$, 301. Found, 301.

Example 45

2-{1-[2-(morpholin-4-yl)ethyl]-1H-imidazol-4-yl}pyridine-4-carboxylic acid

A. 2-{1-[2-(morpholin-4-yl)ethyl]-1H-imidazol-4-yl}pyridine-4-carbonitrile

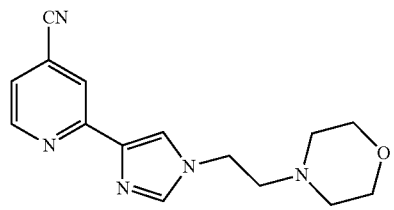 [SMILES: N#Cc1ccnc(-c2cn(CCN3CCOCC3)cn2)c1]

The title compound was prepared from 2-(1H-imidazol-4-yl)pyridine-4-carbonitrile and 4-(2-chloroethyl)morpholine hydrogen chloride according to the procedure for the preparation of Example 43, part A. [M+H] Calc'd for $C_{15}H_{17}N_5O$, 284. Found, 284.

B. 2-{1-[2-(morpholin-4-yl)ethyl]-1H-imidazol-4-yl}pyridine-4-carboxylic acid

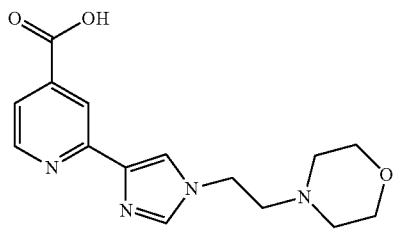 [SMILES: O=C(O)c1ccnc(-c2cn(CCN3CCOCC3)cn2)c1]

The title compound was prepared in 74% yield (two steps) from 2-{1-[2-(morpholin-4-yl)ethyl]-1H-imidazol-4-yl}pyridine-4-carbonitrile according to the procedure for the preparation of Example 1. ¹H NMR (400 MHz, DMSO-d₆): δ 1.66 (4H, m), 2.50 (4H, m), 2.78 (2H, t, J=6.3 Hz), 4.11 (2H, t, J=6.3 Hz), 7.55 (1H, dd, J=1.6 Hz and 5.0 Hz), 7.78 (1H, s), 7.85 (1H, s), 8.28 (1H, s), 8.58 (1H, d, J=5.0 Hz). [M+H] Calc'd for $C_{15}H_{18}N_4O_3$, 303. Found, 303.

Example 46

2-{1-[2-(1H-pyrazol-1-yl)ethyl]-1H-imidazol-4-yl}pyridine-4-carboxylic acid

A. 2-{1-[2-(1H-pyrazol-1-yl)ethyl]-1H-imidazol-4-yl}pyridine-4-carbonitrile

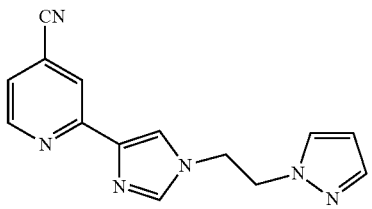 [SMILES: N#Cc1ccnc(-c2cn(CCn3cccn3)cn2)c1]

The title compound was prepared from 2-(1H-imidazol-4-yl)pyridine-4-carbonitrile and 4-(2-chloroethyl)-1H-pyrazole according to the procedure for the preparation of Example 43, part A. [M+H] Calc'd for $C_{14}H_{12}N_6$, 265. Found, 265.

B. 2-{1-[2-(1H-pyrazol-1-yl)ethyl]-1H-imidazol-4-yl}pyridine-4-carboxylic acid

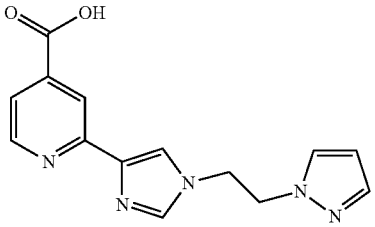 [SMILES: O=C(O)c1ccnc(-c2cn(CCn3cccn3)cn2)c1]

The title compound was prepared in 47% yield (two steps) from 2-{1-[2-(1H-pyrazol-1-yl)ethyl]-1H-imidazol-4-yl}pyridine-4-carbonitrile according to the procedure for the preparation of Example 1. $^1$H NMR (400 MHz, DMSO-d$_6$): δ 4.51 (4H, dd, J=5.7 Hz and 16.6 Hz), 6.19 (1H, s), 7.40 (1H, s), 7.48 (1H, d), 7.53 (d, 1H, J=2.3 Hz), 7.61 (1H, s), 7.95 (1H, s), 8.19 (1H, s), 8.27 (1H, d, J=2.5 Hz), 8.42 (1H, s), 8.57 (1H, d, J=5.0 Hz). [M+H] Calc'd for $C_{14}H_{13}N_5O_2$, 284. Found, 284.

Example 47

2-[1-(pyridin-2-ylmethyl)-1H-imidazol-4-yl]pyridine-4-carboxylic acid

A. 2-[1-(pyridin-2-ylmethyl)-1H-imidazol-4-yl]pyridine-4-carbonitrile

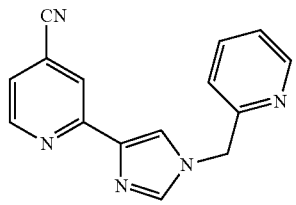 [SMILES: N#Cc1ccnc(-c2cn(Cc3ccccn3)cn2)c1]

The title compound was prepared from 2-(1H-imidazol-4-yl)pyridine-4-carbonitrile and 2-(chloroethyl)pyridine hydrogen chloride according to the procedure for the preparation of Example 43, part A. [M+H] Calc'd for $C_{15}H_{11}N_5$, 262. Found, 262.

B. 2-[1-(pyridin-2-ylmethyl)-1H-imidazol-4-yl]pyridine-4-carboxylic acid

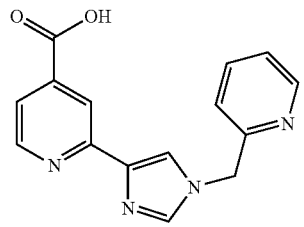 [SMILES: O=C(O)c1ccnc(-c2cn(Cc3ccccn3)cn2)c1]

The title compound was prepared in 60% yield (two steps) from 2-[1-(pyridin-2-ylmethyl)-1H-imidazol-4-yl]pyridine-4-carbonitrile according to the procedure for the preparation of Example 1. $^1$H NMR (400 MHz, DMSO-d$_6$): δ 5.36 (2H, s), 7.29 (1H, d, J=7.8 Hz), 7.34 (1H, m), 7.49 (1H, d, J=4.8 Hz), 7.72 (1H, s), 7.82 (1H, dd, J=1.3 Hz and 7.7 Hz), 7.84 (1H, s), 8.25 (1H, s), 8.39 (1H, d, J=4.8 Hz), 8.57 (1H, dd, J=0.72 Hz and 4.8 Hz). [M+H] Calc'd for $C_{15}H_{12}N_4O_2$, 281. Found, 281.

Example 48

2-(1-{2-[2-(dimethylamino)ethoxy]ethyl}-1H-imidazol-4-yl)pyridine-4-carboxylic acid A. 2-{1-[2-(2-chloroethoxy)ethyl]-1H-imidazol-4-yl}pyridine-4-carbonitrile

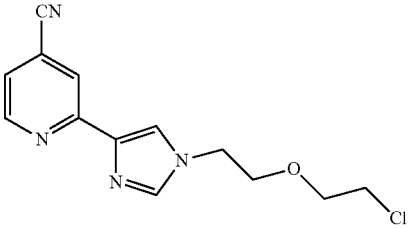 [SMILES: N#Cc1ccnc(-c2cn(CCOCCCl)cn2)c1]

The title compound was prepared from 2-(1H-imidazol-4-yl)pyridine-4-carbonitrile and bis(2-chloroethyl)ether according to the procedure for the preparation of Example 43, part A. [M+H] Calc'd for $C_{13}H_{13}ClN_4O$, 278. Found, 277, 279.

B. 2-(1-{2-[2-(dimethylamino)ethoxy]ethyl}-1H-imidazol-4-yl)pyridine-4-carbonitrile

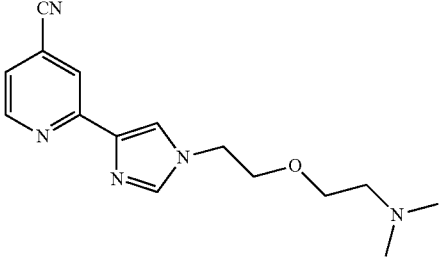 [SMILES: CN(C)CCOCCn1cnc(-c2cc(C#N)ccn2)c1]

To a solution of 2-{1-[2-(2-chloroethoxy)ethyl]-1H-imidazol-4-yl}pyridine-4-carbonitrile obtained from part A in 2 mL of THF was added N,N-dimethylamine hydrogen chloride (121 mg, 1.5 mmol), potassium carbonate (276 mg, 2 mmol) and potassium iodide (66 mg, 0.4 mmol). The reaction mixture was stirred in a sealed tube at 90° C. for 18 hr. After which, it was purified by ISCO flash column chromatography (MeOH/DCM=0-100%). [M+H] Calc'd for $C_{15}H_{19}N_5O$, 286. Found, 286.

C. 2-(1-{2-[2-(dimethylamino)ethoxy]ethyl}-1H-imidazol-4-yl)pyridine-4-carboxylic acid

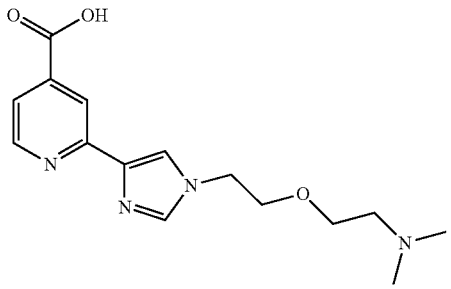 [SMILES: CN(C)CCOCCn1cnc(-c2cc(C(=O)O)ccn2)c1]

The title compound was prepared in 20% yield (three steps) from 2-(1-{2-[2-(dimethylamino)ethoxy]ethyl}-1H-imidazol-4-yl)pyridine-4-carbonitrile according to the procedure for the preparation of Example 1. $^1$H NMR (400 MHz, DMSO-$d_6$): δ 2.16 (6H, s), 2.37 (2H, t, J=5.9 Hz), 3.48 (2H, t, J=5.9 Hz), 3.70 (2H, t, J=5.1 Hz), 4.16 (2H, t, J=5.2 Hz), 7.44 (1H, d, J=4.6 Hz), 7.68 (1H, s), 7.70 (1H, s), 8.20 (1H, s), 8.36 (1H, d, J=4.8 Hz). [M+H] Calc'd for $C_{15}H_{20}N_4O_3$, 305. Found, 305.

Example 49

2-[1-(1-methylpiperidin-4-yl)-1H-imidazol-4-yl]pyridine-4-carboxylic acid

A. 2-[1-(1-methylpiperidin-4-yl)-1H-imidazol-4-yl]pyridine-4-carbonitrile

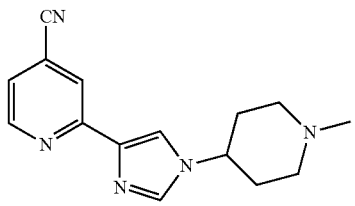 [SMILES: CN1CCC(n2cnc(-c3cc(C#N)ccn3)c2)CC1]

The title compound was prepared from 2-(1H-imidazol-4-yl)pyridine-4-carbonitrile and 4-chloro-1-methylpiperidine according to the procedure for the preparation of Example 43, part A. [M+H] Calc'd for $C_{15}H_{17}N_5$, 268. Found, 268.

B. 2-[1-(1-methylpiperidin-4-yl)-1H-imidazol-4-yl]pyridine-4-carboxylic acid

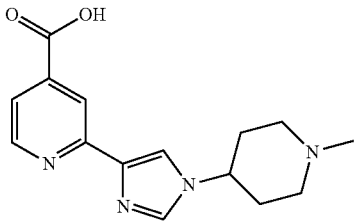 [SMILES: CN1CCC(n2cnc(-c3cc(C(=O)O)ccn3)c2)CC1]

The title compound was prepared in 14% yield (two steps) from 2-[1-(1-methylpiperidin-4-yl)-1H-imidazol-4-yl]pyridine-4-carbonitrile according to the procedure for the preparation of Example 1. $^1$H NMR (400 MHz, DMSO-$d_6$): δ 1.91-2.08 (4H, m), 2.20 (3H, s), 2.59 (2H, m), 2.85 (2H, m), 4.06 (1H, m), 7.44 (1H, dd, J=4.8 Hz), 7.73 (1H, s), 7.80 (1H, s), 8.20 (1H, s), 8.36 (1H, d, J=4.9 Hz). [M+H] Calc'd for $C_{15}H_{18}N_4O_2$, 287. Found, 287.

Example 50

2-{1-[(1-methylpiperidin-4-yl)methyl]-1H-imidazol-4-yl}pyridine-4-carboxylic acid A. 2-{1-[(1-methylpiperidin-4-yl)methyl]-1H-imidazol-4-yl}pyridine-4-carbonitrile

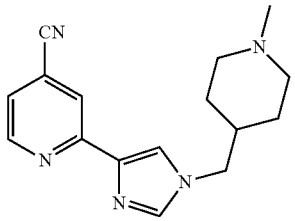 [SMILES: CN1CCC(Cn2cnc(-c3cc(C#N)ccn3)c2)CC1]

The title compound was prepared from 2-(1H-imidazol-4-yl)pyridine-4-carbonitrile and 4-bromomethyl-1-methylpiperidine hydrogen bromide according to the procedure for the preparation of Example 43, part A (heating to 120°). [M+H] Calc'd for $C_{16}H_{19}N_5$, 282. Found, 282.

B. 2-{1-[(1-methylpiperidin-4-yl)methyl]-1H-imidazol-4-yl}pyridine-4-carboxylic acid

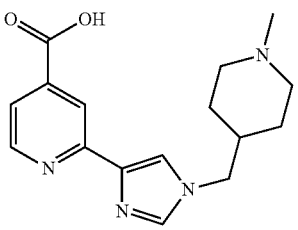 [SMILES: CN1CCC(Cn2cnc(-c3cc(C(=O)O)ccn3)c2)CC1]

The title compound was prepared in 28% yield (two steps) from 2-{1-[(1-methylpiperidin-4-yl)methyl]-1H-imidazol-4-yl}pyridine-4-carbonitrile according to the procedure for the preparation of Example 1. $^1$H NMR (400 MHz, DMSO-$d_6$): δ 1.81 (2H, m), 1.92 (2H, m), 2.07 (2H, m), 2.21 (3H, s), 2.37 (1H, m), 2.54 (2H, m), 3.98 (2H, t, J=7.1 Hz), 7.45 (1H, dd, J=1.4 Hz and 4.9 Hz), 7.69 (1H, s), 7.71 (1H, s), 8.21 (1H, s), 8.37 (1H, d, J=4.9 Hz). [M+H] Calc'd for $C_{16}H_{20}N_4O_2$, 301. Found, 301.

Example 51

2-[1-(tetrahydrofuran-2-ylmethyl)-1H-imidazol-4-yl]pyridine-4-carboxylic acid

A. 2-[1-(tetrahydrofuran-2-ylmethyl)-1H-imidazol-4-yl]pyridine-4-carbonitrile

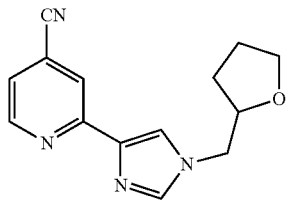 [SMILES: N#Cc1ccnc(-c2cn(CC3CCCO3)cn2)c1]

The title compound was prepared from 2-(1H-imidazol-4-yl)pyridine-4-carbonitrile and tetrahydrofurfuryl bromide according to the procedure for the preparation of Example 43, part A (heating to 120°). [M+H] Calc'd for $C_{14}H_{14}N_4O$, 255. Found, 255.

B. 2-[1-(tetrahydrofuran-2-ylmethyl)-1H-imidazol-4-yl]pyridine-4-carboxylic acid

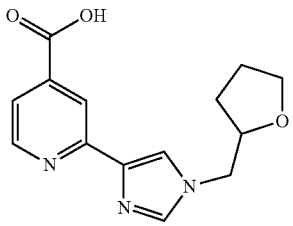 [SMILES: O=C(O)c1ccnc(-c2cn(CC3CCCO3)cn2)c1]

The title compound was prepared in 27% yield (two steps) from 2-[1-(tetrahydrofuran-2-ylmethyl)-1H-imidazol-4-yl]pyridine-4-carbonitrile according to the procedure for the preparation of Example 1. $^1$H NMR (400 MHz, DMSO-$d_6$): δ 1.53 (1H, m), 1.57 (2H, m), 1.92 (1H, m), 3.66 (1H, m), 3.79 (1H, m), 4.00 (1H, m), 4.10 (2H, m), 7.41 (1H, d, J=4.1 Hz), 7.69 (1H, s), 7.71 (1H, s), 8.25 (1H, s), 8.44 (1H, d, J=4.2 Hz). [M+H] Calc'd for $C_{14}H_{15}N_3O_3$, 274. Found, 274.

Example 52

2-[1-(pyrrolidin-3-yl)-1H-imidazol-4-yl]pyridine-4-carboxylic acid

A. tert-butyl 3-[4-(4-cyanopyridin-2-yl)-1H-imidazol-1-yl]pyrrolidine-1-carboxylate

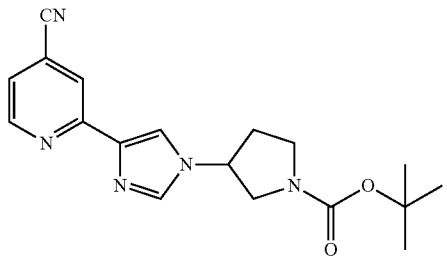 [SMILES: CC(C)(C)OC(=O)N1CCC(n2cnc(-c3cc(C#N)ccn3)c2)C1]

The title compound was prepared from 2-(1H-imidazol-4-yl)pyridine-4-carbonitrile and 1-boc-3-bromopyrrolidine according to the procedure for the preparation of Example 43, part A (heating to 120°). [M+H] Calc'd for $C_{18}H_{21}N_5O_2$, 340. Found, 340.

B. 2-[1-(pyrrolidin-3-yl)-1H-imidazol-4-yl]pyridine-4-carboxylic acid

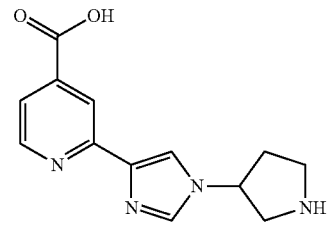 [SMILES: O=C(O)c1ccnc(-c2cn(C3CCNC3)cn2)c1]

The above obtained cpd (tert-butyl 3-[4-(4-cyanopyridin-2-yl)-1H-imidazol-1-yl]pyrrolidine-1-carboxylate) was first treated with 10N NaOH/EtOH (0.5 mL/2 mL) at 90° C. for 1 hr to give the acid intermediate. After purification on ISCO flash column chromatography (MeOH/DCM=0-100%), the product was dissolved in MeOH and treated with HCl in dioxane to give the title cpd which after purification on flash column as light pink solid (5 mg, 16% in two steps). $^1$H NMR (400 MHz, DMSO-$d_6$): δ 3.35 (2H, m), 3.47 (2H, m), 3.72 (2H, m), 5.10 (1H, m), 7.76 (1H, d, J=4.1 Hz), 8.36 (1H, s), 8.46 (1H, br s), 8.78 (1H, d, J=4.8 Hz), 9.51 (1H, br s). [M+H] Calc'd for $C_{13}H_{14}N_4O_2$, 259. Found, 259.

Example 53

2-[1-(pyrrolidin-2-ylmethyl)-1H-imidazol-4-yl]pyridine-4-carboxylic acid

A. tert-butyl 2-{[4-(4-cyanopyridin-2-yl)-1H-imidazol-1-yl]methyl}pyrrolidine-1-carboxylate

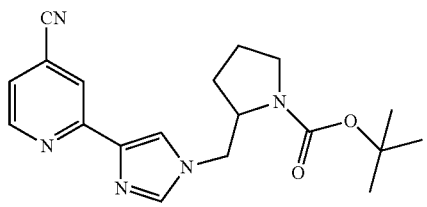 [SMILES: CC(C)(C)OC(=O)N1CCCC1Cn1cnc(-c2cc(C#N)ccn2)c1]

The title compound was prepared from 2-(1H-imidazol-4-yl)pyridine-4-carbonitrile and tert-butyl-2-(bromomethyl)pyrrolidine-1-carboxylate according to the procedure for the preparation of Example 43, part A (heating to 120°). [M+H] Calc'd for $C_{19}H_{23}N_5O_2$, 354. Found, 354.

B. 2-[1-(pyrrolidin-2-ylmethyl)-1H-imidazol-4-yl]pyridine-4-carboxylic acid

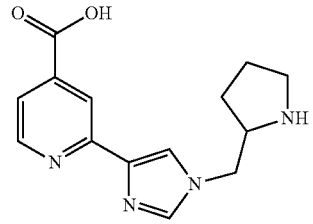 [SMILES: O=C(O)c1ccnc(-c2cn(CC3CCCN3)cn2)c1]

The title compound was prepared in 49% yield from tert-butyl 2-{[4-(4-cyanopyridin-2-yl)-1H-imidazol-1-yl]methyl}pyrrolidine-1-carboxylate according to the procedure for the preparation of Example 52, part B. ¹H NMR (400 MHz, DMSO-d₆): δ 1.81 (2H, m), 1.92 (2H, m), 2.07 (2H, m), 2.21 (3H, s), 2.37 (1H, m), 2.54 (2H, m), 3.98 (2H, t, J=7.1 Hz), 7.86 (1H, d, J=5.0 Hz), 8.39 (1H, s), 8.61 (1H, s), 8.86 (1H, d, J=5.0 Hz), 9.20 (1H, br s), 9.73 (1H, br s), 10.04 (1H, br s). [M+H] Calc'd for $C_{14}H_{16}N_4O_2$, 273. Found, 273.

Example 54

2-{1-[(4-methylmorpholin-2-yl)methyl]-1H-imidazol-4-yl}pyridine-4-carboxylic acid A. 2-{1-[(4-methylmorpholin-2-yl)methyl]-1H-imidazol-4-yl}pyridine-4-carbonitrile

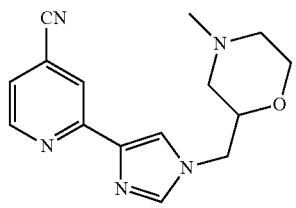 [SMILES: CN1CCOC(Cn2cnc(-c3cc(C#N)ccn3)c2)C1]

The title compound was prepared from 2-(1H-imidazol-4-yl)pyridine-4-carbonitrile and 2-(chloromethyl)-4-methylmorpholine according to the procedure for the preparation of Example 43, part A (heating to 120°). [M+H] Calc'd for $C_{15}H_{17}N_5O$, 284. Found, 284.

B. 2-{1-[(4-methylmorpholin-2-yl)methyl]-1H-imidazol-4-yl}pyridine-4-carboxylic acid

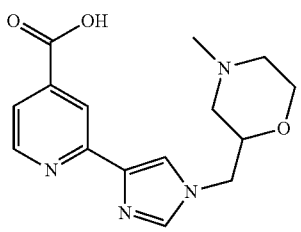 [SMILES: CN1CCOC(Cn2cnc(-c3cc(C(=O)O)ccn3)c2)C1]

The title compound was prepared in 47% yield (two steps) from 2-{1-[(4-methylmorpholin-2-yl)methyl]-1H-imidazol-4-yl}pyridine-4-carbonitrile according to the procedure for the preparation of Example 1. ¹H NMR (400 MHz, DMSO-d₆): δ 1.69 (1H, t, J=10.6 Hz), 1.95 (1H, dt, J=3.2 Hz and 11.3 Hz), 2.55 (1H, m), 2.66 (1H, d, J=11.0 Hz), 3.45 (3H, s), 3.48 (1H, dt, J=2.2 Hz and 11.1 Hz), 3.73 (1H, m), 3.80 (1H, d, J=10.6 Hz), 4.02 (2H, m), 7.46 (1H, dd, J=1.4 Hz and 4.9 Hz), 7.65 (2H, s), 8.21 (1H, s), 8.37 (1H, d, J=4.9 Hz). [M+H] Calc'd for $C_{15}H_{18}N_4O_3$, 303. Found, 303.

Example 55

2-{1-[(1-methylpiperidin-3-yl)methyl]-1H-imidazol-4-yl}pyridine-4-carboxylic acid A. 2-{1-[(1-methylpiperidin-3-yl)methyl]-1H-imidazol-4-yl}pyridine-4-carbonitrile

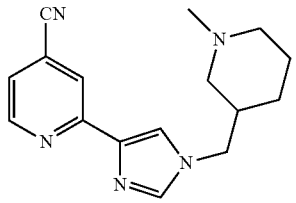 [SMILES: CN1CCCC(Cn2cnc(-c3cc(C#N)ccn3)c2)C1]

The title compound was prepared from 2-(1H-imidazol-4-yl)pyridine-4-carbonitrile and 3-chloromethyl-methyl piperidine according to the procedure for the preparation of Example 43, part A (heating to 120°). [M+H] Calc'd for $C_{16}H_{19}N_5$, 282. Found, 282.

B. 2-{1-[(1-methylpiperidin-3-yl)methyl]-1H-imidazol-4-yl}pyridine-4-carboxylic acid

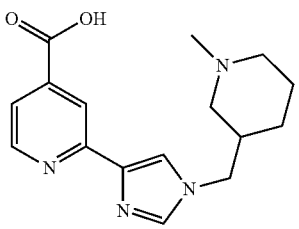 [SMILES: CN1CCCC(Cn2cnc(-c3cc(C(=O)O)ccn3)c2)C1]

The title compound was prepared in 42% yield (two steps) from 2-{1-[(1-methylpiperidin-3-yl)methyl]-1H-imidazol-4-yl}pyridine-4-carbonitrile according to the procedure for the preparation of Example 1. ¹H NMR (400 MHz, DMSO-d₆): δ 0.92 (1H, m), 1.40-1.88 (5H, m), 1.91 (1H, m), 1.96 (1H, m), 2.11 (1H, m), 2.16 (3H, s), 3.92 (2H, d, J=7.3 Hz), 7.46 (1H, dd, J=1.4 Hz and 4.9 Hz), 7.65 (1H, d, J=1.1 Hz), 7.67 (1H, d, J=1.1 Hz), 8.22 (1H, s), 8.37 (1H, d, J=4.9 Hz). [M+H] Calc'd for $C_{16}H_{20}N_4O_2$, 301. Found, 301.

Example 56 methyl 2-(1-{2-[benzyl(methyl)amino]ethyl}-1H-imidazol-4-yl)pyridine-4-carboxylate methyl 2-(1-{2-[(methylsulfonyl)oxy]ethyl}-1H-imidazol-4-yl)pyridine-4-carboxylate A. 5-bromo-1H-imidazole

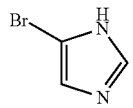

To a solution of imidazole (30 g, 0.44 mol) in chloroform (180 mL) was added bromine (69 g, 500 mmol) in chloroform (50 mL) dropwise at room temperature. Then the mixture was stirred for 1 h. The mixture was filtered and the solids suspended in water and stirred for 30 min. The suspension was filtered and the beige solid was dried to give 22 g of an off white solid.

B. 1,1',1"-[(2-bromoethoxy)methanetriyl]tribenzene

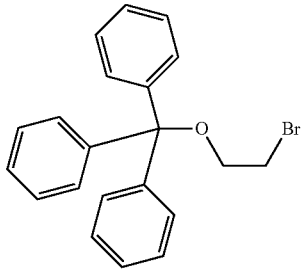 [SMILES: BrCCOC(c1ccccc1)(c1ccccc1)c1ccccc1]

2-Bromo-ethanol (6.3 g, 5.0 mmol), Et$_3$N (10 mL, 72 mmol) and trityl chloride (14.6 g, 52.5 mmol) in anhydrous CH$_2$Cl$_2$ (50 mL) was stirred at room temperature overnight and concentrated in vacuo. The residue was purified by column chromatography on silica gel (hexane/EtOAc, 4:1) to give the title product (12 g).

C. 4-bromo-1-[2-(trityloxy)ethyl]-1H-imidazole

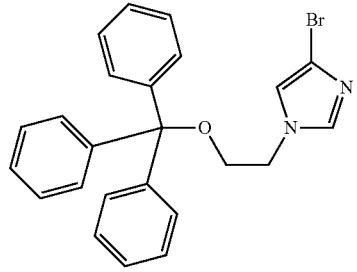 [SMILES: Brc1cn(CCOC(c2ccccc2)(c2ccccc2)c2ccccc2)cn1]

To a solution of 5-bromo-1H-imidazole as prepared in part A (2.2 g, 15 mmol) in DMF (22 mL) at 0° C. was added NaH (658 mg, 60% dispersion, 2.42 mmol) in small portions. The resulting solution was allowed to warm to r.t. and then stirred for 1 hr. The solution was cooled to 0° C. and 1,1',1"-[(2-bromoethoxy)methanetriyl]tribenzene (5.5 g, 15 mmol) in DMF (10 mL) was added drop-wise. The resulting solution was allowed to warm to r.t. where stirring continued until the reaction was judged complete by TLC (16 hr). The suspension was diluted with water and extracted with DCM (2×50 mL). The organics were dried (MgSO4), filtered, and concentrated to a solid that was recrystallized (EtOAc/Hex) to give 4.47 g of the title compound (69%).

D. 4-tri-n-butyltin-1-[2-(trityloxy)ethyl]-1H-imidazole

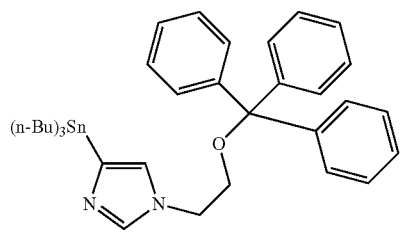

Bis(tributyltin) (13.93 g, 24 mmol), triphenylphosphine (314 mg, 1.2 mmol), sodium carbonate (1.27 g, 12 mmol), and palladium acetate (134 mg, 0.6 mmol) were added to a solution of 4-bromo-[2-(trityloxy)ethyl]-1H-imidazole (5.2 g, 12 mmol) in DMF/Toluene (1:1, 50 mL). The suspension was degassed with argon for 10 minutes and then heated to 100° C. in a sealed glass vessel for 15 hrs. The dark green solution was cooled to r.t. and filtered through a pad of celite; washing with EtOAc. The filtrate was diluted with water (100 mL) and extracted with EtOAc (2×100 mL). The organics were washed with water (2×100 mL), dried (MgSO4), filtered, concentrated, and chromatographed on silica gel (EtOAc:Hex, 1:1) to give the title compound (5.2 g) as a thick oil. $^1$HNMR (400 MHz, CDCl$_3$): δ 0.9-1.7 (27H, m), 3.34 (2H, t, J=5 Hz), 4.08 (2H, t, J=5 Hz), 7.19-7.31 (15H, m).

E. methyl 2-{1-[2-(trityl)oxy)ethyl]-1H-imidazol-4-yl}pyridine-4-carboxylate

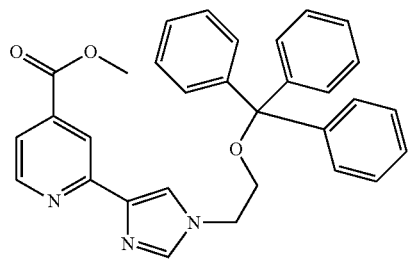 [SMILES: COC(=O)c1ccnc(-c2cn(CCOC(c3ccccc3)(c3ccccc3)c3ccccc3)cn2)c1]

To a solution of methyl 2-chloro-4-pyridinecarboxylate (934 mg, 5.43 mmol) and 4-tri-n-butyltin-1-[2-(trityloxy)ethyl]-1H-imidazole (3.5 g, 5.43 mmol) in toluene (30 mL) was added tetrakis(triphenylphosphine)palladium(O) (314 mg, 0.27 mmol). The solution was degassed with argon for 5 minutes and sealed in a high pressure glass tube equipped with a stir bar. The tube was immersed in a preheated oil bath (115° C.). The solution was stirred for 7 hrs and cooled to r.t. The solvent was evaporated and the residue was chromatographed on silica gel (EtOAc:Hex, 1:1) to give the title compound (2.07 g) as a thick oil which crystallized to a white solid on standing at r.t.

F. methyl 2-[1-(2-hydroxyethyl)-1H-imidazol-4-yl]pyridine-4-carboxylate

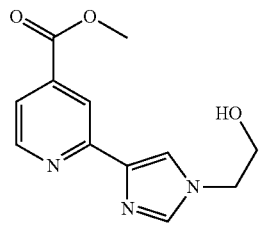 [SMILES: COC(=O)c1ccnc(-c2cn(CCO)cn2)c1]

To a solution of methyl 2-{1-[2-(trityl)oxy)ethyl]-1H-imidazol-4-yl}pyridine-4-carboxylate (2 g, 4.1 mmol) in MeOH (10 mL) was added 2N HCl (10 mL). The solution was stirred at r.t. for 3 hrs, diluted with water (100 mL), and extracted with EtOAc (2×50 mL). The organics were washed with NaHCO$_3$ (5% solution, 50 mL), and brine (50 mL). The organics were then dried (MgSO4), filtered and concentrated to a white solid which was triturated with ether/hexanes (10:90) to give the title compound (700 mg).

G. methyl 2-(1-{2-[(methylsulfonyl)oxy]ethyl}-1H-imidazol-4-yl)pyridine-4-carboxylate

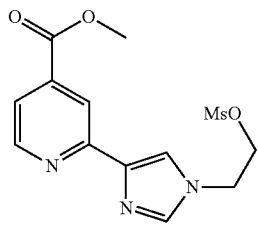 [SMILES: COC(=O)c1ccnc(-c2cn(CCOS(C)(=O)=O)cn2)c1]

To a 0° C. solution of methyl 2-[1-(2-hydroxyethyl)-1H-imidazol-4-yl]pyridine-4-carboxylate (500 mg, 2 mmol) in DCM (10 mL) was added TEA (255 mg, 2.5 mmol) followed by drop-wise addition of a solution of methanesulfonyl chloride (255 mg, 2.22 mmol) in DCM (2 mL). The solution was stirred at 0° C. for 1 hr and then allowed to warm to r.t. where stirring was continued for 1 hr. MeOH (1 mL) was then added and stirring was continued for 30 min. The solution was diluted with DCM (50 mL), washed with water (50 mL), dried (MgSO4), filtered, and concentrated to give the title compound as an oily residue (649 mg).

H. methyl 2-(1-{2-[benzyl(methyl)amino]ethyl}-1H-imidazol-4-yl)pyridine-4-carboxylate

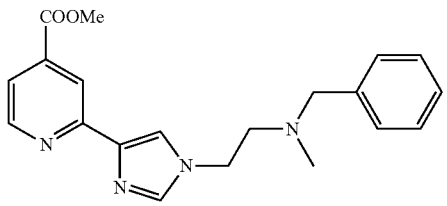 [SMILES: COC(=O)c1ccnc(-c2cn(CCN(C)Cc3ccccc3)cn2)c1]

A solution of methyl 2-(1-{2-[(methylsulfonyl)oxy]ethyl}-1H-imidazol-4-yl)pyridine-4-carboxylate (150 mg, 0.46 mmol) and N-methylbenzylamine (558 mg, 4.6 mmol) in toluene (8 mL) was heated at 110° C. in a sealed tube for 7 hrs. The solution was concentrated to an oily residue and chromatographed on silica gel (EtOAc/Hex, 1:1) to give the title compound (118 mg) as an amber oil: $^1$HNMR (400 MHz, CDCl$_3$): δ 2.28 (3H, s), 2.78 (2H, t, J=4.2 Hz), 3.61 (2H, s), 3.94 (3H, s), 4.03 (2H, t, J=4.2 Hz), 7.19-7.27 (5H, m), 7.58 (1H, s), 7.61 (1H, s), 7.64 (1H, m), 8.47 (1H, s), 8.63 (1H, m). [M+H] Calc'd for C$_{20}$H$_{22}$N$_4$O$_2$, 351. Found, 351.

Example 57

2-(1-{2-[benzyl(methyl)amino]ethyl}-1H-imidazol-4-yl)pyridine-4-carboxylic acid

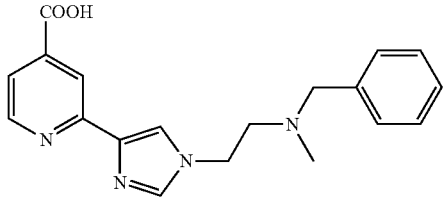 [SMILES: CN(CCn1cnc(-c2cc(C(=O)O)ccn2)c1)Cc1ccccc1]

To a solution of methyl 2-(1-{2-[benzyl(methyl)amino]ethyl}-1H-imidazol-4-yl)pyridine-4-carboxylate (100 mg, 0.26 mmol) in MeOH (5 mL) was added 10 N NaOH solution (1 g). The mixture was stirred and refluxed for 1 hr and then cooled to r.t. The pH was carefully adjusted to 6.5 and the resulting mixture was concentrated to a residue. The residue was diluted with MeOH (10 mL) and filtered. The solids were washed with additional MeOH (10 mL). The filtrate was concentrated to an oily residue and chromatographed on silica gel (90% MeOH, 10% pH 7 buffer [potassium phosphate based] to give an amber oil. This oil was then chromatographed on reverse phase C18 silica gel [40-63 microns (mesh 230-400); 60 Å; 500 m2/g; pore volume 0.8 ml/g] using 80% MeOH/10% DI H2O to give the title compound (28 mg) as a beige solid: $^1$HNMR (400 MHz, DMSO): δ 2.18 (3H, s), 2.69 (2H, m), 3.51 (2H, m), 4.18 (2H, m), 7.17-7.23 (5H, m), 7.58 (1H, s), 7.73 (2H, m), 8.34 (1H, s), 8.54 (1H, s). [M+H] Calc'd for C$_{19}$H$_{20}$N$_4$O$_2$, 337. Found, 337.

Example 58

2-(1-{2-[methyl(phenyl)amino]ethyl}-1H-imidazol-4-yl)pyridine-4-carboxylic acid

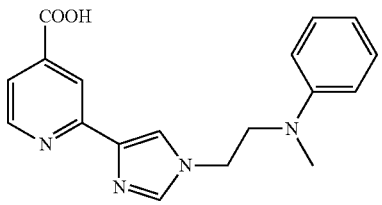 [SMILES: CN(CCn1cnc(-c2cc(C(=O)O)ccn2)c1)c1ccccc1]

A solution of methyl 2-(1-{2-[(methylsulfonyl)oxy]ethyl}-1H-imidazol-4-yl)pyridine-4-carboxylate (100 mg, 0.31 mmol) and N-methylaniline (328 mg, 3.1 mmol) in toluene (5 mL) was heated at 110° C. in a sealed tube for 36 hrs. The solution was concentrated to an oily residue which was dissolved in MeOH (5 mL). To this solution was added 10 N NaOH solution (1 g). The mixture was stirred and refluxed for 1 hr and then cooled to RT. The pH was carefully adjusted to 7 whereupon a precipitate formed. The solid was filtered and dried to give the title compound (41 mg) as an off white solid: $^1$HNMR (400 MHz, CD$_3$OD): δ 2.79 (3H, s), 3.64 (2H, t, J=4.4 Hz), 4.21 (2H, t, J=4.4 Hz), 6.62 (1H, m), 6.68 (2H, m), 7.18 (2H, m), 7.57 (1H, m), 7.66 (1H, s), 7.84 (1H, s), 8.23 (1H, s), 8.63 (1H, m). [M+H] Calc'd for C$_{18}$H$_{18}$N$_4$O$_2$, 323. Found, 323.

Example 59

2-(1-{2-[(cyclopropylmethyl)(methyl)amino]ethyl}-1H-imidazol-4-yl)pyridine-4-carboxylic acid

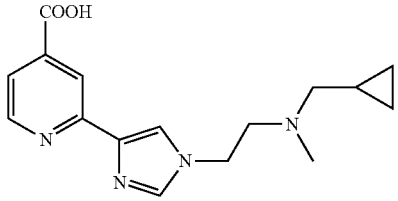 [SMILES: CN(CCn1cnc(-c2cc(C(=O)O)ccn2)c1)CC1CC1]

A solution of methyl 2-(1-{2-[(methylsulfonyl)oxy]ethyl}-1H-imidazol-4-yl)pyridine-4-carboxylate (100 mg, 0.31 mmol) and cyclopropylmethyl(methyl)amine (260 mg, 3.1 mmol) in toluene (5 mL) was heated at 110° C. in a sealed tube for 24 hrs. The solution was concentrated to an oily residue which was dissolved in MeOH (5 mL). To this solution was added 10 N NaOH solution (1 g). The mixture was stirred and refluxed for 1 hr and then cooled to RT. The pH was carefully adjusted to 6.5 and the resulting mixture was concentrated to a residue. The residue was diluted with MeOH (10 mL) and filtered. The solids were washed with additional MeOH (10 mL). The filtrate was concentrated to an oily residue and chromatographed on silica gel (90% MeOH, 10% pH 7 buffer [potassium phosphate based] to give a foam. The foam was then chromatographed on reverse phase C18 silica gel [40-63 microns (mesh 230-400); 60 Å; 500 m2/g; pore volume 0.8 ml/g] using 80% MeOH/10% DI H$_2$O to give the title compound (32 mg) as a beige solid: $^1$HNMR (400 MHz, CD$_3$OD): δ 0.29 (2H, s), 0.73 (2H, s), 1.05 (1H, m), 2.77 (5H, m), 3.51 (2H, t, J=4.2 Hz), 4.45 (2H, t, J=4.2 Hz), 7.79 (1H, s), 7.92 (2H, m), 8.43 (1H, s), 8.64 (1H, s). [M+H] Calc'd for C$_{16}$H$_{20}$N$_4$O$_2$, 301. Found, 301.

Example 60

2-{1-[2-(2-oxopyrrolidin-1-yl)ethyl]-1H-imidazol-4-yl}pyridine-4-carboxylic acid A. 2-{1-[2-(2-oxopyrrolidin-1-yl)ethyl]-1H-imidazol-4-yl}pyridine-4-carbonitrile

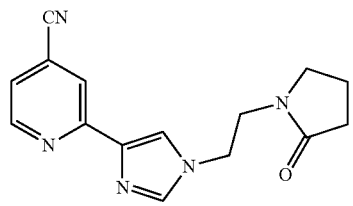 [SMILES: N#Cc1ccnc(-c2cn(CCN3CCCC3=O)cn2)c1]

The title compound was prepared from 2-(1H-imidazol-4-yl)pyridine-4-carbonitrile and 1-(2-chloroethyl)-2-pyrrolidinone according to the procedure for the preparation of Example 43, part A (heating to 120°). [M+H] Calc'd for C$_{15}$H$_{15}$N$_5$O, 282. Found, 282.

B. 2-{1-[2-(2-oxopyrrolidin-1-yl)ethyl]-1H-imidazol-4-yl}pyridine-4-carboxylic acid

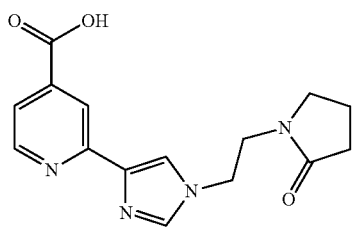 [SMILES: O=C(O)c1ccnc(-c2cn(CCN3CCCC3=O)cn2)c1]

The title compound was prepared in 58% yield (two steps) from 2-{1-[2-(2-oxopyrrolidin-1-yl)ethyl]-1H-imidazol-4-yl}pyridine-4-carbonitrile according to the procedure for the preparation of Example 1. $^1$H NMR (400 MHz, DMSO-d$_6$): δ 2.16 (2H, t, J=7.9 Hz), 2.78 (2H, t, J=6.4 Hz), 3.19 (2H, t, J=7.0 Hz), 3.56 (2H, t, J=5.6 Hz), 4.15 (2H, t, J=5.7 Hz), 7.48 (1H, dd, J=1.3 Hz and 4.9 Hz), 7.69 (1H, d, J=0.9 Hz), 7.73 (1H, s), 8.23 (1H, s), 8.42 (1H, d, J=4.9 Hz). [M+H] Calc'd for C$_{15}$H$_{16}$N$_4$O$_3$, 301. Found, 301.

Example 61

2-{1-[2-(pyrrolidin-1-yl)propyl]-1H-imidazol-4-yl}pyridine-4-carboxylic acid

A. 2-{1-[2-(pyrrolidin-1-yl)propyl]-1H-imidazol-4-yl}pyridine-4-carbonitrile

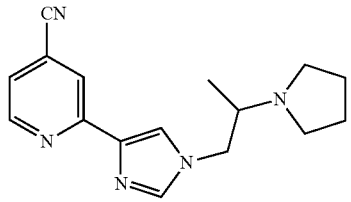 [SMILES: CC(Cn1cnc(-c2cc(C#N)ccn2)c1)N1CCCC1]

The title compound was prepared from 2-(1H-imidazol-4-yl)pyridine-4-carbonitrile and 1-(2-chloro-1-methylethyl) pyrrolidine hydrogen chloride according to the procedure for the preparation of Example 43, part A (heating to 120°). [M+H] Calc'd for C$_{16}$H$_{19}$N$_5$, 282. Found, 282.

B. 2-{1-[2-(pyrrolidin-1-yl)propyl]-1H-imidazol-4-yl}pyridine-4-carboxylic acid

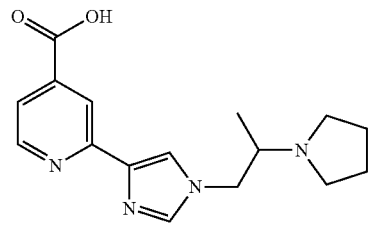 [SMILES: CC(Cn1cnc(-c2cc(C(=O)O)ccn2)c1)N1CCCC1]

The title compound was prepared in 69% yield (two steps) from 2-{1-[2-(pyrrolidin-1-yl)propyl]-1H-imidazol-4-yl}pyridine-4-carbonitrile according to the procedure for the preparation of Example 1. $^1$H NMR (400 MHz, DMSO-d$_6$): δ 0.93 (3H, d, J=6.4 Hz), 1.67 (4H, m), 2.59 (4H, m), 2.79 (1H, m), 4.01 (1H, dd, J=6.0 Hz and 6.1 Hz), 4.13 (1H, dd, J=5.1 Hz and 5.1 Hz), 7.52 (1H, dd, J=1.3 Hz and 4.9 Hz), 7.71 (1H, s), 7.72 (1H, s), 8.26 (1H, s), 8.51 (1H, d, J=4.9 Hz). [M+H] Calc'd for C$_{16}$H$_{20}$N$_4$O$_2$, 301. Found, 301.

Example 62

2-(1-methyl-1H-imidazol-4-yl)-4-(2H-tetrazol-5-yl)pyridine

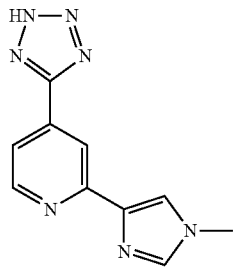 [SMILES: Cn1cnc(-c2cc(-c3nn[nH]n3)ccn2)c1]

To a solution of 2-(1-methyl-1H-imidazol-4-yl)pyridine-4-carbonitrile (50 mg, 0.36 mmol) in 2 mL of DMF was added sodium azide (65 mg, 1 mmol) and ammonium chloride (54 mg, 1 mmol). The reaction mixture was heated at 90° C. for 20 hrs with vigorous stirring. It was then purified by ISCO flash column chromatography (MeOH/DCM=0-100%) to give the title compound as light pink solid (45 mg, 73%). $^1$H NMR (400 MHz, DMSO-d$_6$): δ 3.73 (3H, s), 7.71 (1H, dd, J=1.5 Hz and 5.1 Hz), 7.74 (2H, s), 8.46 (1H, s), 8.51 (1H, d, J=5.0 Hz). [M+H] Calc'd for C$_{10}$H$_9$N$_7$, 228. Found, 228.

Example 63

2-{1-[2-(pyrrolidin-1-yl)ethyl]-1H-imidazol-4-yl}-4-(2H-tetrazol-5-yl)pyridine

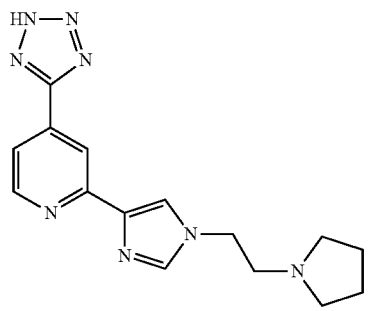 [SMILES: c1cc(-c2nn[nH]n2)cc(-c2cn(CCN3CCCC3)cn2)n1]

The title compound was prepared in 27% yield from 2-{1-[2-(pyrrolidin-1-yl)ethyl]-1H-imidazol-4-yl}pyridine-4-carbonitrile (Example 43, part A) according to the procedure in Example 62. $^1$H NMR (400 MHz, DMSO-d$_6$): δ 1.72 (4H, m), 2.55 (4H, m), 2.93 (2H, m), 4.18 (2H, t, J=5.4 Hz), 7.68 (1H, dd, J=1.6 Hz and 4.9 Hz), 7.77 (1H, s), 7.79 (1H, s), 8.44 (1H, d, J=5.1 Hz), 8.45 (1H, s). [M+H] Calc'd for C$_{15}$H$_{18}$N$_8$, 311. Found, 311.

Example 64

N-cyano-2-(1-{2-[(cyclopropylmethyl)(methyl)amino]ethyl}-1H-imidazol-4-yl)pyridine-4-carboxamide

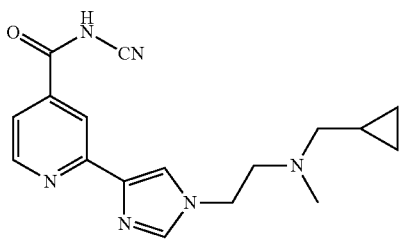 [SMILES: CN(CCn1cnc(-c2cc(C(=O)NC#N)ccn2)c1)CC1CC1]

A mixture of 2-(1-{2-[(cyclopropylmethyl)(methyl)amino]ethyl}-1H-imidazol-4-yl)pyridine-4-carboxylic acid (10 mg, 0.03 mmol, Example 59), cyanamide (4 mg, 0.1 mmol), HATU (38 mg, 0.1 mmol), TEA (29 µL, 0.2 mmol) in DMF (2 mL) was stirred at r.t. for 1 hr. The reaction mixture was purified by ISCO flash column chromatography (MeOH/DCM=0-50%) to give the title compound as off-white solid (6 mg, 60%). $^1$HNMR (400 MHz, DMSO-d$_6$): δ 0.43 (2H, m), 0.79 (2H, m), 1.15 (1H, m), 2.30 (5H, m), 2.76 (2H, m), 4.11 (2H, t, J=4.2 Hz), 7.29 (1H, m), 7.73 (1H, d, J=11.4 Hz), 8.27 (1H, s), 8.29 (1H, s), 8.49 (1H, s). [M+H] Calc'd for C$_{17}$H$_{20}$N$_6$O, 325. Found, 325.

Example 65

N-benzyl-2-fluoro-5-[3-methyl-5-[4-(2H-tetrazol-5-yl)pyridin-2-yl]imidazol-4-yl]benzamide A. N-benzyl-5-[5-(4-cyanopyridin-2-yl)-3-methylimidazol-4-yl]-2-fluorobenzamide

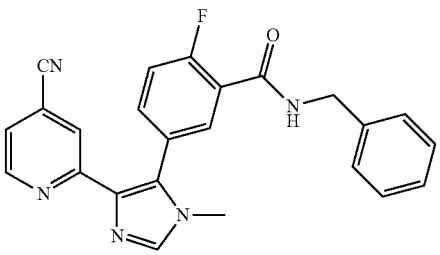 [SMILES: Cn1cnc(-c2cc(C#N)ccn2)c1-c1ccc(F)c(C(=O)NCc2ccccc2)c1]

The title compound was prepared from 2-(5-bromo-1-methyl-1H-imidazol-4-yl)pyridine-4-carbonitrile (PREPARATION 2) and 3-(benzylcarbamoyl)-4-fluorophenyl boronic acid according to the procedure for the preparation of Example 3, part A. [M+H] Calc'd for C$_{24}$H$_{18}$FN$_5$O, 412. Found, 412.

B. N-benzyl-2-fluoro-5-[3-methyl-5-[4-(2H-tetrazol-5-yl)pyridin-2-yl]imidazol-4-yl]benzamide

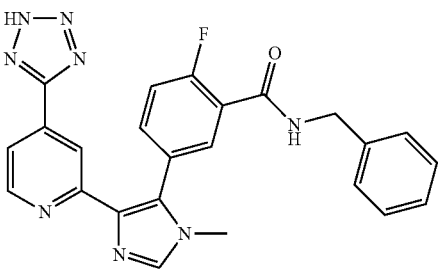 [SMILES: Cn1cnc(-c2cc(-c3nn[nH]n3)ccn2)c1-c1ccc(F)c(C(=O)NCc2ccccc2)c1]

The title compound was prepared in 9% yield (two steps) from N-benzyl-5-[5-(4-cyanopyridin-2-yl)-3-methylimidazol-4-yl]-2-fluorobenzamide according to the procedure for the preparation of Example 128, part C. $^1$H NMR (400 MHz, DMSO): 3.54 (3H, s), 4.47 (2H, d, J=5.8 Hz), 7.24 (1H, m), 7.32 (4H, d), 7.40 (1H, t, J=9.3 Hz), 7.64 (1H, m), 7.73 (2H, d, J=5.1 Hz), 8.00 (1H, s), 8.42 (1H, d, J=4.7 Hz), 8.54 (1H, s), 8.97 (1H, br s). [M+H] Calc'd for C$_{24}$H$_{19}$FN$_8$O, 455. Found, 455.

Example 66

2-[1-[2-[methyl-[(3-methylphenyl)methyl]amino]ethyl]imidazol-4-yl]pyridine-4-carboxylic acid

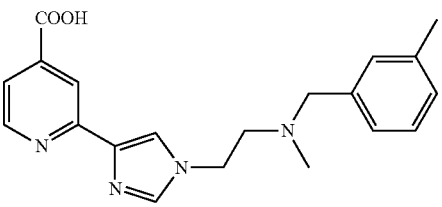 [SMILES: Cc1cccc(CN(C)CCn2cnc(-c3cc(C(=O)O)ccn3)c2)c1]

The title compound was prepared in 57% yield from methyl 2-(1-{2-[(methylsulfonyl)oxy]ethyl}-1H-imidazol-4-yl)pyridine-4-carboxylate (PREPARATION 6) and 3-methyl-N-methylbenzylamine according to the procedure for the preparation of Example 58. ¹HNMR (400 MHz, DMSO): δ 2.20 (3H, s), 2.29 (3H, s), 2.68 (2H, t, J=6 Hz), 3.85 (2H, s), 4.02 (1H, t, J=5.9 Hz), 4.15 (1H, t, J=6.0 Hz), 6.96 (1H, m), 7.11 (2H, t, J=9.0 Hz), 7.18-7.27 (2H, m), 7.51 (1H, d, J=3.6 Hz), 7.74 (1H, s), 8.28 (1H, s), 8.47 (1H, d, J=4.8 Hz). [M+H] Calc'd for $C_{20}H_{22}N_4O_2$, 351. Found, 351.

Example 67

2-[1-[2-[methyl-[(4-methylphenyl)methyl]amino]ethyl]imidazol-4-yl]pyridine-4-carboxylic acid

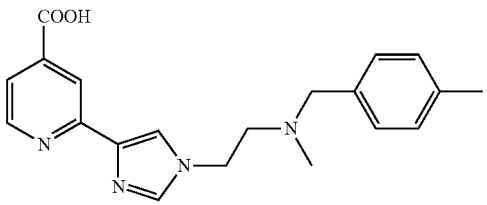 [SMILES: Cc1ccc(CN(C)CCn2cnc(-c3cc(C(=O)O)ccn3)c2)cc1]

The title compound was prepared in 71% yield from methyl 2-(1-{2-[(methylsulfonyl)oxy]ethyl}-1H-imidazol-4-yl)pyridine-4-carboxylate (PREPARATION 6) and 4-methyl-N-methylbenzylamine according to the procedure for the preparation of Example 58. ¹HNMR (400 MHz, DMSO): δ 2.33 (3H, s), 2.61 (3H, s), 2.69 (2H, t, J=6 Hz), 3.80 (2H, s), 4.00 (1H, t, J=5.7 Hz), 4.13 (1H, t, J=5.8 Hz), 7.23 (2H, t, J=8.9 Hz), 7.44 (1H, m), 7.51 (1H, d, J=6.9 Hz), 7.52 (1H, s), 7.73 (1H, d, J=5.1 Hz), 8.24 (1H, m), 8.35 (1H, s), 8.76 (1H, d, J=4.8 Hz). [M+H] Calc'd for $C_{20}H_{22}N_4O_2$, 351. Found, 351.

Example 68

2-[1-[2-[methyl-[[4-(trifluoromethyl)phenyl]methyl]amino]ethyl]imidazol-4-yl]pyridine-4-carboxylic acid

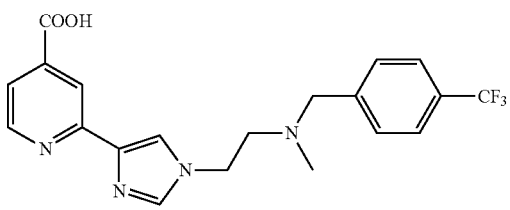 [SMILES: CN(CCn1cnc(-c2cc(C(=O)O)ccn2)c1)Cc1ccc(C(F)(F)F)cc1]

The title compound was prepared in 5% yield from methyl 2-(1-{2-[(methylsulfonyl)oxy]ethyl}-1H-imidazol-4-yl)pyridine-4-carboxylate (PREPARATION 6) and 4-trifluoromethyl-N-methylbenzylamine according to the procedure for the preparation of Example 58. ¹HNMR (400 MHz, DMSO): δ 2.22 (3H, s), 2.73 (2H, t, J=5.8 Hz), 3.62 (2H, s), 4.16 (2H, t, J=5.9 Hz), 7.12 (1H, m), 7.21 (1H, m), 7.38 (2H, d, J=7.8 Hz), 7.54 (2H, d, J=8.2 Hz), 7.75 (1H, s), 8.29 (1H, s), 8.54 (1H, d, J=4.8 Hz). [M+H] Calc'd for $C_{20}H_{19}F_3N_4O_2$, 405. Found, 405.

Example 69

2-[1-[2-[(3-fluorophenyl)methyl-methylamino]ethyl]imidazol-4-yl]pyridine-4-carboxylic acid

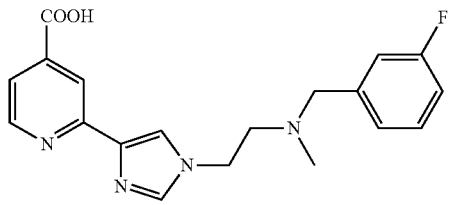 [SMILES: CN(CCn1cnc(-c2cc(C(=O)O)ccn2)c1)Cc1cccc(F)c1]

The title compound was prepared in 9% yield from methyl 2-(1-{2-[(methylsulfonyl)oxy]ethyl}-1H-imidazol-4-yl)pyridine-4-carboxylate (PREPARATION 6) and 3-fluoro-N-methylbenzylamine according to the procedure for the preparation of Example 58. ¹HNMR (400 MHz, DMSO): δ 2.20 (3H, s), 2.71 (2H, t, J=6.2 Hz), 4.02 (1H, t, J=5.8 Hz), 4.16 (2H, t, J=6.2 Hz), 4.39 (1H, t, J=5.9 Hz), 6.93 (1H, d, J=9.8 Hz), 7.00 (2H, d, J=7.8 Hz), 7.25 (1H, m), 7.57 (1H, m), 7.74 (1H, s), 7.79 (1H, d, J=4.2 Hz), 8.30 (1H, s), 8.59 (1H, m). [M+H] Calc'd for $C_{19}H_{19}FN_4O_2$, 355. Found, 355.

Example 70

2-[1-[2-[ethyl-[(4-fluorophenyl)methyl]amino]ethyl]imidazol-4-yl]pyridine-4-carboxylic acid

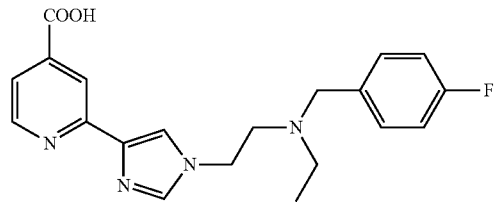 [SMILES: CCN(CCn1cnc(-c2cc(C(=O)O)ccn2)c1)Cc1ccc(F)cc1]

The title compound was prepared in 14% yield from methyl 2-(1-{2-[(methylsulfonyl)oxy]ethyl}-1H-imidazol-4-yl)pyridine-4-carboxylate (PREPARATION 6) and 4-fluoro-N-ethylbenzylamine according to the procedure for the preparation of Example 58. ¹HNMR (400 MHz, DMSO): δ 0.90 (3H, t, J=6.9 Hz), 2.74 (2H, t, J=6.4 Hz), 3.58 (2H, s), 4.08 (2H, t, J=5.9 Hz), 7.03 (2H, t, J=8.9 Hz), 7.23 (2H, dd, J=7.0 Hz and 2.6 Hz), 7.43 (1H, d, J=5.2 Hz), 7.66 (1H, d, J=4.4 Hz), 8.21 (1H, s), 8.35 (1H, d, J=4.5 Hz), 8.54 (1H, s). [M+H] Calc'd for $C_{20}H_{21}FN_4O_2$, 369. Found, 369.

Example 71

2-[1-[2-[cyclopropyl-[(4-fluorophenyl)methyl]amino]ethyl]imidazol-4-yl]pyridine-4-carboxylic acid

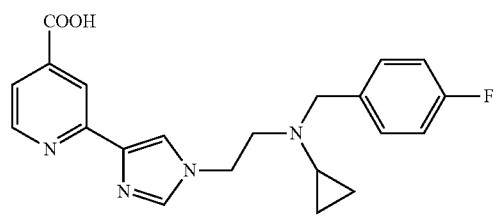 [SMILES: O=C(O)c1ccnc(-c2cn(CCN(Cc3ccc(F)cc3)C3CC3)cn2)c1]

The title compound was prepared in 9% yield from methyl 2-(1-{2-[(methylsulfonyl)oxy]ethyl}-1H-imidazol-4-yl)pyridine-4-carboxylate (PREPARATION 6) and N-[(4-fluorophenyl)methyl]cyclopropylamine according to the procedure for the preparation of Example 58. ¹HNMR (400 MHz, DMSO): δ 0.16 (2H, m), 0.39 (2H, m), 1.82 (1H, m), 2.87 (2H, t, J=6.4 Hz), 3.74 (2H, s), 4.10 (2H, t, J=6.2 Hz), 7.09 (2H, t, J=8.9 Hz), 7.28 (2H, dd, J=7.1 Hz and 2.7 Hz), 7.51 (1H, d, J=4.5 Hz), 7.67 (2H, d, J=1.6 Hz), 8.25 (1H, s), 8.47 (1H, d, J=4.8 Hz). [M+H] Calc'd for $C_{21}H_{21}FN_4O_2$, 381. Found, 381.

Example 72

2-[1-[2-[(4,4-difluorocyclohexyl)methylamino]ethyl]imidazol-4-yl]pyridine-4-carboxylic acid

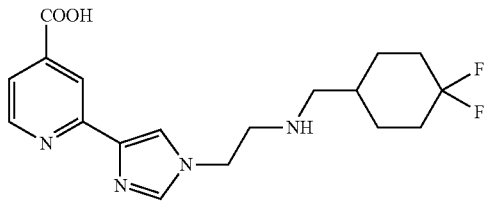 [SMILES: O=C(O)c1ccnc(-c2cn(CCNCC3CCC(F)(F)CC3)cn2)c1]

The title compound was prepared in 13% yield from methyl 2-(1-{2-[(methylsulfonyl)oxy]ethyl}-1H-imidazol-4-yl)pyridine-4-carboxylate (PREPARATION 6) and (4,4-difluorocyclohexyl)methanamine hydrogen chloride according to the procedure for the preparation of Example 58. ¹HNMR (400 MHz, DMSO): δ 1.13 (2H, m), 1.75 (4H, m), 1.96 (2H, m), 2.42 (2H, d, J=6.7 Hz), 2.88 (2H, t, J=6.0 Hz), 4.06 (2H, t, J=6.0 Hz), 7.53 (1H, dd, J=4.9 Hz), 7.73 (1H, s), 7.79 (1H, s), 8.25 (1H, s), 8.55 (1H, d, J=4.9 Hz). [M+H] Calc'd for $C_{18}H_{22}F_2N_4O_2$, 365. Found, 365.

Example 73

2-[1-[2-[(3,3-difluorocyclobutyl)methylamino]ethyl]imidazol-4-yl]pyridine-4-carboxylic acid

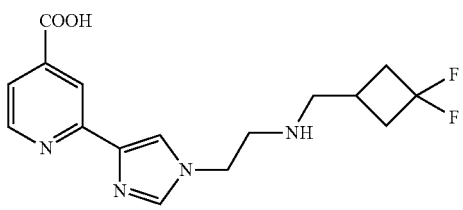 [SMILES: O=C(O)c1ccnc(-c2cn(CCNCC3CC(F)(F)C3)cn2)c1]

The title compound was prepared in 7% yield from methyl 2-(1-{2-[(methylsulfonyl)oxy]ethyl}-1H-imidazol-4-yl)pyridine-4-carboxylate (PREPARATION 6) and (4,4-difluorocyclobutyl)methanamine hydrogen chloride according to the procedure for the preparation of Example 58. ¹HNMR (400 MHz, DMSO): δ 2.24 (5H, m), 2.88 (2H, t, J=6.2 Hz), 4.05 (2H, t, J=6.0 Hz), 7.52 (1H, dd, J=4.7 Hz), 7.72 (1H, s), 7.78 (1H, s), 8.25 (1H, s), 8.54 (1H, d, J=4.6 Hz). [M+H] Calc'd for $C_{16}H_{18}F_2N_4O_2$, 337. Found, 337.

Example 74

2-[1-[2-[(4-fluorophenyl)methylamino]ethyl]imidazol-4-yl]pyridine-4-carboxylic acid

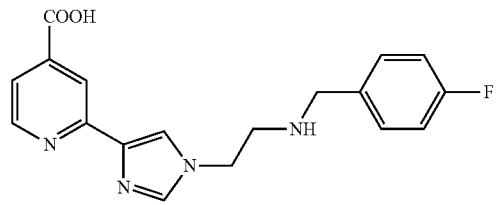 [SMILES: O=C(O)c1ccnc(-c2cn(CCNCc3ccc(F)cc3)cn2)c1]

The title compound was prepared in 20% yield from methyl 2-(1-{2-[(methylsulfonyl)oxy]ethyl}-1H-imidazol-4-yl)pyridine-4-carboxylate (PREPARATION 6) and 4-fluorobenzylamine according to the procedure for the preparation of Example 58. ¹HNMR (400 MHz, DMSO): δ 2.86 (2H, t, J=6.0 Hz), 3.70 (2H, s), 4.09 (2H, t, J=6.0 Hz), 7.08 (2H, t, J=8.9 Hz), 7.33 (2H, dd, J=7.1 Hz and 2.6 Hz), 7.55 (1H, dd, J=3.2 Hz and 1.5 Hz), 7.75 (1H, d, J=1.0 Hz), 7.81 (1H, s), 8.27 (1H, s), 8.59 (1H, d, J=4.9 Hz). [M+H] Calc'd for $C_{18}H_{17}FN_4O_2$, 341. Found, 341.

Example 75

2-[1-[2-[[2-(trifluoromethyl)phenyl]methylamino]ethyl]imidazol-4-yl]pyridine-4-carboxylic acid

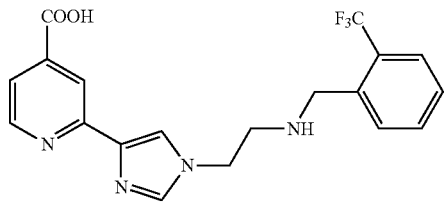 [SMILES: O=C(O)c1ccnc(-c2cn(CCNCc3ccccc3C(F)(F)F)cn2)c1]

The title compound was prepared in 6% yield from methyl 2-(1-{2-[(methylsulfonyl)oxy]ethyl}-1H-imidazol-4-yl)pyridine-4-carboxylate (PREPARATION 6) and 2-(trifluoromethyl)benzylamine according to the procedure for the preparation of Example 58. ¹HNMR (400 MHz, DMSO): δ 2.89 (2H, t, J=5.9 Hz), 3.88 (2H, s), 4.10 (2H, t, J=5.9 Hz), 7.42 (1H, t, J=7.7 Hz), 7.50 (1H, d, J=5.0 Hz), 7.59 (1H, d, J=7.6 Hz), 7.65 (2H, d, J=8.6 Hz), 7.74 (1H, s), 7.77 (1H, s), 8.25 (1H, s), 8.49 (1H, d, J=4.8 Hz). [M+H] Calc'd for $C_{17}H_{19}F_3N_4O_2$, 391. Found, 391.

Example 76

2-[1-[2-(1,3-dihydroisoindol-2-yl)ethyl]imidazol-4-yl]pyridine-4-carboxylic acid

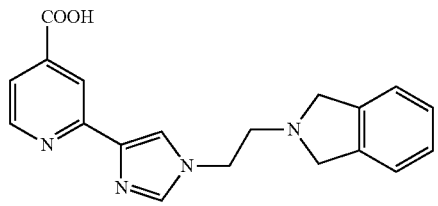 [SMILES: O=C(O)c1ccnc(-c2cn(CCN3Cc4ccccc4C3)cn2)c1]

The title compound was prepared in 15% yield from methyl 2-(1-{2-[(methylsulfonyl)oxy]ethyl}-1H-imidazol- 4-yl)pyridine-4-carboxylate (PREPARATION 6) and isoindoline according to the procedure for the preparation of Example 58. ¹HNMR (400 MHz, DMSO): δ 3.10 (2H, t, J=6.0 Hz), 3.99 (4H, s), 4.21 (2H, t, J=6.0 Hz), 7.17-7.24 (4H, m), 7.56 (1H, d, J=3.8 Hz), 7.82 (1H, s), 7.88 (1H, s), 8.27 (1H, s), 8.59 (1H, d, J=5.0 Hz). [M+H] Calc'd for $C_{19}H_{18}N_4O_2$, 335. Found, 335.

Example 77

2-[1-[2-[(2-methoxyphenyl)methylamino]ethyl]imidazol-4-yl]pyridine-4-carboxylic acid

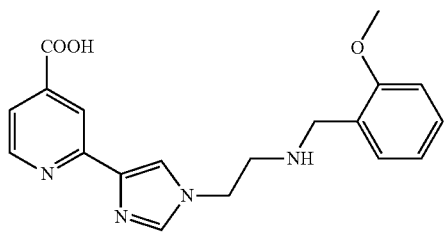 [SMILES: COc1ccccc1CNCCn1cnc(-c2cc(C(=O)O)ccn2)c1]

The title compound was prepared in 19% yield from methyl 2-(1-{2-[(methylsulfonyl)oxy]ethyl}-1H-imidazol-4-yl)pyridine-4-carboxylate (PREPARATION 6) and 2-methoxybenzylamine according to the procedure for the preparation of Example 58. ¹HNMR (400 MHz, DMSO): δ 2.91 (2H, t, J=5.9 Hz), 3.72 (2H, s), 3.75 (3H, s), 4.13 (2H, t, J=6.0 Hz), 6.88 (1H, t, J=7.4 Hz), 6.95 (1H, d, J=8.2 Hz), 7.20 (1H, t, J=8.8 Hz), 7.25 (1H, d, J=7.4 Hz), 7.56 (1H, dd, J=6.4 and 1.4 Hz), 7.75 (1H, s), 7.82 (1H, s), 8.28 (1H, s), 8.59 (1H, d, J=5.0 Hz). [M+H] Calc'd for $C_{19}H_{20}N_4O_3$, 353. Found, 353.

Example 78

2-[1-[2-[(2-chlorophenyl)methylamino]ethyl]imidazol-4-yl]pyridine-4-carboxylic acid

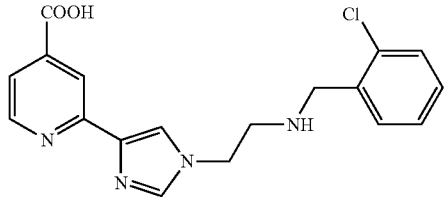 [SMILES: O=C(O)c1ccnc(-c2cn(CCNCc3ccccc3Cl)cn2)c1]

The title compound was prepared in 8% yield from methyl 2-(1-{2-[(methylsulfonyl)oxy]ethyl}-1H-imidazol-4-yl)pyridine-4-carboxylate (PREPARATION 6) and 2-chlorobenzylamine according to the procedure for the preparation of Example 58. ¹HNMR (400 MHz, DMSO): δ 2.90 (2H, t, J=6.0 Hz), 3.80 (2H, s), 4.11 (2H, t, J=6.0 Hz), 7.23-7.27 (2H, m), 7.38 (1H, dd, J=4.5 and 1.5 Hz), 7.45 (1H, dd, J=4.6 and 2.2 Hz), 7.55 (1H, dd, J=3.2 and 1.5 Hz), 7.76 (1H, s), 7.81 (1H, s), 8.27 (1H, s), 8.56 (1H, d, J=5.0 Hz). [M+H] Calc'd for $C_{18}H_{17}ClN_4O_2$, 358. Found, 358.

Example 79

2-[1-[2-(5-fluoro-1,3-dihydroisoindol-2-yl)ethyl]imidazol-4-yl]pyridine-4-carboxylic acid

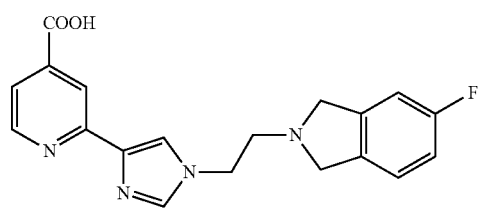 [SMILES: O=C(O)c1ccnc(-c2cn(CCN3Cc4ccc(F)cc4C3)cn2)c1]

The title compound was prepared in 76% yield from methyl 2-(1-{2-[(methylsulfonyl)oxy]ethyl}-1H-imidazol-4-yl)pyridine-4-carboxylate (PREPARATION 6) and 5-fluoro-2,3-dihydro-1H-isoindole according to the procedure for the preparation of Example 58. ¹HNMR (400 MHz, DMSO): δ 3.08 (2H, t, J=6.0 Hz), 3.88 (2H, s), 3.92 (2H, s), 4.19 (2H, t, J=6.0 Hz), 6.98 (1H, td, J=9.6 and 2.5 Hz), 7.08 (1H, dd, J=5.5 and 2.0 Hz), 7.24 (1H, dd, J=6.7 and 3.0 Hz), 7.52 (1H, d, J=3.8 Hz), 7.80 (1H, s), 7.84 (1H, s), 8.26 (1H, s), 8.53 (1H, d, J=5.0 Hz). [M+H] Calc'd for $C_{19}H_{17}FN_4O_2$, 353. Found, 353.

Example 80

2-[1-[2-[(2-ethylphenyl)methylamino]ethyl]imidazol-4-yl]pyridine-4-carboxylic acid

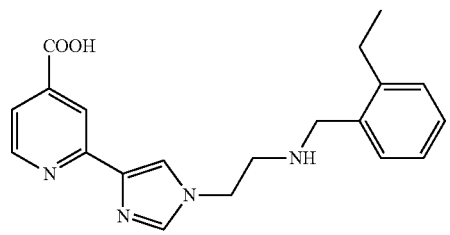 [SMILES: CCc1ccccc1CNCCn1cnc(-c2cc(C(=O)O)ccn2)c1]

The title compound was prepared in 87% yield from methyl 2-(1-{2-[(methylsulfonyl)oxy]ethyl}-1H-imidazol-4-yl)pyridine-4-carboxylate (PREPARATION 6) and 2-ethylbenzylamine according to the procedure for the preparation of Example 58. ¹HNMR (400 MHz, DMSO): δ 1.11 (3H, t, J=7.5 Hz), 2.61 (2H, q, J=7.6 Hz), 2.92 (2H, t, J=6.1 Hz), 3.71 (2H, s), 4.09 (2H, t, J=5.9 Hz), 7.11-7.16 (3H, m&s), 7.27 (1H, d, J=7.6 Hz), 7.44 (1H, dd, J=6.2 and 1.4 Hz), 7.69 (1H, s), 7.71 (1H, s), 8.21 (1H, s), 8.36 (1H, d, J=4.8 Hz). [M+H] Calc'd for $C_{20}H_{22}N_4O_2$, 351. Found, 351.

Example 81

2-[1-[2-(4-chloro-1,3-dihydroisoindol-2-yl)ethyl]imidazol-4-yl]pyridine-4-carboxylic acid

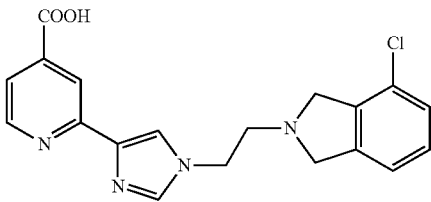 [SMILES: O=C(O)c1ccnc(-c2cn(CCN3Cc4cccc(Cl)c4C3)cn2)c1]

The title compound was prepared in 10% yield from methyl 2-(1-{2-[(methylsulfonyl)oxy]ethyl}-1H-imidazol-4-yl)pyridine-4-carboxylate (PREPARATION 6) and 4-chloroisoindoline hydrogen chloride according to the procedure for the preparation of Example 58. $^1$HNMR (400 MHz, DMSO): δ 3.15 (2H, m), 4.05 (4H, br s), 4.25 (2H, m), 7.19-7.27 (2H, m), 7.59 (1H, dd, J=4.9 Hz), 7.66 (1H, dd, J=6.7 and 3.0 Hz), 7.94 (1H, s), 8.11 (1H, s), 8.28 (1H, s), 8.33 (1H, s), 8.65 (1H, d, J=5.2 Hz). [M+H] Calc'd for $C_{19}H_{17}ClN_4O_2$, 369. Found, 369.

Example 82

2-[1-[2-(5-chloro-1,3-dihydroisoindol-2-yl)ethyl]imidazol-4-yl]pyridine-4-carboxylic acid

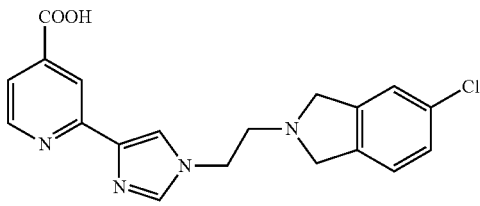 [SMILES: O=C(O)c1ccnc(-c2cn(CCN3Cc4ccc(Cl)cc4C3)cn2)c1]

The title compound was prepared in 17% yield from methyl 2-(1-{2-[(methylsulfonyl)oxy]ethyl}-1H-imidazol-4-yl)pyridine-4-carboxylate (PREPARATION 6) and 5-chloroisoindoline hydrogen chloride according to the procedure for the preparation of Example 58. $^1$HNMR (400 MHz, DMSO): δ 3.08 (2H, t, J=5.9 Hz), 3.90 (2H, s), 3.92 (2H, s), 4.20 (2H, t, J=6.0 Hz), 7.24 (2H, s), 7.31 (1H, s), 7.56 (1H, d, J=4.8 Hz), 7.80 (1H, s), 7.88 (1H, s), 8.27 (1H, s), 8.61 (1H, d, J=4.9 Hz). [M+H] Calc'd for $C_{19}H_{17}ClN_4O_2$, 369. Found, 369.

Example 83

2-[1-[2-(4-cyano-1,3-dihydroisoindol-2-yl)ethyl]imidazol-4-yl]pyridine-4-carboxylic acid

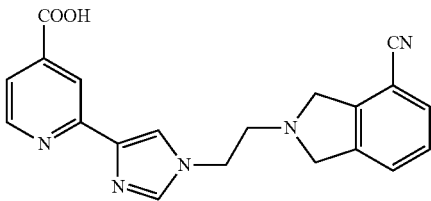

The title compound was prepared in 11% yield from methyl 2-(1-{2-[(methylsulfonyl)oxy]ethyl}-1H-imidazol-4-yl)pyridine-4-carboxylate (PREPARATION 6) and 4-cyanoisoindoline hydrogen chloride according to the procedure for the preparation of Example 58. $^1$HNMR (400 MHz, DMSO): δ 3.13 (2H, t, J=6.0 Hz), 4.03 (2H, s), 4.13 (2H, s), 4.23 (2H, t, J=4.5 Hz), 7.41 (1H, d, J=7.6 Hz), 7.55 (2H, m), 7.66 (1H, d, J=5.7 Hz), 7.80 (1H, s), 7.87 (1H, s), 8.26 (1H, s), 8.57 (1H, d, J=4.9 Hz). [M+H] Calc'd for $C_{20}H_{17}N_5O_2$, 360. Found, 360.

Example 84

2-[1-[2-[5-(trifluoromethyl)-1,3-dihydroisoindol-2-yl]ethyl]imidazol-4-yl]pyridine-4-carboxylic acid

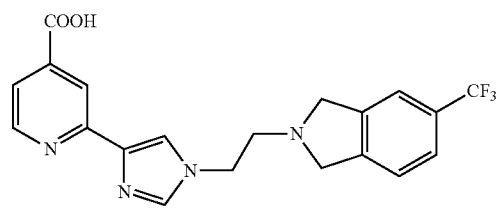 [SMILES: O=C(O)c1ccnc(-c2cn(CCN3Cc4ccc(C(F)(F)F)cc4C3)cn2)c1]

The title compound was prepared in 8% yield from methyl 2-(1-{2-[(methylsulfonyl)oxy]ethyl}-1H-imidazol-4-yl)pyridine-4-carboxylate (PREPARATION 6) and 5-trifluoromethylisoindoline according to the procedure for the preparation of Example 58. $^1$HNMR (400 MHz, DMSO): δ 3.12 (2H, t, J=6.0 Hz), 4.10 (4H, s), 4.21 (2H, t, J=5.9 Hz), 7.45 (1H, d, J=8.0 Hz), 7.55 (2H, d, J=8.8 Hz), 7.60 (1H, s), 7.81 (1H, s), 7.86 (1H, s), 8.26 (1H, s), 8.56 (1H, m). [M+H] Calc'd for $C_{20}H_{17}F_3N_4O_2$, 403. Found, 403.

Example 85

2-[1-[2-[(4-chlorophenyl)methyl-cyclopropylamino]ethyl]imidazol-4-yl]pyridine-4-carboxylic acid

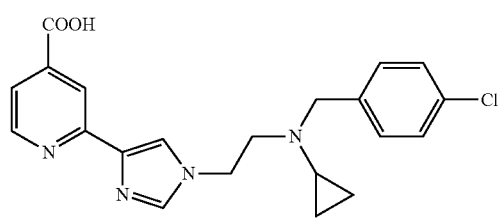 [SMILES: O=C(O)c1ccnc(-c2cn(CCN(Cc3ccc(Cl)cc3)C3CC3)cn2)c1]

The title compound was prepared in 8% yield from methyl 2-(1-{2-[(methylsulfonyl)oxy]ethyl}-1H-imidazol-4-yl)pyridine-4-carboxylate (PREPARATION 6) and (4-chlorobenzyl)cyclopropylamine according to the procedure for the preparation of Example 58. $^1$HNMR (400 MHz, DMSO): δ 0.17 (2H, m), 0.40 (2H, m), 1.83 (1H, m), 2.88 (2H, t, J=6.4 Hz), 3.72 (2H, s), 4.10 (2H, t, J=6.2 Hz), 7.26 (1H, d, J=8.4 Hz), 7.32 (2H, t, J=8.4 Hz), 7.45 (1H, dd, J=3.7 Hz), 7.64 (2H, d, J=4.4 Hz), 8.21 (1H, s), 8.31 (1H, s), 8.40 (1H, d, J=4.8 Hz). [M+H] Calc'd for $C_{21}H_{21}ClN_4O_2$, 398. Found, 398.

Example 86

2-[1-[2-[cyclopropyl-[(3,4-dichlorophenyl)methyl]amino]ethyl]imidazol-4-yl]pyridine-4-carboxylic acid

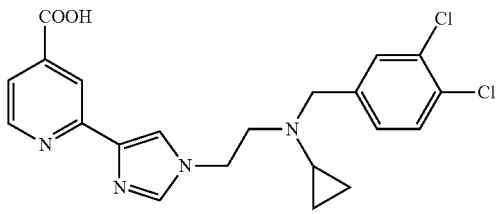 [SMILES: O=C(O)c1ccnc(-c2cn(CCN(Cc3ccc(Cl)c(Cl)c3)C3CC3)cn2)c1]

The title compound was prepared in 7% yield from methyl 2-(1-{2-[(methylsulfonyl)oxy]ethyl}-1H-imidazol-4-yl)pyridine-4-carboxylate (PREPARATION 6) and (3,4-dichlorobenzyl)cyclopropylamine according to the procedure for the preparation of Example 58. ¹HNMR (400 MHz, DMSO): δ 0.14 (2H, m), 0.40 (2H, m), 1.85 (1H, m), 2.90 (2H, t, J=6.2 Hz), 3.74 (2H, s), 4.14 (2H, t, J=6.2 Hz), 7.21 (1H, dd, J=8.3 and 1.8 Hz), 7.45-7.56 (3H, m), 7.70 (1H, s), 7.72 (1H, s), 8.26 (1H, s), 8.56 (1H, d). [M+H] Calc'd for $C_{21}H_{20}Cl_2N_4O_2$, 432. Found, 432.

Example 87

2-[1-[2-(4-chloro-N-methylanilino)ethyl]imidazol-4-yl]pyridine-4-carboxylic acid

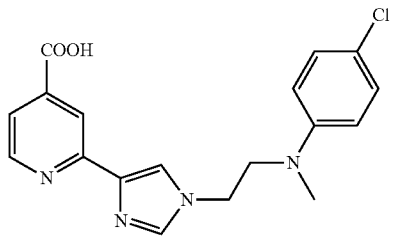 [SMILES: CN(CCn1cnc(-c2cc(C(=O)O)ccn2)c1)c1ccc(Cl)cc1]

The title compound was prepared in 19% yield from methyl 2-(1-{2-[(methylsulfonyl)oxy]ethyl}-1H-imidazol-4-yl)pyridine-4-carboxylate (PREPARATION 6) and 4-chloro-N-methylaniline according to the procedure for the preparation of Example 58. ¹HNMR (400 MHz, DMSO): δ 2.77 (3H, s), 3.71 (2H, t, J=6.4 Hz), 4.17 (2H, t, J=6.4 Hz), 6.71 (1H, d, J=9.0 Hz), 6.99 (1H, m), 7.15 (1H, s), 7.17 (1H, s), 7.57 (1H, m), 7.65 (1H, s), 7.78 (1H, s), 8.24 (1H, s), 8.41 (1H, d, J=5.2 Hz). [M+H] Calc'd for $C_{18}H_{17}ClN_4O_2$, 358. Found, 358.

Example 88

2-[1-[2-(3,4-dihydro-2H-quinolin-1-yl)ethyl]imidazol-4-yl]pyridine-4-carboxylic acid

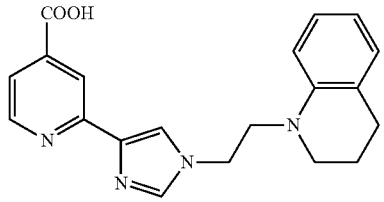 [SMILES: O=C(O)c1ccnc(-c2cn(CCN3CCCc4ccccc43)cn2)c1]

The title compound was prepared in 17% yield from methyl 2-(1-{2-[(methylsulfonyl)oxy]ethyl}-1H-imidazol-4-yl)pyridine-4-carboxylate (PREPARATION 6) and 1,2,3,4-tetrahydroquinoline according to the procedure for the preparation of Example 58. ¹HNMR (400 MHz, DMSO): δ 1.76 (2H, t, J=5.5 Hz), 2.64 (2H, t, J=6.2 Hz), 3.08 (2H, t, J=5.5 Hz), 3.62 (2H, t, J=6.2 Hz), 4.20 (2H, t, J=6.2 Hz), 6.48 (1H, t, J=7.1 Hz), 6.61 (1H, d, J=8.1 Hz), 6.86 (1H, d, J=6.6 Hz), 6.95 (1H, t, J=7.7 Hz), 7.53 (1H, d, J=3.6 Hz), 7.71 (1H, s), 7.84 (1H, s), 8.25 (1H, s), 8.53 (1H, d, J=5.0 Hz). [M+H] Calc'd for $C_{20}H_{20}N_4O_2$, 349. Found, 349.

Example 89

2-[1-[2-(6-chloro-3,4-dihydro-2H-quinolin-1-yl)ethyl]imidazol-4-yl]pyridine-4-carboxylic acid

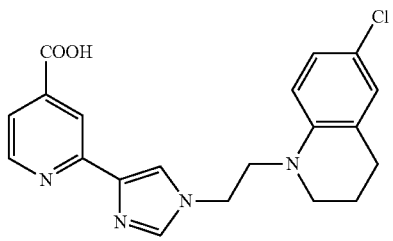 [SMILES: O=C(O)c1ccnc(-c2cn(CCN3CCCc4cc(Cl)ccc43)cn2)c1]

The title compound was prepared in 9% yield from methyl 2-(1-{2-[(methylsulfonyl)oxy]ethyl}-1H-imidazol-4-yl)pyridine-4-carboxylate (PREPARATION 6) and 6-chloro-1,2,3,4-tetrahydroquinoline according to the procedure for the preparation of Example 58. ¹HNMR (400 MHz, DMSO): δ 1.74 (2H, t, J=5.1 Hz), 2.64 (2H, t, J=6.5 Hz), 3.06 (2H, t, J=5.5 Hz), 3.63 (2H, t, J=6.2 Hz), 4.18 (2H, t, J=6.0 Hz), 6.62 (1H, d, J=8.9 Hz), 6.92 (1H, s), 6.94 (1H, t, J=8.7 Hz), 7.49 (1H, d, J=4.8 Hz), 7.69 (1H, s), 7.81 (1H, s), 8.23 (1H, s), 8.46 (1H, d, J=4.1 Hz). [M+H] Calc'd for $C_{20}H_{19}ClN_4O_2$, 384. Found, 384.

Example 90

2-[1-[2-(6-fluoro-3,4-dihydro-2H-quinolin-1-yl)ethyl]imidazol-4-yl]pyridine-4-carboxylic acid

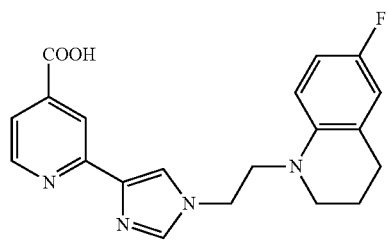 [SMILES: O=C(O)c1ccnc(-c2cn(CCN3CCCc4cc(F)ccc43)cn2)c1]

The title compound was prepared in 13% yield from methyl 2-(1-{2-[(methylsulfonyl)oxy]ethyl}-1H-imidazol-4-yl)pyridine-4-carboxylate (PREPARATION 6) and 6-fluoro-1,2,3,4-tetrahydroquinoline according to the procedure for the preparation of Example 58. ¹HNMR (400 MHz, DMSO): δ 1.75 (2H, t, J=5.5 Hz), 2.64 (2H, t, J=6.2 Hz), 3.06 (2H, t, J=5.4 Hz), 3.60 (2H, t, J=6.2 Hz), 4.19 (2H, t, J=6.3 Hz), 6.60 (1H, m), 6.74 (1H, s), 6.76 (1H, d, J=8.5 Hz), 7.53

(1H, d, J=4.6 Hz), 7.72 (1H, s), 7.85 (1H, s), 8.25 (1H, s), 8.55 (1H, d). [M+H] Calc'd for $C_{20}H_{19}FN_4O_2$, 367. Found, 367.

Example 91

2-[1-[2-(5-fluoro-2,3-dihydroindol-1-yl)ethyl]imidazol-4-yl]pyridine-4-carboxylic acid

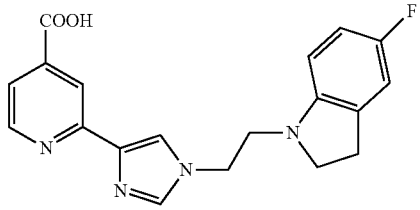 [SMILES: O=C(O)c1ccnc(-c2cn(CCN3CCc4cc(F)ccc43)cn2)c1]

The title compound was prepared in 11% yield from methyl 2-(1-{2-[(methylsulfonyl)oxy]ethyl}-1H-imidazol-4-yl)pyridine-4-carboxylate (PREPARATION 6) and 5-fluoro-2,3-dihydro-(1H)-indole according to the procedure for the preparation of Example 58. $^1$HNMR (400 MHz, DMSO): δ 2.88 (2H, t, J=8.4 Hz), 3.42 (2H, t, J=6.2 Hz), 4.25 (2H, t, J=6.1 Hz), 6.49 (1H, m), 6.76 (1H, td, J=2.2 and 8.8 Hz), 6.89 (1H, dd, J=6.4 Hz), 7.57 (1H, d, J=5.0 Hz), 7.83 (1H, s), 7.94 (1H, s), 8.27 (1H, s), 8.62 (1H, d, J=4.8 Hz). [M+H] Calc'd for $C_{19}H_{17}FN_4O_2$, 353. Found, 353.

Example 92

2-[1-[2-(4-fluorophenyl)ethyl]imidazol-4-yl]pyridine-4-carboxylic acid

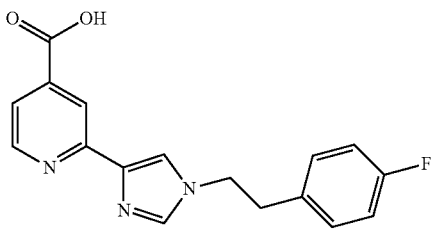 [SMILES: O=C(O)c1ccnc(-c2cn(CCc3ccc(F)cc3)cn2)c1]

The title compound was prepared in 48% yield from methyl 2-(1H-imidazol-4-yl)pyridine-4-carboxylate (PREPARATION 5) and 4-fluorophenethyl bromide according to the procedure for the preparation of Example 44, followed by saponification using NaOH in MeOH. $^1$HNMR (400 MHz, DMSO): δ 3.09 (2H, t, J=7.1 Hz), 4.27 (2H, t, J=7.2 Hz), 7.11 (2H, t, J=8.8 Hz), 7.24 (2H, t, J=7.1 Hz), 7.57 (1H, d, J=3.8 Hz), 7.63 (1H, s), 7.82 (1H, s), 8.26 (1H, s), 8.63 (1H, d, J=5.0 Hz). [M+H] Calc'd for $C_{17}H_{14}FN_3O_2$, 312. Found, 312.

Example 93

2-[1-[2-(2-fluorophenyl)ethyl]imidazol-4-yl]pyridine-4-carboxylic acid

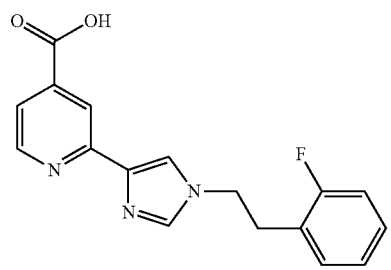 [SMILES: O=C(O)c1ccnc(-c2cn(CCc3ccccc3F)cn2)c1]

The title compound was prepared in 48% yield from methyl 2-(1H-imidazol-4-yl)pyridine-4-carboxylate (PREPARATION 5) and 2-fluorophenethyl bromide according to the procedure for the preparation of Example 44, followed by saponification using NaOH in MeOH. $^1$HNMR (400 MHz, DMSO): δ 3.14 (2H, t, J=6.9 Hz), 4.29 (2H, t, J=7.0 Hz), 7.13 (2H, m), 7.27 (2H, m), 7.58 (1H, d, J=4.0 Hz), 7.63 (1H, s), 7.80 (1H, s), 8.25 (1H, s), 8.62 (1H, d, J=4.9 Hz). [M+H] Calc'd for $C_{17}H_{14}FN_3O_2$, 312. Found, 312.

Example 94

2-[1-[2-(4-methoxyphenyl)ethyl]imidazol-4-yl]pyridine-4-carboxylic acid

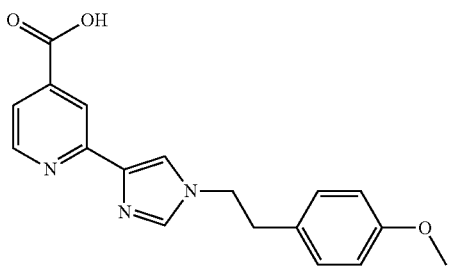 [SMILES: COc1ccc(CCn2cnc(-c3cc(C(=O)O)ccn3)c2)cc1]

The title compound was prepared in 39% yield from methyl 2-(1H-imidazol-4-yl)pyridine-4-carboxylate (PREPARATION 5) and 4-methoxyphenethyl bromide according to the procedure for the preparation of Example 44, followed by saponification using NaOH in MeOH. $^1$HNMR (400 MHz, DMSO): δ 3.02 (2H, t, J=7.2 Hz), 3.71 (3H, s), 4.24 (2H, t, J=7.2 Hz), 6.83 (2H, t, J=8.6 Hz), 7.12 (2H, t, J=8.6 Hz), 7.58 (1H, d, J=3.7 Hz), 7.62 (1H, s), 7.82 (1H, s), 8.26 (1H, s), 8.63 (1H, d, J=4.9 Hz). [M+H] Calc'd for $C_{18}H_{17}N_3O_3$, 324. Found, 324.

Example 95

2-[1-[2-(2-methoxyphenyl)ethyl]imidazol-4-yl]pyridine-4-carboxylic acid

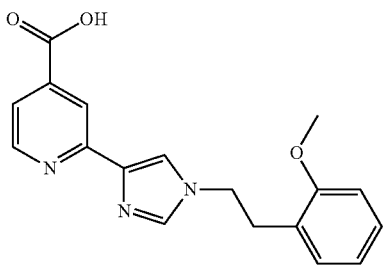 [SMILES: COc1ccccc1CCn1cnc(-c2cc(C(=O)O)ccn2)c1]

The title compound was prepared in 18% yield from 2-(1H-imidazol-4-yl)pyridine-4-carbonitrile (PREPARATION 4) and 2-methoxyphenethyl bromide according to the procedure for the preparation of Example 43. $^1$HNMR (400 MHz, DMSO): δ 3.05 (2H, t, J=7.1 Hz), 3.79 (3H, s), 4.22 (2H, t, J=7.1 Hz), 6.83 (1H, t, J=7.3 Hz), 6.97 (1H, d, J=8.1 Hz), 7.06 (1H, d, J=7.8 Hz), 7.21 (1H, t, J=9.0 Hz), 7.53 (1H, d, J=3.9 Hz), 7.53 (1H, s), 7.70 (1H, s), 8.20 (1H, s), 8.52 (1H, m). [M+H] Calc'd for $C_{18}H_{17}N_3O_3$, 324. Found, 324.

Example 96

2-[1-[2-(2-methylphenyl)ethyl]imidazol-4-yl]pyridine-4-carboxylic acid

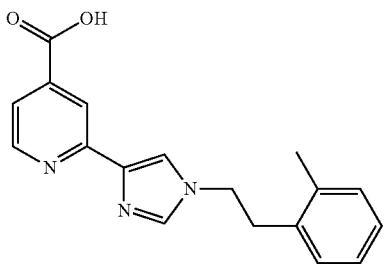 [SMILES: Cc1ccccc1CCn1cnc(-c2cc(C(=O)O)ccn2)c1]

The title compound was prepared in 27% yield from 2-(1H-imidazol-4-yl)pyridine-4-carbonitrile (PREPARATION 4) and 2-methylphenethyl bromide according to the procedure for the preparation of Example 43. $^1$HNMR (400 MHz, DMSO): δ 2.23 (3H, s), 3.08 (2H, t, J=7.4 Hz), 4.24 (2H, t, J=7.2 Hz), 7.12 (4H, m), 7.58 (1H, dd, J=1.5 and 5.0 Hz), 7.66 (1H, s), 7.84 (1H, s), 8.27 (1H, s), 8.63 (1H, d, J=5.1 Hz). [M+H] Calc'd for $C_{18}H_{17}N_3O_2$, 308. Found, 308.

Example 97

2-[1-[2-(2-chlorophenyl)ethyl]imidazol-4-yl]pyridine-4-carboxylic acid

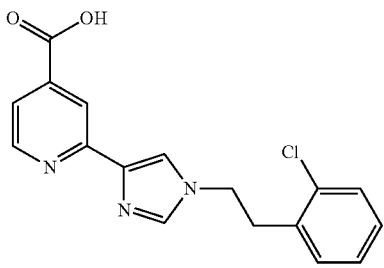

The title compound was prepared in 18% yield from 2-(1H-imidazol-4-yl)pyridine-4-carbonitrile (PREPARATION 4) and 2-chlorophenethyl bromide according to the procedure for the preparation of Example 43. $^1$HNMR (400 MHz, DMSO): δ 3.26 (2H, t, J=5.6 Hz), 4.32 (2H, t, J=7.3 Hz), 7.45 (2H, m), 7.59 (2H, m), 7.67 (1H, s), 7.71 (1H, d, J=7.7 Hz), 7.81 (1H, s), 8.27 (1H, s), 8.64 (1H, d, J=4.9 Hz). [M+H] Calc'd for $C_{17}H_{14}ClN_3O_2$, 329. Found, 329.

Example 98

2-[1-[2-[2-(trifluoromethyl)phenyl]ethyl]imidazol-4-yl]pyridine-4-carboxylic acid

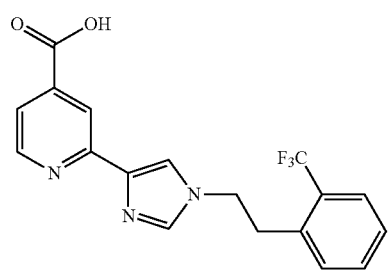 [SMILES: O=C(O)c1ccnc(-c2cn(CCc3ccccc3C(F)(F)F)cn2)c1]

The title compound was prepared in 12% yield from 2-(1H-imidazol-4-yl)pyridine-4-carbonitrile (PREPARATION 4) and 2-(trifluoromethyl)phenethyl bromide according to the procedure for the preparation of Example 43. $^1$HNMR (400 MHz, DMSO): δ 3.23 (2H, t, J=7.2 Hz), 4.30 (2H, t, J=7.1 Hz), 7.27 (3H, m), 7.45 (2H, m), 7.58 (1H, dd, J=1.4 and 4.9 Hz), 7.64 (1H, s), 7.80 (1H, s), 8.26 (1H, s), 8.62 (1H, d, J=4.9 Hz). [M+H] Calc'd for $C_{15}H_{14}F_3N_3O_2$, 362. Found, 362.

Example 99

2-[1-(2,3-dihydro-1H-inden-2-yl)imidazol-4-yl]pyridine-4-carboxylic acid

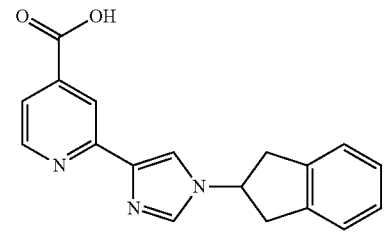 [SMILES: O=C(O)c1ccnc(-c2cn(C3Cc4ccccc4C3)cn2)c1]

The title compound was prepared in 48% yield from methyl 2-(1H-imidazol-4-yl)pyridine-4-carboxylate (PREPARATION 5) and 2-bromo-2,3-dihydro-1H-indene according to the procedure for the preparation of Example 44, followed by saponification using NaOH in MeOH. $^1$HNMR (400 MHz, DMSO): δ 2.21 (2H, d), 3.52 (2H, d), 5.22 (1H, m), 7.23 (2H, m), 7.32 (2H, m), 7.45 (1H, t, J=5.4 Hz), 7.59 (1H, s), 7.82 (1H, s), 8.21 (1H, s), 8.35 (1H, d). [M+H] Calc'd for $C_{18}H_{15}N_3O_2$, 306. Found, 306.

Example 100

2-(1-benzylimidazol-4-yl)pyridine-4-carboxylic acid

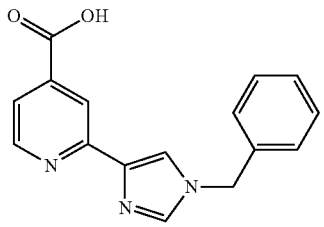 [SMILES: O=C(O)c1ccnc(-c2cn(Cc3ccccc3)cn2)c1]

The title compound was prepared in 30% yield from 2-(1H-imidazol-4-yl)pyridine-4-carbonitrile (PREPARATION 4) and benzyl bromide according to the procedure for the preparation of Example 43 using room temperature, followed by hydrolysis. $^1$H NMR (400 MHz, DMSO-$d_6$): δ 5.26 (2H, s), 7.35 (5H, m), 7.58 (1H, d, J=4.9 Hz), 7.83 (1H, s), 7.91 (1H, s), 8.28 (1H, s), 8.63 (1H, d, J=4.9 Hz). [M+H] Calc'd for $C_{16}H_{13}N_3O_2$, 280. Found, 280.

Example 101

2-[1-[(4-fluorophenyl)methyl]imidazol-4-yl]pyridine-4-carboxylic acid

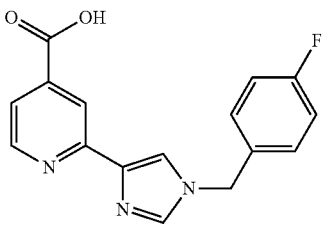 [SMILES: O=C(O)c1ccnc(-c2cn(Cc3ccc(F)cc3)cn2)c1]

The title compound was prepared in 22% yield from 2-(1H-imidazol-4-yl)pyridine-4-carbonitrile (PREPARATION 4) and 4-fluorobenzyl bromide according to the procedure for the preparation of Example 43 using room temperature, followed by hydrolysis. $^1$H NMR (400 MHz, DMSO-$d_6$): δ 5.46 (2H, s), 7.21 (2H, t, J=8.9 Hz), 7.43 (2H, d, J=7.1 Hz), 7.54 (1H, d, J=5.8 Hz), 7.79 (1H, s), 7.89 (1H, s), 8.26 (1H, s), 8.53 (1H, d, J=4.9 Hz). [M+H] Calc'd for $C_{16}H_{12}FN_3O_2$, 298. Found, 298.

Example 102

2-[1-[(2-fluorophenyl)methyl]imidazol-4-yl]pyridine-4-carboxylic acid

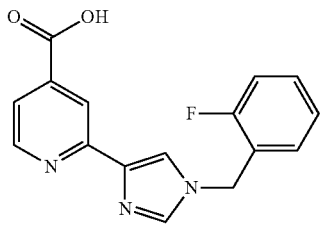 [SMILES: O=C(O)c1ccnc(-c2cn(Cc3ccccc3F)cn2)c1]

The title compound was prepared in 17% yield from 2-(1H-imidazol-4-yl)pyridine-4-carbonitrile (PREPARATION 4) and 2-fluorobenzyl bromide according to the procedure for the preparation of Example 43 using room temperature, followed by hydrolysis. $^1$H NMR (400 MHz, DMSO-$d_6$): δ 5.38 (2H, s), 7.25 (2H, m), 7.40 (2H, m), 7.56 (1H, d, J=4.5 Hz), 7.74 (1H, s), 7.87 (1H, s), 8.28 (1H, s), 8.53 (1H, d, J=4.8 Hz). [M+H] Calc'd for $C_{16}H_{12}FN_3O_2$, 298. Found, 298.

Example 103

2-[1-[(3-fluorophenyl)methyl]imidazol-4-yl]pyridine-4-carboxylic

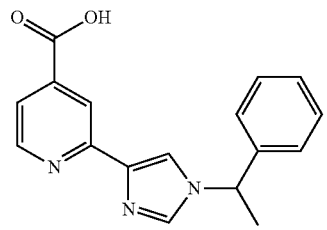 [SMILES: CC(c1ccccc1)n1cnc(-c2cc(C(=O)O)ccn2)c1]

The title compound was prepared in 11% yield from 2-(1H-imidazol-4-yl)pyridine-4-carbonitrile (PREPARATION 4) and (1-bromomethyl)benzene according to the procedure for the preparation of Example 43 using room temperature, followed by hydrolysis. $^1$H NMR (400 MHz, DMSO-$d_6$): δ 1.85 (3H, d, J=6.9 Hz), 5.60 (1H, m), 7.31 (1H, m), 7.34 (4H, m), 7.50 (1H, m), 7.81 (1H, s), 7.92 (1H, s), 8.24 (1H, s), 8.47 (1H, br s). [M+H] Calc'd for $C_{17}H_{15}N_3O_2$, 294. Found, 294.

Example 104

2-[1-[(3-fluorophenyl)methyl]imidazol-4-yl]pyridine-4-carboxylic

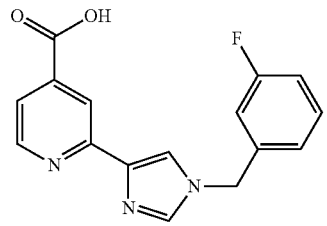 [SMILES: O=C(O)c1ccnc(-c2cn(Cc3cccc(F)c3)cn2)c1]

The title compound was prepared in 13% yield from 2-(1H-imidazol-4-yl)pyridine-4-carbonitrile (PREPARATION 4) and 3-fluorobenzyl bromide according to the procedure for the preparation of Example 43 using room temperature, followed by hydrolysis. $^1$H NMR (400 MHz, DMSO-$d_6$): δ 5.40 (2H, s), 7.21 (3H, m), 7.42 (1H, m), 7.56 (1H, d, J=4.0 Hz), 7.87 (1H, s), 7.92 (1H, s), 8.27 (1H, s), 8.58 (1H, d). [M+H] Calc'd for $C_{16}H_{12}FN_3O_2$, 298. Found, 298.

Example 105

2-[1-[2-(2-chlorophenyl)-2-methylpropyl]imidazol-4-yl]pyridine-4-carboxylic acid

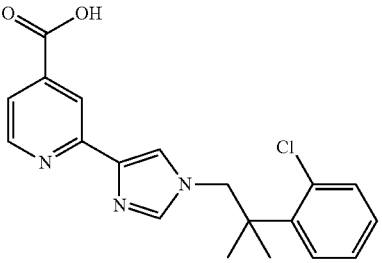 [SMILES: CC(C)(Cn1cnc(-c2cc(C(=O)O)ccn2)c1)c1ccccc1Cl]

The title compound was prepared in 17% yield from 2-(1H-imidazol-4-yl)pyridine-4-carbonitrile (PREPARATION 4)

and 1-(2-bromo-1,1-dimethylethyl)-2-chlorobenzene according to the procedure for the preparation of Example 43. ¹HNMR (400 MHz, DMSO): δ 1.48 (6H, s), 4.52 (2H, s), 7.24-7.36 (5H, m), 7.54 (2H, m), 8.19 (1H, s), 8.56 (1H, d, J=5.0 Hz). [M+H] Calc'd for $C_{19}H_{18}ClN_3O_2$, 357. Found, 357.

Example 106

2-[1-(1-phenylpropan-2-yl)imidazol-4-yl]pyridine-4-carboxylic acid

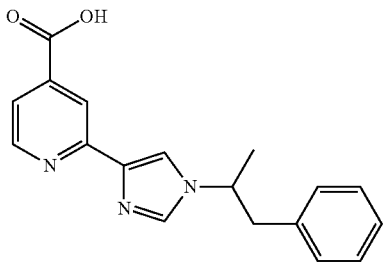 [SMILES: CC(Cc1ccccc1)n1cnc(-c2cc(C(=O)O)ccn2)c1]

The title compound was prepared in 13% yield from 2-(1H-imidazol-4-yl)pyridine-4-carbonitrile (PREPARATION 4) and 2-bromo-1-phenylpropane according to the procedure for the preparation of Example 43. ¹HNMR (400 MHz, DMSO): δ 0.85 (3H, t, J=7.2 Hz), 2.24 (1H, m), 2.33 (1H, m), 5.30 (1H, t, J=7.8 Hz), 7.21-7.31 (3H, m), 7.38 (2H, d, J=7.4 Hz), 7.58 (1H, dd, J=1.6 and 4.9 Hz), 7.93 (1H, s), 7.97 (1H, s), 8.27 (1H, s), 8.60 (1H, d, J=4.7 Hz). [M+H] Calc'd for $C_{18}H_{17}N_3O_2$, 308. Found, 308.

Example 107

2-[1-(1-phenylpropyl)imidazol-4-yl]pyridine-4-carboxylic acid

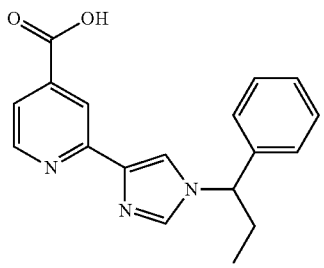 [SMILES: CCC(c1ccccc1)n1cnc(-c2cc(C(=O)O)ccn2)c1]

The title compound was prepared in 24% yield from 2-(1H-imidazol-4-yl)pyridine-4-carbonitrile (PREPARATION 4) and 1-bromopropylbenzene according to the procedure for the preparation of Example 43 using room temperature, followed by hydrolysis. ¹H NMR (400 MHz, DMSO-d₆): δ 0.85 (3H, t, J=7.2 Hz), 2.22 (1H, m), 2.33 (1H, m), 5.30 (1H, t, J=7.8 Hz), 7.31 (1H, t, J=7.4 Hz), 7.38 (2H, t, J=7.2 Hz), 7.46 (2H, d, J=8.7 Hz), 7.56 (1H, dd, J=1.4 and 5.0 Hz), 7.91 (1H, s), 7.96 (1H, s), 8.27 (1H, s), 8.55 (1H, d, J=4.9 Hz). [M+H] Calc'd for $C_{18}H_{17}N_3O_2$, 308. Found, 308.

Example 108

2-[1-(2-methyl-1-phenylpropyl)imidazol-4-yl]pyridine-4-carboxylic acid

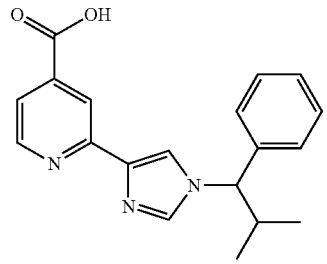 [SMILES: CC(C)C(c1ccccc1)n1cnc(-c2cc(C(=O)O)ccn2)c1]

The title compound was prepared in 16% yield from 2-(1H-imidazol-4-yl)pyridine-4-carbonitrile (PREPARATION 4) and 1-bromo-2-methylbenzene according to the procedure for the preparation of Example 43 using room temperature, followed by hydrolysis. ¹H NMR (400 MHz, DMSO-d₆): δ 0.79 (3H, d, J=6.5 Hz), 0.85 (3H, d, J=6.4 Hz), 2.80 (1H, m), 4.90 (1H, d, J=11.2 Hz), 7.32 (1H, t, J=7.4 Hz), 7.38 (2H, t, J=7.2 Hz), 7.49 (1H, d, J=4.1 Hz), 7.59 (1H, s), 7.61 (1H, s), 7.93 (1H, s), 8.22 (1H, s), 8.40 (1H, br s). [M+H] Calc'd for $C_{19}H_{19}N_3O_2$, 322. Found, 322.

Example 109

2-[1-(6-fluoro-2,3-dihydro-1H-inden-1-yl)imidazol-4-yl]pyridine-4-carboxylic acid

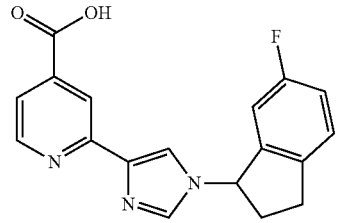 [SMILES: O=C(O)c1ccnc(-c2cn(C3CCc4ccc(F)cc43)cn2)c1]

The title compound was prepared in 5% yield from 2-(1H-imidazol-4-yl)pyridine-4-carbonitrile (PREPARATION 4) and 1-bromo-6-fluoro-2,3-dihydro-1H-indene according to the procedure for the preparation of Example 43 using room temperature, followed by hydrolysis. ¹H NMR (400 MHz, DMSO-d₆): δ 2.33 (2H, m), 2.66 (2H, m), 5.87 (1H, t, J=6.8 Hz), 6.96 (1H, dd, J=2.2 and 8.8 Hz), 7.14 (1H, dt, J=2.8 and 9.1 Hz), 7.41 (1H, t, J=5.2 Hz), 7.46 (1H, d, J=4.1 Hz), 7.52 (1H, s), 7.84 (1H, s), 8.23 (1H, s), 8.35 (1H, d, J=4.6 Hz). [M+H] Calc'd for $C_{18}H_{14}FN_3O_2$, 324. Found, 324.

Example 110

2-[1-(4-fluoro-2,3-dihydro-1H-inden-1-yl)imidazol-4-yl]pyridine-4-carboxylic acid

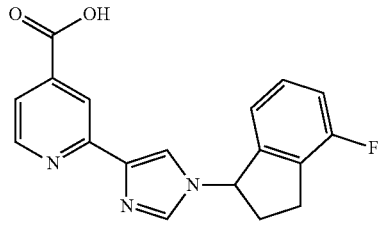 [SMILES: O=C(O)c1ccnc(-c2cn(C3CCc4c(F)cccc43)cn2)c1]

The title compound was prepared in 10% yield from 2-(1H-imidazol-4-yl)pyridine-4-carbonitrile (PREPARATION 4) and 1-bromo-4-fluoro-2,3-dihydro-1H-indene according to the procedure for the preparation of Example 43 using room temperature, followed by hydrolysis. $^1$H NMR (400 MHz, DMSO-d$_6$): δ 2.36 (2H, m), 2.74 (1H, m), 2.98 (1H, m), 5.95 (1H, t, J=6.9 Hz), 6.98 (1H, J=7.4 Hz), 7.15 (1H, t, J=8.8 Hz), 7.28 (1H, q, J=8.0 Hz), 7.51 (1H, d, J=4.6 Hz), 7.60 (1H, s), 7.88 (1H, s), 8.26 (1H, s), 8.46 (1H, d, J=5.1 Hz). [M+H] Calc'd for C$_{18}$H$_{14}$FN$_3$O$_2$, 324. Found, 324.

Example 111

2-[1-[(3-phenylphenyl)methyl]imidazol-4-yl]pyridine-4-carboxylic acid

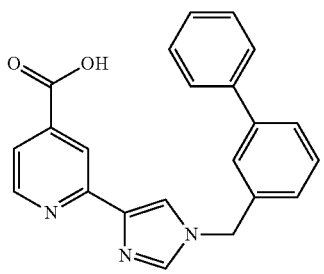 [SMILES: O=C(O)c1ccnc(-c2cn(Cc3cccc(-c4ccccc4)c3)cn2)c1]

The title compound was prepared in 70% yield from 2-(1H-imidazol-4-yl)pyridine-4-carbonitrile (PREPARATION 4) and 3-phenylbenzyl bromide according to the procedure for the preparation of Example 43 using room temperature, followed by hydrolysis. $^1$H NMR (400 MHz, DMSO-d$_6$): δ 5.32 (2H, s), 7.35 (2H, t, J=8.3 Hz), 7.47 (2H, t, J=7.6 Hz), 7.54 (1H, d, J=3.6 Hz), 7.61-7.67 (2H, m), 7.72 (1H, s), 7.87 (1H, s), 7.96 (1H, s), 8.26 (1H, s), 8.55 (1H, d, J=4.9 Hz). [M+H] Calc'd for C$_{22}$H$_{17}$N$_3$O$_2$, 356. Found, 356.

Example 112

2-[1-(2-naphthalen-1-ylethyl)imidazol-4-yl]pyridine-4-carboxylic acid

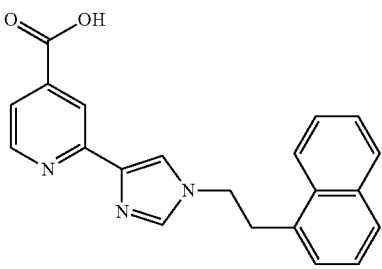 [SMILES: O=C(O)c1ccnc(-c2cn(CCc3cccc4ccccc34)cn2)c1]

The title compound was prepared in 30% yield from 2-(1H-imidazol-4-yl)pyridine-4-carbonitrile (PREPARATION 4) and 1-(2-bromoethyl)naphthalene according to the procedure for the preparation of Example 43. $^1$HNMR (400 MHz, DMSO): δ 3.58 (2H, t, J=7.6 Hz), 4.37 (2H, t, J=7.6 Hz), 7.36 (1H, d, J=6.2 Hz), 7.42 (1H, t, J=7.2 Hz), 7.51-7.60 (2H, m), 7.65 (1H, s), 7.83 (2H, t, J=6.0 Hz), 7.94 (1H, d, J=8.5 Hz), 8.23 (1H, s), 8.25 (1H, s), 8.39 (2H, s), 8.44 (1H, d, J=4.8 Hz). [M+H] Calc'd for C$_{21}$H$_{17}$N$_3$O$_2$, 344. Found, 344.

Example 113

2-[1-[2-(3-chlorophenyl)ethyl]imidazol-4-yl]pyridine-4-carboxylic acid

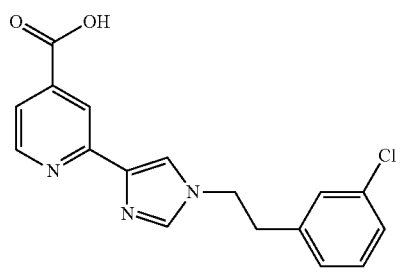 [SMILES: O=C(O)c1ccnc(-c2cn(CCc3cccc(Cl)c3)cn2)c1]

The title compound was prepared in 20% yield from 2-(1H-imidazol-4-yl)pyridine-4-carbonitrile (PREPARATION 4) and 3-chlorophenethyl bromide according to the procedure for the preparation of Example 43. $^1$HNMR (400 MHz, DMSO): δ 3.12 (2H, t, J=7.3 Hz), 4.29 (2H, t, J=7.3 Hz), 7.17 (1H, d, J=7.1 Hz), 7.26-7.33 (2H, m), 7.35 (1H, s), 7.58 (1H, dd, J=1.6 and 5.0 Hz), 7.66 (1H, s), 7.84 (1H, s), 8.26 (1H, s), 8.63 (1H, d, J=4.7 Hz). [M+H] Calc'd for C$_{17}$H$_{14}$ClN$_3$O$_2$, 329. Found, 329.

Example 114

2-[1-(2-cyclohexylethyl)imidazol-4-yl]pyridine-4-carboxylic acid

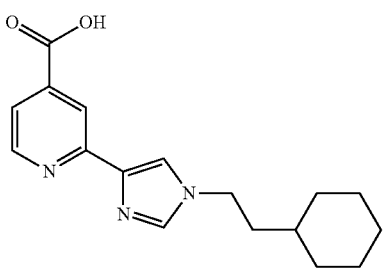 [SMILES: O=C(O)c1ccnc(-c2cn(CCC3CCCCC3)cn2)c1]

The title compound was prepared in 31% yield from 2-(1H-imidazol-4-yl)pyridine-4-carbonitrile (PREPARATION 4) and 1-bromo-2-cyclohexylethane according to the procedure for the preparation of Example 43. $^1$HNMR (400 MHz, DMSO): δ 0.91-0.97 (2H, m), 1.10-1.21 (5H, m), 1.61-1.73 (7H, m), 4.03 (2H, t, J=7.3 Hz), 7.52 (1H, d, J=4.6 Hz), 7.73 (2H, s), 8.29 (1H, s), 8.47 (1H, d, J=4.6 Hz). [M+H] Calc'd for C$_{17}$H$_{21}$N$_3$O$_2$, 300. Found, 300.

Example 115

2-[1-(cyclohexylmethyl)imidazol-4-yl]pyridine-4-carboxylic acid

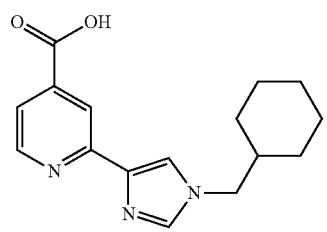 [SMILES: O=C(O)c1ccnc(-c2cn(CC3CCCCC3)cn2)c1]

The title compound was prepared in 19% yield from 2-(1H-imidazol-4-yl)pyridine-4-carbonitrile (PREPARATION 4) and (bromomethyl)cyclohexane according to the procedure for the preparation of Example 43. $^1$HNMR (400 MHz, DMSO): δ 0.89-0.98 (2H, m), 1.10-1.23 (3H, m), 1.54-1.73 (6H, m), 3.85 (2H, d, J=7.1 Hz), 7.49 (1H, d, J=5.2 Hz), 7.67 (2H, d, J=6.9 Hz), 8.24 (1H, s), 8.41 (1H, d). [M+H] Calc'd for $C_{16}H_{19}N_3O_2$, 286. Found, 286.

Example 116

2-[1-(1,2,3,4-tetrahydronaphthalen-1-ylmethyl)imidazol-4-yl]pyridine-4-carboxylic acid

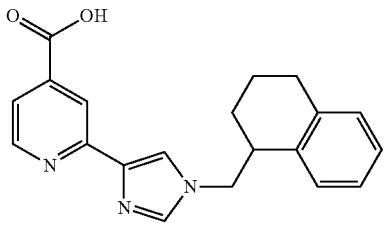 [SMILES: O=C(O)c1ccnc(-c2cn(CC3CCCc4ccccc43)cn2)c1]

The title compound was prepared in 5% yield from 2-(1H-imidazol-4-yl)pyridine-4-carbonitrile (PREPARATION 4) and 1-(bromomethyl)-1,2,3,4-tetrahydronaphthalene according to the procedure for the preparation of Example 43. $^1$HNMR (400 MHz, DMSO): δ 1.46-1.49 (1H, m), 1.63-1.67 (2H, m), 1.83-1.86 (1H, m), 2.73-2.89 (3H, d), 4.09-4.15 (1H, m), 4.27-4.31 (1H, m), 7.09-7.15 (3H, m), 7.29 (1H, t, J=4.4 Hz), 7.49 (1H, d, J=3.8 Hz), 7.72 (1H, s), 7.79 (1H, s), 8.26 (1H, s), 8.41 (1H, d). [M+H] Calc'd for $C_{20}H_{19}N_3O_2$, 334. Found, 334.

Example 117

2-[1-[[3-(trifluoromethyl)phenyl]methyl]imidazol-4-yl]pyridine-4-carboxylic acid

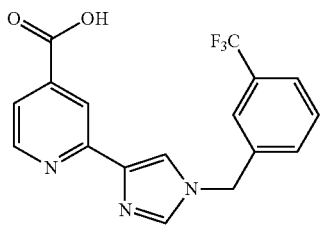

The title compound was prepared in 13% yield from 2-(1H-imidazol-4-yl)pyridine-4-carbonitrile (PREPARATION 4) and 3-trifluoromethylbenzyl bromide according to the procedure for the preparation of Example 43 using room temperature, followed by hydrolysis. $^1$H NMR (400 MHz, DMSO-$d_6$): δ 5.36 (2H, s), 7.52 (1H, d, J=4.1 Hz), 7.62-7.71 (3H, m), 7.79 (1H, s), 7.84 (1H, s), 7.94 (1H, s), 8.25 (1H, s), 8.51 (1H, d, J=4.7 Hz). [M+H] Calc'd for $C_{17}H_{12}F_3N_3O_2$, 348. Found, 348.

Example 118 methyl 2-[1-[2-(2-fluorophenyl)ethyl]imidazol-4-yl]pyridine-4-carboxylate

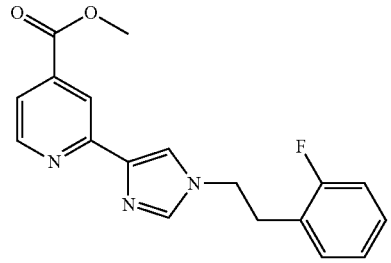 [SMILES: COC(=O)c1ccnc(-c2cn(CCc3ccccc3F)cn2)c1]

The title compound was prepared in 41% yield from 2-[1-[2-(2-fluorophenyl)ethyl]imidazol-4-yl]pyridine-4-carboxylic acid (Example 93) according to the procedure for the preparation of Example 8. $^1$HNMR (400 MHz, DMSO): δ 3.14 (2H, t, J=7.2 Hz), 3.91 (3H, s), 4.29 (2H, t, J=7.0 Hz), 7.09-7.18 (2H, m), 7.23-7.28 (2H, m), 7.60 (1H, dd, J=1.4 and 4.9 Hz), 7.65 (1H, s), 7.83 (1H, s), 8.27 (1H, s), 8.67 (1H, d, J=5.2 Hz). [M+H] Calc'd for $C_{18}H_{16}FN_3O_2$, 326. Found, 326.

Example 119 methyl 2-[1-[(3-phenylphenyl)methyl]imidazol-4-yl]pyridine-4-carboxylate

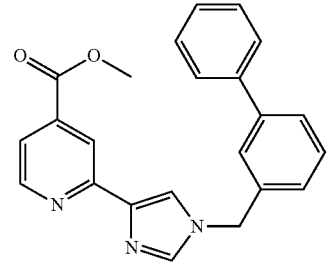 [SMILES: COC(=O)c1ccnc(-c2cn(Cc3cccc(-c4ccccc4)c3)cn2)c1]

The title compound was prepared in 60% yield from 2-[1-[(3-phenylphenyl)methyl]imidazol-4-yl]pyridine-4-carboxylic acid (Example 111) according to the procedure for the preparation of Example 8. $^1$H NMR (400 MHz, DMSO-$d_6$): δ 3.93 (3H, s), 5.63 (2H, s), 7.42 (1H, t, J=7.5 Hz), 7.47-7.56 (3H, m), 7.69 (4H, d, J=7.7 Hz), 7.86 (3H, d, J=9.3 Hz), 8.42 (1H, s). [M+H] Calc'd for $C_{23}H_{19}N_3O_2$, 370. Found, 370.

Example 120

2-[5-[2-(cyclopropylmethoxy)-4-fluorophenyl]-1-methylimidazol-4-yl]pyridine-4-carboxylic acid

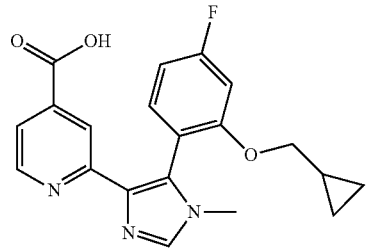 [SMILES: Cn1cnc(-c2cc(C(=O)O)ccn2)c1-c1ccc(F)cc1OCC1CC1]

The title compound was prepared in 10% yield from 2-(5-bromo-1-methyl-1H-imidazol-4-yl)pyridine-4-carboxylic acid methyl ester and 2-(cyclopropylmethoxy)-4-fluorophenylboronic acid according to the procedure for the preparation of Example 3, part A followed by hydrolysis. $^1$H NMR (400 MHz, DMSO-$d_6$): δ 0.10 (2H, m), 0.32-0.39 (2H, m), 0.88-0.93 (1H, m), 3.44 (3H, s), 3.69 (1H, m), 3.81 (1H, m), 6.80 (1H, td, J=2.4 and 8.4 Hz), 6.96 (1H, dd, J=2.4 and 11.6 Hz), 7.27 (1H, t, J=7.7 Hz), 7.45 (1H, dd, J=1.5 and 5.1 Hz), 7.84 (1H, s), 8.28 (1H, s), 8.31 (1H, d, J=5.0 Hz). [M+H] Calc'd for $C_{20}H_{18}FN_3O_3$, 368. Found, 368.

Example 121

2-[5-[2-(cyclopropylmethoxy)-4,5-difluorophenyl]-1-methylimidazol-4-yl]pyridine-4-carboxylic acid

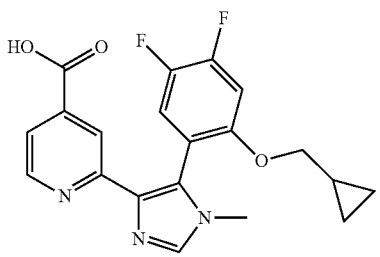 [SMILES: Cn1cnc(-c2cc(C(=O)O)ccn2)c1-c1cc(F)c(F)cc1OCC1CC1]

The title compound was prepared in 5% yield from 2-(5-bromo-1-methyl-1H-imidazol-4-yl)pyridine-4-carboxylic acid methyl ester and 2-(cyclopropylmethoxy)-4,5-difluorophenylboronic acid pinacol ester according to the procedure for the preparation of Example 3, part A followed by hydrolysis. $^1$H NMR (400 MHz, DMSO-$d_6$): δ 0.29-0.32 (2H, m), 0.53-0.58 (2H, m), 1.22 (1H, m), 3.43 (3H, s), 3.82 (2H, d, J=7.0 Hz), 6.82 (1H, br s), 7.09-7.14 (1H, m), 7.27 (1H, t, J=7.7 Hz), 7.42 (1H, d, J=3.6 Hz), 7.90 (1H, s), 8.20 (1H, d, J=4.3 Hz), 8.30 (1H, s). [M+H] Calc'd for $C_{20}H_{12}F_2N_3O_3$, 386. Found, 386.

Example 122

2-[5-[2-(cyclopropylmethoxy)-6-fluorophenyl]-1-methylimidazol-4-yl]pyridine-4-carboxylic acid

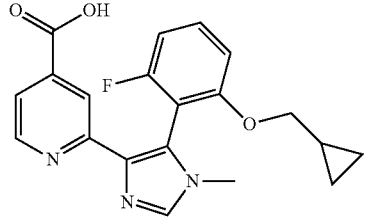 [SMILES: Cn1cnc(-c2cc(C(=O)O)ccn2)c1-c1c(F)cccc1OCC1CC1]

The title compound was prepared in 3% yield from 2-(5-bromo-1-methyl-1H-imidazol-4-yl)pyridine-4-carboxylic acid methyl ester and 2-(cyclopropylmethoxy)-6-fluorophenylboronic acid according to the procedure for the preparation of Example 3, part A followed by hydrolysis. $^1$H NMR (400 MHz, DMSO-$d_6$): δ 0.12 (2H, m), 0.33-0.40 (2H, m), 0.83-0.94 (1H, m), 3.60-3.70 (1H, m), 3.72-3.84 (1H, m), 6.84 (1H, t, J=8.4 Hz), 6.92 (1H, d, J=8.2 Hz), 7.35 (1H, t, J=5.0 Hz), 7.40 (1H, t, J=7.8 Hz), 7.86 (1H, s), 8.08 (1H, d, J=4.7 Hz), 8.27 (1H, s). [M+H] Calc'd for $C_{20}H_{18}FN_3O_3$, 368. Found, 368.

Example 123

2-[5-[2-(cyclopropylmethoxy)-5-methylphenyl]-1-methylimidazol-4-yl]pyridine-4-carboxylic acid

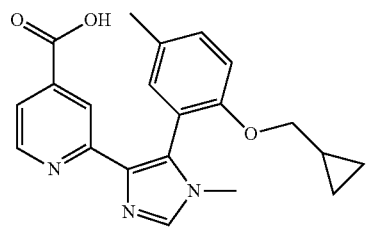 [SMILES: Cc1ccc(OCC2CC2)c(-c2c(-c3cc(C(=O)O)ccn3)ncn2C)c1]

The title compound was prepared in 17% yield from 2-(5-bromo-1-methyl-1H-imidazol-4-yl)pyridine-4-carboxylic acid methyl ester and 2-(cyclopropylmethoxy)-6-fluorophenylboronic acid according to the procedure for the preparation of Example 3, part A followed by hydrolysis. $^1$H NMR (400 MHz, DMSO-$d_6$): δ 0.07-0.10 (2H, m), 0.29-0.37 (2H, m), 0.83-0.86 (1H, m), 2.23 (3H, s), 3.42 (3H, s), 3.59-3.63 (1H, m), 3.72-3.77 (1H, m), 6.95 (1H, d, J=8.5 Hz), 7.04 (1H, s), 7.16 (1H, d, J=8.6 Hz), 7.44 (1H, d, J=4.7 Hz), 7.82 (1H, s), 8.27 (1H, s), 8.31 (1H, d, J=5.1 Hz). [M+H] Calc'd for $C_{21}H_{21}N_3O_3$, 364. Found, 364.

PREPARATION 7:
2-(1H-imidazol-4-yl)pyridine-4-carboxamide

A. methyl 2-formylpyridine-4-carboxylate

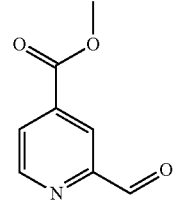

To a solution of methyl 2-(hydroxymethyl)pyridine-4-carboxylate (30 g, 179.64 mmol) in DCM (1 L) was added MnO$_2$ (93.77 g, 1.0778 mol) at r.t. and stirred overnight. The reaction mixture was then filtered and concentrated to afford the title compound (21.3 g, 72%). [M+H] Calc'd for $C_8H_7NO_3$, 166. Found, 166.

B. 2-[4-(4-methylphenyl) sulfonyl-4,5-dihydro-1,3-oxazol-5-yl]pyridine-4-carboxamide

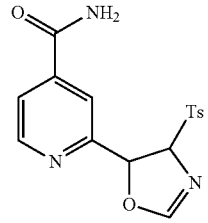 [SMILES: Cc1ccc(S(=O)(=O)C2N=COC2c2cc(C(N)=O)ccn2)cc1]

To a solution of methyl 2-formylpyridine-4-carboxylate (12 g, 72.7 mmol) and TsMic (12 g, 72.7 mmol) in EtOH (200 mL), was added KCN (487 mg, 7.27 mmol) at r.t., stirred for 20 min, filtered, the solid dried to give the title compound (23 g, 88%). [M+H] Calc'd for $C_{16}H_{15}N_3O_4S$, 361. Found, 361.

C. 2-(1H-imidazol-4-yl)pyridine-4-carboxamide

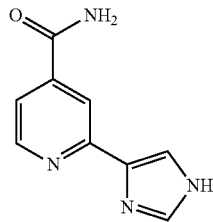 [SMILES: NC(=O)c1ccnc(-c2c[nH]cn2)c1]

2-[4-(4-methylphenyl)sulfonyl-4,5-dihydro-1,3-oxazol-5-yl]pyridine-4-carboxamide (23 g, 63.98 mmol) was added to a solution of $NH_3$ in MeOH (5 g/120 mL) and stirred overnight at 125° C., concentrated and purified by flash column chromatography to give the title compound (5 g, 36.8%). [M+H] Calc'd for $C_9H_8N_4O$, 189. Found, 189.

Example 124

2-[1-[2-(2-chlorophenyl)ethyl]-5-(4-fluorophenyl)imidazol-4-yl]pyridine-4-carboxylic acid A. 2-[1-[2-(2-chlorophenyl)ethyl]imidazol-4-yl]pyridine-4-carboxamide

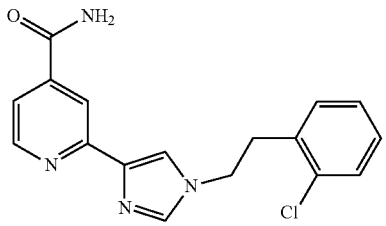 [SMILES: NC(=O)c1ccnc(-c2cn(CCc3ccccc3Cl)cn2)c1]

A mixture of 2-(1H-imidazol-4-yl)pyridine-4-carboxamide (400 mg, 2.13 mmol, PREPARATION 7), 1-(2-bromoethyl)-2-chloro-benzene (557 mg, 2.55 mmol) and $K_2CO_3$ (587 mg, 4.26 mmol) in DMF (10 mL) was stirred overnight at 80° C. LC/MS showed the reaction was completed. It was then purified by flash column chromatography to give the title compound (228 mg, 33%) as a yellow solid. [M+H] Calc'd for $C_{17}H_{15}ClN_4O$, 327. Found, 327.

B. 2-[1-[2-(2-chlorophenyl)ethyl]imidazol-4-yl]pyridine-4-carbonitrile

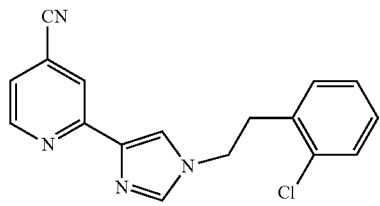 [SMILES: N#Cc1ccnc(-c2cn(CCc3ccccc3Cl)cn2)c1]

To a solution of 2-[1-[2-(2-chlorophenyl)ethyl]imidazol-4-yl]pyridine-4-carboxamide (1 eq) and pyridine (3 eq) in DCM was added TFAA (2 eq) slowly at 0° C., then the mixture was stirred for 2 hr at 0° C., the solution was washed by $H_2O$, $NaHCO_3$ and brine. The collected organic fractions were concentrated and purified by FCC (PE/EA=1/4) to give the title compound (53%). [M+H] Calc'd for $C_{17}H_{13}ClN_4$, 309. Found, 309.

C. 2-[5-bromo-1-[2-(2-chlorophenyl)ethyl]imidazol-4-yl]pyridine-4-carbonitrile

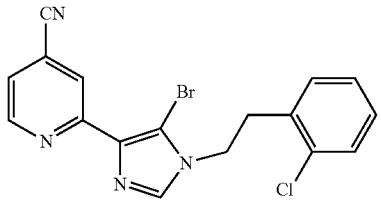 [SMILES: N#Cc1ccnc(-c2ncn(CCc3ccccc3Cl)c2Br)c1]

To a solution of 2-[1-[2-(2-chlorophenyl)ethyl]imidazol-4-yl]pyridine-4-carbonitrile (1 eq) in DCM (10 mL) was added NBS (1.05 eq) at rt and stirred for 3 hr at rt. Washed by $H_2O$, dried and concentrated to afford the title compound (95%). [M+H] Calc'd for $C_{17}H_{12}BrClN_4$, 387. Found, 387.

D. 2-[1-[2-(2-chlorophenyl)ethyl]-5-(4-fluorophenyl)imidazol-4-yl]pyridine-4-carbonitrile

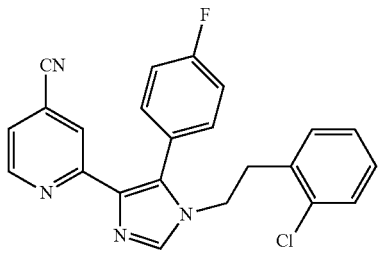 [SMILES: N#Cc1ccnc(-c2ncn(CCc3ccccc3Cl)c2-c2ccc(F)cc2)c1]

A mixture of 2-[5-bromo-1-[2-(2-chlorophenyl)ethyl]imidazol-4-yl]pyridine-4-carbonitrile (1 eq), 4-fluorophenylboronic acid, $Pd(dppf)Cl_2$ (0.1 eq) and $Na_2CO_3$ (2 eq, 2 M) in dioxane was refluxed overnight under $N_2$. The reaction mixture was concentrated and purified by FCC (DCM/MeOH=20/1) to give the title compound (48%). [M+H] Calc'd for $C_{23}H_{16}ClFN_4$, 403. Found, 403.

E. 2-[1-[2-(2-chlorophenyl)ethyl]-5-(4-fluorophenyl)imidazol-4-yl]pyridine-4-carboxylic acid

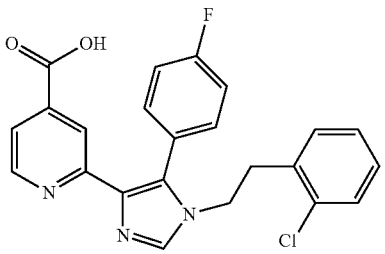 [SMILES: O=C(O)c1ccnc(-c2ncn(CCc3ccccc3Cl)c2-c2ccc(F)cc2)c1]

A mixture of 2-[1-[2-(2-chlorophenyl)ethyl]-5-(4-fluorophenyl)imidazol-4-yl]pyridine-4-carbonitrile (1 eq) and NaOH (5 eq, 2 M) in MeOH was refluxed overnight, concentrated and acidified to pH=3-4, purified by HPLC to give the title compound (43%). $^1H$ NMR (300 MHz, $CD_3OD$): δ 3.07 (2H, t, J=6.6 Hz), 4.27 (2H, t, J=6.6 Hz), 7.00-7.33 (8H, m), 7.68 (1H, d, J=5.1 Hz), 7.93-7.95 (2H, m), 8.52 (1H, d, J=4.8 Hz). [M+H] Calc'd for $C_{23}H_{17}ClFN_3O_2$, 422. Found, 422.

Example 125

2-[1-(cyclopropylmethyl)-5-(4-fluorophenyl)imidazol-4-yl]pyridine-4-carboxylic acid A. 2-[1-(cyclopropylmethyl)imidazol-4-yl]pyridine-4-carboxamide

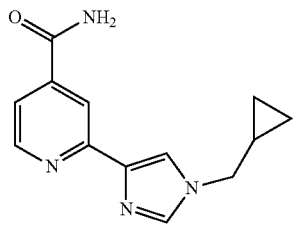 [SMILES: NC(=O)c1ccnc(-c2cn(CC3CC3)cn2)c1]

The title compound was prepared in 60% yield from 2-(1H-imidazol-4-yl)pyridine-4-carboxamide (PREPARATION 7) and cyclopropylmethyl bromide according to the procedure for the preparation of Example 124, part A. [M+H] Calc'd for $C_{13}H_{14}N_4O$, 327. Found, 327.

B. 2-[1-(cyclopropylmethyl)imidazol-4-yl]pyridine-4-carbonitrile

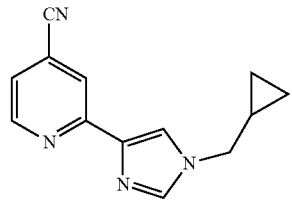 [SMILES: N#Cc1ccnc(-c2cn(CC3CC3)cn2)c1]

The title compound was prepared in 43% yield from 2-[1-(cyclopropylmethyl)imidazol-4-yl]pyridine-4-carboxamide according to the procedure for the preparation of Example 124, part B. [M+H] Calc'd for $C_{13}H_{12}N_4$, 225. Found, 225.

C. 2-[5-bromo-1-(cyclopropylmethyl)imidazol-4-yl]pyridine-4-carbonitrile

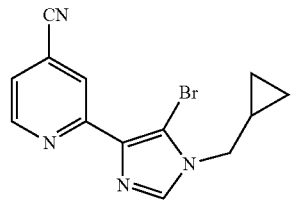 [SMILES: N#Cc1ccnc(-c2ncn(CC3CC3)c2Br)c1]

The title compound was prepared in 80% yield from 2-[1-(cyclopropylmethyl)imidazol-4-yl]pyridine-4-carbonitrile according to the procedure for the preparation of Example 124, part C. [M+H] Calc'd for $C_{13}H_{11}BrN_4$, 303. Found, 303.

D. 2-[1-(cyclopropylmethyl)-5-(4-fluorophenyl)imidazol-4-yl]pyridine-4-carbonitrile

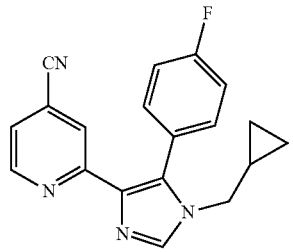 [SMILES: N#Cc1ccnc(-c2ncn(CC3CC3)c2-c2ccc(F)cc2)c1]

The title compound was prepared in 50% yield from 2-[5-bromo-1-(cyclopropylmethyl)imidazol-4-yl]pyridine-4-carbonitrile according to the procedure for the preparation of Example 124, part D. [M+H] Calc'd for $C_{19}H_{15}FN_4$, 319. Found, 319.

E. 2-[1-(cyclopropylmethyl)-5-(4-fluorophenyl)imidazol-4-yl]pyridine-4-carboxylic acid

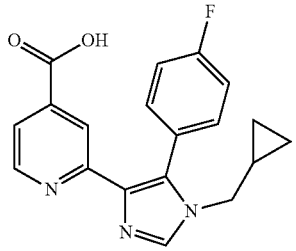 [SMILES: O=C(O)c1ccnc(-c2ncn(CC3CC3)c2-c2ccc(F)cc2)c1]

The title compound was prepared in 44% yield from 2-[1-(cyclopropylmethyl)-5-(4-fluorophenyl)imidazol-4-yl]pyridine-4-carbonitrile according to the procedure for the preparation of Example 124, part E. $^1$H NMR (300 MHz, $CD_3OD$): δ 0.23-0.26 (2H, m), 0.52-0.58 (2H, m), 1.05 (1H, m), 3.79 (2H, d, J=7.2 Hz), 7.18-7.24 (2H, m), 7.40-7.44 (2H, m), 7.63 (1H, d, J=6.3 Hz), 7.92-7.97 (2H, m), 8.47 (1H, d, J=4.5 Hz). [M+H] Calc'd for $C_{19}H_{16}FN_3O_2$, 338. Found, 338.

Example 126

2-[5-(4-chlorophenyl)-1-(cyclopropylmethyl)imidazol-4-yl]pyridine-4-carboxylic acid

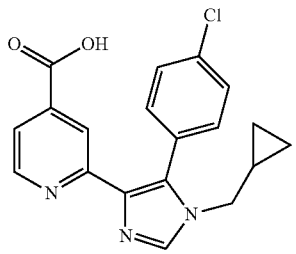 [SMILES: O=C(O)c1ccnc(-c2ncn(CC3CC3)c2-c2ccc(Cl)cc2)c1]

The title compound was prepared in 26% yield according to the procedure for the preparation of Example 125. $^1$H NMR (300 MHz, $CD_3OD$): δ 0.35-0.37 (2H, m), 0.67-0.70 (2H, m), 1.18-1.21 (1H, m), 3.93 (2H, d, J=5.1 Hz), 7.60-7.73 (5H, m), 7.87-7.88 (1H, m), 8.83 (1H, m), 9.13 (1H, m). [M+H] Calc'd for $C_{19}H_{16}ClN_3O_2$, 354. Found, 354.

Example 127

2-[1-[(2-chlorophenyl)methyl]-5-(4-fluorophenyl)imidazol-4-yl]pyridine-4-carboxylic acid A. 2-[5-bromo-1-[(2-chlorophenyl)methyl]imidazol-4-yl]pyridine-4-carbonitrile

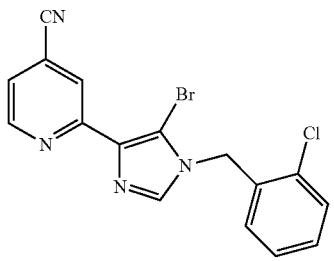 [SMILES: N#Cc1ccnc(-c2ncn(Cc3ccccc3Cl)c2Br)c1]

The title compound was prepared in 82% yield from 2-[1-[(2-chlorophenyl)methyl]imidazol-4-yl]pyridine-4-carbonitrile according to the procedure for the preparation of Example 124, part C. [M+H] Calc'd for $C_{16}H_{10}BrClN_4$, 373. Found, 373.

B. 2-[1-[(2-chlorophenyl)methyl]-5-(4-fluorophenyl)imidazol-4-yl]pyridine-4-carbonitrile

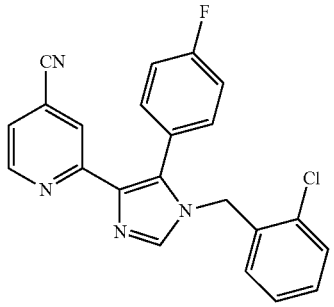 [SMILES: N#Cc1ccnc(-c2ncn(Cc3ccccc3Cl)c2-c2ccc(F)cc2)c1]

A mixture of 2-[5-bromo-1-[(2-chlorophenyl)methyl]imidazol-4-yl]pyridine-4-carbonitrile (270 mg, 0.726 mmol), 4-fluorophenylboronic acid (203 mg, 1.452 mmol), Pd(dppf)Cl$_2$ (60 mg, 0.0726 mmol) and Na$_2$CO$_3$ (0.3 mL, 1.452 mmol, 2 M) in dioxane (10 mL) was refluxed overnight under N$_2$, concentrated and purified by FCC (DCM/MeOH=20/1) to give the title compound (250 mg, 88%). [M+H] Calc'd for $C_{22}H_{14}ClFN_4$, 389. Found, 389.

C. 2-[1-[(2-chlorophenyl)methyl]-5-(4-fluorophenyl)imidazol-4-yl]pyridine-4-carboxylic acid

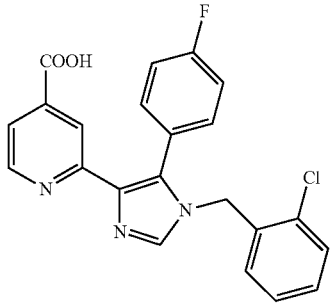 [SMILES: O=C(O)c1ccnc(-c2ncn(Cc3ccccc3Cl)c2-c2ccc(F)cc2)c1]

The title compound was prepared in 24% yield from 2-[1-[(2-chlorophenyl)methyl]-5-(4-fluorophenyl)imidazol-4-yl]pyridine-4-carbonitrile according to the procedure for the preparation of Example 124, part E. $^1$H NMR (300 MHz, CD$_3$OD): δ 5.28 (2H, s), 6.85-6.88 (1H, m), 7.09-7.39 (7H, m), 7.66 (1H, d, J=6.3 Hz), 7.95 (1H, s), 7.80 (1H, s), 8.50 (1H, d, J=5.4 Hz). [M+H] Calc'd for $C_{22}H_{15}ClFN_3O_2$, 408. Found, 408.

Example 128

2-[1-[2-(2-ethoxyphenyl)ethyl]imidazol-4-yl]-4-(2H-tetrazol-5-yl)pyridine

A. 2-[1-[2-(2-ethoxyphenyl)ethyl]imidazol-4-yl]pyridine-4-carboxamide

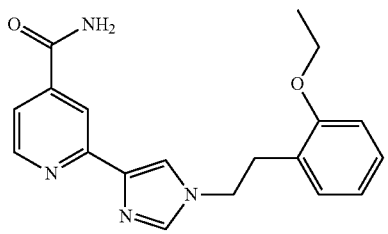 [SMILES: CCOc1ccccc1CCn1cnc(-c2cc(C(N)=O)ccn2)c1]

A mixture of 2-(1H-imidazol-4-yl)pyridine-4-carboxamide (200 mg, 1.06 mmol, PREPARATION 7), methanesulfonic acid 2-(2-ethoxy-phenyl)-ethyl ester (311 mg, 1.28 mmol) and K$_2$CO$_3$ (294 mg, 2.13 mmol) in DMF (10 mL) was stirred overnight at 70° C., LC/MS showed the reaction was completed, purified by FCC (DCM/MeOH=20/1) to give the title compound (189 mg, 53%) as a yellow solid. [M+H] Calc'd for $C_{19}H_{20}N_4O_2$, 337. Found, 337.

B. 2-[1-[2-(2-ethoxyphenyl)ethyl]imidazol-4-yl]pyridine-4-carbonitrile

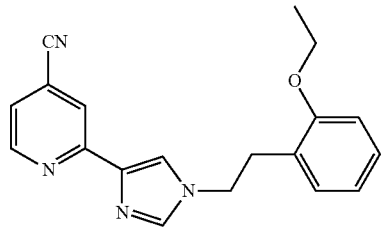 [SMILES: CCOc1ccccc1CCn1cnc(-c2cc(C#N)ccn2)c1]

The title compound was prepared in 47% yield from 2-[1-[2-(2-ethoxyphenyl)ethyl]imidazol-4-yl]pyridine-4-carboxamide according to the procedure for the preparation of Example 124, part B. [M+H] Calc'd for $C_{19}H_{18}N_4O$, 319. Found, 319.

C. 2-[1-[2-(2-ethoxyphenyl)ethyl]imidazol-4-yl]-4-(2H-tetrazol-5-yl)pyridine

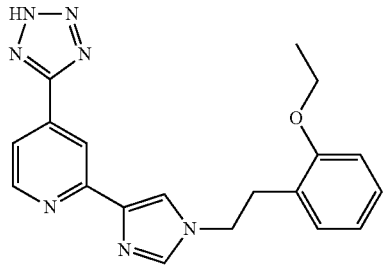 [SMILES: CCOc1ccccc1CCn1cnc(-c2cc(-c3nn[nH]n3)ccn2)c1]

To a mixture of 2-[1-[2-(2-ethoxyphenyl)ethyl]imidazol-4-yl]pyridine-4-carbonitrile (1 eq) and NH₄Cl (10 eq) in DMF was added NaN₃ at rt, then stirred for 2 hr at 110° C. in a microwave oven, LC/MS showed the reaction was completed, acidified to PH=3-4 by conc. HCl, stirred for 1 hr, then adjusted to PH=7-8 by NaOH, concentrated and purified by HPLC to give the title compound (56%). ¹H NMR (400 MHz, DMSO): δ 1.36 (3H, t, J=6.4 Hz), 3.06-3.09 (2H, m), 4.02-4.03 (2H, m), 4.25-4.29 (2H, m), 6.82-7.19 (4H, m), 7.69 (1H, s), 7.76-7.81 (2H, m), 8.47 (1H, s), 8.61 (1H, d, J=6.0 Hz). [M+H] Calc'd for C₁₉H₁₉N₇O, 362. Found, 362.

Example 129

2-[1-[(2-chlorophenyl)methyl]imidazol-4-yl]-4-(2H-tetrazol-5-yl)pyridine

A. 2-[1-[(2-chlorophenyl)methyl]imidazol-4-yl]pyridine-4-carboxamide

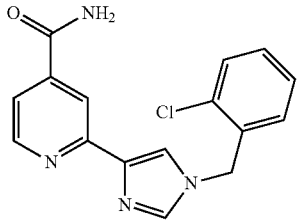 [SMILES: NC(=O)c1ccnc(-c2cn(Cc3ccccc3Cl)cn2)c1]

A mixture of 2-(1H-imidazol-4-yl)pyridine-4-carboxamide (PREPARATION 7)), 1-bromomethyl-2-chlorobenzene (260 mg, 1.28 mmol) and K₂CO₃ (176 mg, 1.28 mmol) in DMF (8 mL) was stirred overnight at rt, LC/MS showed the reaction was completed, purified by FCC to give the title compound (83 mg, 42%) as a yellow solid. [M+H] Calc'd for C₁₆H₁₃ClN₄O, 313. Found, 313.

B. 2-[1-[(2-chlorophenyl)methyl]imidazol-4-yl]pyridine-4-carbonitrile

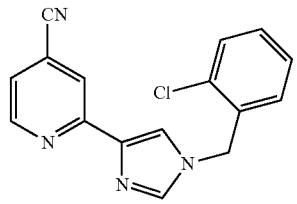 [SMILES: N#Cc1ccnc(-c2cn(Cc3ccccc3Cl)cn2)c1]

The title compound was prepared in 93% yield from 2-[1-[(2-chlorophenyl)methyl]imidazol-4-yl]pyridine-4-carboxamide according to the procedure for the preparation of Example 124, part B. [M+H] Calc'd for C₁₆H₁₁ClN₄, 295. Found, 295.

C. 2-[1-[(2-chlorophenyl)methyl]imidazol-4-yl]-4-(2H-tetrazol-5-yl)pyridine

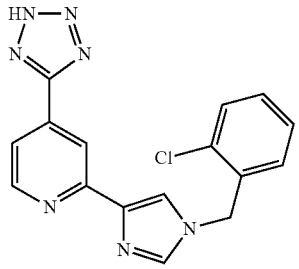 [SMILES: Clc1ccccc1Cn1cnc(-c2cc(-c3nn[nH]n3)ccn2)c1]

The title compound was prepared in 28% yield from 2-[1-[(2-chlorophenyl)methyl]imidazol-4-yl]pyridine-4-carbonitrile according to the procedure for the preparation of Example 128, part C. ¹H NMR (400 MHz, DMSO): δ 5.42 (2H, s), 7.29-7.31 (1H, m), 7.38-7.41 (2H, m), 7.52-7.55 (1H, m), 7.81 (1H, d, J=5.2 Hz), 7.87 (1H, s), 7.99 (1H, s), 8.52 (1H, s), 8.68 (1H, d, J=4.4 Hz). [M+H] Calc'd for C₁₆H₁₂ClN₇, 338. Found, 338.

Example 130

2-[1-[(3-chlorophenyl)methyl]imidazol-4-yl]-4-(2H-tetrazol-5-yl)pyridine

A. 2-[1-[(3-chlorophenyl)methyl]imidazol-4-yl]pyridine-4-carboxamide

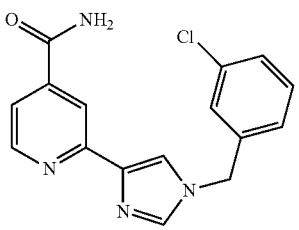 [SMILES: NC(=O)c1ccnc(-c2cn(Cc3cccc(Cl)c3)cn2)c1]

The title compound was prepared in 51% yield from 2-(1H-imidazol-4-yl)pyridine-4-carboxamide according to the procedure for the preparation of Example 129, part A. [M+H] Calc'd for C₁₆H₁₃ClN₄O, 313. Found, 313.

B. 2-[1-[(3-chlorophenyl)methyl]imidazol-4-yl]pyridine-4-carbonitrile

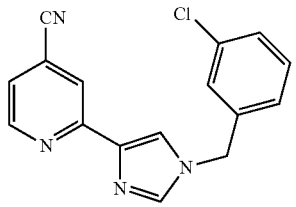 [SMILES: N#Cc1ccnc(-c2cn(Cc3cccc(Cl)c3)cn2)c1]

The title compound was prepared in 40% yield from 2-[1-[(3-chlorophenyl)methyl]imidazol-4-yl]pyridine-4-carboxamide according to the procedure for the preparation of Example 124, part B. [M+H] Calc'd for C₁₆H₁₁ClN₄, 295. Found, 295.

C. 2-[1-[(3-chlorophenyl)methyl]imidazol-4-yl]-4-(2H-tetrazol-5-yl)pyridine

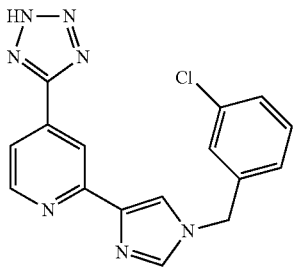 [SMILES: Clc1cccc(Cn2cnc(-c3cc(-c4nn[nH]n4)ccn3)c2)c1]

The title compound was prepared in 34% yield from 2-[1-[(3-chlorophenyl)methyl]imidazol-4-yl]pyridine-4-carbonitrile according to the procedure for the preparation of Example 128, part C. ¹H NMR (300 MHz, DMSO): δ 5.31

(2H, s), 7.41-7.49 (4H, m), 7.82 (1H, m), 7.98 (1H, s), 8.04 (1H, s), 8.52 (1H, s), 8.68 (1H, d, J=5.1 Hz). [M+H] Calc'd for $C_{16}H_{12}ClN_7$, 338. Found, 338.

Example 131

2-[1-[(4-chlorophenyl)methyl]imidazol-4-yl]-4-(2H-tetrazol-5-yl)pyridine

A. 2-[1-[(4-chlorophenyl)methyl]imidazol-4-yl]pyridine-4-carboxamide

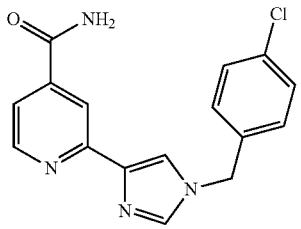 [SMILES: NC(=O)c1ccnc(-c2cn(Cc3ccc(Cl)cc3)cn2)c1]

The title compound was prepared in 46% yield from 2-(1H-imidazol-4-yl)pyridine-4-carboxamide according to the procedure for the preparation of Example 129, part A. [M+H] Calc'd for $C_{16}H_{13}ClN_4O$, 313. Found, 313.

B. 2-[1-[(4-chlorophenyl)methyl]imidazol-4-yl]pyridine-4-carbonitrile

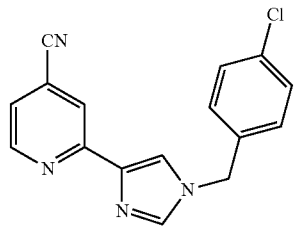 [SMILES: N#Cc1ccnc(-c2cn(Cc3ccc(Cl)cc3)cn2)c1]

The title compound was prepared in 80% yield from 2-[1-[(4-chlorophenyl)methyl]imidazol-4-yl]pyridine-4-carboxamide according to the procedure for the preparation of Example 124, part B. [M+H] Calc'd for $C_{16}H_{11}ClN_4$, 295. Found, 295.

C. 2-[1-[(4-chlorophenyl)methyl]imidazol-4-yl]-4-(2H-tetrazol-5-yl)pyridine

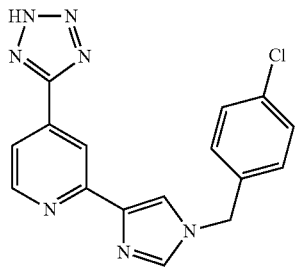 [SMILES: Clc1ccc(Cn2cnc(-c3cc(-c4nn[nH]n4)ccn3)c2)cc1]

The title compound was prepared in 58% yield from 2-[1-[(4-chlorophenyl)methyl]imidazol-4-yl]pyridine-4-carbonitrile according to the procedure for the preparation of Example 128, part C. $^1$H NMR (300 MHz, DMSO): δ 5.30 (2H, s), 7.39-7.48 (4H, m), 7.80-7.82 (1H, m), 7.94 (1H, s), 8.02 (1H, s), 8.51 (1H, s), 8.68 (1H, d, J=5.1 Hz). [M+H] Calc'd for $C_{16}H_{12}ClN_7$, 338. Found, 338.

Example 132

2-[1-[2-(2-chlorophenyl)ethyl]-5-(4-fluorophenyl)imidazol-4-yl]-4-(2H-tetrazol-5-yl)pyridine

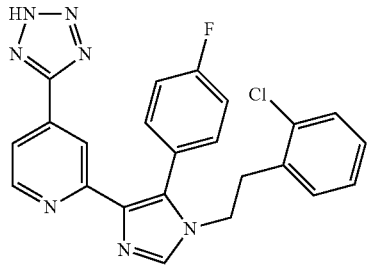

The title compound was prepared in 36% yield from 2-[1-[2-(2-chlorophenyl)ethyl]-5-(4-fluorophenyl)imidazol-4-yl]pyridine-4-carbonitrile (Example 124, part D) according to the procedure for the preparation of Example 128, part C. $^1$H NMR (300 MHz, DMSO): δ 3.07 (2H, t, J=6.6 Hz), 4.26 (2H, t, J=6.6 Hz), 7.19-7.48 (8H, m), 7.77-7.79 (1H, m), 7.95-7.98 (1H, m), 8.83 (1H, br), 9.22 (1H, br). [M+H] Calc'd for $C_{23}H_{17}ClFN_7$, 446. Found, 446.

Example 133

2-[5-(4-chlorophenyl)-1-[2-(2-chlorophenyl)ethyl]imidazol-4-yl]-4-(2H-tetrazol-5-yl)pyridine

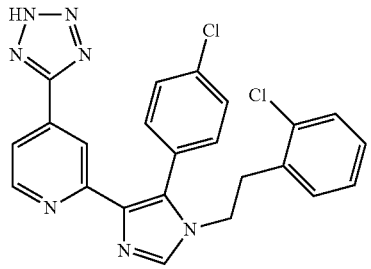 [SMILES: Fc1ccc(-c2c(-c3cc(-c4nn[nH]n4)ccn3)ncn2CCc2ccccc2Cl)cc1]

The title compound was prepared in 20% yield from 2-[5-(4-chlorophenyl)-1-[2-(2-chlorophenyl)ethyl]imidazol-4-yl]pyridine-4-carbonitrile according to the procedure for the preparation of Example 128, part C. $^1$H NMR (300 MHz, DMSO): δ 2.97 (2H, t, J=6.6 Hz), 4.15 (2H, t, J=6.6 Hz), 7.11-7.37 (8H, m), 7.76-7.78 (1H, m), 8.26-8.37 (2H, m), 8.52 (1H, d, J=4.5 Hz). [M+H] Calc'd for $C_{23}H_{17}Cl_2N_7$, 462. Found, 462.

Example 134

2-[5-(4-fluorophenyl)-1-(2,2,2-trifluoroethyl)imidazol-4-yl]-4-(2H-tetrazol-5-yl)pyridine A. 2-[1-(2,2,2-trifluoroethyl)imidazol-4-yl]pyridine-4-carboxamide

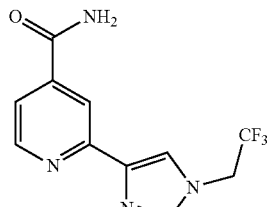

The title compound was prepared in 60% yield from 2-(1H-imidazol-4-yl)pyridine-4-carboxamide (PREPARATION 7) and toluene-4-sulfonic acid 2,2,2-trifluoro-ethyl ester according to the procedure for the preparation Example 128, part A. [M+H] Calc'd for $C_{11}H_9F_3N_4O$, 271. Found, 271.

B. 2-[1-(2,2,2-trifluoroethyl)imidazol-4-yl]pyridine-4-carbonitrile

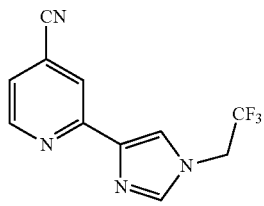 [SMILES: N#Cc1ccnc(-c2cn(CC(F)(F)F)cn2)c1]

The title compound was prepared in 40% yield from 2-[1-(2,2,2-trifluoroethyl)imidazol-4-yl]pyridine-4-carboxamide according to the procedure for the preparation of Example 124, part B. [M+H] Calc'd for $C_{11}H_7F_3N_4$, 253. Found, 253.

C. 2-[5-bromo-1-(2,2,2-trifluoroethyl)imidazol-4-yl]pyridine-4-carbonitrile

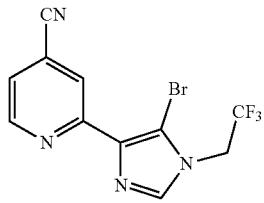 [SMILES: N#Cc1ccnc(-c2ncn(CC(F)(F)F)c2Br)c1]

The title compound was prepared in 40% yield from 2-[1-(2,2,2-trifluoroethyl)imidazol-4-yl]pyridine-4-carbonitrile according to the procedure for the preparation of Example 124, part C. [M+H] Calc'd for $C_{11}H_6BrF_3N_4$, 331. Found, 331.

D. 2-[5-(4-fluorophenyl)-1-(2,2,2-trifluoroethyl)imidazol-4-yl]pyridine-4-carbonitrile

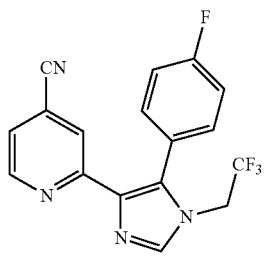 [SMILES: N#Cc1ccnc(-c2ncn(CC(F)(F)F)c2-c2ccc(F)cc2)c1]

The title compound was prepared in 48% yield from 2-[5-bromo-1-(2,2,2-trifluoroethyl)imidazol-4-yl]pyridine-4-carbonitrile according to the procedure for the preparation of Example 124, part D. [M+H] Calc'd for $C_{17}H_{10}F_4N_4$, 347. Found, 347.

E. 2-[5-(4-fluorophenyl)-1-(2,2,2-trifluoroethyl)imidazol-4-yl]-4-(2H-tetrazol-5-yl)pyridine

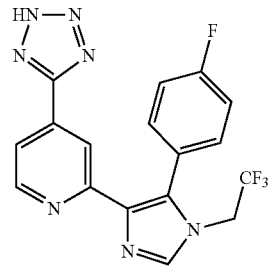 [SMILES: Fc1ccc(-c2c(-c3cc(-c4nn[nH]n4)ccn3)ncn2CC(F)(F)F)cc1]

The title compound was prepared in 68% yield from 2-[5-(4-fluorophenyl)-1-(2,2,2-trifluoroethyl)imidazol-4-yl]pyridine-4-carbonitrile according to the procedure for the preparation of Example 128, part C. $^1$H NMR (300 MHz, DMSO): δ 4.86-4.89 (2H, m), 7.59-7.35 (2H, m), 7.45-7.49 (2H, m), 7.74 (1H, d, J=6.3 Hz), 8.11 (1H, s), 8.47 (1H, d, J=4.2 Hz), 8.54 (1H, s). [M+H] Calc'd for $C_{17}H_{11}F_4N_7$, 390. Found, 390.

Example 135

2-[1-(cyclopropylmethyl)-5-(4-fluorophenyl)imidazol-4-yl]-4-(2H-tetrazol-5-yl)pyridine

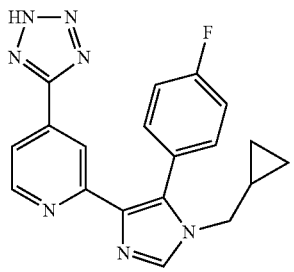 [SMILES: Fc1ccc(-c2c(-c3cc(-c4nn[nH]n4)ccn3)ncn2CC2CC2)cc1]

The title compound was prepared in 23% yield from 2-[1-(cyclopropylmethyl)-5-(4-fluorophenyl)imidazol-4-yl]pyridine-4-carbonitrile (Example 125, part D) according to the procedure for the preparation of Example 128, part C. $^1$H NMR (300 MHz, DMSO): δ 0.19-0.21 (2H, m), 0.43-0.46 (2H, m), 0.94 (1H, m), 3.71 (2H, d, J=7.2 Hz), 7.23-7.34 (2H, m), 7.49-7.52 (2H, m), 7.70 (1H, d, J=6.6 Hz), 8.07 (1H, s), 8.37 (1H, d, J=5.1 Hz), 8.46 (1H, s). [M+H] Calc'd for $C_{19}H_{16}FN_7$, 362. Found, 362.

Example 136

2-[5-(4-chlorophenyl)-1-(cyclopropylmethyl)imidazol-4-yl]-4-(2H-tetrazol-5-yl)pyridine

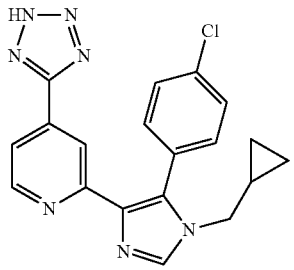

The title compound was prepared in 23% yield from 2-[5-(4-chlorophenyl)-1-(cyclopropylmethyl)-imidazol-4-yl]pyridine-4-carbonitrile according to the procedure for the preparation of Example 128, part C. ¹H NMR (300 MHz, DMSO): δ 0.17-0.221 (2H, m), 0.41-0.45 (2H, m), 0.91-0.94 (1H, m), 3.69 (2H, d, J=4.8 Hz), 7.48-7.63 (5H, m), 7.98-7.99 (1H, m), 8.21-8.22 (1H, m), 8.46 (1H, s). [M+H] Calc'd for C₁₉H₁₆ClN₇, 378. Found, 378.

Example 137

2-[1-[(2-chlorophenyl)methyl]-5-(4-fluorophenyl) imidazol-4-yl]-4-(2H-tetrazol-5-yl)pyridine

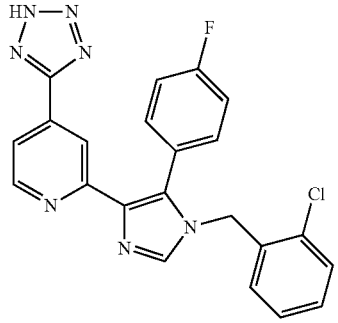 [SMILES: Fc1ccc(-c2c(-c3cc(-c4nn[nH]n4)ccn3)ncn2Cc2ccccc2Cl)cc1]

The title compound was prepared in 41% yield from 2-[1-[(2-chlorophenyl)methyl]-5-(4-fluorophenyl)imidazol-4-yl]pyridine-4-carbonitrile (Example 127, part B) according to the procedure for the preparation of Example 128, part C. ¹H NMR (300 MHz, DMSO): δ 5.24 (2H, s), 6.75-6.78 (1H, m), 7.16-7.41 (7H, m), 7.74 (1H, d, J=4.5 Hz), 8.10 (1H, s), 8.44 (1H, d, J=5.4 Hz), 8.53 (1H, s). [M+H] Calc'd for C₂₂H₁₅ClFN₇, 432. Found, 432.

Example 138

[5-[2-[1-[(2-chlorophenyl)methyl]-5-(4-fluorophenyl)imidazol-4-yl]pyridin-4-yl]tetrazol-2-yl]methyl acetate

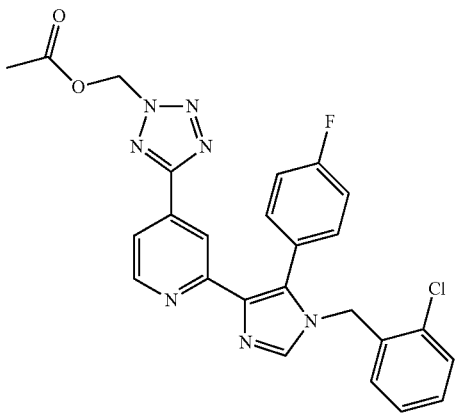 [SMILES: CC(=O)OCn1nnc(-c2ccnc(-c3ncn(Cc4ccccc4Cl)c3-c3ccc(F)cc3)c2)n1]

To a solution of 2-[1-[(2-chlorophenyl)methyl]-5-(4-fluorophenyl)imidazol-4-yl]-4-(2H-tetrazol-5-yl)pyridine (50 mg, 0.12 mmol, Example 137) in DMF (5 mL) was added acetic acid bromomethyl ester (20 mg, 0.12 mmol), t-BuOK (27 mg, 0.24 mmol) and KI (40 mg, 0.24 mmol) at 0° C., then the mixture was stirred for 72 hr at rt, H₂O was added, extracted with EA, dried, concentrated and purified by HPLC to give the title compound (5 mg, 8.6%). ¹H NMR (300 MHz, CD₃OD): δ 2.13 (3H, s), 5.38 (2H, s), 6.55 (2H, s), 6.97-6.98 (1H, m), 7.23-7.49 (7H, m), 7.85 (1H, s), 8.10 (1H, d, J=6.0 Hz), 8.28 (1H, m), 8.64 (1H, m). [M+H] Calc'd for C₂₅H₁₉ClFN₇O₂, 504. Found, 504.

Example 139

[5-[2-[1-[(2-chlorophenyl)methyl]-5-(4-fluorophenyl)imidazol-4-yl]pyridin-4-yl]tetrazol-2-yl]methyl 2,2-dimethylpropanoate

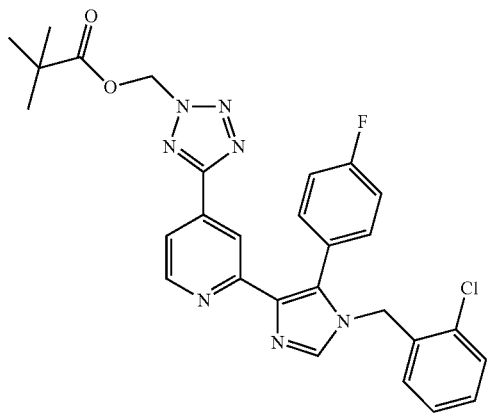 [SMILES: CC(C)(C)C(=O)OCn1nnc(-c2ccnc(-c3ncn(Cc4ccccc4Cl)c3-c3ccc(F)cc3)c2)n1]

The title compound was prepared in 24% yield from 2-[1-[(2-chlorophenyl)methyl]-5-(4-fluorophenyl)imidazol-4-yl]-4-(2H-tetrazol-5-yl)pyridine (Example 137) and 2,2-dimethyl-propionic acid chloromethyl ester according to the procedure for the preparation of Example 138. ¹H NMR (300 MHz, CD₃OD): δ 1.22 (9H, s), 5.30 (2H, s), 6.61 (2H, s), 6.61-6.62 (1H, m), 6.86-6.88 (2H, m), 7.09-7.39 (5H, m), 7.88 (1H, d, J=6.6 Hz), 7.96 (1H, s), 8.29 (1H, s), 8.55 (1H, d, J=5.1 Hz). [M+H] Calc'd for C₂₈H₂₅ClFN₇O₂, 546. Found, 546.

Example 140

4-(2H-tetrazol-5-yl)-2-[1-[2-[2-(trifluoromethyl)phenyl]ethyl]imidazol-4-yl]pyridine

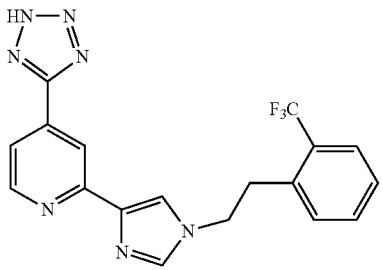 [SMILES: FC(F)(F)c1ccccc1CCn1cnc(-c2cc(-c3nn[nH]n3)ccn2)c1]

The title compound was prepared from 2-[1-[2-[2-(trifluoromethyl)phenyl]ethyl]imidazol-4-yl]pyridine-4-carbonitrile according to the procedure for the preparation of Example 128, part C. ¹H NMR (400 MHz, DMSO): 4.35 (2H, t, J=7.5 Hz), 7.47 (2H, t, J=8.7 Hz), 7.62 (1H, t, J=7.0 Hz), 7.72 (1H, d, J=8.0 Hz), 7.81 (1H, d, J=5.8 Hz), 7.93 (1H, br s), 8.50 (1H, s), 8.69 (1H, d, J=5.2 Hz). [M+H] Calc'd for $C_{18}H_{14}F_3N_7$, 386. Found, 362.

Example 141

2-[1-[2-(2-chlorophenyl)ethyl]imidazol-4-yl]-4-(2H-tetrazol-5-yl)pyridine

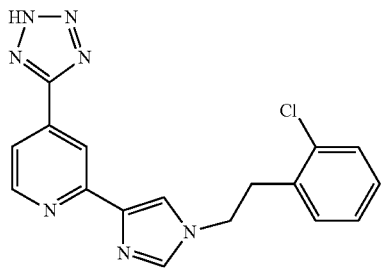 [SMILES: Clc1ccccc1CCn1cnc(-c2cc(-c3nn[nH]n3)ccn2)c1]

The title compound was prepared in 57% yield from 2-[1-[2-(2-chlorophenyl)ethyl]imidazol-4-yl]pyridine-4-carbonitrile according to the procedure for the preparation of Example 128, part C. $^1$H NMR (400 MHz, DMSO): 3.25 (2H, t, J=7.3 Hz), 4.32 (2H, t, J=7.2 Hz), 7.26 (2H, t, J=8.6 Hz), 7.46 (1H, t, J=6.8 Hz), 7.72 (1H, s), 7.78 (1H, d, J=3.9 Hz), 7.86 (1H, s), 8.50 (1H, s), 8.57 (1H, d, J=5.0 Hz). [M+H] Calc'd for $C_{17}H_{14}ClN_7$, 353. Found, 353.

Example 142

2-[1-(2-naphthalen-1-ylethyl)imidazol-4-yl]-4-(2H-tetrazol-5-yl)pyridine

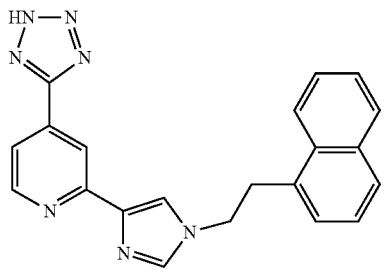 [SMILES: c1ccc2c(CCn3cnc(-c4cc(-c5nn[nH]n5)ccn4)c3)cccc2c1]

The title compound was prepared in 41% yield from 2-[1-(2-naphthalen-1-ylethyl)imidazol-4-yl]pyridine-4-carbonitrile according to the procedure for the preparation of Example 128, part C. $^1$H NMR (400 MHz, DMSO): 3.61 (2H, t, J=7.5 Hz), 4.41 (2H, t, J=7.4 Hz), 7.43 (1H, t, J=7.1 Hz), 7.53 (1H, m), 7.57 (2H, m), 7.82 (1H, s), 7.83 (2H, m), 7.94 (1H, d, J=8.2 Hz), 8.03 (1H, s), 8.25 (1H, d, J=8.3 Hz), 8.50 (1H, s), 8.63 (1H, d, J=5.2 Hz). [M+H] Calc'd for $C_{21}H_{17}N_7$, 368. Found, 368.

Example 143

2-[1-(1,2,3,4-tetrahydronaphthalen-1-ylmethyl)imidazol-4-yl]-4-(2H-tetrazol-5-yl)pyridine

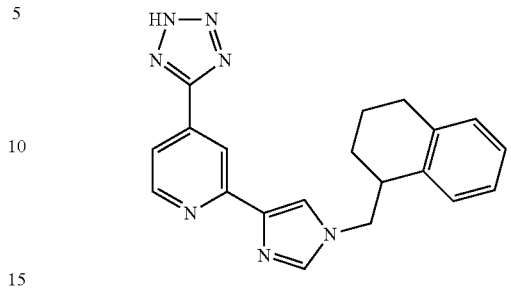

The title compound was prepared in 17% yield from 2-[1-(1,2,3,4-tetrahydronaphthalen-1-ylmethyl)imidazol-4-yl]pyridine-4-carbonitrile according to the procedure for the preparation of Example 128, part C. $^1$H NMR (400 MHz, DMSO): 1.51 (1H, m), 1.64-1.68 (3H, m), 1.83 (1H, m), 2.73 (2H, m), 4.16 (1H, m), 4.32 (1H, m), 7.11 (1H, t, J=4.4 Hz), 7.15 (2H, m), 7.82 (3H, m), 7.95 (1H, s), 8.51 (1H, s), 8.58 (1H, d, J=5.0 Hz). [M+H] Calc'd for $C_{20}H_{19}N_7$, 358. Found, 358.

Example 144

2-[1-(1-phenylpropyl)imidazol-4-yl]-4-(2H-tetrazol-5-yl)pyridine

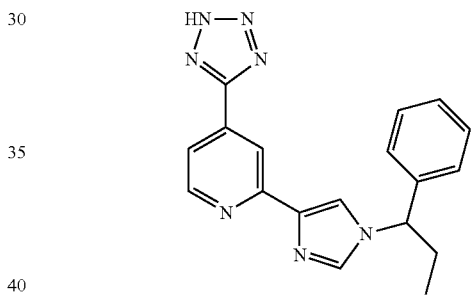

The title compound was prepared in 16% yield from 2-[1-(1-phenylpropyl)imidazol-4-yl]pyridine-4-carbonitrile according to the procedure for the preparation of Example 128, part C. $^1$H NMR (400 MHz, DMSO): 0.86 (3H, t, J=7.2 Hz), 2.26 (1H, m), 2.34 (2H, m), 5.33 (1H, t, J=8.0 Hz), 7.32 (1H, t, J=7.2 Hz), 7.39 (2H, t, J=7.5 Hz), 7.47 (1H, s), 7.49 (1H, s), 7.79 (1H, d, J=5.0 Hz), 8.06 (1H, s), 8.08 (1H, s), 8.50 (1H, s), 8.65 (1H, d, J=5.1 Hz). [M+H] Calc'd for $C_{18}H_{17}N_7$, 332. Found, 332.

Example 145

2-[1-(2-methyl-1-phenylpropyl)imidazol-4-yl]-4-(2H-tetrazol-5-yl)pyridine

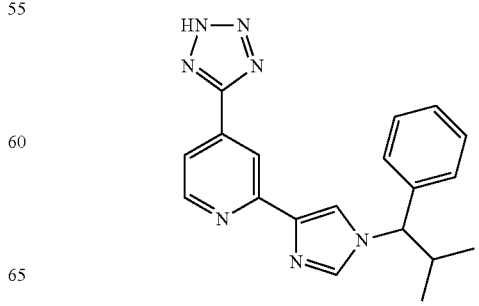

213

The title compound was prepared in 10% yield from 2-[1-(2-methyl-1-phenylpropyl)imidazol-4-yl]pyridine-4-carbonitrile according to the procedure for the preparation of Example 128, part C. $^1$H NMR (400 MHz, DMSO): 0.80 (3H, t, J=6.6 Hz), 0.88 (3H, d, J=6.4 Hz), 4.96 (1H, d, J=11.2 Hz), 7.30 (1H, t, J=7.5 Hz), 7.39 (2H, t, J=7.4 Hz), 7.61 (1H, s), 7.63 (1H, s), 7.78 (1H, d, J=4.2 Hz), 8.07 (1H, s), 8.12 (1H, s), 8.48 (1H, s), 8.62 (1H, d, J=4.8 Hz). [M+H] Calc'd for $C_{19}H_{19}N_7$, 346. Found, 346.

Example 146

2-[1-(1,2,3,4-tetrahydronaphthalen-2-ylmethyl)imidazol-4-yl]-4-(2H-tetrazol-5-yl)pyridine

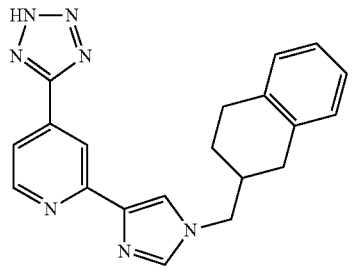 [SMILES: c1ccc2c(c1)CCC(Cn1cnc(-c3cc(-c4nn[nH]n4)ccn3)c1)C2]

The title compound was prepared in 7% yield from 2-[1-(1,2,3,4-tetrahydronaphthalen-2-ylmethyl)imidazol-4-yl]pyridine-4-carbonitrile according to the procedure for the preparation of Example 128, part C. $^1$H NMR (400 MHz, DMSO): 1.23-1.44 (1H, m), 1.82-1.85 (1H, m), 2.28-2.33 (2H, m), 2.67-2.85 (3H, m), 4.10 (1H, d, J=7.2 Hz), 7.07 (4H, m), 7.81 (1H, d, J=4.6 Hz), 7.97 (1H, s), 8.02 (1H, s), 8.54 (1H, s), 8.69 (1H, d, J=5.1 Hz). [M+H] Calc'd for $C_{20}H_{19}N_7$, 358. Found, 358.

Example 147

2-[1-(2,3-dihydro-1H-inden-2-ylmethyl)imidazol-4-yl]-4-(2H-tetrazol-5-yl)pyridine

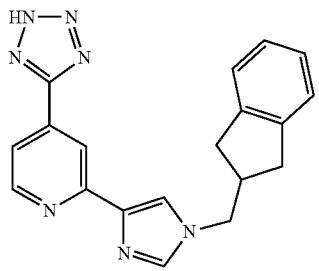 [SMILES: c1ccc2c(c1)CC(Cn1cnc(-c3cc(-c4nn[nH]n4)ccn3)c1)C2]

The title compound was prepared in 3% yield from 2-[1-(2,3-dihydro-1H-inden-2-ylmethyl)imidazol-4-yl]pyridine-4-carbonitrile according to the procedure for the preparation of Example 128, part C. $^1$H NMR (400 MHz, DMSO): 1.78-1.91 (1H, m), 2.07-2.14 (1H, m), 2.67-2.91 (3H, m), 3.67 (1H, m), 4.15 (1H, m), 4.39 (1H, m), 7.14-7.25 (3H, m), 7.24 (1H, d, J=6.6 Hz), 7.77-7.79 (2H, m), 7.91 (1H, s), 8.50 (1H, s), 8.61 (1H, d, J=4.7 Hz). [M+H] Calc'd for $C_{19}H_{17}N_7$, 344. Found, 344.

214

Example 148

2-[5-(4-fluoro-2-phenylmethoxyphenyl)-1-methylimidazol-4-yl]-4-(2H-tetrazol-5-yl)pyridine A. 2-[5-(4-fluoro-2-phenylmethoxyphenyl)-1-methylimidazol-4-yl]pyridine-4-carbonitrile

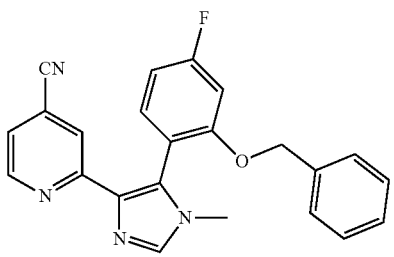 [SMILES: Cn1cnc(-c2cc(C#N)ccn2)c1-c1ccc(F)cc1OCc1ccccc1]

The title compound was prepared from 2-(5-bromo-1-methyl-1H-imidazol-4-yl)pyridine-4-carbonitrile (PREPARATION 2) and 2-benzyloxyl-4-fluorophenylboronic acid according to the procedure for the preparation of Example 3, part A. [M+H] Calc'd for $C_{23}H_{17}FN_4O$, 385. Found, 385.

B. 2-[5-(4-fluoro-2-phenylmethoxyphenyl)-1-methylimidazol-4-yl]-4-(2H-tetrazol-5-yl)pyridine

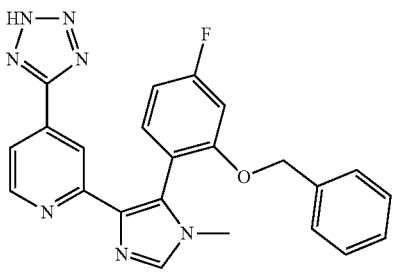 [SMILES: Cn1cnc(-c2cc(-c3nn[nH]n3)ccn2)c1-c1ccc(F)cc1OCc1ccccc1]

The title compound was prepared in 3% yield (two steps) from 2-[5-(4-fluoro-2-phenylmethoxyphenyl)-1-methylimidazol-4-yl]pyridine-4-carbonitrile according to the procedure for the preparation of Example 128, part C. $^1$H NMR (400 MHz, DMSO): 3.43 (3H, s), 4.99 (1H, m), 5.10 (1H, m), 6.90 (1H, t, J=6.5 Hz), 7.05 (1H, m), 7.17 (3H, m), 7.38 (1H, t, J=7.4 Hz), 7.47 (1H, m), 7.68-7.75 (2H, m), 7.80 (1H, br s), 8.36 (1H, d, J=5.0 Hz), 8.43 (1H, s). [M+H] Calc'd for $C_{23}H_{18}FN_7O$, 428. Found, 428.

Example 149

2-[5-(2-butoxy-4-fluorophenyl)-1-methylimidazol-4-yl]-4-(2H-tetrazol-5-yl)pyridine A. 2-[5-(2-butoxy-4-fluorophenyl)-1-methylimidazol-4-yl]pyridine-4-carbonitrile

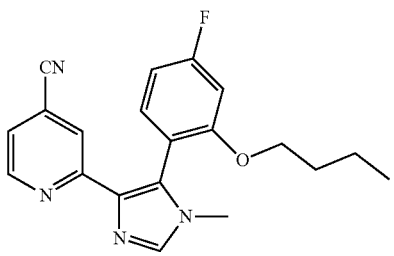 [SMILES: CCCCOc1cc(F)ccc1-c1c(-c2cc(C#N)ccn2)ncn1C]

The title compound was prepared from 2-(5-bromo-1-methyl-1H-imidazol-4-yl)pyridine-4-carbonitrile (PREPARATION 2) and 2-butoxy-4-fluorophenylboronic acid according to the procedure for the preparation of Example 3, part A. [M+H] Calc'd for $C_{20}H_{19}FN_4O$, 351. Found, 351.

B. 2-[5-(2-butoxy-4-fluorophenyl)-1-methylimidazol-4-yl]-4-(2H-tetrazol-5-yl)pyridine

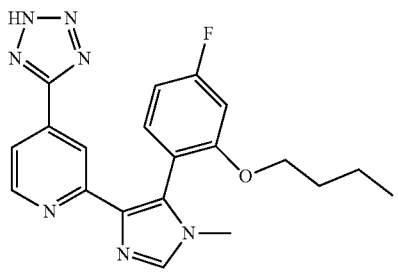 [SMILES: CCCCOc1cc(F)ccc1-c1c(-c2cc(-c3nn[nH]n3)ccn2)ncn1C]

The title compound was prepared in 9% yield (two steps) from 2-[5-(2-butoxy-4-fluorophenyl)-1-methylimidazol-4-yl]pyridine-4-carbonitrile according to the procedure for the preparation of Example 128, part C. $^1$H NMR (400 MHz, DMSO): 0.64 (3H, t, J=7.4 Hz), 1.04 (2H, q, J=10.3 Hz), 1.34 (2H, m), 3.42 (3H, s), 3.85 (1H, m), 3.96 (1H, m), 6.88 (1H, t, J=8.4 Hz), 7.05 (1H, d, J=10.6 Hz), 7.38 (1H, t, J=7.5 Hz), 7.73 (1H, br s), 8.05 (1H, br s), 8.38 (1H, br s), 8.42 (1H, d, J=5.3 Hz). [M+H] Calc'd for $C_{20}H_{20}FN_7O$, 394. Found, 394.

Example 150

2-[5-[2-(cyclopropylmethoxy)-4-fluorophenyl]-1-methylimidazol-4-yl]-4-(2H-tetrazol-5-yl)pyridine A. 2-[5-[2-(cyclopropylmethoxy)-4-fluorophenyl]-1-methylimidazol-4-yl]pyridine-4-carbonitrile

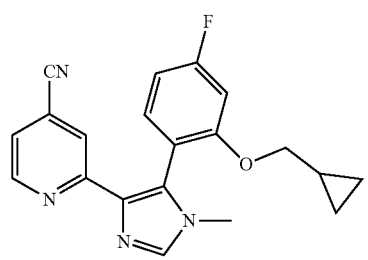 [SMILES: Cn1cnc(-c2cc(C#N)ccn2)c1-c1ccc(F)cc1OCC1CC1]

The title compound was prepared from 2-(5-bromo-1-methyl-1H-imidazol-4-yl)pyridine-4-carbonitrile (PREPARATION 2) and 2-(cyclopropylmethoxy)-4-fluorophenylboronic acid according to the procedure for the preparation of Example 3, part A. [M+H] Calc'd for $C_{20}H_{17}FN_4O$, 349. Found, 349.

B. 2-[5-[2-(cyclopropylmethoxy)-4-fluorophenyl]-1-methylimidazol-4-yl]-4-(2H-tetrazol-5-yl)pyridine

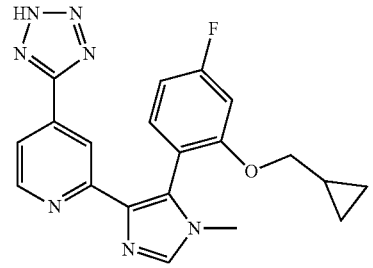 [SMILES: Cn1cnc(-c2cc(-c3nn[nH]n3)ccn2)c1-c1ccc(F)cc1OCC1CC1]

The title compound was prepared in 12% yield (two steps) from 2-[5-[2-(cyclopropylmethoxy)-4-fluorophenyl]-1-methylimidazol-4-yl]pyridine-4-carbonitrile according to the procedure for the preparation of Example 128, part C. $^1$H NMR (400 MHz, DMSO): 0.11 (2H, m), 0.33 2H, m), 0.91 (1H, m), 3.46 (3H, s), 3.74 (1H, m), 3.86 (1H, m), 6.87 (1H, d t, J=2.0 and 8.43 Hz), 7.04 (1H, d, J=9.6 Hz), 7.36 (1H, t, J=7.7 Hz), 7.74 (1H, d, J=4.2 Hz), 8.11 (1H, br s), 8.39 (1H, br s), 8.44 (1H, d, J=5.2 Hz). [M+H] Calc'd for $C_{20}H_{18}FN_7O$, 392. Found, 392.

Example 151

2-[1-[(2,6-dichlorophenyl)methyl]imidazol-4-yl]-4-(2H-tetrazol-5-yl)pyridine

A. 2-[1-[(2,6-dichlorophenyl)methyl]imidazol-4-yl]pyridine-4-carbonitrile

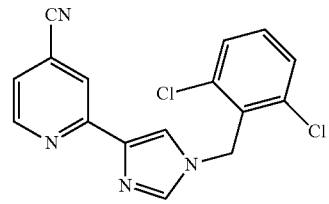 [SMILES: N#Cc1ccnc(-c2cn(Cc3c(Cl)cccc3Cl)cn2)c1]

The title compound was prepared from 2-(1H-imidazol-4-yl)pyridine-4-carbonitrile (PREPARATION 4) and 2,6-dichlorobenzyle bromide according to the procedure for the preparation of Example 43, part A using room temp. [M+H] Calc'd for $C_{16}H_{10}Cl_2N_4$, 330. Found, 330.

B. 2-[1-[(2,6-dichlorophenyl)methyl]imidazol-4-yl]-4-(2H-tetrazol-5-yl)pyridine

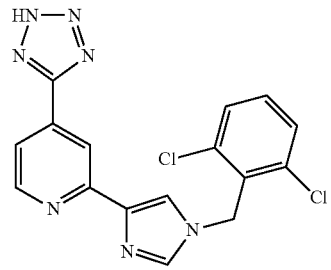 [SMILES: Clc1cccc(Cl)c1Cn1cnc(-c2cc(-c3nn[nH]n3)ccn2)c1]

The title compound was prepared in 6% yield from 2-[1-[(2,6-dichlorophenyl)methyl]imidazol-4-yl]pyridine-4-carbonitrile according to the procedure for the preparation of Example 128, part C. ¹H NMR (400 MHz, DMSO): δ 5.53 (2H, s), 7.49 (1H, t, J=8.1 Hz), 7.61 (2H, d, J=7.9 Hz), 7.66 (1H, s), 7.78 (1H, d, J=4.1 Hz), 7.95 (1H, s), 8.48 (1H, s), 8.60 (1H, d, J=5.0 Hz). [M+H] Calc'd for $C_{16}H_{11}Cl_2N_7$, 373. Found, 373.

Example 152

4-(2H-tetrazol-5-yl)-2-[1-[[2-(2,2,2-trifluoroethoxy)phenyl]methyl]imidazol-4-yl]pyridine A. 2-[1-[[2-(2,2,2-trifluoroethoxy)phenyl]methyl]imidazol-4-yl]pyridine-4-carbonitrile

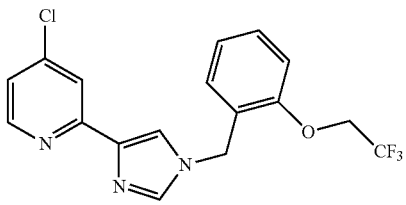 [SMILES: FC(F)(F)COc1ccccc1Cn1cnc(-c2cc(Cl)ccn2)c1]

The title compound was prepared from 2-(1H-imidazol-4-yl)pyridine-4-carbonitrile (PREPARATION 4) and 1-(bromomethyl)-2-(2,2,2-trifluoromethoxy)benzene according to the procedure for the preparation of Example 43, part A using room temp. [M+H] Calc'd for $C_{18}H_{13}F_3N_4O$, 359. Found, 359.

B. 4-(2H-tetrazol-5-yl)-2-[1-[[2-(2,2,2-trifluoroethoxy)phenyl]methyl]imidazol-4-yl]pyridine

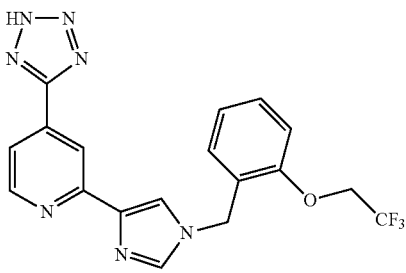 [SMILES: FC(F)(F)COc1ccccc1Cn1cnc(-c2cc(-c3nn[nH]n3)ccn2)c1]

The title compound was prepared in 3% yield from 2-[1-[[2-(2,2,2-trifluoroethoxy)phenyl]methyl]imidazol-4-yl]pyridine-4-carbonitrile according to the procedure for the preparation of Example 128, part C. ¹H NMR (400 MHz, DMSO): δ 4.86 (2H, q, J=8.5 Hz), 5.24 (2H, s), 7.07 (1H, t, J=7.3 Hz), 7.16 (1H, d, J=8.5 Hz), 7.32-7.40 (2H, m), 7.73 (1H, d, J=5.3 Hz), 7.75 (1H, s), 7.82 (1H, s), 8.50 (1H, s), 8.53 (1H, d, J=5.0 Hz). [M+H] Calc'd for $C_{18}H_{14}F_3N_7O$, 402. Found, 402.

Example 153

2-[1-[[2-(2-methylpropoxy)phenyl]methyl]imidazol-4-yl]-4-(2H-tetrazol-5-yl)pyridine A. 2-[1-[[2-(2-methylpropoxy)phenyl]methyl]imidazol-4-yl]pyridine-4-carbonitrile

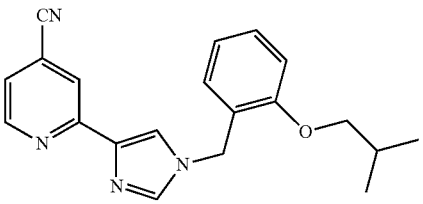 [SMILES: CC(C)COc1ccccc1Cn1cnc(-c2cc(C#N)ccn2)c1]

The title compound was prepared from 2-(1H-imidazol-4-yl)pyridine-4-carbonitrile (PREPARATION 4) and 1-(bromomethyl)-2-(2-methylpropoxyl)benzene according to the procedure for the preparation of Example 43, part A using room temp. [M+H] Calc'd for $C_{20}H_{20}N_4O$, 333. Found, 333.

B. 2-[1-[[2-(2-methylpropoxy)phenyl]methyl]imidazol-4-yl]-4-(2H-tetrazol-5-yl)pyridine

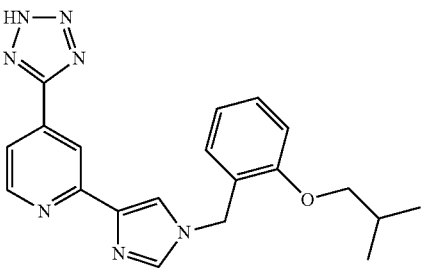 [SMILES: CC(C)COc1ccccc1Cn1cnc(-c2cc(-c3nn[nH]n3)ccn2)c1]

The title compound was prepared in 17% yield from 2-[1-[[2-(2-methylpropoxy)phenyl]methyl]imidazol-4-yl]pyridine-4-carbonitrile according to the procedure for the preparation of Example 128, part C. ¹H NMR (400 MHz, DMSO): δ 1.00 (6H, d, J=6.7 Hz), 2.08 (1H, m), 3.81 (2H, d, J=6.3 Hz), 5.25 (2H, s), 6.95 (1H, t, J=7.1 Hz), 7.03 (1H, d, J=8.3 Hz), 7.27 (1H, d, J=7.4 Hz), 7.32 (1H, t, J=7.8 Hz), 7.80 (1H, d, J=5.8 Hz), 7.83 (1H, s), 7.93 (1H, s), 8.50 (1H, s), 8.67 (1H, d, J=5.3 Hz). [M+H] Calc'd for $C_{20}H_{21}N_7O$, 376. Found, 376.

Example 154

2-[1-[[2-chloro-3-(trifluoromethyl)phenyl]methyl]imidazol-4-yl]-4-(2H-tetrazol-5-yl)pyridine A. 2-[1-[[2-chloro-3-(trifluoromethyl)phenyl]methyl]imidazol-4-yl]pyridine-4-carbonitrile

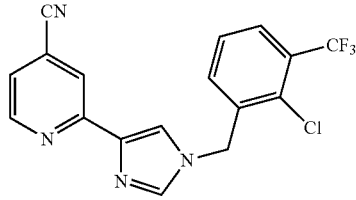 [SMILES: N#Cc1ccnc(-c2cn(Cc3cccc(C(F)(F)F)c3Cl)cn2)c1]

The title compound was prepared from 2-(1H-imidazol-4-yl)pyridine-4-carbonitrile (PREPARATION 4) and 2-chloro-3-(trifluoromethyl)benzyl bromide according to the procedure for the preparation of Example 43, part A using room temp. [M+H] Calc'd for $C_{17}H_{10}ClF_3N_4$, 363. Found, 363.

B. 2-[1-[[2-chloro-3-(trifluoromethyl)phenyl]methyl]imidazol-4-yl]-4-(2H-tetrazol-5-yl)pyridine

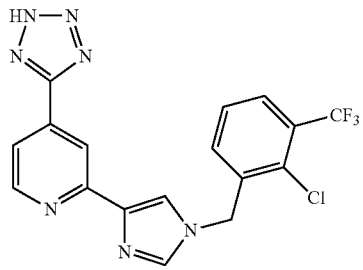 [SMILES: FC(F)(F)c1cccc(Cn2cnc(-c3cc(-c4nn[nH]n4)ccn3)c2)c1Cl]

The title compound was prepared in 20% yield from 2-[1-[[2-chloro-3-(trifluoromethyl)phenyl]methyl]imidazol-4-yl]pyridine-4-carbonitrile according to the procedure for the preparation of Example 128, part C. $^1$H NMR (400 MHz, DMSO): δ 5.54 (2H, s), 7.45 (1H, d, J=7.8 Hz), 7.60 (1H, d, J=7.7 Hz), 7.82 (1H, d, J=3.6 Hz), 7.87 (1H, d, J=7.8 Hz), 7.93 (1H, s), 8.02 (1H, s), 8.54 (1H, s), 8.69 (1H, d, J=5.0 Hz). [M+H] Calc'd for $C_{17}H_{11}ClF_3N_7$, 406. Found, 406.

Example 155

2-[1-(naphthalen-1-ylmethyl)imidazol-4-yl]-4-(2H-tetrazol-5-yl)pyridine

A. 2-[1-(naphthalen-1-ylmethyl)imidazol-4-yl]pyridine-4-carbonitrile

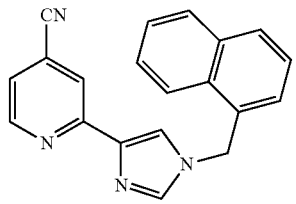 [SMILES: N#Cc1ccnc(-c2cn(Cc3cccc4ccccc34)cn2)c1]

The title compound was prepared from 2-(1H-imidazol-4-yl)pyridine-4-carbonitrile (PREPARATION 4) and 1-(bromomethyl)naphthalene according to the procedure for the preparation of Example 43, part A using room temp. [M+H] Calc'd for $C_{20}H_{14}N_4$, 311. Found, 311.

B. 2-[1-(naphthalen-1-ylmethyl)imidazol-4-yl]-4-(2H-tetrazol-5-yl)pyridine

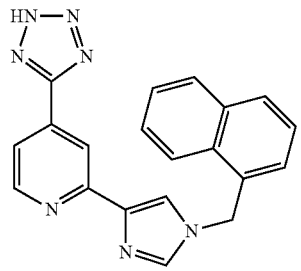 [SMILES: c1ccc2c(Cn3cnc(-c4cc(-c5nn[nH]n5)ccn4)c3)cccc2c1]

The title compound was prepared in 19% yield from 2-[1-(naphthalen-1-ylmethyl)imidazol-4-yl]pyridine-4-carbonitrile according to the procedure for the preparation of Example 128, part C. $^1$H NMR (400 MHz, DMSO): δ 5.82 (2H, s), 7.45 (1H, d, J=7.0 Hz), 7.53-7.7.65 (3H, m), 7.79 (1H, d, J=4.6 Hz), 7.88 (1H, s), 7.95-8.01 (2H, m), 8.09 (1H, s), 8.23 (1H, d, J=8.3 Hz), 8.51 (1H, s), 8.65 (1H, d, J=4.8 Hz). [M+H] Calc'd for $C_{20}H_{15}N_7$, 354. Found, 354.

Example 156

4-(2H-tetrazol-5-yl)-2-[1-[[2-(trifluoromethoxy)phenyl]methyl]imidazol-4-yl]pyridine A. 2-[1-[[2-(trifluoromethoxy)phenyl]methyl]imidazol-4-yl]pyridine-4-carbonitrile

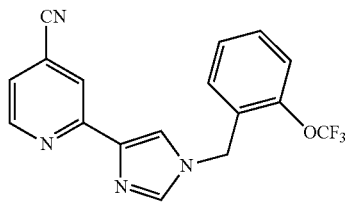 [SMILES: N#Cc1ccnc(-c2cn(Cc3ccccc3OC(F)(F)F)cn2)c1]

The title compound was prepared from 2-(1H-imidazol-4-yl)pyridine-4-carbonitrile (PREPARATION 4) and 2-(trifluoromethoxy)benzyl bromide according to the procedure for the preparation of Example 43, part A using room temp. [M+H] Calc'd for $C_{17}H_{11}F_3N_4O$, 345. Found, 345.

B. 4-(2H-tetrazol-5-yl)-2-[1-[[2-(trifluoromethoxy)phenyl]methyl]imidazol-4-yl]pyridine

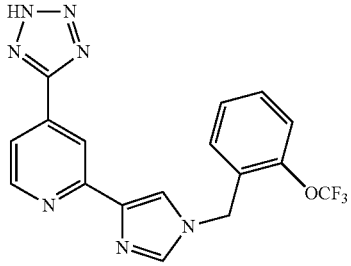 [SMILES: FC(F)(F)Oc1ccccc1Cn1cnc(-c2cc(-c3nn[nH]n3)ccn2)c1]

The title compound was prepared in 22% yield from 2-[1-[[2-(trifluoromethoxy)phenyl]methyl]imidazol-4-yl]pyridine-4-carbonitrile according to the procedure for the preparation of Example 128, part C. $^1$H NMR (400 MHz, DMSO): δ 5.41 (2H, s), 7.37-7.53 (4H, m), 7.81 (1H, d, J=4.9 Hz), 7.85 (1H, s), 7.96 (1H, s), 8.52 (1H, s), 8.68 (1H, d, J=5.0 Hz). [M+H] Calc'd for $C_{17}H_{12}F_3N_7O$, 388. Found, 388.

Example 157

2-[1-[1-(2-chlorophenyl)ethyl]imidazol-4-yl]-4-(2H-tetrazol-5-yl)pyridine

A. 2-[1-[1-(2-chlorophenyl)ethyl]imidazol-4-yl]pyridine-4-carbonitrile

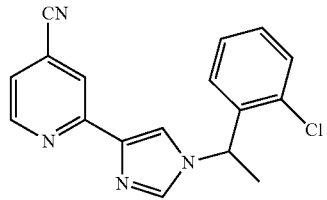 [SMILES: CC(c1ccccc1Cl)n1cnc(-c2cc(C#N)ccn2)c1]

The title compound was prepared from 2-(1H-imidazol-4-yl)pyridine-4-carbonitrile (PREPARATION 4) and 1-(1-bromomethyl)-2-chloroenzene according to the procedure for the preparation of Example 43, part A using room temp. [M+H] Calc'd for $C_{17}H_{13}ClN_4$, 309. Found, 309.

B. 2-[1-[1-(2-chlorophenyl)ethyl]imidazol-4-yl]-4-(2H-tetrazol-5-yl)pyridine

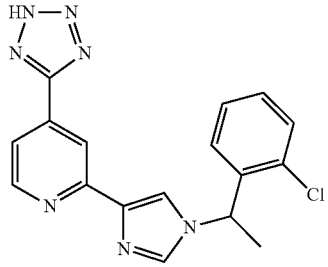 [SMILES: CC(c1ccccc1Cl)n1cnc(-c2cc(-c3nn[nH]n3)ccn2)c1]

The title compound was prepared in 19% yield from 2-[1-[1-(2-chlorophenyl)ethyl]imidazol-4-yl]pyridine-4-carbonitrile according to the procedure for the preparation of Example 128, part C. $^1$H NMR (400 MHz, DMSO): δ 1.89 (3H, d, J=7.0 Hz), 5.96 (1H, q, J=7.0 Hz), 7.38-7.43 (2H, m), 7.47-7.53 (2H, m), 7.82 (1H, d, J=4.9 Hz), 7.98 (1H, s), 8.08 (1H, s), 8.52 (1H, s), 8.68 (1H, d, J=5.1 Hz). [M+H] Calc'd for $C_{17}H_{14}ClN_7$, 352. Found, 352.

Example 158

2-[1-[(2,3-dichlorophenyl)methyl]imidazol-4-yl]-4-(2H-tetrazol-5-yl)pyridine

A. 2-[1-[(2,3-dichlorophenyl)methyl]imidazol-4-yl]pyridine-4-carbonitrile

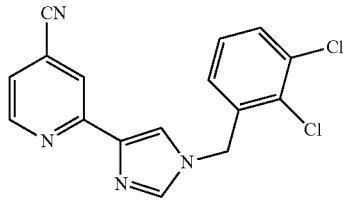 [SMILES: N#Cc1ccnc(-c2cn(Cc3cccc(Cl)c3Cl)cn2)c1]

The title compound was prepared from 2-(1H-imidazol-4-yl)pyridine-4-carbonitrile (PREPARATION 4) and 2,3-dichlorobenzylbromide according to the procedure for the preparation of Example 43, part A using room temp. [M+H] Calc'd for $C_{16}H_{10}Cl_2N_4$, 330. Found, 330.

B. 2-[1-[(2,3-dichlorophenyl)methyl]imidazol-4-yl]-4-(2H-tetrazol-5-yl)pyridine

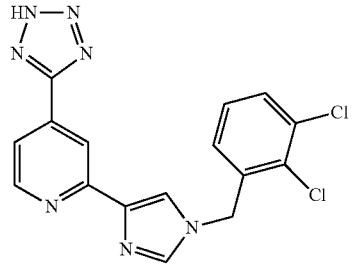 [SMILES: Clc1cccc(Cn2cnc(-c3cc(-c4nn[nH]n4)ccn3)c2)c1Cl]

The title compound was prepared in 19% yield from 2-[1-[(2,3-dichlorophenyl)methyl]imidazol-4-yl]pyridine-4-carbonitrile according to the procedure for the preparation of Example 128, part C. $^1$H NMR (400 MHz, DMSO): δ 5.48 (2H, s), 7.17 (1H, d, J=7.8 Hz), 7.41 (1H, t, J=7.9 Hz), 7.67 (1H, d, J=8.0 Hz), 7.81 (1H, d, J=1.3 Hz), 7.90 (1H, s), 8.01 (1H, s), 8.53 (1H, s), 8.69 (1H, d, J=5.2 Hz). [M+H] Calc'd for $C_{16}H_{11}Cl_2N_7$, 374. Found, 374.

Example 159

2-[5-[4-fluoro-3-(2,2,2-trifluoroethoxy)phenyl]-1-methylimidazol-4-yl]-4-(2H-tetrazol-5-yl)pyridine A. 2-[5-[4-fluoro-3-(2,2,2-trifluoroethoxy)phenyl]-1-methylimidazol-4-yl]pyridine-4-carbonitrile

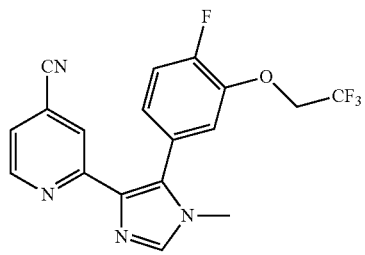 [SMILES: Cn1cnc(-c2cc(C#N)ccn2)c1-c1ccc(F)c(OCC(F)(F)F)c1]

The title compound was prepared from 2-(5-bromo-1-methyl-1H-imidazol-4-yl)pyridine-4-carbonitrile (PREPARATION 2) and 4-fluoro-3-(2,2,2-trifluoroethoxy)phenyl boronic acid according to the procedure for the preparation of Example 3, part A. [M+H] Calc'd for $C_{18}H_{12}F_4N_4O$, 377. Found, 377.

B. 2-[5-[4-fluoro-3-(2,2,2-trifluoroethoxy)phenyl]-1-methylimidazol-4-yl]-4-(2H-tetrazol-5-yl)pyridine

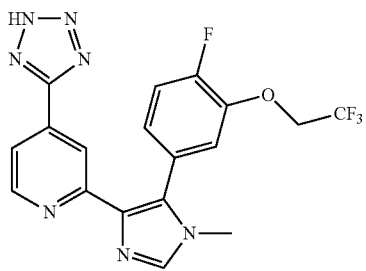 [SMILES: Cn1cnc(-c2cc(-c3nn[nH]n3)ccn2)c1-c1ccc(F)c(OCC(F)(F)F)c1]

The title compound was prepared in 12% yield (two steps) from 2-[5-[4-fluoro-3-(2,2,2-trifluoroethoxy)phenyl]-1-methylimidazol-4-yl]-4-(2H-tetrazol-5-yl)pyridine according to the procedure for the preparation of Example 128, part C. $^1$H NMR (400 MHz, DMSO): 3.48 (3H, s), 4.85 (2H, q, J=8.7 Hz), 7.17 (1H, m), 7.39 (1H, t, J=7.8 Hz), 7.47 (1H, d, J=7.6 Hz), 7.73 (1H, br s), 8.01 (1H, br s), 8.48 (2H, d, J=5.1 Hz). [M+H] Calc'd for $C_{18}H_{13}F_4N_7O$, 420. Found, 420.

Example 160

2-[5-(4-fluoro-3-phenylmethoxyphenyl)-1-methylimidazol-4-yl]-4-(2H-tetrazol-5-yl)pyridine A. 2-[5-(4-fluoro-3-phenylmethoxyphenyl)-1-methylimidazol-4-yl]pyridine-4-carbonitrile

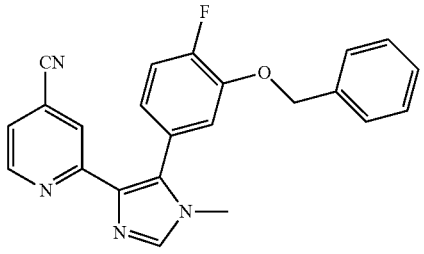 [SMILES: Cn1cnc(-c2cc(C#N)ccn2)c1-c1ccc(F)c(OCc2ccccc2)c1]

The title compound was prepared from 2-(5-bromo-1-methyl-1H-imidazol-4-yl)pyridine-4-carbonitrile (PREPARATION 2) and 3-benzyloxy-4-fluorophenyl boronic acid according to the procedure for the preparation of Example 3, part A. [M+H] Calc'd for $C_{23}H_{17}FN_4O$, 385. Found, 385.

B. 2-[5-(4-fluoro-3-phenylmethoxyphenyl)-1-methylimidazol-4-yl]-4-(2H-tetrazol-5-yl)pyridine

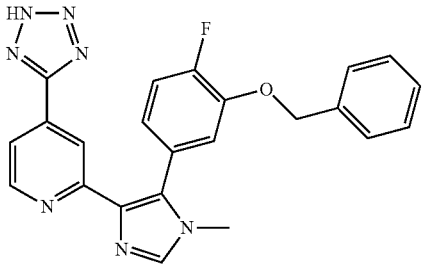 [SMILES: Cn1cnc(-c2cc(-c3nn[nH]n3)ccn2)c1-c1ccc(F)c(OCc2ccccc2)c1]

The title compound was prepared in 12% yield (two steps) from 2-[5-(4-fluoro-3-phenylmethoxyphenyl)-1-methylimidazol-4-yl]pyridine-4-carbonitrile according to the procedure for the preparation of Example 128, part C. $^1$H NMR (400 MHz, DMSO): 3.54 (3H, s), 5.18 (2H, s), 7.05 (1H, m), 7.32-7.44 (7H, m), 7.73 (1H, br s), 7.98 (1H, br s), 8.42 (1H, br s), 8.46 (1H, br s). [M+H] Calc'd for $C_{23}H_{18}FN_7O$, 428. Found, 428.

Example 161

2-[5-(4-chloro-3-phenylmethoxyphenyl)-1-methylimidazol-4-yl]-4-(2H-tetrazol-5-yl)pyridin A. 2-[5-(4-chloro-3-phenylmethoxyphenyl)-1-methylimidazol-4-yl]pyridine-4-carbonitrile

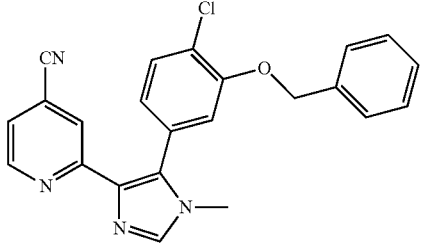

The title compound was prepared from 2-(5-bromo-1-methyl-1H-imidazol-4-yl)pyridine-4-carbonitrile (PREPARATION 2) and 3-benzyloxy-4-chlorophenyl boronic acid according to the procedure for the preparation of Example 3, part A. [M+H] Calc'd for $C_{23}H_{17}ClN_4O$, 401. Found, 401.

B. 2-[5-(4-chloro-3-phenylmethoxyphenyl)-1-methylimidazol-4-yl]-4-(2H-tetrazol-5-yl)pyridin

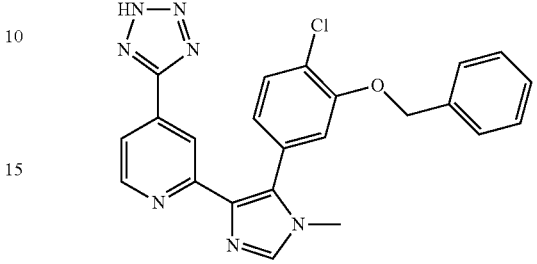

The title compound was prepared in 14% yield (two steps) from 2-[5-(4-chloro-3-phenylmethoxyphenyl)-1-methylimidazol-4-yl]pyridine-4-carbonitrile according to the procedure for the preparation of Example 128, part C. $^1$H NMR (400 MHz, DMSO): 3.57 (3H, s), 5.22 (2H, s), 7.06 (1H, dd, J=1.4 and 8.1 Hz), 7.32-7.45 (6H, m), 7.52 (1H, d, J=8.1 Hz), 7.74 (1H, d, J=4.7 Hz), 8.02 (1H, s), 8.46 (1H, d, J=5.1 Hz), 8.50 (1H, s). [M+H] Calc'd for $C_{23}H_{18}ClN_7O$, 444. Found, 444.

Example 162

2-fluoro-5-[3-methyl-5-[4-(2H-tetrazol-5-yl)pyridin-2-yl]imidazol-4-yl]phenol

A. 2-[5-(4-fluoro-3-hydroxyphenyl)-1-methylimidazol-4-yl]pyridine-4-carbonitrile

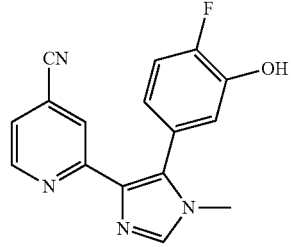 [SMILES: Cn1cnc(-c2cc(C#N)ccn2)c1-c1ccc(F)c(O)c1]

The title compound was prepared from 2-(5-bromo-1-methyl-1H-imidazol-4-yl)pyridine-4-carbonitrile (PREPARATION 2) and 4-fluoro-3-hydroxyphenyl boronic acid according to the procedure for the preparation of Example 3, part A. [M+H] Calc'd for $C_{16}H_{11}FN_4O$, 295. Found, 295.

B. 2-fluoro-5-[3-methyl-5-[4-(2H-tetrazol-5-yl)pyridin-2-yl]imidazol-4-yl]phenol

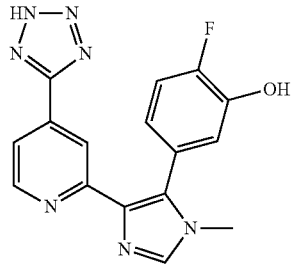 [SMILES: Cn1cnc(-c2cc(-c3nn[nH]n3)ccn2)c1-c1ccc(F)c(O)c1]

The title compound was prepared in 6% yield (two steps) from 2-[5-(4-fluoro-3-hydroxyphenyl)-1-methylimidazol-4-yl]pyridine-4-carbonitrile according to the procedure for the preparation of Example 128, part C. $^1$H NMR (400 MHz, DMSO): 3.51 (3H, s), 6.89 (1H, m), 7.03 (1H, dd, J=1.8 and 8.5 Hz), 7.26 (1H, dt, J=2.9 and 8.4 Hz), 7.77 (1H, d, J=5.2 Hz), 8.08 (1H, s), 8.38 (1H, s), 8.51 (1H, d, J=5.2 Hz). [M+H] Calc'd for $C_{16}H_{12}FN_7O$, 338. Found, 338.

Example 163

2-fluoro-5-[3-methyl-5-[4-(2H-tetrazol-5-yl)pyridin-2-yl]imidazol-4-yl]-N-phenylbenzamide A. 5-[5-(4-cyanopyridin-2-yl)-3-methylimidazol-4-yl]-2-fluoro-N-phenylbenzamide

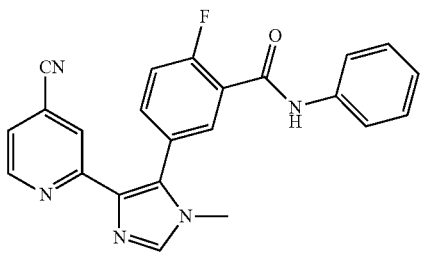 [SMILES: Cn1cnc(-c2cc(C#N)ccn2)c1-c1ccc(F)c(C(=O)Nc2ccccc2)c1]

The title compound was prepared from 2-(5-bromo-1-methyl-1H-imidazol-4-yl)pyridine-4-carbonitrile (PREPARATION 2) and 4-fluoro-3-(phenyl carbamoyl)phenyl boronic acid according to the procedure for the preparation of Example 3, part A. [M+H] Calc'd for $C_{23}H_{16}FN_5O$, 398. Found, 398.

B. 2-fluoro-5-[3-methyl-5-[4-(2H-tetrazol-5-yl)pyridin-2-yl]imidazol-4-yl]-N-phenylbenzamide

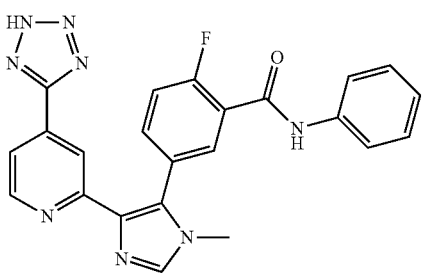 [SMILES: Cn1cnc(-c2cc(-c3nn[nH]n3)ccn2)c1-c1ccc(F)c(C(=O)Nc2ccccc2)c1]

The title compound was prepared in 11% yield (two steps) from 5-[5-(4-cyanopyridin-2-yl)-3-methylimidazol-4-yl]-2-fluoro-N-phenylbenzamide according to the procedure for the preparation of Example 128, part C. $^1$H NMR (400 MHz, DMSO): 3.57 (3H, s), 7.11 (1H, t, J=7.4 Hz), 7.35 (2H, t, J=7.9 Hz), 7.45 (1H, t, J=9.3 Hz), 7.68-7.78 (5H, m), 8.14 (1H, s), 8.46 (1H, d, J=5.1 Hz), 8.57 (1H, s), 10.48 (1H, s). [M+H] Calc'd for $C_{23}H_{17}FN_8O$, 441. Found, 441.

Example 164

2-[5-(4-fluoronaphthalen-1-yl)-1-methylimidazol-4-yl]-4-(2H-tetrazol-5-yl)pyridine A. 2-[5-(4-fluoronaphthalen-1-yl)-1-methylimidazol-4-yl]pyridine-4-carbonitrile

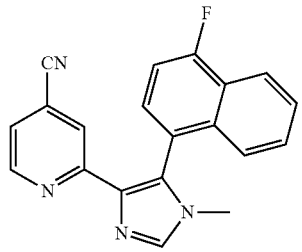 [SMILES: Cn1cnc(-c2cc(C#N)ccn2)c1-c1ccc(F)c2ccccc12]

The title compound was prepared from 2-(5-bromo-1-methyl-1H-imidazol-4-yl)pyridine-4-carbonitrile (PREPARATION 2) and 4-fluoronaphthalene-1-boronic acid according to the procedure for the preparation of Example 3, part A. [M+H] Calc'd for $C_{20}H_{13}FN_4$, 329. Found, 329.

B. 2-[5-(4-fluoronaphthalen-1-yl)-1-methylimidazol-4-yl]-4-(2H-tetrazol-5-yl)pyridine

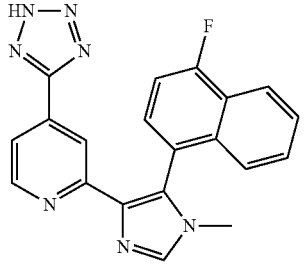 [SMILES: Cn1cnc(-c2cc(-c3nn[nH]n3)ccn2)c1-c1ccc(F)c2ccccc12]

The title compound was prepared in 13% yield (two steps) from 2-[5-(4-fluoronaphthalen-1-yl)-1-methylimidazol-4-yl]pyridine-4-carbonitrile according to the procedure for the preparation of Example 128, part C. $^1$H NMR (400 MHz, DMSO): 3.57 (3H, s), 7.11 (1H, t, J=7.4 Hz), 7.35 (2H, t, J=7.9 Hz), 7.45 (1H, t, J=9.3 Hz), 7.68-7.78 (5H, m), 8.14 (1H, s), 8.46 (1H, d, J=5.1 Hz), 8.57 (1H, s), 10.48 (1H, s). [M+H] Calc'd for $C_{20}H_{14}FN_7$, 372. Found, 372.

Example 165

2-(1-(2-chlorobenzyl)-1H-imidazol-4-yl)-4-(2-methyl-2H-tetrazol-5-yl)pyridine

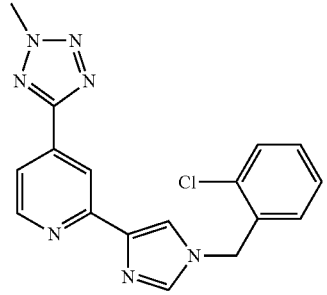 [SMILES: Cn1nnc(-c2ccnc(-c3cn(Cc4ccccc4Cl)cn3)c2)n1]

The title compound was prepared in 95% yield from 2-[1-[(2-chlorophenyl)methyl]imidazol-4-yl]-4-(2H-tetrazol-5- yl)pyridine (Example 129), MeI and potassium carbonate in DMF. $^1$H NMR (400 MHz, DMSO): δ 4.49 (3H, s), 5.41 (2H, s), 7.27-7.30 (1H, m), 7.38-7.40 (2H, m), 7.52-7.55 (1H, m), 7.79 (1H, d, J=5.2 Hz), 7.84 (1H, s), 7.96 (1H, s), 8.50 (1H, s), 8.67 (1H, d, J=5.1 Hz). [M+H] Calc'd for $C_{17}H_{14}ClN_7$, 352. Found, 352.

Example 166

(5-(2-(1-(2-chlorobenzyl)-1H-imidazol-4-yl)pyridin-4-yl)-2H-tetrazol-2-yl)methyl pivalate

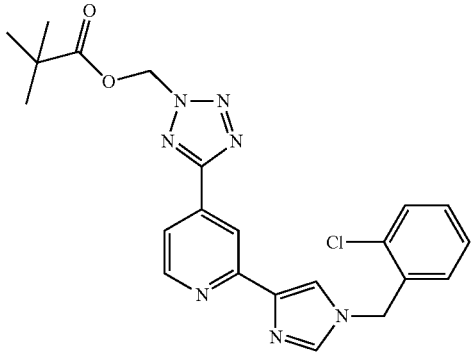 [SMILES: CC(C)(C)C(=O)OCn1nnc(-c2ccnc(-c3cn(Cc4ccccc4Cl)cn3)c2)n1]

The title compound was prepared in 15% yield from 2-[1-[(2-chlorophenyl)methyl]imidazol-4-yl]-4-(2H-tetrazol-5-yl)pyridine (Example 129), chloroethyl pivalate and potassium carbonate in DMF. $^1$H NMR (400 MHz, DMSO): δ 1.10 (9H, s), 5.41 (2H, s), 6.70 (2H, s), 7.28-7.30 (1H, m), 7.38-7.40 (2H, m), 7.52-7.54 (1H, m), 7.81-7.83 (3H, m), 7.94 (1H, s), 8.51 (1H, s), 8.68 (1H, d, J=5.1 Hz). [M+H] Calc'd for $C_{22}H_{22}ClN_7O_2$, 452. Found, 452.

Example 167

(5-(2-(1-(2-chlorobenzyl)-1H-imidazol-4-yl)pyridin-4-yl)-2H-tetrazol-2-yl)methyl acetate

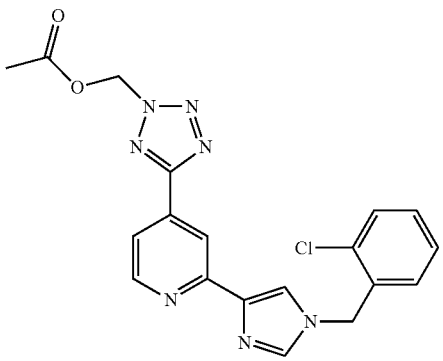 [SMILES: CC(=O)OCn1nnc(-c2ccnc(-c3cn(Cc4ccccc4Cl)cn3)c2)n1]

The title compound was prepared in 15% yield from 2-[1-[(2-chlorophenyl)methyl]imidazol-4-yl]-4-(2H-tetrazol-5-yl)pyridine (Example 129), chloromethyl acetate and potassium carbonate in DMF. $^1$H NMR (400 MHz, DMSO): δ 2.12 (3H, s), 5.41 (2H, s), 6.67 (2H, s), 7.27-7.29 (1H, m), 7.38-7.41 (2H, m), 7.53-7.55 (1H, m), 7.81 (1H, s), 7.94 (1H, s), 8.51 (1H, s), 8.68 (1H, d, J=5.0 Hz). [M+H] Calc'd for $C_{19}H_{16}ClN_7O_2$, 410. Found, 410.

Example 168

(5-(2-(1-((1,2,3,4-tetrahydronaphthalen-1-yl)methyl)-1H-imidazol-4-yl)pyridin-4-yl)-2H-tetrazol-2-yl)methyl pivalate

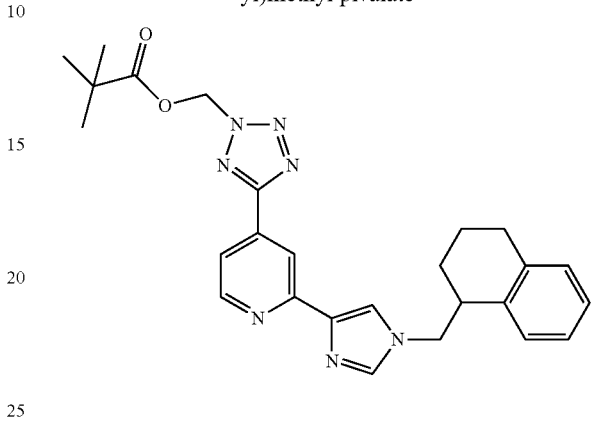

The title compound was prepared in 18% yield from 2-[1-(1,2,3,4-tetrahydronaphthalen-1-ylmethyl)imidazol-4-yl]-4-(2H-tetrazol-5-yl)pyridine according to the procedure for the preparation of Example 167. $^1$H NMR (400 MHz, DMSO): 1.12 (9H, s), 1.49 (1H, m), 1.64-1.66 (2H, m), 1.84 (1H, m), 2.67 (3H, m), 4.17 (1H, m), 4.32 (1H, m), 6.71 (2H, s), 7.12 (1H, t, J=3.7 Hz), 7.15 (2H, m), 7.30 (1H, t, J=4.9 Hz), 7.82 (1H, s), 7.83 (1H, s), 7.95 (1H, s), 8.52 (1H, s), 8.70 (1H, d, J=5.0 Hz). [M+H] Calc'd for $C_{26}H_{29}N_7O_2$, 472. Found, 472.

Example 169

2-(1-(3-chlorobenzyl)-5-(2-(cyclopropylmethoxy)-4-fluorophenyl)-1H-imidazol-4-yl)-4-(2H-tetrazol-5-yl)pyridine

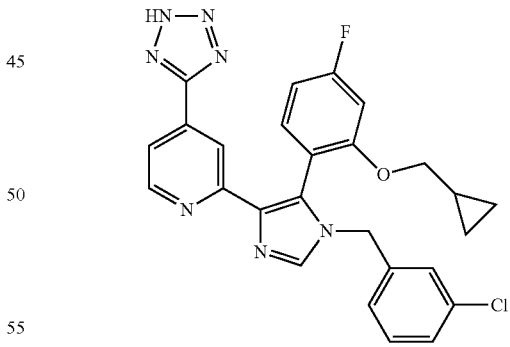

The title compound was prepared from 2-[1-[(3-chlorophenyl)methyl]imidazol-4-yl]pyridine-4-carbonitrile (Example 130, part B) according to the procedure for the preparation of Example 137. $^1$H NMR (300 MHz, DMSO): δ 0.05 (2H, m), 0.33 (2H, m), 0.89 (1H, m), 3.63 (1H, m), 3.73 (1H, m), 5.08 (1H, d, J=16 Hz), 5.16 (1H, d, J=15 Hz), 6.77 (1H, t, J=8.0 Hz), 6.87-6.94 (3H, s & m), 7.17 (1H, t, J=7.0 Hz), 7.23-7.29 (2H, s & m), 7.73 (1H, m), 8.16 (1H, m), 8.42 (1H, d, J=5.0 Hz), 8.53 (1H, s). [M+H] Calc'd for $C_{26}H_{21}ClFN_7O$, 502. Found, 502.

II. Biological Evaluation

Example 1

In Vitro Enzyme Inhibition Assay

This assay determines the ability of a test compound to inhibit Jarid1A, Jarid1B, JMJD2C, and JMJD2A demethylase activity. Baculovirus expressed Jarid1A (GenBank Accession #NM_001042603, AA1-1090) was purchased from BPS Bioscience (Cat#50110). Baculovirus expressed Jarid1B (GenBank Accession #NM_006618, AA 2-751) was purchased from BPS Bioscience (Cat #50121) or custom made by MolecularThroughput. Baculovirus expressed JMJD2C (GenBank Accession #BC143571, AA 2-372) was purchased from BPS Bioscience (Cat#50105). Baculovirus expressed JMJD2A (GenBank Accession #NM_014663, AA 1-350) was purchased from BPS Bioscience (Cat#50123). Baculovirus expressed FBXL10 (GenBank Accession #NM_032590, AA 1-650) was purchased from BPS Bioscience (Cat#50120).

Jarid1A Assay

The enzymatic assay of Jarid1A activity is based upon Time Resolved-Fluorescence Resonance Energy Transfer (TR-FRET) detection. The ability of test compounds to inhibit the activity of Jarid1A was determined in 384-well plate format under the following reaction conditions: 1 nM Jarid1A, 300 nM H3K4me3-biotin labeled peptide (Anaspec cat #64357), 2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-mono- or di-methylated histone H3 lysine 4 (H3K4me1-2) antibody (PerkinElmer) in the presence of 5 mM EDTA in LANCE detection buffer (PerkinElmer) at a final concentration of 25 nM and 1 nM, respectively.

The assay reaction was initiated by the following: 2 µl of the mixture of 900 nM H3K4me3-biotin labeled peptide and 6 µM alpha-ketoglutaric acid with 2 µl of 11-point serial diluted inhibitor in 3% DMSO was added to each well of plate, followed by the addition of 2 µl of 3 nM Jarid1A to initiate the reaction. The reaction mixture was incubated at room temperature for 30 minutes, and terminated by the addition of 6 µl of 5 mM EDTA in LANCE detection buffer containing 50 nM Phycolink Streptavidin-allophycocyanin and 2 nM Europium-anti-H3K4me1-2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

Jarid1B Assay

The ability of test compounds to inhibit the activity of Jarid1B was determined in 384-well plate format under the following reaction conditions: 0.8 nM Jarid1B, 300 nM H3K4me3-biotin labeled peptide (Anaspec cat #64357), 2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-mono- or di-methylated histone H3 lysine 4 (H3K4me1-2) antibody (PerkinElmer) in the presence of 5 mM EDTA in LANCE detection buffer (PerkinElmer) at a final concentration of 25 nM and 1 nM, respectively.

The assay reaction was initiated by the following: 2 µl of the mixture of 900 nM H3K4me3-biotin labeled peptide and 6 µM alpha-ketoglutaric acid with 2 µl of 11-point serial diluted inhibitor in 3% DMSO was added to each well of the plate, followed by the addition of 2 µl of 2.4 nM Jarid1B to initiate the reaction. The reaction mixture was incubated at room temperature for 30 minutes, and terminated by the addition of 6 µl of 5 mM EDTA in LANCE detection buffer containing 50 nM Phycolink Streptavidin-allophycocyanin and 2 nM Europium-anti-H3K4me1-2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

JMJD2C Assay

The ability of test compounds to inhibit the activity of JMJD2C was determined in 384-well plate format under the following reaction conditions: 0.3 nM JMJD2C, 300 nM H3K9me3-biotin labeled peptide (Anaspec cat #64360), 2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 µl of the mixture of 900 nM H3K9me3-biotin labeled peptide and 6 µM alpha-ketoglutaric acid with 2 µl of 11-point serial diluted inhibitor in 3% DMSO were added to each well of the plate, followed by the addition of 2 µl of 0.9 nM JMJD2C to initiate the reaction. The reaction mixture was incubated at room temperature for 30 minutes, and terminated by the addition of 6 µl of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

JMJD2A Assay

The ability of test compounds to inhibit the activity of JMJD2A was determined in 384-well plate format under the following reaction conditions: 2 nM JMJD2A, 300 nM H3K9me3-biotin labeled peptide (Anaspec cat #64360), 2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 µl of the mixture of 900 nM H3K9me3-biotin labeled peptide and 6 µM alpha-ketoglutaric acid with 2 µl of 11-point serial diluted inhibitor in 3% DMSO were added to each well of plate, followed by the addition of 2 µl of 6 nM JMJD2A to initiate the reaction. The reaction mixture was incubated at room temperature for 30 minutes, and terminated by the addition of 6 µl of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

FBXL10 Assay

The ability of test compounds to inhibit the activity of FBXL10 was determined in 384-well plate format under the following reaction conditions: 0.3 nM FBXL10, 30 nM H3K36me2-biotin labeled peptide (Anaspec cat #64442), 0.2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 5 µM ammonium iron(II) sulfate. Reaction product was determined quantitatively by AlphaScreen detection after the addition of detection reagents anti-H3K36me1 antibody, AlphaScreen® Streptavidin-coated Donor beads, and AlphaScreen® Protein A Acceptor beads in 50 mM HEPES, pH7.3, 10 mM NaCl, 0.005% Brij35, 5 mM EDTA, 2 mg/ml BSA to final 10 µg/ml beads.

The assay reaction was initiated by the following: 3 µl of the mixture of 90 nM H3K36me2-biotin labeled peptide and 0.6 µM alpha-ketoglutaric acid with 3 µl of 11-point serial diluted inhibitor in 3% DMSO were added to each well of 384 well Proxiplate (Perkin Elmer), followed by the addition of 3 µl of 0.9 nM FBXL10 to initiate the reaction. The reaction mixture was incubated at room temperature for 30 minutes, and terminated by the addition of 3 µl of 50 mM HEPES, pH7.3, 10 mM NaCl, 0.005% Brij35, 5 mM EDTA, 2 mg/ml BSA containing appropriate dilution of anti H3K36me1 antibody. Plates were incubated at room temperature for 40 minutes, followed by addition of 3 µl of 50 µg/ml AlphaScreen® Streptavidin-coated Donor beads and AlphaScreen® Protein A Acceptor beads in 50 mM HEPES, pH7.3, 10 mM NaCl, 0.005% Brij35, 5 mM EDTA, 2 mg/ml BSA. Plates were read by EnVisionMultilabel Reader in AlphaScreen mode after a minimum of 2 hour or up to overnight incubation at room temperature. The AlphaScreen signal for each well was used to determine inhibition constant ($IC_{50}$).

The ability of the compounds disclosed herein to inhibit demethylase activity was quantified and the respective $IC_{50}$ value was determined. Table 3 provides the $IC_{50}$ values of various compounds disclosed herein.

TABLE 3

| Ex. | NAME | $IC_{50}$ Jarid1A (nM) | $IC_{50}$ Jarid1B (nM) | $IC_{50}$ JMJD2C (nM) | $IC_{50}$ JMJD2A (nM) | $IC_{50}$ FBXL10 (nM) |
|---|---|---|---|---|---|---|
| 1 | 2-(1-methyl-1H-imidazol-4-yl)pyridine-4-carboxylic acid | A | A | A | A | A |
| 2 | 2-(5-bromo-1-methyl-1H-imidazol-4-yl)pyridine-4-carboxylic acid | A | A | B | | B |
| 3 | 2-[5-(3-hydroxy-4-methylphenyl)-1-methyl-1H-imidazol-4-yl]pyridine-4-carboxylic acid | A | A | C | | B |
| 4 | 2-[1-methyl-5-(4-methylphenyl)-1H-imidazol-4-yl]pyridine-4-carboxylic acid | A | A | C | | B |
| 5 | 2-[5-(4-ethylphenyl)-1-methyl-1H-imidazol-4-yl]pyridine-4-carboxylic acid | A | A | C | | B |
| 6 | 2-{1-methyl-5-[4-(trifluoromethyl)phenyl]-1H-imidazol-4-yl}pyridine-4-carboxylic acid | A | A | C | | B |
| 7 | 2-[5-(4-cyclopropylphenyl)-1-methyl-1H-imidazol-4-yl]pyridine-4-carboxylic acid | A | A | C | | B |
| 8 | methyl 2-[5-(4-cyclopropylphenyl)-1-methyl-1H-imidazol-4-yl]pyridine-4-carboxylate | | | | | |
| 9 | 2-[5-(4-tert-butylphenyl)-1-methyl-1H-imidazol-4-yl]pyridine-4-carboxylic acid | B | B | C | | |
| 10 | 2-{1-methyl-5-[3-(methylcarbamoyl)phenyl]-1H-imidazol-4-yl}pyridine-4-carboxylic acid | B | B | C | | |
| 11 | 2-{5-[3-(hydroxymethyl)phenyl]-1-methyl-1H-imidazol-4-yl}pyridine-4-carboxylic acid | B | B | C | | B |
| 12 | 2-[5-(4-methoxyphenyl)-1-methyl-1H-imidazol-4-yl]pyridine-4-carboxylic acid | B | B | C | | B |
| 13 | 2-{1-methyl-5-[4-(trifluoromethoxy)phenyl]-1H-imidazol-4-yl}pyridine-4-carboxylic acid | B | B | C | | B |
| 14 | 2-[5-(4-ethoxyphenyl)-1-methyl-1H-imidazol-4-yl]pyridine-4-carboxylic acid | B | B | C | | B |

TABLE 3-continued

| Ex. | NAME | IC$_{50}$ Jarid1A (nM) | IC$_{50}$ Jarid1B (nM) | IC$_{50}$ JMJD2C (nM) | IC$_{50}$ JMJD2A (nM) | IC$_{50}$ FBXL10 (nM) |
|---|---|---|---|---|---|---|
| 15 | 2-{1-methyl-5-[4-(1H-pyrazol-1-yl)phenyl]-1H-imidazol-4-yl}pyridine-4-carboxylic acid | A | A | B | | B |
| 16 | 2-{5-[4-(cyclopropylmethoxy)phenyl]-1-methyl-1H-imidazol-4-yl}pyridine-4-carboxylic acid | A | A | B | | B |
| 17 | 2-(5-{4-[1-(hydroxymethyl)cyclopropyl]phenyl}-1-methyl-1H-imidazol-4-yl)pyridine-4-carboxylic acid | A | A | B | | |
| 18 | 2-{1-methyl-5-[4-(pyrrolidin-1-yl)phenyl]-1H-imidazol-4-yl}pyridine-4-carboxylic acid | A | A | B | | |
| 19 | 2-[5-(4-chlorophenyl)-1-methyl-1H-imidazol-4-yl]pyridine-4-carboxylic acid | A | A | B | | A |
| 20 | 2-[5-(3-chlorophenyl)-1-methyl-1H-imidazol-4-yl]pyridine-4-carboxylic acid | A | A | B | | A |
| 21 | 2-[5-(4-ethynylphenyl)-1-methyl-1H-imidazol-4-yl]pyridine-4-carboxylic acid | A | A | B | | A |
| 22 | 2-[5-(1H-indol-6-yl)-1-methyl-1H-imidazol-4-yl]pyridine-4-carboxylic acid | A | A | B | | A |
| 23 | 2-[5-(4-fluorophenyl)-1-methyl-1H-imidazol-4-yl]pyridine-4-carboxylic acid | A | A | B | B | A |
| 24 | 2-[5-(3-fluorophenyl)-1-methyl-1H-imidazol-4-yl]pyridine-4-carboxylic acid | A | A | B | | A |
| 25 | 2-(5-{4-[1-(methoxymethyl)cyclopropyl]phenyl}-1-methyl-1H-imidazol-4-yl)pyridine-4-carboxylic acid | A | A | C | | |
| 26 | 2-[5-(4-chloro-2-methylphenyl)-1-methyl-1H-imidazol-4-yl]pyridine-4-carboxylic acid | A | B | C | | |
| 27 | 2-{5-[4-chloro-2-(trifluoromethyl)phenyl]-1-methyl-1H-imidazol-4-yl}pyridine-4-carboxylic acid | A | A | C | | A |
| 28 | 2-[5-(3,4-dichlorophenyl)-1-methyl-1H-imidazol-4-yl]pyridine-4-carboxylic acid | A | A | B | | B |
| 29 | 2-[5-(4-chloro-3-fluorophenyl)-1-methyl-1H-imidazol-4-yl]pyridine-4-carboxylic acid | A | A | B | | A |
| 30 | 2-[5-(4-chloro-3-methoxyphenyl)-1-methyl-1H-imidazol-4-yl]pyridine-4-carboxylic acid | A | A | B | | A |
| 31 | 2-{5-[4-chloro-3-(trifluoromethyl)phenyl]-1-methyl-1H-imidazol-4-yl}pyridine-4-carboxylic acid | A | A | B | | B |
| 32 | 2-[5-(4-chloro-2-ethoxyphenyl)-1-methyl-1H-imidazol-4-yl]pyridine-4-carboxylic acid | A | A | C | | B |
| 33 | 2-[5-(2,4-dichlorophenyl)-1-methyl-1H-imidazol-4-yl]pyridine-4-carboxylic acid | A | A | B | | A |
| 34 | 2-(1-methyl-5-{4-[1-(trifluoromethyl)cyclopropyl]phenyl}-1H-imidazol-4-yl)pyridine-4-carboxylic acid | A | A | B | | |
| 35 | 2-[5-(4-chloro-3-fluorophenyl)-1-propyl-1H-imidazol-4-yl]pyridine-4-carboxylic acid | A | A | B | | A |
| 36 | 2-[5-(4-chloro-3-fluorophenyl)-1-(3-methoxypropyl)-1H-imidazol-4-yl]pyridine-4-carboxylic acid | A | A | C | | A |
| 37 | 2-[5-(4-chloro-3-fluorophenyl)-1-(2-methoxyethyl)-1H-imidazol-4-yl]pyridine-4-carboxylic acid | A | A | C | | A |

TABLE 3-continued

| Ex. | NAME | IC$_{50}$ Jarid1A (nM) | IC$_{50}$ Jarid1B (nM) | IC$_{50}$ JMJD2C (nM) | IC$_{50}$ JMJD2A (nM) | IC$_{50}$ FBXL10 (nM) |
|---|---|---|---|---|---|---|
| 38 | 2-[1-[2-[(4-fluorophenyl)methyl-methylamino]ethyl]imidazol-4-yl]pyridine-4-carboxylic acid | A | A | A | A | A |
| 39 | 2-{5-(4-chloro-3-fluorophenyl)-1-[2-(dimethylamino)ethyl]-1H-imidazol-4-yl}pyridine-4-carboxylic acid | A | A | A | | A |
| 40 | 2-{1-[2-(dimethylamino)ethyl]-1H-imidazol-4-yl}pyridine-4-carboxylic acid | A | A | A | | |
| 41 | 2-(1-propyl-1H-imidazol-4-yl)pyridine-4-carboxylic acid | A | A | A | | A |
| 42 | 2-{1-[3-(dimethylamino)propyl]-1H-imidazol-4-yl}pyridine-4-carboxylic acid | A | A | A | | |
| 43 | 2-{1-[2-(pyrrolidin-1-yl)ethyl]-1H-imidazol-4-yl}pyridine-4-carboxylic acid | A | A | A | A | C |
| 44 | methyl 2-{1-[2-(pyrrolidin-1-yl)ethyl]-1H-imidazol-4-yl}pyridine-4-carboxylate | | | | | |
| 45 | 2-{1-[2-(morpholin-4-yl)ethyl]-1H-imidazol-4-yl}pyridine-4-carboxylic acid | C | B | D | | |
| 46 | 2-{1-[2-(1H-pyrazol-1-yl)ethyl]-1H-imidazol-4-yl}pyridine-4-carboxylic acid | B | B | C | | B |
| 47 | 2-[1-(pyridin-2-ylmethyl)-1H-imidazol-4-yl]pyridine-4-carboxylic acid | A | A | B | | A |
| 48 | 2-(1-{2-[2-(dimethylamino)ethoxy]ethyl}-1H-imidazol-4-yl)pyridine-4-carboxylic acid | A | A | A | A | B |
| 49 | 2-[1-(1-methylpiperidin-4-yl)-1H-imidazol-4-yl]pyridine-4-carboxylic acid | A | A | A | | B |
| 50 | 2-{1-[(1-methylpiperidin-4-yl)methyl]-1H-imidazol-4-yl}pyridine-4-carboxylic acid | A | A | A | A | C |
| 51 | 2-[1-(tetrahydrofuran-2-ylmethyl)-1H-imidazol-4-yl]pyridine-4-carboxylic acid | A | A | B | | A |
| 52 | 2-[1-(pyrrolidin-3-yl)-1H-imidazol-4-yl]pyridine-4-carboxylic acid | A | A | A | | B |
| 53 | 2-[1-(pyrrolidin-2-ylmethyl)-1H-imidazol-4-yl]pyridine-4-carboxylic acid | A | A | A | | B |
| 54 | 2-{1-[(4-methylmorpholin-2-yl)methyl]-1H-imidazol-4-yl}pyridine-4-carboxylic acid | A | A | A | | A |
| 55 | 2-{1-[(1-methylpiperidin-3-yl)methyl]-1H-imidazol-4-yl}pyridine-4-carboxylic acid | A | A | A | | A |
| 56 | methyl 2-(1-{2-[benzyl(methyl)amino]ethyl}-1H-imidazol-4-yl)pyridine-4-carboxylate | | | | | |
| 57 | 2-(1-{2-[benzyl(methyl)amino]ethyl}-1H-imidazol-4-yl)pyridine-4-carboxylic acid | A | A | A | | A |
| 58 | 2-(1-{2-[methyl(phenyl)amino]ethyl}-1H-imidazol-4-yl)pyridine-4-carboxylic acid | A | A | B | B | A |
| 59 | 2-(1-{2-[(cyclopropylmethyl)(methyl)amino]ethyl}-1H-imidazol-4-yl)pyridine-4-carboxylic acid | A | A | A | A | B |
| 60 | 2-{1-[2-(2-oxopyrrolidin-1-yl)ethyl]-1H-imidazol-4-yl}pyridine-4-carboxylic acid | A | A | B | A | A |

TABLE 3-continued

| Ex. | NAME | IC$_{50}$ Jarid1A (nM) | IC$_{50}$ Jarid1B (nM) | IC$_{50}$ JMJD2C (nM) | IC$_{50}$ JMJD2A (nM) | IC$_{50}$ FBXL10 (nM) |
|---|---|---|---|---|---|---|
| 61 | 2-{1-[2-(pyrrolidin-1-yl)propyl]-1H-imidazol-4-yl}pyridine-4-carboxylic acid | A | A | A | | |
| 62 | 2-(1-methyl-1H-imidazol-4-yl)-4-(2H-tetrazol-5-yl)pyridine | B | B | D | D | A |
| 63 | 2-{1-[2-(pyrrolidin-1-yl)ethyl]-1H-imidazol-4-yl}-4-(2H-tetrazol-5-yl)pyridine | A | A | B | C | B |
| 64 | N-cyano-2-(1-{2-[(cyclopropylmethyl)(methyl)amino]ethyl}-1H-imidazol-4-yl)pyridine-4-carboxamide | A | A | B | D | D |
| 65 | N-benzyl-2-fluoro-5-[3-methyl-5-[4-(2H-tetrazol-5-yl)pyridin-2-yl]imidazol-4-yl]benzamide | | | C | | A |
| 66 | 2-[1-[2-[methyl-[(3-methylphenyl)methyl]amino]ethyl]imidazol-4-yl]pyridine-4-carboxylic acid | A | A | A | A | A |
| 67 | 2-[1-[2-[methyl-[(4-methylphenyl)methyl]amino]ethyl]imidazol-4-yl]pyridine-4-carboxylic acid | A | A | A | A | A |
| 68 | 2-[1-[2-[methyl-[[4-(trifluoromethyl)phenyl]methyl]amino]ethyl]imidazol-4-yl]pyridine-4-carboxylic acid | A | A | A | A | A |
| 69 | 2-[1-[2-[(3-fluorophenyl)methyl-methylamino]ethyl]imidazol-4-yl]pyridine-4-carboxylic acid | A | A | A | A | A |
| 70 | 2-[1-[2-[ethyl-[(4-fluorophenyl)methyl]amino]ethyl]imidazol-4-yl]pyridine-4-carboxylic acid | A | A | A | A | A |
| 71 | 2-[1-[2-[cyclopropyl-[(4-fluorophenyl)methyl]amino]ethyl]imidazol-4-yl]pyridine-4-carboxylic acid | A | A | A | A | A |
| 72 | 2-[1-[2-[(4,4-difluorocyclohexyl)methylamino]ethyl]imidazol-4-yl]pyridine-4-carboxylic acid | A | A | A | | A |
| 73 | 2-[1-[2-[(3,3-difluorocyclobutyl)methylamino]ethyl]imidazol-4-yl]pyridine-4-carboxylic acid | A | A | A | | A |
| 74 | 2-[1-[2-[(4-fluorophenyl)methylamino]ethyl]imidazol-4-yl]pyridine-4-carboxylic acid | A | A | A | | A |
| 75 | 2-[1-[2-[[2-(trifluoromethyl)phenyl]methyl-amino]ethyl]imidazol-4-yl]pyridine-4-carboxylic acid | A | A | A | | |
| 76 | 2-[1-[2-(1,3-dihydroisoindol-2-yl)ethyl]imidazol-4-yl]pyridine-4-carboxylic acid | A | A | A | | A |
| 77 | 2-[1-[2-[(2-methoxyphenyl)methylamino]ethyl]imidazol-4-yl]pyridine-4-carboxylic acid | A | A | A | | A |
| 78 | 2-[1-[2-[(2-chlorophenyl)methylamino]ethyl]imidazol-4-yl]pyridine-4-carboxylic acid | A | A | A | | A |
| 79 | 2-[1-[2-(5-fluoro-1,3-dihydroisoindol-2-yl)ethyl]imidazol-4-yl]pyridine-4-carboxylic acid | A | A | A | | A |
| 80 | 2-[1-[2-[(2-ethylphenyl)methylamino]ethyl]imidazol-4-yl]pyridine-4-carboxylic acid | A | A | A | | A |
| 81 | 2-[1-[2-(4-chloro-1,3-dihydroisoindol-2- | A | A | A | | A |

TABLE 3-continued

| Ex. | NAME | IC$_{50}$ Jarid1A (nM) | IC$_{50}$ Jarid1B (nM) | IC$_{50}$ JMJD2C (nM) | IC$_{50}$ JMJD2A (nM) | IC$_{50}$ FBXL10 (nM) |
|---|---|---|---|---|---|---|
|  | yl)ethyl]imidazol-4-yl]pyridine-4-carboxylic acid |  |  |  |  |  |
| 82 | 2-[1-[2-(5-chloro-1,3-dihydroisoindol-2-yl)ethyl]imidazol-4-yl]pyridine-4-carboxylic acid | A | A | A |  | A |
| 83 | 2-[1-[2-(4-cyano-1,3-dihydroisoindol-2-yl)ethyl]imidazol-4-yl]pyridine-4-carboxylic acid | A | A | A |  | A |
| 84 | 2-[1-[2-[5-(trifluoromethyl)-1,3-dihydroisoindol-2-yl]ethyl]imidazol-4-yl]pyridine-4-carboxylic acid | A | A | A |  | A |
| 85 | 2-[1-[2-[(4-chlorophenyl)methyl-cyclopropylamino]ethyl]imidazol-4-yl]pyridine-4-carboxylic acid | A | A | B |  | A |
| 86 | 2-[1-[2-[cyclopropyl-[(3,4-dichlorophenyl)methyl]amino]ethyl]imidazol-4-yl]pyridine-4-carboxylic acid | A | A | B |  | A |
| 87 | 2-[1-[2-(4-chloro-N-methylanilino)ethyl]imidazol-4-yl]pyridine-4-carboxylic acid | A | A | B | B | A |
| 88 | 2-[1-[2-(3,4-dihydro-2H-quinolin-1-yl)ethyl]imidazol-4-yl]pyridine-4-carboxylic acid | A | A | B | A | A |
| 89 | 2-[1-[2-(6-chloro-3,4-dihydro-2H-quinolin-1-yl)ethyl]imidazol-4-yl]pyridine-4-carboxylic acid | A | A | B | B | A |
| 90 | 2-[1-[2-(6-fluoro-3,4-dihydro-2H-quinolin-1-yl)ethyl]imidazol-4-yl]pyridine-4-carboxylic acid | A | A | B | A | A |
| 91 | 2-[1-[2-(5-fluoro-2,3-dihydroindol-1-yl)ethyl]imidazol-4-yl]pyridine-4-carboxylic acid | A | A | B | B | B |
| 92 | 2-[1-[2-(4-fluorophenyl)ethyl]imidazol-4-yl]pyridine-4-carboxylic acid | A | A | A |  | A |
| 93 | 2-[1-[2-(2-fluorophenyl)ethyl]imidazol-4-yl]pyridine-4-carboxylic acid | A | A | A |  | A |
| 94 | 2-[1-[2-(4-methoxyphenyl)ethyl]imidazol-4-yl]pyridine-4-carboxylic acid | A | A | A |  |  |
| 95 | 2-[1-[2-(2-methoxyphenyl)ethyl]imidazol-4-yl]pyridine-4-carboxylic acid | A | A | B | B | A |
| 96 | 2-[1-[2-(2-methylphenyl)ethyl]imidazol-4-yl]pyridine-4-carboxylic acid | A | A | B | B | A |
| 97 | 2-[1-[2-(2-chlorophenyl)ethyl]imidazol-4-yl]pyridine-4-carboxylic acid | A | A | B | A | A |
| 98 | 2-[1-[2-[2-(trifluoromethyl)phenyl]ethyl]imidazol-4-yl]pyridine-4-carboxylic acid | A | A | A | A | A |
| 99 | 2-[1-(2,3-dihydro-1H-inden-2-yl)imidazol-4-yl]pyridine-4-carboxylic acid | A | A | B | B | A |
| 100 | 2-(1-benzylimidazol-4-yl)pyridine-4-carboxylic acid | A | A | B |  | A |
| 101 | 2-[1-[(4-fluorophenyl)methyl]imidazol-4-yl]pyridine-4-carboxylic acid | A | A | B | B | A |
| 102 | 2-[1-[(2-fluorophenyl)methyl]imidazol-4-yl]pyridine-4-carboxylic acid | A | A | B | B | A |
| 103 | 2-[1-(1-phenylethyl)imidazol-4-yl]pyridine-4-carboxylic acid | A | A | A | A | A |
| 104 | 2-[1-[(3-fluorophenyl)methyl]imidazol-4-yl]pyridine-4-carboxylic | A | A | B |  | A |

TABLE 3-continued

| Ex. | NAME | IC$_{50}$ Jarid1A (nM) | IC$_{50}$ Jarid1B (nM) | IC$_{50}$ JMJD2C (nM) | IC$_{50}$ JMJD2A (nM) | IC$_{50}$ FBXL10 (nM) |
|---|---|---|---|---|---|---|
| 105 | 2-[1-[2-(2-chlorophenyl)-2-methylpropyl]imidazol-4-yl]pyridine-4-carboxylic acid | A | A | C | B | A |
| 106 | 2-[1-(1-phenylpropan-2-yl)imidazol-4-yl]pyridine-4-carboxylic acid | A | A | B | | A |
| 107 | 2-[1-(1-phenylpropyl)imidazol-4-yl]pyridine-4-carboxylic acid | A | A | B | A | A |
| 108 | 2-[1-(2-methyl-1-phenylpropyl)imidazol-4-yl]pyridine-4-carboxylic acid | A | A | B | B | A |
| 109 | 2-[1-(6-fluoro-2,3-dihydro-1H-inden-1-yl)imidazol-4-yl]pyridine-4-carboxylic acid | A | A | C | B | A |
| 110 | 2-[1-(4-fluoro-2,3-dihydro-1H-inden-1-yl)imidazol-4-yl]pyridine-4-carboxylic acid | A | A | B | B | A |
| 111 | 2-[1-[(3-phenylphenyl)methyl]imidazol-4-yl]pyridine-4-carboxylic acid | A | A | C | C | A |
| 112 | 2-[1-(2-naphthalen-1-ylethyl)imidazol-4-yl]pyridine-4-carboxylic acid | A | A | B | B | A |
| 113 | 2-[1-[2-(3-chlorophenyl)ethyl]imidazol-4-yl]pyridine-4-carboxylic acid | A | A | B | | A |
| 114 | 2-[1-(2-cyclohexylethyl)imidazol-4-yl]pyridine-4-carboxylic acid | A | A | B | | A |
| 115 | 2-[1-(cyclohexylmethyl)imidazol-4-yl]pyridine-4-carboxylic acid | A | A | B | | A |
| 116 | 2-[1-(1,2,3,4-tetrahydronaphthalen-1-ylmethyl)imidazol-4-yl]pyridine-4-carboxylic acid | A | A | B | A | A |
| 117 | 2-[1-[[3-(trifluoromethyl)phenyl]methyl]imidazol-4-yl]pyridine-4-carboxylic acid | | | B | | A |
| 118 | methyl 2-[1-[2-(2-fluorophenyl)ethyl]imidazol-4-yl]pyridine-4-carboxylate | | | | | |
| 119 | methyl 2-[1-[(3-phenylphenyl)methyl]imidazol-4-yl]pyridine-4-carboxylate | | | | | |
| 120 | 2-[5-[2-(cyclopropylmethoxy)-4-fluorophenyl]-1-methylimidazol-4-yl]pyridine-4-carboxylic acid | B | A | C | D | A |
| 121 | 2-[5-[2-(cyclopropylmethoxy)-4,5-difluorophenyl]-1-methylimidazol-4-yl]pyridine-4-carboxylic acid | | | C | | A |
| 122 | 2-[5-[2-(cyclopropylmethoxy)-6-fluorophenyl]-1-methylimidazol-4-yl]pyridine-4-carboxylic acid | | | C | | A |
| 123 | 2-[5-[2-(cyclopropylmethoxy)-5-methylphenyl]-1-methylimidazol-4-yl]pyridine-4-carboxylic acid | | | C | | B |
| 124 | 2-[1-[2-(2-chlorophenyl)ethyl]-5-(4-fluorophenyl)imidazol-4-yl]pyridine-4-carboxylic acid | | | B | | A |
| 125 | 2-[1-(cyclopropylmethyl)-5-(4-fluorophenyl)imidazol-4-yl]pyridine-4-carboxylic acid | | | B | | A |
| 126 | 2-[5-(4-chlorophenyl)-1-(cyclopropylmethyl)imidazol-4-yl]pyridine-4-carboxylic acid | | | C | | A |
| 127 | 2-[1-[(2-chlorophenyl)methyl]-5-(4-fluorophenyl)imidazol-4-yl]pyridine-4-carboxylic acid | | | C | | A |
| 128 | 2-[1-[2-(2-ethoxyphenyl)ethyl]imidazol-4-yl]-4-(2H-tetrazol-5-yl)pyridine | | | C | | A |
| 129 | 2-[1-[(2-chlorophenyl)methyl]imidazol-4-yl]-4-(2H-tetrazol-5-yl)pyridine | B | A | C | D | A |

TABLE 3-continued

| Ex. | NAME | IC$_{50}$ Jarid1A (nM) | IC$_{50}$ Jarid1B (nM) | IC$_{50}$ JMJD2C (nM) | IC$_{50}$ JMJD2A (nM) | IC$_{50}$ FBXL10 (nM) |
|---|---|---|---|---|---|---|
| 130 | 2-[1-[(3-chlorophenyl)methyl]imidazol-4-yl]-4-(2H-tetrazol-5-yl)pyridine | | | C | | A |
| 131 | 2-[1-[(4-chlorophenyl)methyl]imidazol-4-yl]-4-(2H-tetrazol-5-yl)pyridine | | | C | | A |
| 132 | 2-[1-[2-(2-chlorophenyl)ethyl]-5-(4-fluorophenyl)imidazol-4-yl]-4-(2H-tetrazol-5-yl)pyridine | | | C | | A |
| 133 | 2-[5-(4-chlorophenyl)-1-[2-(2-chlorophenyl)ethyl]imidazol-4-yl]-4-(2H-tetrazol-5-yl)pyridine | | | C | | B |
| 134 | 2-[5-(4-fluorophenyl)-1-(2,2,2-trifluoroethyl)imidazol-4-yl]-4-(2H-tetrazol-5-yl)pyridine | | | C | | A |
| 135 | 2-[1-(cyclopropylmethyl)-5-(4-fluorophenyl)imidazol-4-yl]-4-(2H-tetrazol-5-yl)pyridine | | | C | | A |
| 136 | 2-[5-(4-chlorophenyl)-1-(cyclopropylmethyl)imidazol-4-yl]-4-(2H-tetrazol-5-yl)pyridine | | | C | | A |
| 137 | 2-[1-[(2-chlorophenyl)methyl]-5-(4-fluorophenyl)imidazol-4-yl]-4-(2H-tetrazol-5-yl)pyridine | | | C | | A |
| 138 | [5-[2-[1-[(2-chlorophenyl)methyl]-5-(4-fluorophenyl)imidazol-4-yl]pyridin-4-yl]tetrazol-2-yl]methyl acetate | | | C | | C |
| 139 | [5-[2-[1-[(2-chlorophenyl)methyl]-5-(4-fluorophenyl)imidazol-4-yl]pyridin-4-yl]tetrazol-2-yl]methyl 2,2-dimethylpropanoate | | | C | | C |
| 140 | 4-(2H-tetrazol-5-yl)-2-[1-[2-[2-(trifluoromethyl)phenyl]ethyl]imidazol-4-yl]pyridine | B | A | C | D | A |
| 141 | 2-[1-[2-(2-chlorophenyl)ethyl]imidazol-4-yl]-4-(2H-tetrazol-5-yl)pyridine | B | B | C | D | A |
| 142 | 2-[1-(2-naphthalen-1-ylethyl)imidazol-4-yl]-4-(2H-tetrazol-5-yl)pyridine | | A | C | D | A |
| 143 | 2-[1-(1,2,3,4-tetrahydronaphthalen-1-ylmethyl)imidazol-4-yl]-4-(2H-tetrazol-5-yl)pyridine | | B | C | D | A |
| 144 | 2-[1-(1-phenylpropyl)imidazol-4-yl]-4-(2H-tetrazol-5-yl)pyridine | B | A | C | D | A |
| 145 | 2-[1-(2-methyl-1-phenylpropyl)imidazol-4-yl]-4-(2H-tetrazol-5-yl)pyridine | B | B | C | D | A |
| 146 | 2-[1-(1,2,3,4-tetrahydronaphthalen-2-ylmethyl)imidazol-4-yl]-4-(2H-tetrazol-5-yl)pyridine | | | C | | A |
| 147 | 2-[1-(2,3-dihydro-1H-inden-2-ylmethyl)imidazol-4-yl]-4-(2H-tetrazol-5-yl)pyridine | | | C | | A |
| 148 | 2-[5-(4-fluoro-2-phenylmethoxyphenyl)-1-methylimidazol-4-yl]-4-(2H-tetrazol-5-yl)pyridine | | | C | | A |
| 149 | 2-[5-(2-butoxy-4-fluorophenyl)-1-methylimidazol-4-yl]-4-(2H-tetrazol-5-yl)pyridine | | | C | | A |
| 150 | 2-[5-[2-(cyclopropylmethoxy)-4-fluorophenyl]-1-methylimidazol-4-yl]-4-(2H-tetrazol-5-yl)pyridine | B | A | C | D | A |
| 151 | 2-[1-[(2,6-dichlorophenyl)methyl]imidazol-4-yl]-4-(2H-tetrazol-5-yl)pyridine | | | C | | A |

TABLE 3-continued

| Ex. | NAME | IC$_{50}$ Jarid1A (nM) | IC$_{50}$ Jarid1B (nM) | IC$_{50}$ JMJD2C (nM) | IC$_{50}$ JMJD2A (nM) | IC$_{50}$ FBXL10 (nM) |
|---|---|---|---|---|---|---|
| 152 | 4-(2H-tetrazol-5-yl)-2-[1-[[2-(2,2,2-trifluoroethoxy)phenyl]methyl]imidazol-4-yl]pyridine | | | C | | A |
| 153 | 2-[1-[[2-(2-methylpropoxy)phenyl]methyl]imidazol-4-yl]-4-(2H-tetrazol-5-yl)pyridine | | | C | | B |
| 154 | 2-[1-[[2-chloro-3-(trifluoromethyl)phenyl]methyl]imidazol-4-yl]-4-(2H-tetrazol-5-yl)pyridine | B | A | C | D | A |
| 155 | 2-[1-(naphthalen-1-ylmethyl)imidazol-4-yl]-4-(2H-tetrazol-5-yl)pyridine | | | C | | A |
| 156 | 4-(2H-tetrazol-5-yl)-2-[1-[[2-(trifluoromethoxy)phenyl]methyl]imidazol-4-yl]pyridine | | | C | | A |
| 157 | 2-[1-[1-(2-chlorophenyl)ethyl]imidazol-4-yl]-4-(2H-tetrazol-5-yl)pyridine | | | C | | A |
| 158 | 2-[1-[(2,3-dichlorophenyl)methyl]imidazol-4-yl]-4-(2H-tetrazol-5-yl)pyridine | | | C | | A |
| 159 | 2-[5-[4-fluoro-3-(2,2,2-trifluoroethoxy)phenyl]-1-methylimidazol-4-yl]-4-(2H-tetrazol-5-yl)pyridine | | | C | | B |
| 160 | 2-[5-(4-fluoro-3-phenylmethoxyphenyl)-1-methylimidazol-4-yl]-4-(2H-tetrazol-5-yl)pyridine | | | C | | A |
| 161 | 2-[5-(4-chloro-3-phenylmethoxyphenyl)-1-methylimidazol-4-yl]pyridine-4-carbonitrile | | | C | | A |
| 162 | 2-fluoro-5-[3-methyl-5-[4-(2H-tetrazol-5-yl)pyridin-2-yl]imidazol-4-yl]phenol | | | C | | A |
| 163 | 2-fluoro-5-[3-methyl-5-[4-(2H-tetrazol-5-yl)pyridin-2-yl]imidazol-4-yl]-N-phenylbenzamide | | | C | | B |
| 164 | 2-[5-(4-fluoronaphthalen-1-yl)-1-methylimidazol-4-yl]-4-(2H-tetrazol-5-yl)pyridine | | | C | | A |
| 165 | 2-(1-(2-chlorobenzyl)-1H-imidazol-4-yl)-4-(2-methyl-2H-tetrazol-5-yl)pyridine | | | C | | C |
| 166 | (5-(2-(1-(2-chlorobenzyl)-1H-imidazol-4-yl)pyridin-4-yl)-2H-tetrazol-2-yl)methyl pivalate | | | C | | C |
| 167 | (5-(2-(1-(2-chlorobenzyl)-1H-imidazol-4-yl)pyridin-4-yl)-2H-tetrazol-2-yl)methyl acetate | | | C | | B |
| 168 | (5-(2-(1-(((1,2,3,4-tetrahydronaphthalen-1-yl)methyl)-1H-imidazol-4-yl)pyridin-4-yl)-2H-tetrazol-2-yl)methyl pivalate | | | | | |
| 169 | 2-(1-(3-chlorobenzyl)-5-(2-(cyclopropylmethoxy)-4-fluorophenyl)-1H-imidazol-4-yl)-4-(2H-tetrazol-5-yl)pyridine | | | C | | B |

Note:
Biochemical assay IC$_{50}$ data are designated within the following ranges:
A: ≤100 nM
B: >100 nM to ≤1,000 nM
C: >1,000 nM to ≤10,000 nM
D: >10,000 nM

Example 2

In Vitro Cell-Based Assay

An assay to measure the degree of cellular inhibition of KDM5A and 5B was developed. This quantitative immuno-blotting assay measures the amount tri-methylated histone H3 at amino acid Lysine number 4, a specific substrate and product of the direct enzymatic activity of the histone demethylases KDM5A and KDM5B from extracts of the ZR-75-1 breast cancer cell line.

Assay Principle

This assay is a fluorometric immunoassay for the quantification of tri-methyl H3K4 extracted from cells treated with test compound and is used as a measure of the cellular inhibition of KDM5A/B.

Assay Method

ZR-75-1 (PTEN null, ER+) breast cancer cells numbering 50,000 (ATCC) were seeded into each well of a 96-well tissue culture treated plate and then exposed to an 11 point dilution of test compound with final concentration ranges of test compound ranging from 1250 μM to 10 nM. Cells were left in the presence of test compound for 72 hours. Extracts were prepared containing all of the cellular histone material using detergent based lysis and sonication methods. These lysates were subsequently normalized for total protein content using a colorimetric bicinchonic acid assay (MicroBCA Pierce/Thermo Scientific). Normalized cell extracts were then subjected to typical immuno-blotting procedures using NuPage reagents (Life Technologies). Electrophoretically separated histones were then transferred and immobilized using polyvinylidene difluoride membrane (Immobilon-FL Millipore). The amount of tri-methylated lysine 4 of histone H3 was detected using an antibody specific to the tri-methylated state (Cell Signaling Technologies) and quantified on an infrared imager using a densitometry software package (Odyssey CLx, Image Studio, Li-Cor). This background subtracted densitometry value was reported as a ration of the GAPDH amount for that sample and then calculated as a percent of the DMSO treated sample. The software package XL-fit (IDBS) was then used to calculate a relative $IC_{50}$ value for the dilution series of a given test compound according to the equation:

$$fit=(D+((Vmax*(x\hat{\,}n))/((x\hat{\,}n)+(Km\hat{\,}n))))$$

Table 4 provides the cellular $IC_{50}$ values of various compounds disclosed herein.

TABLE 4

| Chemical Synthesis Example | Name | $IC_{50}$ ZR-75-1 cell-MOA (μM) |
|---|---|---|
| 1 | 2-(1-methyl-1H-imidazol-4-yl)pyridine-4-carboxylic acid | D |
| 3 | 2-[5-(3-hydroxy-4-methylphenyl)-1-methyl-1H-imidazol-4-yl]pyridine-4-carboxylic acid | D |
| 7 | 2-[5-(4-cyclopropylphenyl)-1-methyl-1H-imidazol-4-yl]pyridine-4-carboxylic acid | D |
| 12 | 2-[5-(4-methoxyphenyl)-1-methyl-1H-imidazol-4-yl]pyridine-4-carboxylic acid | C |
| 15 | 2-{1-methyl-5-[4-(1H-pyrazol-1-yl)phenyl]-1H-imidazol-4-yl}pyridine-4-carboxylic acid | C |
| 16 | 2-{5-[4-(cyclopropylmethoxy)phenyl]-1-methyl-1H-imidazol-4-yl}pyridine-4-carboxylic acid | C |
| 18 | 2-{1-methyl-5-[4-(pyrrolidin-1-yl)phenyl]-1H-imidazol-4-yl}pyridine-4-carboxylic acid | C |
| 19 | 2-[5-(4-chlorophenyl)-1-methyl-1H-imidazol-4-yl]pyridine-4-carboxylic acid | C |
| 20 | 2-[5-(3-chlorophenyl)-1-methyl-1H-imidazol-4-yl]pyridine-4-carboxylic acid | D |
| 22 | 2-[5-(1H-indol-6-yl)-1-methyl-1H-imidazol-4-yl]pyridine-4-carboxylic acid | D |
| 23 | 2-[5-(4-fluorophenyl)-1-methyl-1H-imidazol-4-yl]pyridine-4-carboxylic acid | C |
| 29 | 2-[5-(4-chloro-3-fluorophenyl)-1-methyl-1H-imidazol-4-yl]pyridine-4-carboxylic acid | D |
| 35 | 2-[5-(4-chloro-3-fluorophenyl)-1-propyl-1H-imidazol-4-yl]pyridine-4-carboxylic acid | D |
| 40 | 2-{1-[2-(dimethylamino)ethyl]-1H-imidazol-4-yl}pyridine-4-carboxylic acid | C |
| 41 | 2-(1-propyl-1H-imidazol-4-yl)pyridine-4-carboxylic acid | C |
| 43 | 2-{1-[2-(pyrrolidin-1-yl)ethyl]-1H-imidazol-4-yl}pyridine-4-carboxylic acid | D |
| 62 | 2-(1-methyl-1H-imidazol-4-yl)-4-(2H-tetrazol-5-yl)pyridine | D |
| 71 | 2-[1-[2-[cyclopropyl-[(4-fluorophenyl)methyl]amino]ethyl]imidazol-4-yl]pyridine-4-carboxylic acid | C |
| 72 | 2-[1-[2-[(4,4-difluorocyclohexyl)methylamino]ethyl]imidazol-4-yl]pyridine-4-carboxylic acid | C |
| 88 | 2-[1-[2-(3,4-dihydro-2H-quinolin-1-yl)ethyl]imidazol-4-yl]pyridine-4-carboxylic acid | C |
| 92 | 2-[1-[2-(4-fluorophenyl)ethyl]imidazol-4-yl]pyridine-4-carboxylic acid | C |
| 93 | 2-[1-[2-(2-fluorophenyl)ethyl]imidazol-4-yl]pyridine-4-carboxylic acid | C |
| 95 | 2-[1-[2-(2-methoxyphenyl)ethyl]imidazol-4-yl]pyridine-4-carboxylic acid | D |
| 96 | 2-[1-[2-(2-methylphenyl)ethyl]imidazol-4-yl]pyridine-4-carboxylic acid | C |
| 97 | 2-[1-[2-(2-chlorophenyl)ethyl]imidazol-4-yl]pyridine-4-carboxylic acid | C |
| 98 | 2-[1-[2-[2-(trifluoromethyl)phenyl]ethyl]imidazol-4-yl]pyridine-4-carboxylic acid | D |
| 99 | 2-[1-(2,3-dihydro-1H-inden-2-yl)imidazol-4-yl]pyridine-4-carboxylic acid | C |
| 100 | 2-(1-benzylimidazol-4-yl)pyridine-4-carboxylic acid | C |
| 101 | 2-[1-[(4-fluorophenyl)methyl]imidazol-4-yl]pyridine-4-carboxylic acid | C |
| 102 | 2-[1-[(2-fluorophenyl)methyl]imidazol-4-yl]pyridine-4-carboxylic acid | C |
| 103 | 2-[1-(1-phenylethyl)imidazol-4-yl]pyridine-4-carboxylic acid | C |
| 104 | 2-[1-[(3-fluorophenyl)methyl]imidazol-4-yl]pyridine-4-carboxylic | D |
| 105 | 2-[1-[2-(2-chlorophenyl)-2-methylpropyl]imidazol-4-yl]pyridine-4-carboxylic acid | C |
| 106 | 2-[1-(1-phenylpropan-2-yl)imidazol-4-yl]pyridine-4-carboxylic acid | C |

Note:
Cellular assay $IC_{50}$ data are designated within the following ranges:
A: ≤0.10 μM
B: >0.10 μM to ≤1.0 μM
C: >1.0 μM to ≤10 μM
D: >10 μM

Example 3

In Vivo Xenograph Study

Time release pellets containing 0.72 mg 17-β Estradiol are subcutaneously implanted into nu/nu mice. MCF-7 cells are grown in RPMI containing 10% FBS at 5% $CO_2$, 37° C. Cells are spun down and re-suspended in 50% RPMI (serum free)

and 50% Matrigel at 1×10⁷ cells/mL. MCF-7 cells are subcutaneously injected (100 μL/animal) on the right flank 2-3 days post pellet implantation and tumor volume (length× width²/2) is monitored bi-weekly. When tumors reach an average volume of ~200 mm³ animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

III. Preparation of Pharmaceutical Dosage Forms

Example 1

Oral Tablet

A tablet is prepared by mixing 48% by weight of a compound of Formula (I) or (III), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A compound having the structure of Formula (II):

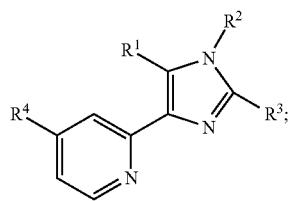

Formula (II)

or a pharmaceutically acceptable salt thereof, wherein:
$R^1$ is hydrogen, or C6-C10aryl;
$R^2$ is C1-C5alkyl, C3-C8cycloalkyl, C6-C10aryl, C3-C8cycloalkyl(C1-C5alkylene), or C6-C10ar(C1-C5alkylene);
$R^3$ is hydrogen;
$R^4$ is —CO₂H, —CO₂R⁶, —C(O)N(H)CN, or —C(O)N(H)OH;
each $R^5$ is independently hydrogen, C1-C5alkyl, C3-C8cycloalkyl, C6-C10aryl, C3-C8cycloalkyl(C1-C5alkylene), or C6-C10ar(C1-C5alkylene); and
$R^6$ is C1-C5alkyl.

2. The compound of claim 1, wherein $R^4$ is —CO₂H.
3. The compound of claim 1, wherein $R^4$ is —CO₂R⁶.
4. The compound of claim 1, wherein $R^4$ is —C(O)N(H)CN.
5. The compound of claim 1, wherein $R^2$ is C1-C5alkyl.
6. The compound of claim 1, wherein $R^2$ is methyl.
7. The compound of claim 1, wherein $R^2$ is C1-C5alkyl substituted with (C1-C5alkyl)-O—.
8. The compound of claim 1, wherein $R^2$ is C1-C5alkyl substituted with (C1-C5alkyl)₂N—.
9. The compound of claim 1, wherein $R^2$ is C1-C5alkyl substituted with (C6-C10aryl)(C1-C5alkyl)amino.
10. The compound of claim 1, wherein $R^2$ is C1-C5alkyl substituted with (C3-C8cycloalkyl)(C1-C5alkyl)amino.
11. The compound of claim 1, wherein $R^2$ is C1-C5alkyl substituted with (C6-C10ar(C1-C5alkylene))(C1-C5alkyl)amino.
12. The compound of claim 1, wherein $R^2$ is C1-C5alkyl substituted with (C3-C8cycloalkyl(C1-C5alkylene))(C1-C5alkyl)amino.
13. The compound of claim 1, wherein $R^1$ is hydrogen.
14. The compound of claim 1, wherein $R^1$ is C6-C10aryl.
15. The compound of claim 14, wherein $R^1$ is phenyl optionally substituted with one or more groups selected from halogen, —OH, —OR⁵, —N(R⁵)₂, —CON(R⁵)₂, C1-C5alkyl, C2-C5alkynyl, C3-C8cycloalkyl, C6-C10aryl, C3-C8cycloalkyl(C1-C5alkylene), and (C6-C10ar(C1-C5alkylene).
16. The compound of claim 14, wherein $R^1$ is phenyl optionally substituted with one or more groups selected from halogen, —OH, —OR⁵, C1-C5alkyl, and C3-C8cycloalkyl.
17. A pharmaceutical composition comprising a compound of claim 1, or a pharmaceutically acceptable salt thereof, and at least one pharmaceutically acceptable excipient.

* * * * *